US011130786B2

(12) United States Patent
Ng et al.

(10) Patent No.: US 11,130,786 B2
(45) Date of Patent: Sep. 28, 2021

(54) ALPHAVIRUS NSP MUTANTS AS VACCINES

(71) Applicants: AGENCY FOR SCIENCE, TECHNOLOGY AND RESEARCH, Singapore (SG); University of Tartu, Tartu (EE)

(72) Inventors: Lisa Fong Poh Ng, Singapore (SG); Yi Hao Chan, Singapore (SG); Andres Merits, Tartu (EE); Age Utt, Tartu (EE)

(73) Assignees: AGENCY FOR SCIENCE, TECHNOLOGY AND RESEARCH, Singapore (SG); UNIVERSITY OF TARTU, Tartu (EE)

( * ) Notice: Subject to any disclaimer, the term of this patent is extended or adjusted under 35 U.S.C. 154(b) by 0 days.

(21) Appl. No.: 16/484,277

(22) PCT Filed: Feb. 7, 2018

(86) PCT No.: PCT/SG2018/050052
§ 371 (c)(1),
(2) Date: Aug. 7, 2019

(87) PCT Pub. No.: WO2018/147802
PCT Pub. Date: Aug. 16, 2018

(65) Prior Publication Data
US 2019/0359656 A1 Nov. 28, 2019

(30) Foreign Application Priority Data
Feb. 7, 2017 (SG) .......................... 10201700950R

(51) Int. Cl.
*C07K 14/005* (2006.01)
*A61P 31/14* (2006.01)
*A61K 9/127* (2006.01)
*A61K 39/12* (2006.01)
*A61K 39/00* (2006.01)

(52) U.S. Cl.
CPC ............ *C07K 14/005* (2013.01); *A61K 9/127* (2013.01); *A61K 39/12* (2013.01); *A61P 31/14* (2018.01); *A61K 2039/5254* (2013.01); *A61K 2039/5258* (2013.01); *A61K 2039/54* (2013.01); *A61K 2039/542* (2013.01); *A61K 2039/543* (2013.01); *A61K 2039/545* (2013.01); *C12N 2770/36122* (2013.01); *C12N 2770/36123* (2013.01); *C12N 2770/36134* (2013.01); *C12N 2770/36171* (2013.01)

(58) Field of Classification Search
CPC ....... C07K 14/005; A61P 31/14; A61K 9/127; A61K 39/12; A61K 2039/5254; A61K 2039/5258; A61K 2039/54; A61K 2039/542; A61K 2039/543; A61K 2039/545; C12N 2770/36122; C12N 2770/36123; C12N 2770/36134; C12N 2770/36171; Y02A 50/30
See application file for complete search history.

(56) References Cited

U.S. PATENT DOCUMENTS

2015/0024002 A1* 1/2015 Perri ...................... A61P 31/14
424/196.11

FOREIGN PATENT DOCUMENTS

WO WO-2012/159638 A1 11/2012

OTHER PUBLICATIONS

Tsetsarkin KA, Vanlandingham DL, Higgs S. Nonstructural polyprotein [Cloning vector pCHIKV-LR ic], GenBank: ABX40005.1. Dep. Nov. 24, 2007.*
Hallengärd et al., "Novel Attenuated Chikungunya Vaccine Candidates Elicit Protective Immunity in C57BL/6 Mice", Journal of Virology, vol. 88, No. 5, Mar. 2014, pp. 2858-2866.
Fros et al., "Chikungunya Virus Nonstructural Protein 2 Inhibits Type I/II Interferon-Stimulated JAK-STAT Signaling" Journal of Virology, vol. 84, No. 20, Oct. 2010, pp. 10877-10887.
Utt et al., "Mutations Conferring a Noncytotoxic Phenotype on Chikungunya Virus Replicons Compromise Enzymatic Properties of Nonstructural Protein 2", Journal of Virology, vol. 89, No. 6, Mar. 2015, pp. 3145-3162.
Teo et al., "Caribbean and La Réunion Chikungunya Virus Isolates Differ in Their Capacity to Induce Proinflammatory Th1 and NK Cell Responses and Acute Joint Pathology", Journal of Virology, vol. 89, No. 15, Aug. 2015, pp. 7955-7969.
Abraham et al., "Correlation of Phylogenetic Clade Diversification and In Vitro Infectivity Differences Among Cosmopolitan Genotype Strains of Chikungunya Virus", Infection, Genetics and Evolution, vol. 37, 2016, pp. 174-184.
Saul et al., "Differences in Processing Determinants of Nonstructural Polyprotein and in the Sequence of Nonstructural Protein 3 Affect Neurovirulence of Semliki Forest Virus", Journal of Virology, vol. 89, No. 21, Nov. 2015, pp. 11030-11045.
Search Report in International Application No. PCT/SG2018/050052 dated Apr. 11, 2018, 3 pages.
Saul et al., "Differences in Processing Determinants of Nonstructural Polyprotein and in the Sequence of Nonstructural Protein 3 Affect Neurovirulence of Semliki Forest Virus", Journal of Virology, vol. 89, No. 21, Aug. 26, 2015, pp. 11030-11045.
Cruz et al., "Modulation of Type I IFN Induction by a Virulence Determinant Within the Alphavirus nsP1 Protein", Virology, vol. 399, No. 1, Jan. 25, 2010, 10 pages.
Hallengard et al., "Novel Attenuated Chikungunya Vaccine Candidates Elicit Protective Immunity in C57BL/6 Mice", Journal of Virology, vol. 88, No. 5, Mar. 1, 2014, pp. 2858-2866.

(Continued)

Primary Examiner — Rachel B Gill
(74) Attorney, Agent, or Firm — Marshall, Gerstein & Borun LLP

(57) ABSTRACT

The present invention generally relates to polypeptides, polynucleotides, expression vectors, infectious clones, virus particles and immunogenic compositions of recombinant alphaviruses which can be used as vaccines. The present disclosure also relates to methods for eliciting an immune response against alphavirus infection using the immunogenic composition comprising the alphavirus mutants described herein.

18 Claims, 40 Drawing Sheets

Specification includes a Sequence Listing.

(56) References Cited

OTHER PUBLICATIONS

Paritidos et al., "Cross-protective Immunity Against Onyong-nyong Virus Afforded by a Novel Recombinant Chikungunya Vaccine", Vaccine, vol. 30, No. 31, Apr. 27, 2012, pp. 4638-4643.
Chan et al., Mutating Chikungunya Virus Non-structural Protein Produces Potent Live-attenuated Vaccine Candidate, Embo Molecular Medicine, vol. 11, No. 6, Apr. 23, 2019, 17 pages.
Extended European Search Report in EP Application No. 18750998.9 dated Aug. 13, 2020, 8 pages.
Invitation to Proceed Further in EP Application No. 18750998.9 dated Sep. 1, 2020, 2 pages.

* cited by examiner (A)

|  | Mock-vaccinated + WT CHIKV | WT CHIKV-vaccinated + WT CHIKV | RH CHIKV-vaccinated + WT CHIKV |
|---|---|---|---|
| Edema | | | |
| Synovitis | | | |
| Muscle degeneration and necrosis | | | |

(iii) Inflammation

Synovial membrane

Vaccination phase: ○ PBS  • WT  ● RH
Re-infection phase: WT CHIKV (iv) Inflammation

Tendon

Vaccination phase: ○ PBS  • WT  ● RH
Re-infection phase: WT CHIKV

FIG. 7 (CONTINUED)

(v) Inflammation (vi) Muscle pathology (A)

Viremia

[Graph: x-axis "Days post-infection (dpi)" from 0 to 15; y-axis "nsP1 genome copies/ 10 μl blood (Log10)" from 0.1 to 100]

Vaccination phase: —●— WT  —■— RH  —○— Mock

Re-infection phase : WT ONNV

FIG. 11

```
VEEV   ---MEKVHVDIEEDSPFLRALQRSFPQFEVEAKQVTDNDHANARAFSHLASKLIETEVDPS
BFV    MAKPVVKIDVEPESHFAKQVQSCFPQFEIEAVQTTPNDHAHARAFSHLATKLIEMETAKD
ONNV   ---MDSVYVDIDADSAFLKALQRAYPMFEVEPKQVTPNDHANARAFSHLAIKLIEQEIDPD
CHIKV  ---MDPVYVDIDADSAFLKALQRAYPMFEVEPRQVTPNDHANARAFSHLAIKLIEQEIDPD
RRV    ---MKVTVDVEADSPFLKALQKAFPAFEVESQQVTPNDHANARAFSHLATKLIEQEVPTN
SFV    MAAKVHVDIEADSPFLKSLQKAFPSFEVESLQVTPNDHANARAFSHLATKLIEQETDKD
MAYV   ---MSKVFVDIEAESPFLKSLQRAFPAFEVEAQQVTPNDHANARAFSHLATKLIEQETEKD
          *  ::  * ::  *: *:  *  :*  :** ***.******:***:* :

VEEV   DTILDIGSAPARRMYSKHKYHCICPMRCAEDPDRLYKYATKLKNCKEITDKELDKKMKE
BFV    QIILDIGSAPARRIYSEHKYHCVCPMKCTEDPERMLGYARKLIAGSAK----GKAEKLRD
ONNV   STILDIGPAPARRMSDRKYHCVCPMRSAEDPERLANYARKLASAAGKVTDKNISGKIND
CHIKV  STILDIGSAPARRMSDRKYHCVCPMRSAEDPERLANYARKLASAAGKVLDRNISGKIGD
RRV    ITILDVGSAPARRLMSDHSYHCICPMKSAEDPERLANYARKLAKAAGEVLDKNVSGKITD
SFV    TLILDIGSAPSRRMMSTHKYHCVCPMRSAEDPERLVCYAKKLAAASGKVLDREIAGKITD
MAYV   TLILDIGSAPARRMMSEHTYHCVCPMRSAEDPERLLYYARKLAKASGEVVDRNIAAKIDD
        ***:*:** ** :  :::***:***:  *** *: :* :*: .: :       *  ::

VEEV   LAAVMSDPDLETETMCLHDDESCRYEGQVAVYQDVYAVDGPTSLYHQANKGVRVAYWIGF
BFV    LRDVLATPDIETQSLCLHTDASCRYRGDVAVYQDVYAIDAPTTLYHQALKGVRTAYWIGF
ONNV   LQAVMAVPNMETSTFCLHTDATCKQRGDVAIYQDVYAVHAPTSLYHQAIKGVRVAYWIGF
CHIKV  LQAVMAVPDTETPTFCLHTDVSCRQRADVAIYQDVYAVHAPTSLYHQAIRGVRVAYWVGF
RRV    LQDVMATPDLESPTFCLHTDETCRTRAEVAVYQDVYAVHAPTSLYHQAMKGVRTVYWIGF
SFV    LQTVMATPDAESPTFCLHTDVTCRTAAEVAVYQDVYAVHAPTSLYHQAMKGVRTAYWIGF
MAYV   LQSVMATPDNESRTFCLHTDQTCRTPAEVAVYQDVYAVHAPTSLYFQAMKGVRTAYWIGF
       *  .:: *: *: : ***.*  *:   .**:*******  **:***:*  :***.****
```

FIG. 11 (CONTINUED)

```
BFV     DTTPFMYDALAGAYPLYSTNWADEQVLESRNIGLCSDKVSEGGKKGRSILRKKFLKQSDR
ONNV    DTTPFMYNAMAGAYPSYSTNWADEQVLKAKNIGLCSTDLSEGRRGKLSIMRGKKLKPCDR
CHIKV   DTTPFMYNAMAGAYPSYSTNWADEQVLKAKNIGLCSTDLTEGRRGKLSIMRGKKLKPCDR
RRV     DTTPFMFEVLAGAYPTYSTNWADEQVLQARNIGLCATSLSEGHRGKLSIMRKKRLRPSDR
SFV     DTTPFMFDALAGAYPTYATNWADEQVLQARNIGLCAASLTEGRLGKLSILRKKQLKPCDT
MAYV    DTTPFMFDTMAGAYPTYATNWADEQVLKARNIGLCSAALTEGHLGKLSIMRKKRMKPSDQ
        ****:: :: ****** ******:: *  ******:*:    :* ***:  *:*:*

VEEV    VLFSVGSTIYHEKRDLLRSWHLPSVFHLRGKQNYTCRCETIVSCDGYVVKRIAISPGLYG
BFV     VMFSVGSTLYTESRKLLQSWHLPSTFHLKGKSSFTCRCDTIVSCEGYVVKITMCPGVTG
ONNV    VLFSVGSTLYPESRKLLQSWHLPSVFHLKGKLSFTCRCDTIVSCEGYVVKRVTMSPGIYG
CHIKV   VLFSVGSTLYPESRKLLKSWHLPSVFHLKGKLSFTCRCDTVVSCEGYVVKRITMSPGLYG
RRV     VMFSVGSTLYIESRRLLKSWHLPSVFHLKGKNSFTCRCDTIVSCEGYVVKKITMSPGTYG
SFV     VMFSVGSTLYTESRKLLKSWHLPSVFHLKGKQSFTCRCDTVVSCEGYVVKKITMCPGLYG
MAYV    IMFSVGSTLYTESRRLLKSWHLPSVFHLKGRQSYTCRCDTVVSCEGYVVKKITMSPGVFG
        :****:* . *:**:**:****.*** *: ..****::*****:**   :*..*

VEEV    KPSGYAATMHREGFLCCKVTDTLNGERVSFPVCTYVPATLCDQMTGILATDVSADDAQKL
BFV     KPIGYAVTHKEGFVVGKVTDTIRGERVSFAVCTYVPTTLCDQMTGILATEVTADDAQKL
ONNV    KTSGYAVTHHADGFLMCKTTDTVDGERVSFSVCTYVPATICDQMTGILATEVTPEDAQKL
CHIKV   KTTGYAVTHHADGFLMCKTTDTVDGERMSFSVCTYVPATICDQMTGILATEVTPEDAQKL
RRV     KTVGYAVTHHADGFLMCKTTDTVRGERVSFSVCTYVPATICDQMTGILATDVTPEDAQKL
SFV     KTVGYAVTYHAEGFLVCKTTDTVKGERVSFPVCTYVPSTICDQMTGILATDVTPEDAQKL
MAYV    KTSGYAVTHHAEGFLVCKITDTIAGERVSFPVCTYVPSTICDQMTGILATEVTPEDAQKL
        *  **** *:  **: .* **:  ***:** *****:* **********:*: *****
```

FIG. 11 (CONTINUED)

```
VEEV  LVGINQRIVVNGRTQRNTNTMKNYLLPVVAQAFARWAKEYKEDQEDERPLGIRDRQLVMG
BFV   LVGINQRIVVNGRTQRNTNTMKNYLLPLVAQALAKWAKEAKQDMEDERPLNERQRTLTCL
ONNV  LVGINQRIVVNGRTQRNTNTMKNYLLPIVAQAFSKWAKECRKDMEDEKLLGVRERTLTCC
CHIKV LVGINQRIVVNGRTQRNTNTMKNYLLPVVAQAFSKWAKECRKDMEDEKLLGVRERTLTCC
RRV   LVGINQRIVVNGRTQRNTNTMKNYLLPVVAQAFSKWAREAKADMEDEKPLGTRERTLTCC
SFV   LVGINQRIVVNGRTQRNTNTMKNYLLPIVAVAFSKWAREYKADLDDEKPLGVRERSLTCC
MAYV  LVGINQRIVVNGRTQRNTNTMKNYLLPVVSQAFSKWAKEYRLDQEDEKNMGMRERTLTCC
      *********************:.::.***:**: : *:* .**::* : *::

VEEV  CCWAFRRHKITSIYKRPDTQTIIKVNSDEHSFVLPRIGSNTLEIGLRTRIRKMLEEHKEP
BFV   CCWAFKRNKRHAIYKRPDTQSIVKVPCEFTSFPLVSLWSAGMSISLRQKLKMMIQARQPT
ONNV  CLWAFRKHKTHTVYKRPDTQSIQKVQAEFDSFVVPSLWSSGLSIPLRTRIKWLLSKAPKH
CHIKV CLWAFKKQKTHTVYKRPDTQSIQKVQAEFDSFVVPSLWSSGLSIPLRTRIKWLLSKVPKT
RRV   CLWAFKSHKTHTMYKRPDTQTIVKVPSTFDSFVIPSLWSSSLSIGLRQRIKILLGPKLSR
SFV   CLWAFKTRKMHTMYKKPDTQTIVKVPSEFNSFVIPSLWSTGLAIPVRSRIKMLLAKKTKR
MAYV  CLWAFKIHKNHTMYKKPDTQTIVRVPSEFNSFVIPNLWSAGLSIEIRHRIRLLLQSRRAE
      * ***: :* ::* ***: *.* ::.* ** : . *..* : .  :  ::

VEEV  SPLIT-AEDVQEAKCAADEAKEVREAELTRAALPPLAADV--EEPTLEADVDLMLQEAGA
BFV   QIAAVTEELIQEAAAVEQEAVDTANAELDHAAWPSIVDTT---ERHVEVEVEEIDQRAGE
ONNV  EQLPH-SGNAEEAAQAEMDAAEEREAELTREAMPPIQATQ--DDVQVEIDVEQLEDRAGA
CHIKV DLIPY-SGDAREARDAEKEABEEREAELTREALPPLQAAQ--EDVQVEIDVEQLEDRAGA
RRV   -DLPY-SGDRNEAREAEKEAEETKEAELTREALPPIVGSN-CADDVDRVDVEELTYRAGA
SFV   -ELIP-VLDASSARDAEQEEKERLEAELTREALPPIVPIAPAETGVVDVEELEYHAGA
MAYV  -PLVP-SMDASEARAAEKEAEAEKEAEFTLAALPPLIPTAPLLDDIPEVDVEELEFRAGA
          .    :.    : :  :  .*  ::  **:            * *: **
```

FIG. 11 (CONTINUED)

```
VEEV    GSVETPRGLIKVTSYAGEDKIGSYAVLSPQAVLKSEKLSCIHPLAEQVIVITHSGRKGRY
BFV     GVVETPRNSIKVSTQIGDALIGSYLILSPQAVLRSEKLACIHDLAEQVKLVTHSGRSGRY
ONNV    GIVETPRGAIKVTAQPSDRVVGEYLVLTPQAVLRSQKLSLIHALAEQVKTCTHSGRAGRY
CHIKV   GIIETPRGAIKVTAQPTDHVVGEYLVLSPQTVLRSQKLSLIHALAEQVKTCTHNGRAGRY
RRV     GVVETPRNALRVTPQERDQLIGAYLILSPQAVLKSEKLTPIHPLAEQVTIMTHSGRSGRY
SFV     GVVETPRSALKVTAQPNDVLLGNYVVLSPQTVLKSSKLAPVHPLAEQVKIITHNGRAGRY
MAYV    GVVETPRNALKVTPQDRDTMVGSYLVLSPQTVLKSAKLQVLHPLAEQVKIITHKGRAGRY
         * :::**    .:     *  **::******  ** :   ::****** :** .******

VEEV    AVEPYHGKVVPEGHAIPVQDFQALSESATIVYNEREFVNRYLHHIATHGGALNTDEEYY
BFV     AVDKYDGRVLVPTGVAIDIQSFQALSESATLVYNEREFVNRKLWHIAVYGAALNTDEEGY
ONNV    AVEAYDGRVLVPSGYAIPQEDFQSLSESATMVFNEREFVNREFVNRKLHHIAMHGPALNTDEESY
CHIKV   AVEAYDGRVLVPSGYAISPEDFQSLSESATMVYNEREFVNREFINRKLHHIAMHGPALNTDEESY
RRV     PVDRYDGRVLVPTGAAIPVSEFQALSESATMVYNEREFINRKLHHIALYGPALNTEEENY
SFV     QVDGYDGRVLLPCGSAIPVPEFQALSESATMVYNEREFVNREFINRKLYHIAVHGPSLNTDEENY
MAYV    QVDAYDGRVLIPTGAAIPVPDFQALSESATMVYNEREFINRKLYHIAVHGAALNTDEEGY
         *  ::** :..  **   :** :******:* :****.*** *  **.  * **:   *

VEEV    KTVKPSEHDGEYLYDIDRKQCVKKELVTGLGLTGELVDPPFHEFAYESLRTRPAAPYQVP
BFV     EKVPVERAESDYVEDVDVDQKMCLKKEQASGWVLCGELVNPPFHEFAYEGLRTRPSAPYKVH
ONNV    ELVRVEKTEHEYVYDVDVDQKKCCKREEATGLVLVGDLTSPPYHEFAYEGLKIRPACPYKTA
CHIKV   ELVRAERTEHEYVYDVDQRRCCKKEEAAGLVLVGDLTNPPYHEFAYEGLKIRPACPYKIA
RRV     EKVRAERAEAEYVFDVDKRMCVKREEASGLVLVGDLINPPFHEFAYEGLKIRPATPFQTT
SFV     EKVRAERTDAEYVFDVDKKCCVKREEASGLVLVGELTNPPFHEFAYEGLKIRPSAPYKTT
MAYV    EKVRAERTDAEYVFDVDRKQCVKREDAEGLVMIGDLVNPPFHEFAYEGLKRRPAAPYKTT
         : .  .  . * ::*.*    *::*:   *::.*:*. **:**** :: *: *:
```

FIG. 11 (CONTINUED)

```
VEEV   TIGVYGVPGSGKSGIIKSAVIKKDLVVSAKKENCAEIIRDVKKMKGLDVNARTVDSVLLN
BFV    TVGVYGVPGSGKSGIIKSAVIKKDLVVSAKKENCAEIIRDVKKMKGLDVNARTVDSVLLN
ONNV   VIGVFGVPGSGKSAIIKNTVIMSDLVLSGKKENCLEIMNDVLKHRALRITAKTVDSVLLN
CHIKV  VIGVFGVPGSGKSAIIKNLVTRQDLVTSGKKENCQEISNDVMRQRKLEISARTVDSLLLN
RRV    VIGVFGVPGSGKSAIIKNLVTRQDLVTSGKKENCQEITTDVMRQRGLEISARTVDSLLLN
SFV    VVGVFGVPGSGKSAIIKSVVITRDLVASGKKENCQEIVNDVKKQRGLDVTARTVDSILLN
MAYV   VVGVFGVPGSGKSGIIKSLVTRADLVTSGKRENCQEIMLDVKRYRDLDITAKTVDSVLLN
       :.*:.*******.**    :*    .**: ****.**** **   : :    :*****

VEEV   GCKHPVETLYIDEAFACHAGTLRALIAIIRPK-KAVLCGDPKQCGFFNMMCLKVHFNHEI
BFV    GVKHTPNILYIDEAFSCHAGTLLATIAIVRPKQKVLCGDPKQCGFFNMMQLKVNYNHDI
ONNV   GCNKPVEVLYVDEAFACHSGTLLALIAMVRPRQKVLCGDPKQCGFFNMMQMKVNYNHNI
CHIKV  GCNRPVDVLYVDEAFACHSGTLLALIALIAMVKPTGKVILCGDPKQCGFFNLMQMKVNYNHNI
RRV    GCRRGVENLYVDEAFACHSGTLLALIAMVKPTGKVILCGDPKQCGFFNLMQLKVNFNHDI
SFV    GCRRAVDILYVDEAFACHSGTLLALIALVKPRSKVVLCGDPKQCGFFNMMQLKVNFNHNI
MAYV   GVKQTVDVLYVDEAFACHAGTLLALIATVRPRKKVVLCGDPKQCGFFNLMQLQVNFNHNI
       *  :  : **:****:**:**:* :** : *: .* :***********::* : :.*::

VEEV   CTQVFHKSISRRCTKSVTSVVSTLFYDKKMRTTNPKETKIVIDTTGSTKPKQDDLILTCF
BFV    CSEVFHKSISRRCTQDITAIVSKLHYQDRMRTTNPRKGDIIDTTGTTKPAKTDLILTCF
ONNV   CTQVYHKSISRRCTLPVTAIVSSLHYESKMRTTNEYNQPIVDTTGITKPEPGDLVLTCF
CHIKV  CTQVYHKSISRRCTLPVTAIVSSLHYEGKMRTTNPIVDTTGSTKPDPGDLVLTCF
RRV    CTQVLHKSISRRCTLPITAIVSTLHYQGKMRTTNLCSAPIQIDTTGTTKPAKGDIVLTCF
SFV    CTEVCHKSISRRCTRPVTAIVSTLHYGGKMRTTNPCNKPIIIDTTGQTKPKPGDIVLTCF
MAYV   CTEVHHKSISRRCTLPITAIVSTLHYEGKMRTTNPYNKPVIIDTTGQTKPYNREDIVLTCF
       *::* ********* .:::::** *.*  ******  .    ***    :: :*:****
```

FIG. 11 (CONTINUED)

```
VEEV   RGWVKQLQIDYKGNEIMTAAASQGLTRKGVYAVRYKVNENPLYAPTSEHVNVLLTRTEDR
BFV    RGWVKQLQQDYRGNEVMTAAASQGLTRASVYAVRTKVNENPLYAQTSEHVNVLLTRTENK
ONNV   RGWVKQLQIDYRGNEVMTAAASQGLTRKGVYAVRQKVNENPLYASTSEHVNVLLTRTEGK
CHIKV  RGWVKQLQIDYRGYEVMTAAASQGLTRKGVYAVRQKVNENPLYASTSEHVNVLLTRTEGK
RRV    RGWVKQLQIDYRGHEVMTAAASQGLTRKGVYAVRQKVNENPLYAPSSEHVNVLLTRTENR
SFV    RGWVKQLQLDYRGHEVMTAAASQGLTRKGVYAVRQKVNENPLYAPASEHVNVLLTRTEDR
MAYV   RGWVKQLQLDYRGHEVMTAAASQGLTRKGVYAVRMKVNENPLYAQSSEHVNVLLTRTEGR
       ****** * :* .*:****** ****:****.*:*******: ****:* *******.:

VEEV   IVWKTLAGDPWIKTLTAKYPGNFTATIEEWQAEHDAIMRHILERPDPTDVFQNKANVCWA
BFV    LVWKTLSTDPWIKTLTNPPRGHYTATIAEWEAEHQGIMKAIQGYAPPVNTFMNKVNVCWA
ONNV   LIWKTLSGDPWIKILQNPPKGNFKATIKEWEAEHASIMAGICNHQMAFDTFQNKANVCWA
CHIKV  LVWKTLSGDPWIKTLQNPPKGNFKATIKEWEVEHASIMAGICSHQMTFDTFQNKANVCWA
RRV    LVWKTLSGDPWIKVLTNIPKGDFSATLEEWQEEHDNIMNALRERSTAVDPFQNKAKVCWA
SFV    LVWKTLAGDPWIKVLSNIPQGNFTATLEEWQEEHDKIMKVIEGPAAPVDAFQNKAKVCWA
MAYV   LVWKTLSGDPWIKTLSNIPKGNFTATLEDWQQEHDAIMRAITQEAAPLDVFQNKAKVCWA
       ::****: **** : .   * :*:*: ** ** .:*  :           **:*.****

VEEV   KALVPVLKTAGIDMTTEQWNTV-DYFETDKAHSAEIVLNQLCVRFFGLDLDSGLFSAPTV
BFV    KTLTPVLETAGISLSAEDWSELLPPFAQDVAYSEVALNIICTKMYGFDLDTGLFSRPSV
ONNV   KCLVPILDTAGIKLSDRQWSQIVQAFKEDRAYSPVALNEICTRIYGVDLDSGLFSKPLI
CHIKV  KSLVPILETAGIKLNDRQWSQIIQAFKEDKAYSPVALNEICTRMYGVDLDSGLFSKPLV
RRV    KCLVQVLETAGIRMTAEEWDTV-LAFREDRAYSPVALNEICTKYYGVDLDSGLFSAQSV
SFV    KSLVPVLDTAGIRLTAEEWSTIITAFKEDRAYSPVALNEICTKYYGVDLDSGLFSAPKV
MAYV   KCLVPVLETAGIRLSAADWSSIILAFKEDRAYSPVALNEICTKVYGVDLDSGLFSAPRV
       * * ::*:*** : :  *.:   .  ::    *   :**  *.:  .:**:****.  *
```

FIG. 11 (CONTINUED)

```
VEEV  PLSIRNNHWDNSPSPNMYGLNKEVVRQLSRRYPQLPRAVATGRVYDMNTGTLRNYDPRIN
BFV   PMTYTKDHWDNRVGGKMYGESQQAYDQLARRHPYLRGREKSGMQIVVTEMRIQRPRSDAN
ONNV  SVYYADNHWDNRPGGKMFGFNPEVALMIEKKYPFTKGKWNINKQICITTRKVDEFNPETN
CHIKV SVYYADNHWDNRPGGKMFGFNPEAASILERKYPFTKGKWNINKQICVTTRRIEDFNPTTN
RRV   SLYYENNHWDNRPGGRMYGFNREVARKFEQRYPFLRGKMDSGLQVNVPERKVQPFNAECN
SFV   SLYYENNHWDNRPGGRMYGFNAATAARLEARHTFLKGQWHTGKQAVIAERKIQPLSVLDN
MAYV  SLHYTTNHWDNSPGGRMYGFSVEAANRIEQRHPFYRGRWASGQ-VLVAERRTQPIDITCN
      : :*   ****  *.  *:.* :                   .             .         *

VEEV  LVPVNRRLPHALVLHHNEHPQSDFSSFVSKLKGRTVLVV-GEKLSVPGKMVDWLSDR--P
BFV   IIPINRRLPHSLVATHEYRRAARAEEFTTTRGYTMLLVSEYNMNLPNKKITWLAPIGTQ
ONNV  IIPANRRLPHSLVAEHHTVRGERMEWLVNKINGHHMLLVSGYNLIILPTKRVTWVAPLGTR
CHIKV IIPANRRLPHSLVAEHRPVKGERMEWLVNKINGHHVLLVSGYNLALPTKRVTWVAPLGVR
RRV   ILPSNRRLPHALVTSYQQCQGERVEWLLKKLPGYHLLLVSEYNLALPHKRVFWIAPPHVS
SFV   VIPINRRLPHALVAEYKTVKGSRVEMLVNKVRGYHVLLVSEYNLALPRRRVTWLSPLNVT
MAYV  LIPFNRRLPHALVTEYHPVKGERVEWLVNKIPGYHLLLVSEYNLILPRRKVTWIAPPTVT
      : *  **** *: *. *              : . . : : : : * :    :       :

VEEV  EATFRARLDLGIPGDVPKYDIIFVNVRTPYKYHHYQQCEDHAIKLSMLTKKACLHLNPGG
BFV   GAHTANLNLGIPPLLGSEDAVVNMPTPFRNHHYQQCEDHAMKLQMLAGDALRHIKPGG
ONNV  GADYTNLELGLPATLGRYDLVVINIHTPFRIHHYQQCVDHAMKLQMLGGDSLRLLKPGG
CHIKV GADYTNLELGLPATLGRYDLVVINIHTPFRIHHYQQCVDHAMKLQMLGGDSLRLLKPGG
RRV   GADRIYDLDLGLPLNAGRYDLVFVNIHTEYRTHHYQQCVDHSMKLQMLGGDSLHLLKPGG
SFV   GADRCYDLSLGLPADAGREDLVFVNIHTEFRIHHYQQCVDHAMKLQMLGGDALRLLKPGG
MAYV  GADLTHDLDLGLPPNAGRYDLVFVNMHTPYRLHHYQQCVDHAMKLQMLGGDALYLLKPGG
      **  :     *      .*   * : :     : * **** *****:* ** ::**
```

```
VEEV     KASRPEQITVCSSFPLPKYRITGVQKIQCSQPILFSPKVPAYIHPRKYLVETPPVDETPE
BFV      KCTNTTQFTVCSSFELPKYHIQGVQRVKCERIIILDPTVPPTYKRPCIRRYPSTISCNSS
ONNV     RMNHTTSIIVCSSFPLPKYKIEGVQKVKCSKALLFDHNVPSRVSPRTYRPADEIIQTPQI
CHIKV    RMNHVTSIIVCSSFPLPKYKIEGVQKVKCSKVMLFDHNVPSRVSPREYRSSQESAQEAST
RRV      RMNNTKAIIVCSSFPLPKYRIEGVQKVKCDRVLIFDQTVPSLVSPRKYIPAAASTHADTV
SFV      RSHQVKSMVVCSSFPLPKYHVDGVQKVKCEKVLLFDPTVPSVVSPRKYAASTTDHSDRSL
MAYV     RMHHTKDLVVCSSFQLPKYRIAGVQRVRCEKVMLFDATPPASVSPVQYLTSHSETT-VSL
         :  .   : ***** ****:: ***:::*.: :::.  . *

VEEV     PSAENQSTE-----------GTPEQPPLITEDETRTRTPEPIIIE-EEEEDSISLLSD-G
BFV      E-DSRSLSTFSVSSD--SSI------GSLPVGDTR-PIPAPRTI----------------
ONNV     PTEACQDAQFVQS----ITDEAVPVPSDLEAC--DATMDWPSIDIVPTRQRSDSFDSEYS
CHIKV    I-TSLTHSQFDLS----VDGEILPVPSDLDAD--APALEP-ALDDGA-------------
RRV      SLDSTVSTGSAWSFPSEATYETMEVVAEVHHS--EPPVPPPRRR----RA-------QVT
SFV      R-----GFDLDWTTDSSSTASDTMSLPSLQSCDIDSIYEPMAPI----VV-------T--
MAYV     S-----SFSITSDSSSLSTFPDLESLEEL---GNDPQ-----SM----RM-------D--
                                    :

VEEV     PTHQVLQVEADIHGPPSVSSSSWSIPHASDFDVDSLSILDTLEGASVTSGATSAETNS-Y
BFV      ------------------------------------------------------------
ONNV     SRSNIQLVTADVHA-----------PMY--------ANSLASSGGSVLSLSSEQAQNGIM
CHIKV    ------------------------------------THTLPSTTGNLA------------
RRV      MHHQELLEVSDMHTPIAARV---EIPVY--------DTAVVVERVAIPCTSEYA------
SFV      ---------ADVH----------------------------PEPAGIADLAADV------
MAYV     ---------ES----------------------------------------VNQ------
```

FIG. 11 (CONTINUED)

```
VEEV   F-------AKSMEFLARPVPAPRTVERNPPHPAPRTRTPSLAPSR--ACSRTSLVS---TPP
BFV    FRP-----VPAPRAPVLRTTPPKPPRTFTVRAEV------------------------
ONNV   ILPDSEDTDSISRVSTPIAPPRRRLGRTINVTCDEREGKILPMASDRLFTAKPYTVALGV
CHIKV  --------AVSDWVMSTVPVAPPRRRRGRNLTVTCDEREGNITPMASVRFFRAELCPVVQET
RRV    --KP----TPAPRAARVVPVPAPRIQRASTYRVSPTPTP-------RVLRASVCSVTTSA
SFV    --HP----EPADHVDLENPIPPPRPKRAAYLASR-------------------------
MAYV   --QP----IP-TAEPVVQPVPPPRPKRARRLAAARMQVQ---------VEVHRPPVV----QR
                                            *  *

VEEV   GVNRVITREELEALTPSRTPS-R-----------------------------SVSRTSLVS
BFV    ----------HQAPPTPVP--PPRPKRAAKLAREMHPGETFGDFGEHEVEELTASPLTFGD
ONNV   STAD-ITAYPIQAPLGS-----------TQPPALEQITFGDITFGDFAEGEIDNLLTGALTFGD
CHIKV  AETR-DTAMSLQAPPSTATEPNHPPI-SFGASSETFPITFGDFNEGEIESLSSELLTFGD
RRV    GVEFPWAPEDLEVLTEPVHCKMREPV-ELPWEPEDVDIQFGDFETS-------D-KIQFGD
SFV    ------AAERPVPAPRKPTPAPRT-AFR-----NKLPLTFGDFDEHEVDALAS-GITFGD
MAYV   TKPVPAPRTSLRPVPAPRSCMPRPAV-ELPWPQETVDVEFGAPT------EEDS-EITFGD
                *                                                 *  *

VEEV   NPPGVNRVITREEFEAF---VAQQQRRFDAGAYIFSSDTGQGHLQQKSVRQTVLSEVVLER
BFV    FAEGEIQGMG---------VEFERLGRAGGYIFSSDTGPGHLQQRSVLQNCTAECIYEP
ONNV   FEPGEVEELTDSEWSTCSDTDEELRIDRAGGYIFSSDTGQGHLQQKSVRQTTLPVNIVEE
CHIKV  FLPGEVDDLTDSDWSTCSDTDDELRIDRAGGYIFSSDTGPGHLQQKSVRQSVLPVNTLEE
RRV    ID----------------FDQFRLGRAGAYIFSSDTGPGHLQQKSVRQHALPCEMLYV
SFV    F-----------------DDVLRLGRAGAYIFSSDTGSGHLQQKSVRQHNLQCAQLDA
MAYV   FSAS-------EWET----ISNSSRLGRAGAYIFSSDVGPGHLQQKSVRQHDLEVPIMDR
           *         *        *** *******.* *******:**.: *
```

FIG. 11 (CONTINUED)

```
VEEV   TELEISYAPRLDQEKEELLRKKLQLNPTPANRSRYQSRKVENMKAITARRILQGLGHYLK
BFV    AKLEKIHAPKLDKTKEDILRSKYQMKPSEANKSRYQSRKVENMKAEIVGRLLDGLGEYLG
ONNV   VHEEKCYPPKLDEIKEQLLLKRLQESASTANRSRYQSRKVENMKATIIHRLKEGCRLYLA
CHIKV  VHEEKCYPPKLDEAKEQLLLKKLQESASMANRSRYQSRKVENMKAAIIQRLKRGCRLYLM
RRV    HEEERTYPPALDEAREKLLQAKMQMAPTEANKSRYQSRKVENMKAVIIDRLKDGARTYLT
SFV    VEEEKMYPPKLDTEREKLLLLKMQMHPSEANKSRYQSRKVENMKATVVDRLTSGARLYTG
MAYV   VVEEKVYPPKFDEAKEKQLLLKLQMHATDANRSRYQSRKVENMKATIIDRLKQGSASYIS
              :  *   :  *:  *        ***********   *    **       *

VEEV   AE-GKVECYRTLHPVPLYSSSVNRAFSSPKVAVEACNAMLKENFPTVASYCIIPEYDAYL
BFV    TEHP-VECYRITYPVPIYSTSVLRGLSSAKTAVRACNAFLEANFPSVTSYKITDEYDAYL
ONNV   SDTPRVPSYRITYPAPVYSPSISIKLNNPETAVCNEFLARNYPTVASYQVTDEYDAYL
CHIKV  SETPKVPTYRTTYPAPVYSPPINVRLSNPESAVAACNEFLARNYPTVSSYQITDEYDAYL
RRV    EQSEKIPTYVSKYPRPVYSPSVEDSLQNPEVAVAACNAFLEANYPTVASYQITDEYDAYL
SFV    ADVGRIPTYAVRYPRPVYSPTVIERFSSPDVAIAACNEYLSRNYPTVSSYQITDEYDAYL
MAYV   AEADKAVTYHVKYAKPRYSVPVMQRLSSATTAVAACNEFLARNYPTVASYQITDEYDAYL
           :        *  *          .    :  *:  : :.* :*:*  * *****

VEEV   DMVDGASCCLDTASFCPAKLRSFPKKHSYLEPTIRSAVPSAIQNTLQNVLAAATKRNCNV
BFV    DMVDGSESCLDRSSFSPSRLRSFPKTHSYLDPQINSAVPSPFQNTLQNVLAAATKRNCNV
ONNV   DMVDGSESCLDRATFNPSKLRSYPKQHSYHAPTIRSAVPSPFQNTLQNVLAAATKRNCNV
CHIKV  DMVDGSESCLDRATFNPSKLRSYPKQHAYHAPSIRSAVPSPFQNTLQNVLAAATKRNCNV
RRV    DMVDGSESCLDRATFCPAKLRCYPKHHAYHQPQVRSAVPSPFQNTLQNVLAAATKRNCNV
SFV    DMVDGSDSCLDRATFCPAKLRCYPKHHAYHQPTVRSAVPSPFQNTLQNVLAAATKRNCNV
MAYV   DMVDGSESCLDRANFCPAKLRCYPKHHAYHVPQIRSAVPSPFQNTLQNVLAAATKRNCNV
       ******. ****  * *::**.:**.::*   ::.****. :*****************
```

FIG. 11 (CONTINUED)

```
VEEV  TQMRELPVLDSAAFNVECFKKYACNNEYWETFKENPIRLTEENVVNYITKLKGPKAAALF
BFV   TQMRELPTYDSAVLNVEAFRKYACKPDVWDEYRDNPICITTENVTTYVAKLKGPKAAALF
ONNV  TQMRELPTMDSAVFNVECFKKYACNQEYWREFASSPIRVTTENLTMYVTKLKGPKAAALF
CHIKV TQMRELPTLDSAVFNVECFKKFACNQEYWEEFAASPIRITENLATYVTKLKGPKAAALF
RRV   TQMRELPTLDSAVLNVECFKKFACNGEYWQEFKDNPIRITTENITTYVTRLKGPKAAALF
SFV   TQMRELPTMDSAVFNVECFKKYACSGEYWEEYAKQPIRITTENITTYVTKLKGPKAAALF
MAYV  TQMRELPTLDSAVYNVECFRKYACNNEYWEEFAAKPIRITTENLTTYVTKLKGGKAAALF
      *******  ***** **  *** ** **  * ** :   ** *  ***:**:****

VEEV  AKTHNLNMLQDIPMDRFVMDLKRDVKVTPGTKHTEERPKVQVIQAADPLATAYLCGIHRE
BFV   AKTHNLIPLHQVPMDKFTVDMKRDVKVTPGTKHTEERPKVQVIQAAEPLATAYLCGIHRE
ONNV  AKTHNLLPLQEVPMDRFTMDMKRDVKVTPGTKHTEERPKVQVIQAAEPLATAYLCGIHRE
CHIKV AKTHNLLPLQEVPMDRFTVDMKRDVKVTPGTKHTEERPKVQVIQAAEPLATAYLCGIHRE
RRV   AKTHNLVPLQEVPMDRFVVDMKRDVKVTPGTKHTEERPKVQVIQAAEPLATAYLCGIHRE
SFV   AKTHNLVPLQEVPMDRFVDMKRDVKVTPGTKHTEERPKVQVIQAAEPLATAYLCGIHRE
MAYV  AKTHNLVPLQEVPMDRFVMDMKRDVKVTPGTKHTEERPKVQVIQAAEPLATAYLCGIHRE
      ******: *::: *:*:* :*:********************:***********

VEEV  LVRRLNAVLLPNIHTLFDMSAEDFDAIIAEHFQPGDCVLETDIASFDKSEDDAMALTALM
BFV   LVRRLNAVLLPNIHTLFDMSAEDFDAIIAEHFKHGDHVLETDIASFDKSQDDSMALTALM
ONNV  LVRRLNAVLLPNVHTLFDMSAEDFDAIISTHFKPGDAVLETDIASFDKSQDDSLALTALM
CHIKV LVRRLNAVLLPNVHTLFDMSAEDFDAIAAHFKPGDTVLETDIASFDKSQDDSLALTAMM
RRV   LVRRLKAVLAPNIHTLFDMSAEDFDAIAAHFQPGDAVLETDIASFDKSQDDSLALTALM
SFV   LVRRLNAVLRPNVHTLFDMSAEDFDAIASHFHPGDPVLETDIASFDKSQDDSLALTGLM
MAYV  LVRRLNAVLLPNIHTLFDMSAEDFDAISEHFKPGDHVLETDIASFDKSQDDSLALTGLM
      *****:*** **:************: :**: ** :*********** **:****.:*
```

FIG. 11 (CONTINUED)

```
VEEV   ILEDLGVDAELLTLIEAAFGEISSIHLPTKTKFKFGAMMKSGMFLTLFVNTVLNIVIASR
BFV    ILEDLGVDQNLMNLIEAAFGEIVSTHLPTGTRFKFGAMMKSGMFLTLFVNTILNVVIACR
ONNV   LLEDLGVDQPILDLIEAAFGEISSCHLPTGTRFKFGAMMKSGMFLTLFVNTLLNITIASR
CHIKV  LLEDLGVDHSLLDLIEAAFGEISSCHLPTGTRFKFGAMMKSGMFLTLFVNTLLNIVIACR
RRV    LLEDLGVDQELLDLIEAAFGEITSVHLPTGTRFKFGAMMKSGMFLTLFINTVLNITIASR
SFV    ILEDLGVDQYLLDLIEAAFGEISSCHLPTGTRFKFGAMMKSGMFLTLFINTVLNITIASR
MAYV   ILEDLGVDNQLLDLIEAAFGQITSCHLPTGTRFKFGAMMKSGMFLTLFINTVLNITIASR
       :****** ::.*********: :.***********:*********:*** ::* ..*:*

VEEV   VLRERLTGSPCAAFIGDDNIVKGVKSDKLMADRCATWLNMEVKIIDAVVGEKAPYFCGGF
BFV    VLEDQLAQSPCAAFIGDDNIIHGIISDKLMADRCATWMNMEVKILDSIVGIRPPYFCGGF
ONNV   VLEERLITSACAAFIGDDNIIHGIISDKLMADRCATWMNMEVKIIDAVVSEKAPYFCGGF
CHIKV  VLEDRLITKSACAAFIGDDNIIHGVVSDELMAARCATWMNMEVKIIDAVVSLKAPYFCGGF
RRV    VLREKLTNSVCAAFIGDDNIVHGVRSDPLMAERCASWVNMEVKIIDATMCEKPPYFCGGF
SFV    VLEQRLTDSACAAFIGDDNIVHGVISDKLMAERCASWNNMEVKIIDAVMGEKPPYFCGGF
MAYV   VLEARLTNSACAAFIGDDNVVHGVVSDKLMADRCATWVNMEVKIIDAVMCAKPPYFCGGF
       **: *: *.*******::*: **:**.***:*::*****:*:  ..:***********

VEEV   ILCDSVTGTACRVADPLKRLFKLGKPLAADDEHDDDRRRALHEESTRWNRVGILSELCKA
BFV    IVCDDVTGTACRVADPLKRLFKLGKPLPLDDGQDEDRRRALHDEVKTWSRVGLRHRVCEA
ONNV   ILHDTVTGTSCRVADPLKRLFKLGKPLAAGDEQDEDRRRALADEVTRWQRTGLITELEKA
CHIKV  ILHDTVTGTACRVADPLKRLFKLGKPLAAGDEQDEDRRRALADEVIRWQRTGLIDELEKA
RRV    ILYDKVTGSACRVADPLKRLFKLGKPLPAGDTQDEDRRRALKDETDRWARVGLKSELEIA
SFV    IVFDSVTQTACRVSDPLKRLFKLGKPLTAEDKQDEDRRRALSDEVSKWFRTGLGAELEVA
MAYV   LVYDHVTRMSCRIADPLKRLFKLGKPLPADDCQDEDRRRALHDEVKKWFRSGLGSEIEVA
       :: *.*  ::**::************ . * :*********::*  * *  *.:*::.
```

FIG. 11 (CONTINUED)

```
VEEV   VESRYETVGTSIIVMAMTTLASSVKSFSYLRGAPITLYG-----
BFV    IEDRYAVHSSELVLLALTTLSKNLKSFRNIRGKPIHLYGGPK---
ONNV   VYSRYEVQGITAVITSMATFASSKENEKKLRGPVVTLYGGPK---
CHIKV  VYSRYEVQGISVVVMSMATFASSRSNFEKLRGPVITLYGGPK---
RRV    LSSRYEVNGTGNIVRAMATLAKSLKNFKKLRGPIVHLYGGPK---
SFV    LTSRYEVEGCKSILIAMATLARDIKAFKKLRGPVIHLYGGPRLVR
MAYV   LATRYEVEGGYNLLLAMSTFAHSMKNFSALRGPVIHLYGGPK---
       ::    * .   :   :::*:: .   *  : *** ::
```

ALPHAVIRUS NSP MUTANTS AS VACCINES

TECHNICAL FIELD

The disclosure generally relates to the field of immunology and virology. The present disclosure relates to polypeptides, polynucleotides, expression vectors, infectious clones, virus particles, and immunogenic compositions of recombinant alphaviruses, for use in these fields, in particular as vaccines against alphavirus infection. The present disclosure also relates to methods for eliciting an immune response against alphavirus infection using the immunogenic compositions of the present disclosure.

BACKGROUND

Alphaviruses are a genus of enveloped, RNA viruses that cause diseases in humans and animals, with symptoms such as fever, rash and arthritis. The alphavirus genome encodes nonstructural (nsP) and structural proteins. More specifically, the genome encodes four nsPs which are involved in virus replication and pathogenesis, and five structural proteins that make up the virion. Substitutions of amino acids at functionally coupled sites in the nsPs were previously shown to affect polypeptide processing and controlled the virulence of the alphavirus Semliki Forest Virus (SFV).

Another alphavirus is Chikungunya virus (CHIKV), an arthropod-borne alphavirus that causes acute febrile illness and chronic debilitating polyarthralgia. The interferon-α/β receptor (IFNAR) dependent Type 1 interferon (IFN) signaling pathway has been shown to be critical in CHIKV induced anti-viral mechanisms. Yet another alphavirus is O'nyong'nyong Virus (ONNV), which is also an arthropod-borne alphavirus that causes symptoms such as fever, rash, headache and arthralgia.

There are presently no known commercial vaccines to prevent such alphavirus infections, such as CHIKV and ONNV infections, or medicine for treating such infections. Therefore, there is a need to provide vaccines against such alphavirus infections, and methods for eliciting an immune response against the alphavirus infections.

SUMMARY

In one aspect, there is provided a recombinant polypeptide comprising an amino acid SEQ ID NO: 1, or a variant thereof, comprising one or more mutations selected from the group consisting of: (a) a mutation at a position equivalent to amino acid position 532 of SEQ ID NO: 1, and (b) a mutation at a position equivalent to amino acid position 1050 of SEQ ID NO: 1.

Advantageously, mutation at a position equivalent to amino acid position 532 of SEQ ID NO: 1 alone, results in higher Type 1 IFN immune response in primary mouse fibroblasts in murine ex-vivo and in vivo infection models. Additionally, when the mutation at position 532 occurs simultaneously in combination with a mutation at position 1050 of SEQ ID NO: 1, both sites being functionally coupled, not only is the Type 1 IFN immune response significantly enhanced, but alphavirus harboring these nsP mutations also exhibited lower infectivity.

In another aspect, there is provided a polynucleotide encoding the polypeptide described herein.

In another aspect, there is provided an expression vector comprising the polynucleotide sequence described herein.

In another aspect, there is provided an infectious clone comprising the polynucleotide sequence described herein.

In another aspect, there is provided a recombinant virus particle comprising the polypeptide described herein.

In another aspect, there is provided a recombinant virus particle comprising the polynucleotide described herein.

In another aspect, there is provided a virus particle derived from the infectious clone described herein.

In another aspect, there is provided an immunogenic composition comprising an infectious clone, a recombinant virus particle and/or a virus particle described herein.

In another aspect, there is provided a method of eliciting an immune response against alphavirus infection in a subject comprising administering an immunogenic composition described herein to the subject. Advantageously, the method is capable of providing protection to subjects administered with the immunogenic composition against wild-type (WT) alphavirus infection, as well as re-infection upon subsequent exposure to alphavirus.

DEFINITION OF TERMS

The following words and terms used herein shall have the meaning indicated:

The term "polypeptide" refers to any polymer of amino acids (dipeptide or greater) linked through peptide bonds or modified peptide bonds, whether produced naturally or synthetically.

The term "polynucleotide" includes a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. The terms "polynucleotide", "nucleic acid", "nucleic acid molecule", and "nucleic acid sequence" are used interchangeably herein unless the context indicates otherwise.

The term "recombinant" when used in reference to a polypeptide, polynucleotide or virus refers to a polypeptide, polynucleotide or virus that is not naturally occurring, or was made artificially. A recombinant virus refers to a virus that may carry a recombinant polynucleotide or a virus that expresses a recombinant polypeptide.

The term "equivalent", when used in reference to the position of an amino acid in a polypeptide sequence or the position of a nucleic acid in a polynucleotide sequence, refers to a position of the amino acid or nucleic acid in the sequence of a given polypeptide or polynucleotide, which corresponds in position (in either primary or tertiary structure) to a position of the amino acid in SEQ ID NO: 1, or its corresponding polynucleotide sequence, as the case may be. Such equivalent positions in a particular sequence can be determined using methods known in the art, for example based on sequence alignment against the reference sequence or by comparing experimentally revealed or predicted 3D-structures of corresponding proteins. For example, amino acid positions 1185-1187 of the non-structural protein of SFV are equivalent to amino acid positions 1183-1185 of the non-structural protein of CHIKV; amino acid positions 532 and 1050 of the non-structural protein P1234 of O'nyong'nyong Virus are equivalent to amino acid positions 532 and 1050 of the non-structural protein P1234 of CHIKV, respectively; amino acid positions 531 and 1048 of the non-structural protein P1234 of Ross River Virus are equivalent to amino acid positions 532 and 1050 of the non-structural protein P1234 of CHIKV, respectively; amino acid positions 530 and 1048 of the non-structural protein P1234 of Barmah Forest Virus are equivalent to amino acid positions 532 and 1050 of the non-structural protein P1234 of CHIKV, respectively; and amino acid positions 543 and 1059 of the non-structural protein P1234 of Venezuelan Equine Encephalitis Virus are equivalent to amino acid positions 532 and 1050 of the non-structural protein P1234 of Chikungunya Virus, respectively.

The term "variant" as used herein includes a reference to substantially similar sequences. These sequence variants may have at least 25%, 30%, 35%, 40%, 45%, 50%, 55%, 60%, 65%, 70%, 75%, 80%, 85%, 90%, 95%, 96%, 97%, 98% or 99% sequence identity to a reference polypeptide or polynucleotide sequence, or to a section within the polypeptide or polynucleotide reference sequence. The reference sequence may be any one of SEQ IN NOs: 1 to 7. For example, a variant of any one of SEQ IN NOs: 1 to 7 may have at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% identity to SEQ ID NOs: 1 to 7. In one example, where the variant sequence includes a mutation, the differences that make up the variants are expected to occur outside of the section where the mutation is located. That is to say that the differences that constitute the variant sequences are outside the location of the mutation. By way of an example, if a sequence comprises a mutation at amino acid residue 515, then the differences that make up the variants are found at any location within the variant sequence other than at amino acid residue 515. In another example, if a sequence comprises a mutation at base pair 1500, the differences that make up the variants are found at any location within the variant sequence other than at base pair 1500.

A polypeptide variant may be a biological variant, which displays substantially the same biological activity as a reference polypeptide. The reference polypeptide may be any one of SEQ ID NO: 1 to SEQ ID NO: 4.

A polypeptide variant may also, or alternatively, be a functional variant, which is a variant having at least 80% (e.g. 80%, 85%, 90%, 95% or 99%) identity to the reference polypeptide sequence, and possessing the same activity as the reference polypeptide sequence. The reference polypeptide may be any one of SEQ ID NO: 1 to SEQ ID NO: 4. For example, SEQ ID NO: 2 is a functional variant of SEQ ID NO: 1.

As used herein, the term "missense mutation" refers to a point mutation in which a single nucleotide change results in a codon that codes for a different amino acid. Missense mutations may or may not affect the activity of a polypeptide. In some cases, missense mutations may render the resulting polypeptide to be nonfunctional.

As used herein, the term "substitution" refers to a mutation in which one or more nucleotides changes result in a codon that codes for a different amino acid. Substitution of an amino acid may or may not affect the activity of a polypeptide. In some cases, substitution of an amino acid may render the resulting polypeptide to be nonfunctional.

As used herein, the term "attenuated" virus refers to a virus which is infectious but not pathogenic; or an infectious virus which may or may not be pathogenic, but which either produces defective particles during each round of replication or produces fewer progeny virions than does the corresponding wild type virus during replication. Pathogenic viruses which are engineered to produce defective particles or a reduced number of progeny virions may be "attenuated" in that even though the virus is capable of causing disease, the titers of virus obtained in a vaccinated individual will provide only subclinical levels of infection.

A "virus particle" may be a complete, incomplete or empty particle. A complete "virus particle" is typically composed of the viral genetic material (DNA or RNA), a protein coat, and in some cases an envelope of lipids that surrounds the protein coat. On the other hand, an incomplete particles or empty "virus particle" typically contains protein, but not the genetic material.

As used herein, the term "infectious clone" may refer to a double-stranded DNA or cDNA copy of a viral genome that is carried on a bacterial plasmid. The DNA (or RNAs which are produced from the DNA) can be introduced into cells (such as C6/36 *Aedes albopictus* cell line, BHK-21 cell line, and VeroE6 cell line) via transfection to produce infectious viruses.

As used herein, the term "expression" may refer to the expression of a polypeptide from a gene. Thus, an "expression vector" may refer to a recombinant polynucleotide capable of expressing polypeptides. Generally, such expression vectors include transcriptional and translational regulatory nucleic acid operably linked to the nucleotide sequence encoding the polypeptide that is to be expressed.

The term "immunogenic composition" as used herein refers to a composition which is capable of stimulating the immune system of a subject. In this way, immune protection may be provided against an antigen not recognized as a self-antigen by the immune system.

The term "administering" and variations of that term including "administer" and "administration", includes contacting, applying, delivering or providing a composition of the disclosure to subject by any appropriate means.

"Immune response" refers to conditions associated with inflammation, trauma, immune disorders, or infectious or genetic disease, and can be characterized by expression of various factors, e.g., cytokines, chemokines, and other signaling molecules, which may affect cellular and systemic defence systems.

The term "subject" refers to patients of human or other mammals, and includes any individual it is desired to be treated using the immunogenic compositions and methods of the disclosure. However, it will be understood that "subject" does not imply that symptoms are present. Suitable mammals that fall within the scope of the disclosure include, but are not restricted to, primates, livestock animals (e.g. sheep, cows, horses, donkeys, pigs), laboratory test animals (e.g. rabbits, mice, rats, guinea pigs, hamsters), companion animals (e.g. cats, dogs) and captive wild animals (e.g. foxes, deer, dingoes).

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of, but not limited to, concentrations of DNA, chemicals, chemical solutions, enzymes or components of a buffer, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from one to six should be considered to have specifically disclosed sub-ranges such as from one to three, from one to four, from one to five, from two to four, from two to six, from three to six etc., as well as individual numbers within that range, for example, one, two, three, four, five, and six. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

The disclosure illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the disclosures embodied therein herein disclosed may be resorted to by those skilled in the art, and that such modifications and variations are considered to be within the scope of this disclosure.

DETAILED DISCLOSURE OF THE EMBODIMENTS

CHIKV infection causes Chikungunya viral disease. The disease may present symptoms such as fever and severe joint pain which is debilitating and can vary in duration. Currently, there is no cure for the disease. The present disclosure provides alphavirus nonstructural protein (nsP) mutants as vaccines against CHIKV. These mutants may be generated by mutagenizing the nsP region of an alphavirus. For example, mutagenesis can be targeted to one or more specific sites of the nsP region of an alphavirus. The resulting alphavirus nsP mutant and/or the recombinant products can be used as vaccines and/or for production of immunogenic compositions for providing immunity to a particular alphavirus strain. For example, the alphavirus can be, but is not limited to, CHIKV, SFV, O'nyong'nyong virus, Ross River virus or Venezuelan Equine Encephalitis virus.

The nsP region in the CHIKV genome encodes four non-structural proteins which have various functions in virus replication and pathogenesis. In one example, the inventors have identified two specific mutations in the nsP region in CHIKV which are located at amino acid positions 532 of SEQ ID NO: 1 and 1050 of SEQ ID NO: 1 which can be useful in preparing recombinant alphavirus to be used as vaccines. In this example, the amino acid at position 532 of SEQ ID NO: 1 is mutated from arginine (R) to histidine (H), while the amino acid at position 1050 of SEQ ID NO: 1 is mutated from glutamic acid (E) to valine (V).

Therefore, in one aspect, there is provided a recombinant polypeptide comprising an amino acid SEQ ID NO: 1, or a variant thereof, comprising one or more mutations selected from the group consisting of: (a) a mutation at a position equivalent to amino acid position 532 of SEQ ID NO: 1, and (b) a mutation at a position equivalent to amino acid position 1050 of SEQ ID NO: 1. In one example, the recombinant polypeptide comprises an amino acid SEQ ID NO: 1, or a variant thereof, with a mutation at a position equivalent to amino acid position 532 of SEQ ID NO: 1. In another example, the recombinant polypeptide comprises an amino acid SEQ ID NO: 1, or a variant thereof, with a mutation at a position equivalent to amino acid position 1050 of SEQ ID NO: 1. In yet another example, the recombinant polypeptide comprises an amino acid SEQ ID NO: 1, or a variant thereof, with a mutation at a position equivalent to amino acid position 532 of SEQ ID NO: 1, and a mutation at a position equivalent to amino acid position 1050 of SEQ ID NO: 1.

SEQ ID NO: 1 is the wild-type polypeptide sequence of the nsP region of CHIKV LR2006 OPY1 strain. A recombinant polypeptide may be generated from SEQ ID NO: 1 through mutagenesis to introduce suitable amino acid substitutions at these nsP positions. Mutagenesis at specific sites, or site-directed mutagenesis, may be conducted using methods known in the art, such as, but not limited to polymerase incomplete primer extension (PIPE) cloning method, primer extension using mutagenic oligonucleotides and inverse PCR. Similar mutations can be introduced into positions equivalent to the amino acid positions 532 and 1050 of SEQ ID NO: 1 in the nsP region of other alphavirus such as, but not limited to, SFV, O'nyong'nyong virus, Ross River virus and Venezuelan Equine Encephalitis virus. The positions "equivalent" to the amino acid positions 532 and 1050 of SEQ ID NO: 1 refer to amino acid positions in a polypeptide sequence which correspond in position to the positions 532 and 1050 of sequence of SEQ ID NO: 1. The position may refer to a position of the amino acids in the primary or tertiary structure of the polypeptides. Such positions may be determined using methods known in the art, for example based on sequence alignment against SEQ ID NO: 1 (such as the sequence alignment shown in FIG. 11).

In one example, the amino acid SEQ ID NO: 1 is derived from a CHIKV strain LR2006 OPY1. The amino acid SEQ ID NO: 1 can also be derived from, but is not limited to, CHIKV strains CNR20235, SGP007, SG011 and IND91.

In one example, the recombinant polypeptide comprises a variant of SEQ ID NO: 1. The variant may be a biological variant that is derived from the nsP polypeptide region of another alphavirus or a functional variant that is derived from any one of SEQ ID NOs: 1 to 4. The variant may be at least 80%, 85%, 90%, or 95% identical to SEQ ID NO: 1. Variants of SEQ ID NO: 1 of the present disclosure may have at least 80% identity, at least 85% identity, at least 90% identity, at least 95% identity or at least 99% sequence identity to SEQ ID NO: 1. The variants may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% sequence identity to SEQ ID NO: 1. The variants may also have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 1.

In another example, the recombinant polypeptide described herein comprises a polypeptide selected from the group consisting of SEQ ID NO: 2, SEQ ID NO: 3, SEQ ID NO: 4, and variants thereof. SEQ ID NO: 2 is a polypeptide sequence of SEQ ID NO: 1 wherein the R at position 532 is mutated to H. SEQ ID NO: 3 is a polypeptide sequence of SEQ ID NO: 1 wherein the E at position 1050 is mutated to V. SEQ ID NO: 4 is a polypeptide sequence of SEQ ID NO: 1 wherein the R at position 532 is mutated to H and the E at position 1050 is mutated to V. Variants of SEQ ID NO: 2, SEQ ID NO: 3, and SEQ ID NO: 4 of the present disclosure may have at least 80% identity, at least 85% identity, at least 90% identity, at least 95% identity or at least 99% sequence identity to any one of SEQ ID NO: 2, SEQ ID NO: 3, and SEQ ID NO: 4. The variants may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% sequence identity to any one of SEQ ID NO: 2, SEQ ID NO: 3, and SEQ ID NO: 4. The variants may also have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NO: 2, SEQ ID NO: 3, and SEQ ID NO: 4.

In one example, the mutation comprises a missense mutation and/or an amino acid substitution. In some examples of the amino acid substitutions as disclosed herein, the amino acid substitution is a conservative amino acid substitution. In other examples, the amino acid substitution is a non-conservative substitution. The terms "conservative amino acid substitution" and "non-conservative amino acid substitution" are used consistently with their meanings in the art. For example, "conservative amino acid substitution" as used herein refers to a substitution or replacement of one amino acid for another amino acid with similar properties within a polypeptide chain. However, it is also known in the art that some amino acids can substitute for each other even though they belong to different groups.

In one example, the substitution at position 532 comprises substitution of R with H.

In another example, the substitution at position 1050 comprises substitution of E with V.

In another example, the substitutions at positions 532 and 1050, comprise substitutions of R with H and E with V, respectively.

As demonstrated in the Examples below, CHIKV nsP mutant which contains the amino acid substitution from R to H at position 532 of SEQ ID NO: 1 (herein referred to as RH CHIKV) show reduced viral infectivity (FIG. 4) and replicative potential in mouse tail fibroblasts (MTFs) (FIG. 1). Simultaneous mutations to CHIKV nsP region from R to H at position 532 and also from E to V at position 1050 of SEQ ID NO: 1 (herein referred to as RHEV CHIKV) similarly show reduced viral infectivity and replicative potential in MTFs (FIG. 1).

Infection of MTFs with RH CHIKV and RHEV CHIKV also resulted in a higher Type 1 IFN immune response (FIG. 2). FIG. 3A shows that mice infected with RH CHIKV and RHEV CHIKV display faster clearance of viremia compared to mice infected with wild-type CHIKV (herein referred to as WT CHIKV). Attenuation of the Chikungunya disease pathology, measured through joint inflammation, is also found to occur in mice infected with RH CHIKV and RHEV CHIKV (FIG. 3B).

Infection with RH CHIKV is found to provide protection from subsequent WT CHIKV infection (FIG. 5). Similarly, infection with RHEV CHIKV is also found to provide protection from subsequent WT CHIKV infection (FIG. 5).

In another aspect, there is provided a polynucleotide encoding the polypeptide described herein.

In one example, the polynucleotide is DNA. In another example, the polynucleotide is RNA.

In one example, the polynucleotide is selected from the group consisting of SEQ ID NO: 5 (which is the polynucleotide sequence encoding SEQ ID NO: 2), SEQ ID NO: 6 (which is the polynucleotide sequence encoding SEQ ID NO: 3), SEQ ID NO: 7 (which is the polynucleotide sequence encoding SEQ ID NO: 4), and variants thereof. In one example, the variant is at least 80%, 85%, 90%, or 95% identical to SEQ ID NO: 5, SEQ ID NO: 6, and SEQ ID NO: 7. Variants of SEQ ID NO: 5, SEQ ID NO: 6, and SEQ ID NO: 7 of the present disclosure may have at least 80% identity, at least 85% identity, at least 90% identity, at least 95% identity or at least 99% sequence identity to any one of SEQ ID NO: 5, SEQ ID NO: 6, and SEQ ID NO: 7. The variants may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% sequence identity to any one of SEQ ID NO: 5, SEQ ID NO: 6, and SEQ ID NO: 7. The variants may also have at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any one of SEQ ID NO: 5, SEQ ID NO: 6, and SEQ ID NO: 7.

In another aspect, there is provided an expression vector comprising the polynucleotide sequence described herein. Examples of suitable expression vectors are, but not limited to, adeno-associated virus expression vectors, baculovirus expression vector and hybrid vectors.

In another aspect, there is provided an infectious clone comprising the polynucleotide sequence described herein. The infectious clone can be constructed by inserting the genome (in DNA or cDNA form) of an infectious virus, such as the polynucleotide sequence described herein, or a genome comprising the polynucleotide described herein, into a plasmid for infection into a host cell, such as an epithelial cell, an endothelial cell, a primary myeloid cell and a lymphoid cell. Exemplary uses of the infectious clones are, but not limited to, use for infectivity assays or for inducing an immune response in the host cell. Plasmids which can be used as the backbone to generate the infectious clones include, but are not limited to, pBluescript II KS and pBR322. These infectious clones may be specifically engineered to not cause mortality but yet still be immunogenic in a subject, such as but not limited to human. Therefore, such infectious clones may be suitable for use as vaccines.

In another aspect, there is provided a recombinant virus particle comprising the polypeptide described herein.

In another aspect, there is provided a recombinant virus particle comprising the polynucleotide described herein.

In one example of the recombinant virus particle, the virus is an alphavirus. Exemplary alphaviruses may be such as, but not limited to, CHIKV, SFV, O'nyong'nyong virus, Ross River virus and Venezuelan Equine Encephalitis virus.

In one example, the alphavirus is derived from a CHKV strain. In one example, the CHIKV strain is LR2006 OPY1.

In one example, the recombinant virus particle is a live attenuated virus. The inventors have demonstrated in FIG. 3B that the exemplary mutant viruses of the disclosure, specifically the RH CHIKV and RHEV CHIKV nsP mutants, are attenuated as they do not induce the typically higher fold change in inflammation to the footpad of mice compared to WT CHIKV. Instead, the mutants exhibit much lower fold change in inflammation to the foot pad of infected mice compared to WT CHIKV. The difference in joint inflammation severity between the nsP mutants and WT CHIKV can be determined using statistical analysis such as Mann-Whitney U-test, Student's t-test and one-way analysis of variance (ANOVA).

In another aspect, there is provided a virus particle derived from the infectious clone described herein.

In another aspect, there is provided an immunogenic composition comprising an infectious clone, a recombinant virus particle and/or a virus particle described herein. In general, suitable compositions may be prepared according to methods which are known to those of ordinary skill in the art and accordingly may include a pharmaceutically acceptable carrier, diluent and/or adjuvant. The carriers, diluents and adjuvants must be "acceptable" in terms of being compatible with the other ingredients of the composition, and not deleterious to the recipient thereof.

One skilled in the art would be able, by routine experimentation, to determine an effective and safe amount of the immunogenic composition for administration to achieve the desired immunogenic response.

Generally, an effective dosage to achieve the desired immunogenic response is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage to achieve the desired immunogenic response may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In another example, the amount of vaccine administered to elicit the desired immunogenic response is quantified based on the number of viruses. The number of viruses can be determined using methods known in the art, such as, but not limited to plaque assay, focus forming assay and endpoint dilution assay. The number of viruses to achieve the desired immunogenic response is expected to be in the range of about 10 to 10 million plaque forming units (PFU).

Generally, an effective PFU to achieve the desired immunogenic response may be about 10 to about 1.5 million PFU, about 1 million to about 2.5 million PFU, about 2 million to about 3.5 million PFU, about 3 million to about 4.5 million PFU, about 4 million to about 5.5 million PFU, about 5 million to about 6.5 million PFU, about 6 million to about 7.5 million PFU, about 7 million to about 8.5 million PFU, about 8 million to about 9.5 million PFU, or about 9 million to about 10 million PFU.

Alternatively, an effective PFU to achieve the desired immunogenic response may be about 100,000 to about 1 million PFU, about 900,000 to about 2 million PFU, about 1.9 million PFU to about 3 million PFU, about 2.9 million PFU to about 4 million PFU, about 3.9 million to about 5 million PFU, about 4.9 million PFU to about 6 million PFU, about 5.9 million PFU to about 7 million PFU, about 6.9 million PFU to about 7 million PFU, about 7.9 million PFU to about 9 million PFU, or about 8.9 million PFU to about 10 million PFU. In one example, the number of nsP mutants administered to elicit the desired immunogenic response may be about 1 million PFU as determined using plaque assay.

In one example of the immunogenic composition, the recombinant virus is a live attenuated CHIKV. In one example, the immunogenic composition further comprises an adjuvant, a preservative, a stabilizer and/or a pharmaceutically acceptable carrier. In one example, the adjuvant is selected from the group consisting of (a) aluminum hydroxide, (b) aluminum phosphate, (c) gamma inulin, (d) algammulin (a combination of aluminum hydroxide and gamma inulin), (e) cholecalciferol in oil, (f) an oil in water emulsion OWEM1, containing squalene, tween-80, Span-85 in 10 mM phosphate-citrate buffer, (f) oil in water emulsion OWEM2 containing squalene, tween-80, Span-85, alpha tocopherol in phosphate-citrate buffer, and (g) an oil in water emulsion OWEM3 containing squalene, tween-80, Span-85, cholecalciferol in phosphate-citrate buffer. In another example, the immunogenic composition may further comprise an expression vector described herein.

In another aspect, there is provided a method of eliciting an immune response against alphavirus infection in a subject comprising administering an immunogenic composition described herein to the subject. As demonstrated in the Examples below, the exemplary RH CHIKV and RHEV CHIKV nsP mutants are capable of inducing the immune response (FIG. 3), which shows that infection with these mutants results in higher levels of Type 1 IFN response compared to infection with WT CHIKV. The exemplary RH CHIKV and RHEV CHIKV nsP mutants are capable of further providing protection from subsequent re-infection with WT CHIKV (FIG. 5).

The immunogenic composition may be administered to the subject by a route selected from the group consisting of intramuscular, intradermal, subcutaneous, intravenous, oral, and intranasal administration. Thus, the immunogenic compositions of the disclosure may be in a form suitable for parenteral administration (that is, subcutaneous, intramuscular or intravenous injection), in the form of a formulation suitable for oral ingestion (such as capsules, tablets, caplets, elixirs, for example), or in an aerosol form suitable for administration by inhalation (such as by intranasal inhalation or oral inhalation).

For administration as an injectable solution or suspension, non-toxic parenterally acceptable diluents or carriers can include Ringer's solution, isotonic saline, phosphate buffered saline, ethanol and 1,2 propylene glycol.

For oral administration, suitable carriers, diluents, excipients and adjuvants include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Drops for oral administration according to the present disclosure may comprise sterile aqueous or oily solutions or suspensions. These may be prepared by dissolving the immunogenic agent in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic.

In one example, the subject to be administered the immunogenic composition is a human at risk of CHIKV infection, such as subjects living in areas (or in close proximity to areas) with a Chikungunya outbreak. The human subjects can be either adults or children. In another example, the subject to be administered the immunogenic composition is a human at risk of O'nyong'nyong virus infection, such as subjects living in areas (or in close proximity to areas) with an O'nyong'nyong outbreak. The method of the disclosure can also be used on other subjects at risk of CHIKV infection such as, but are not limited to, non-human primates, livestock animals (eg. sheep, cows, horses, donkeys, pigs), laboratory test animals (eg. rabbits, mice, rats, guinea pigs, hamsters), companion animals (eg. cats, dogs) and captive wild animals (eg. foxes, deer, dingoes).

The development of the alphavirus nsP mutants of the present disclosure may potentially be manipulated further not only as vaccine for alphavirus, but also as alternative vaccine candidates for all alphavirus because a similar effect of attenuation could be created using other mutations that affect the processing of nsP1/2 site in these viruses.

BRIEF DESCRIPTION OF THE DRAWINGS

The disclosure will be better understood with reference to the detailed description when considered in conjunction with the non-limiting examples and the accompanying drawings, in which.

The graph in (A) shows the proportions of live MTFs that are infected at various time points. Statistical analysis was done using unpaired t-test (*p<0.05).

The graph in (B) shows the viral load of the MTFs at different time points.

The graph in (C) shows the 50% Tissue Culture Infective Dose (TCID50) at 12 hpi. The data are representative of three independent experiments and are presented as mean±SD.

The graph in (D) shows the proportions of live MTFs that are infected at 12 hpi. Statistical analysis was done using unpaired t-test (*p<0.05). The graph in (D) is adapted from the 12 hpi time point for graph (A) with additional data for EV CHIKV.

The graph in (E) shows the viral load of the MTFs at 12 hpi. The data are representative of three independent experiments and are presented as mean±SD. The graph in (E) is adapted from the 12 hpi time point for graph (B) with additional data for EV CHIKV.

Figure 2:
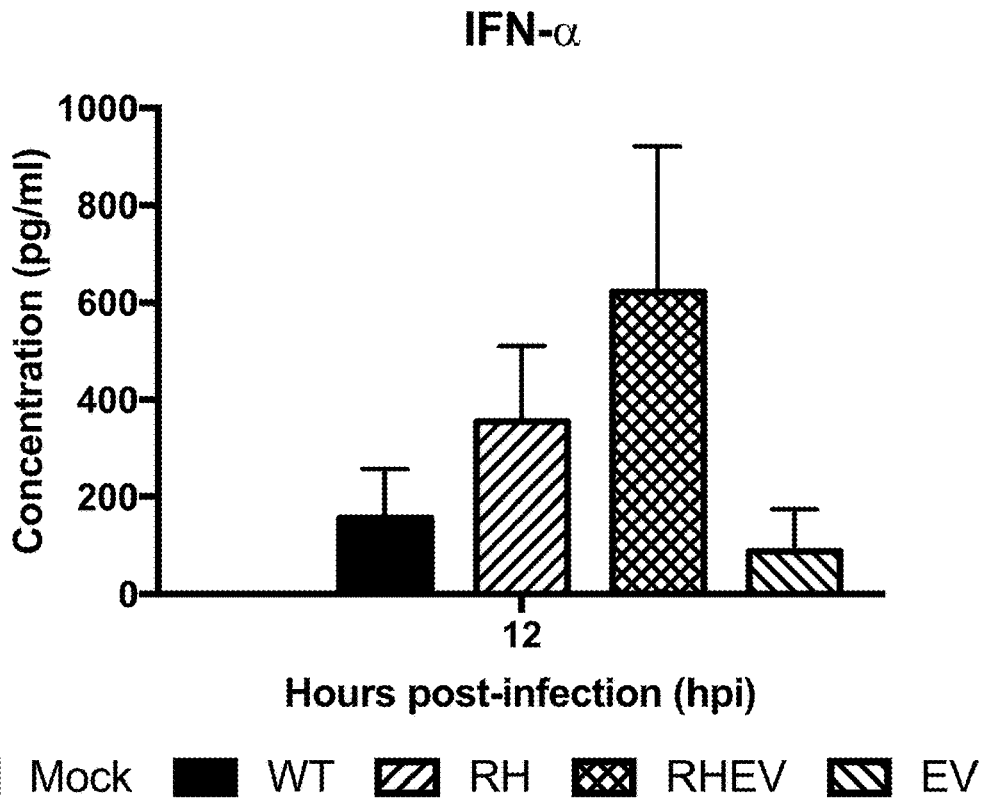
Figure 2:
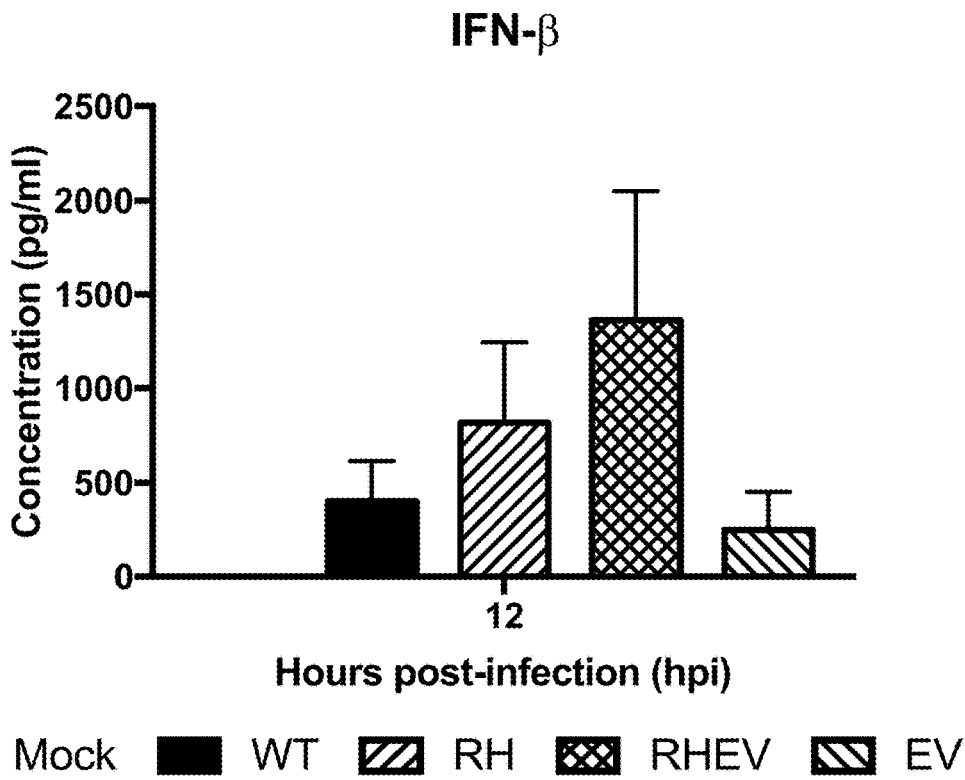

FIG. 2 shows that mutations in the CHIKV nsPs result in more robust Type 1 IFN response. CHIKV-infected MTFs were harvested at 12 hours post infection (hpi), and concentrations of Type 1 IFN were analysed using Luminex® screening assay.

The graph in (A) shows the IFN-α concentration in CHIKV-infected MTFs at 12 hpi.
The graph in (B) shows the IFN-β concentration in CHIKV-infected MTFs at 12 hpi. The data are representative of three independent experiments and are presented as mean±SD.

Figure 3:
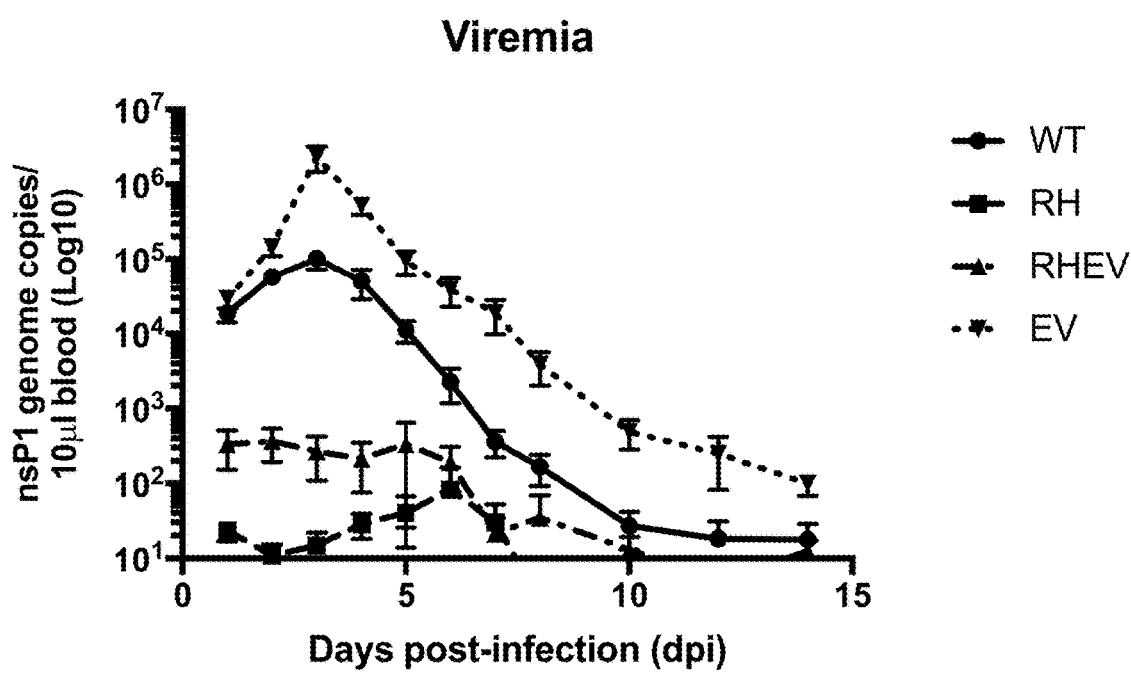
Figure 3:
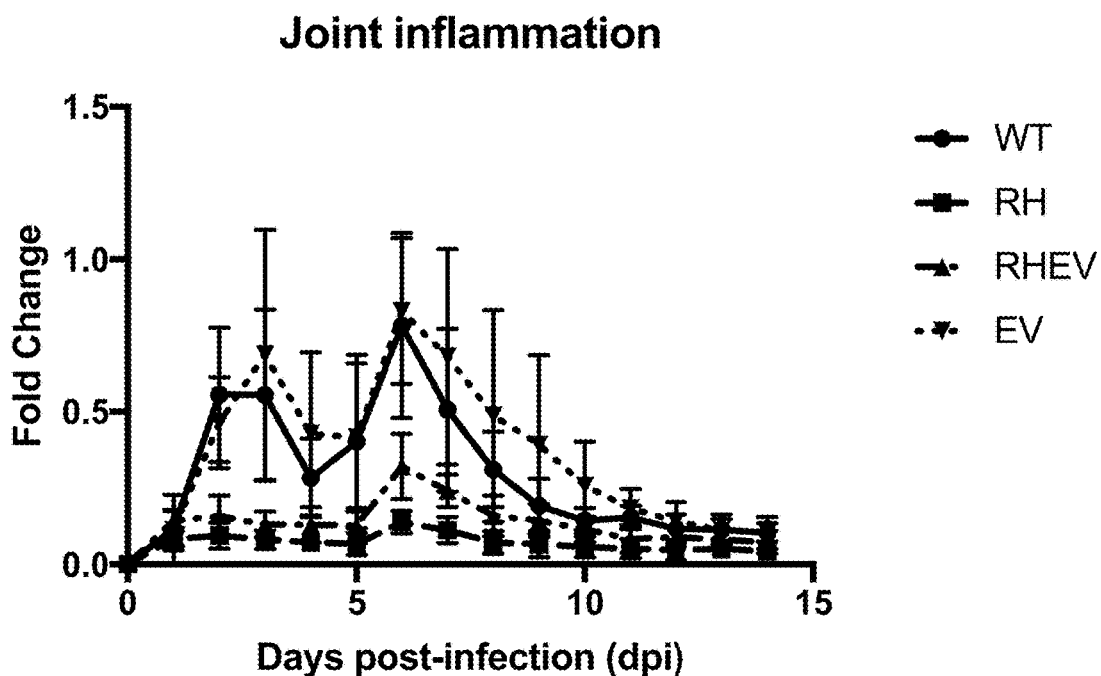

FIG. 3 shows that mutations in the CHIKV nsPs results in faster clearance of viremia and less severe virus-induced joint inflammation. WT C57BL/6 mice were infected with ZsG-tagged WT CHIKV, RH CHIKV, EV CHIKV and RHEV CHIKV at the metatarsal region of the footpad.
The graph in (A) shows viremia progression in virus-infected mice which were monitored over 2 weeks.
The graph in (B) shows joint inflammation of the mice which were monitored over 2 weeks. The data are representative of two independent experiments and are presented as mean±SD (n=11). "Statistical analysis was performed across all CHIKV-infected groups using one-way ANOVA, followed by Dunnett's post test comparing WT CHIKV (*p<0.05, p<0.01, *p<0.001).

Figure 4:
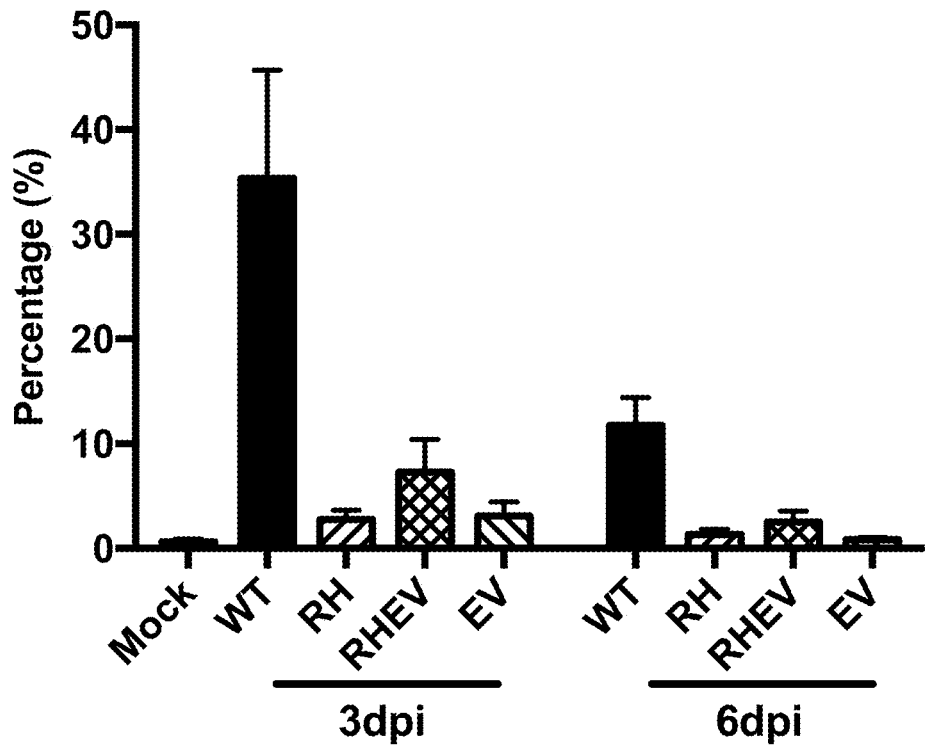
Figure 4:
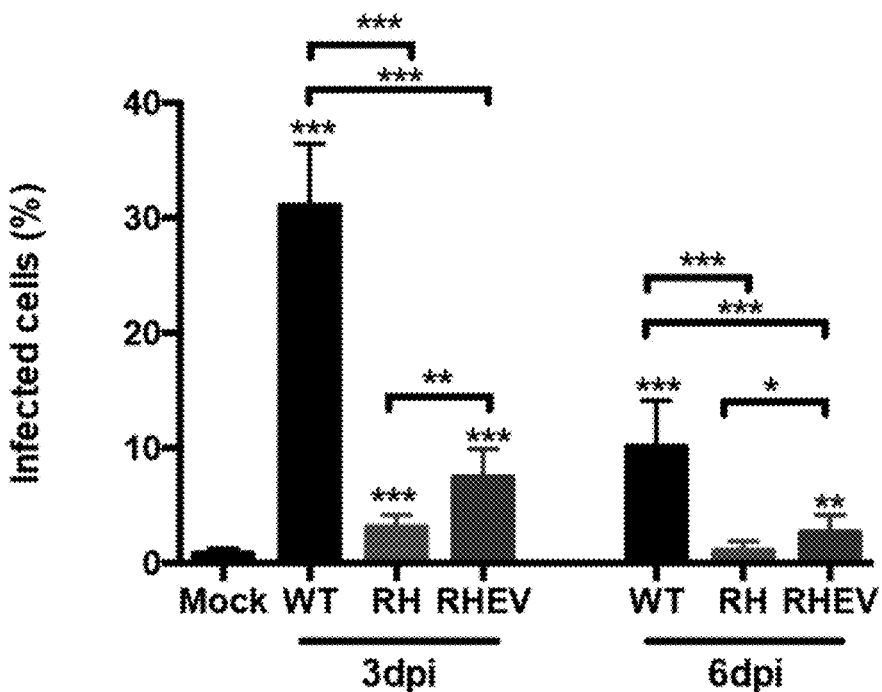
Figure 4:
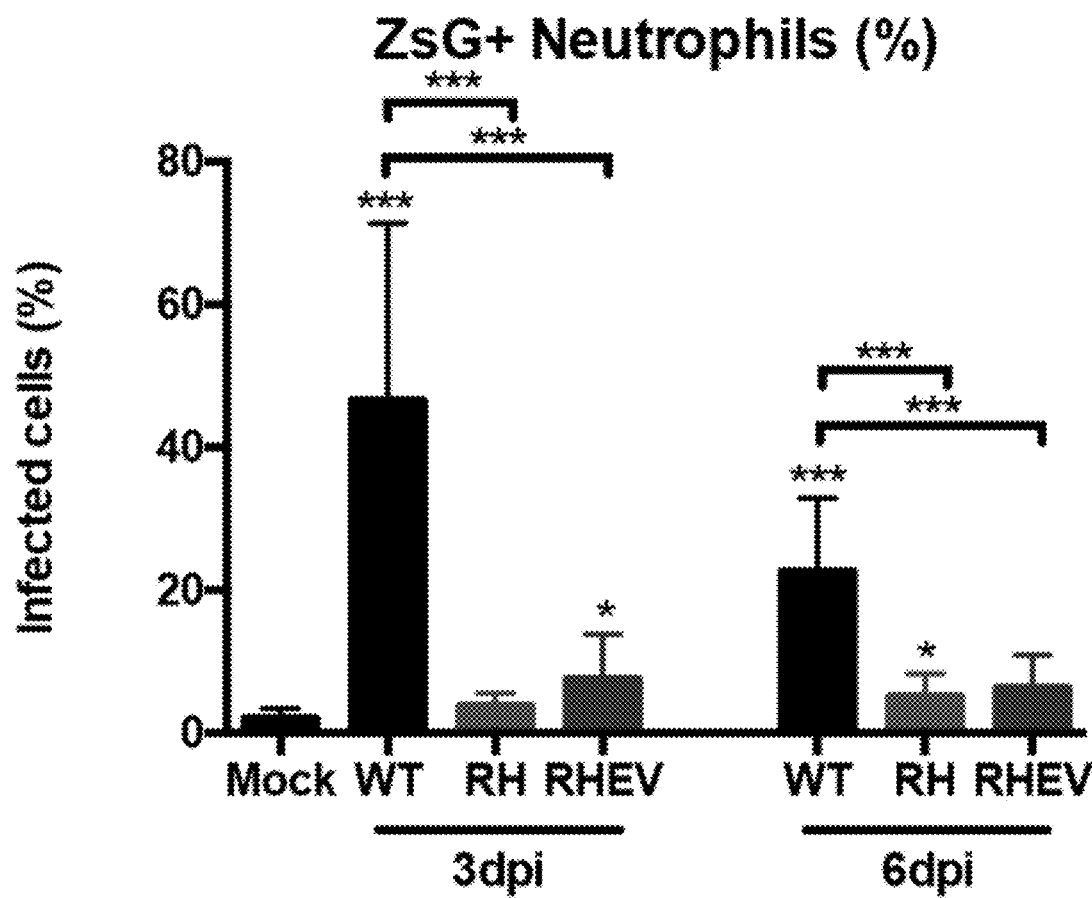
Figure 4:
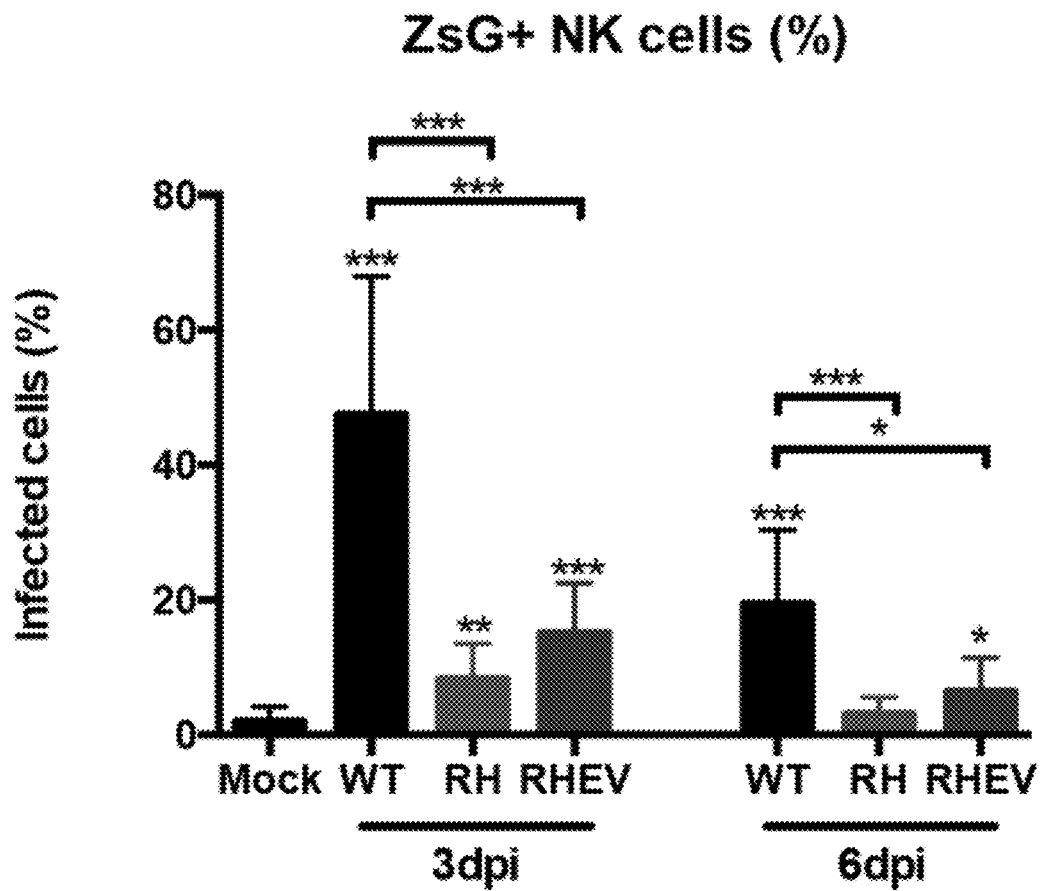
Figure 4:
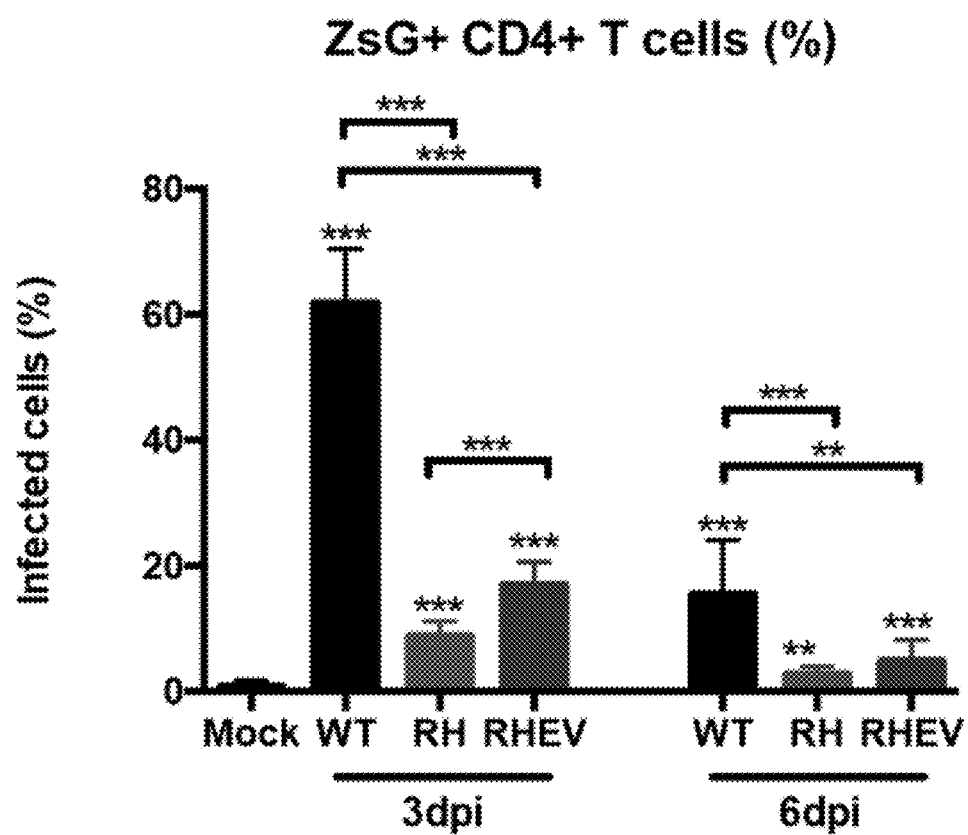
Figure 4:
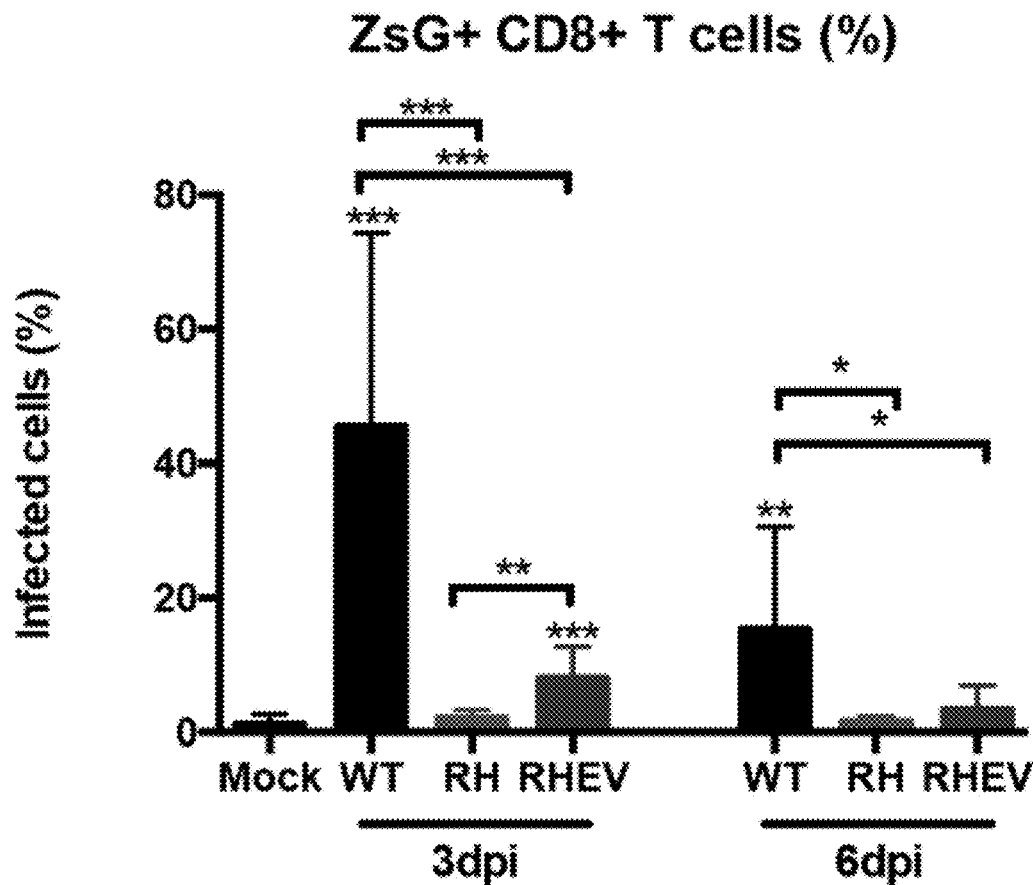
Figure 4:
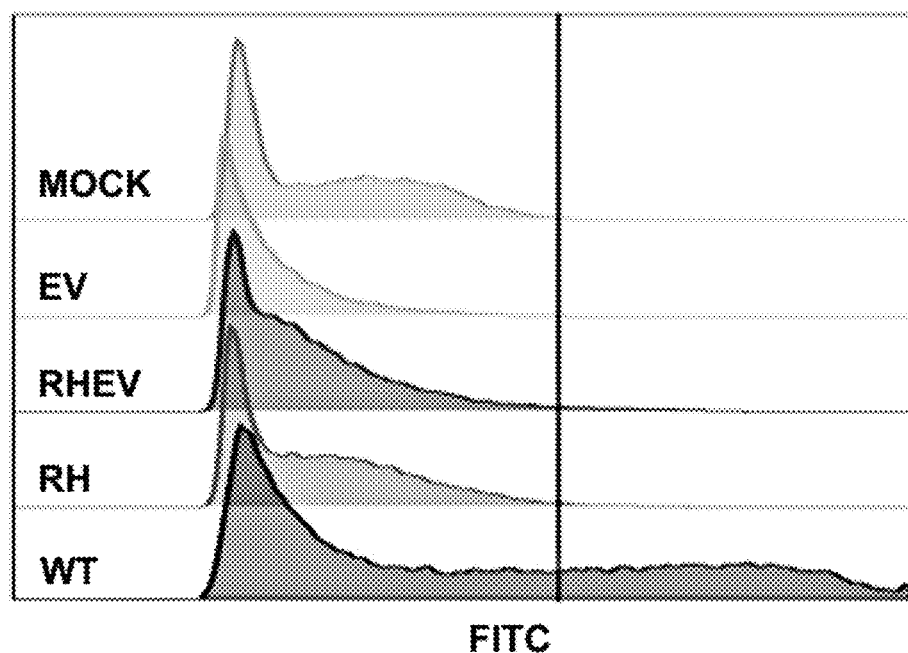

FIG. 4 shows that mutations in the CHIKV nsPs result in lower infectivity at the site of inflammation. WT C57BL/6 mice were infected subcutaneously with ZsG-tagged WT CHIKV, RH CHIKV, EV CHIKV and RHEV CHIKV at the metatarsal region of the footpad.
The graph in (A) shows the level of leukocytes isolated from the footpad at 3 days post infection (dpi) and 6 dpi using WT CHIKV, RH CHIKV, EV CHIKV and RHEV CHIKV, analysed using flow cytometry (G).
Infections with WT CHIKV, RH CHIKV and RHEV CHIKV, in various leukocyte subsets, were assessed, including in (B) monocytes and macrophages, (C) neutrophils, (D) NK cells, (E) CD4+ T cells, and (F) CD8+ T cells.
The data are representative of two independent experiments and are presented as mean±SD (n=8). Statistical analysis was performed using two-tailed Mann Whitney U test (*p<0.05).

Figure 5:
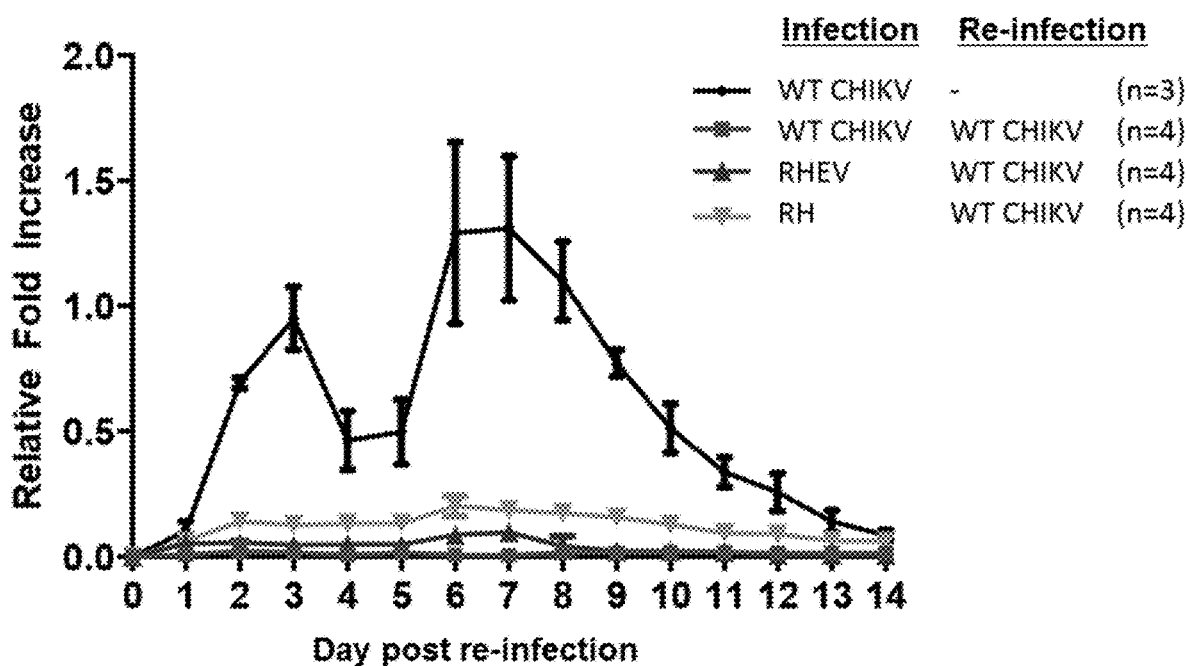
Figure 5:
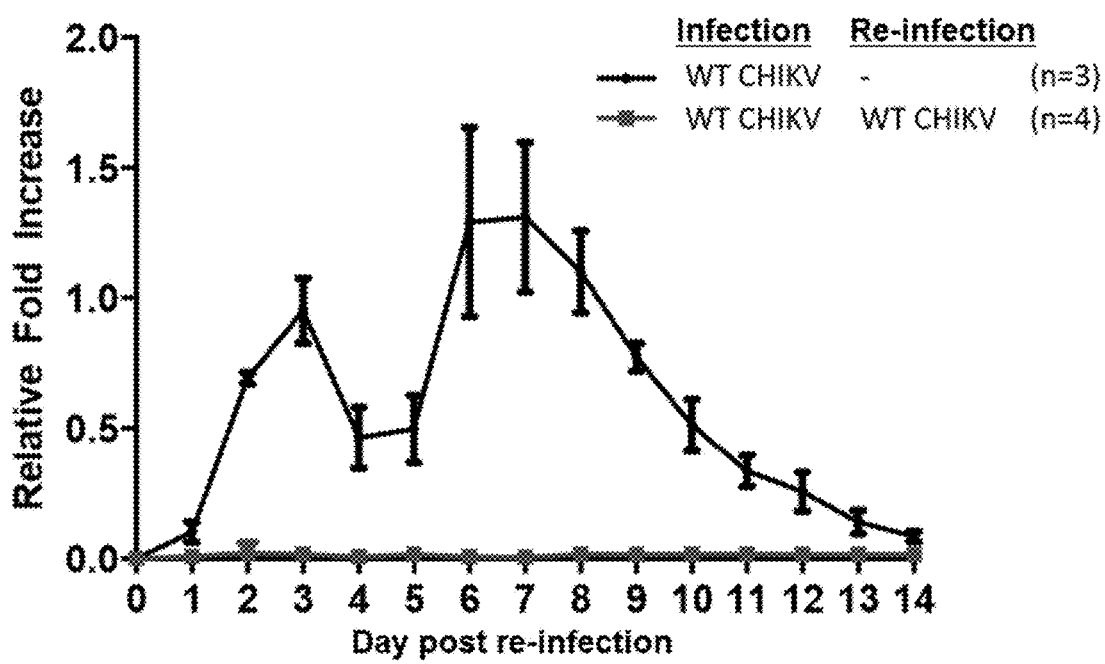
Figure 5:
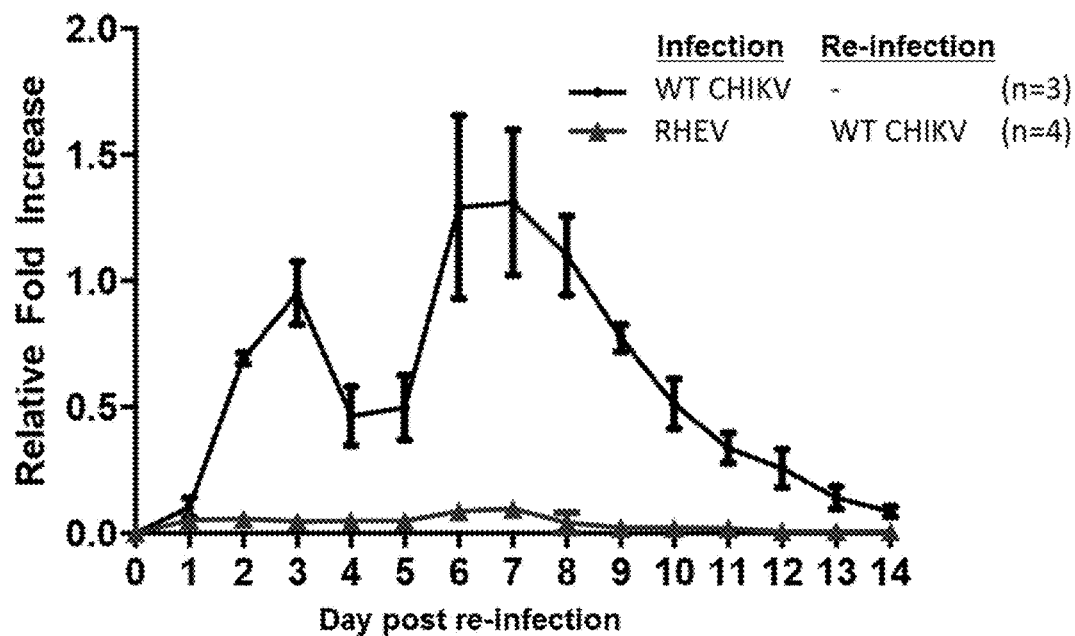
Figure 5:
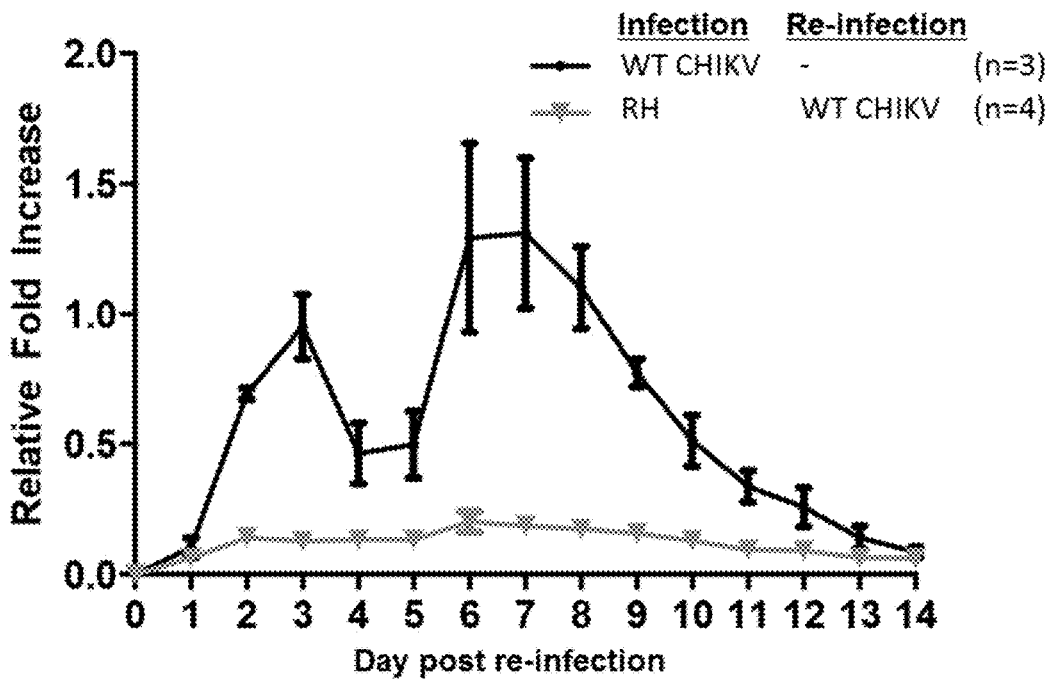

FIG. 5 shows that mice infected with CHIKV nsP mutants are protected from virus infection. WT C57BL/6 mice were re-infected with WT CHIKV 90 dpi after the first infection (with WT CHIKV, RH CHIKV and RHEV CHIKV) at the metatarsal region of the footpad. Joint inflammation of the mice was monitored over 2 weeks.

Figure 6:
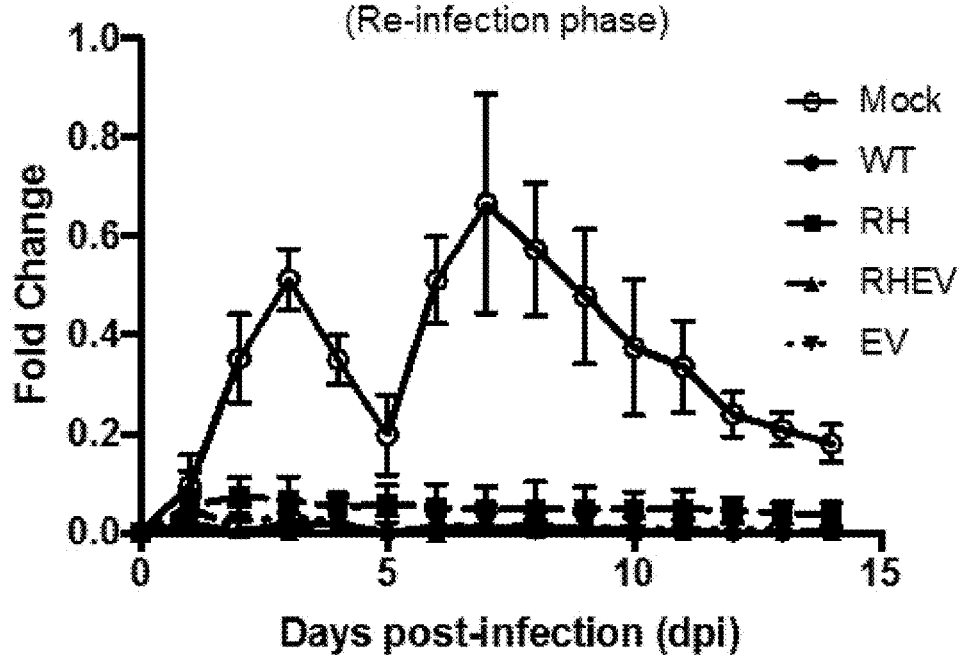
Figure 6:
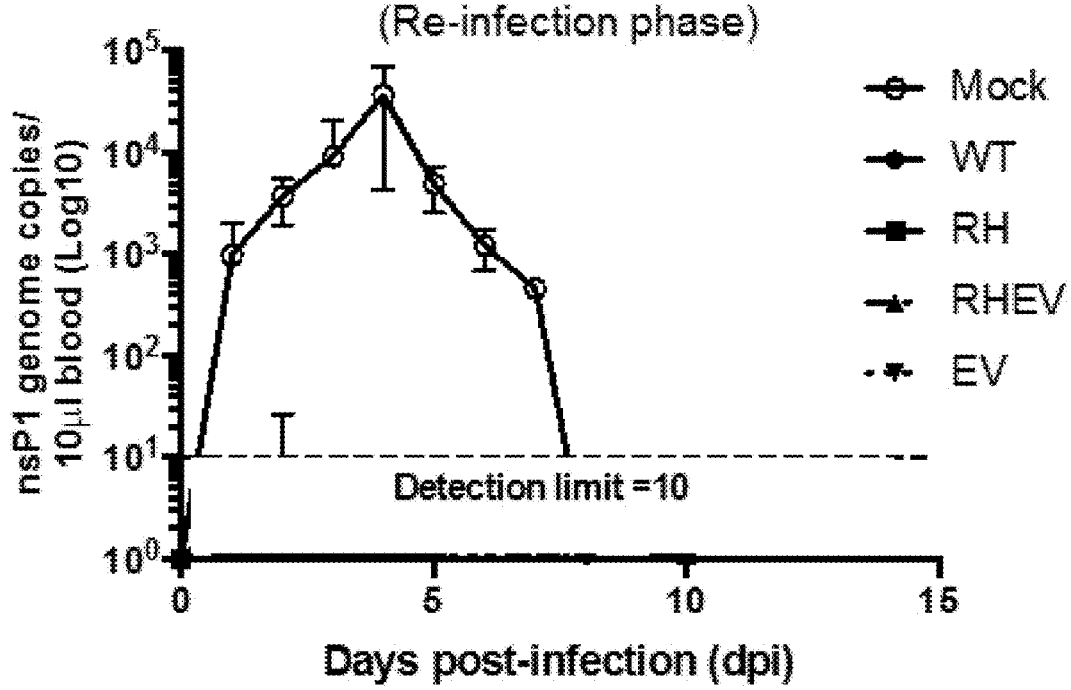
Figure 6:
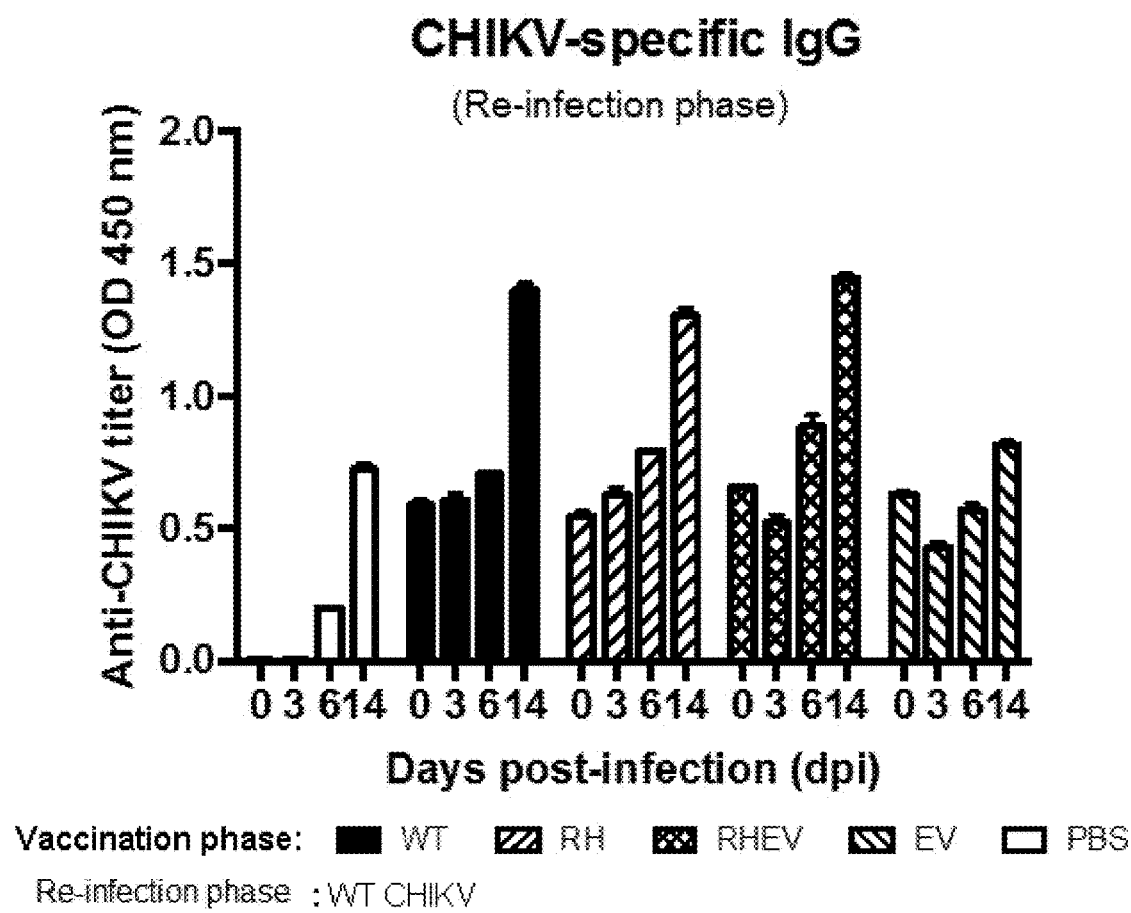
Figure 6:
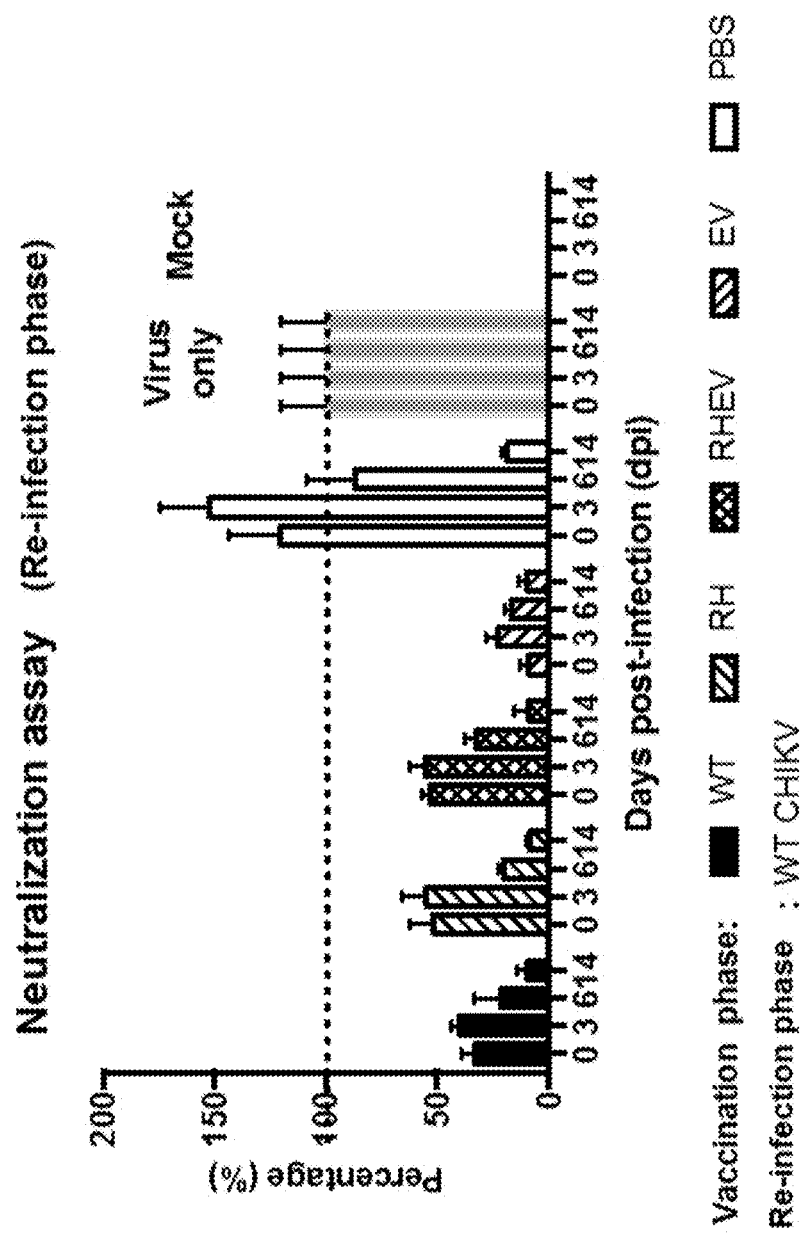

FIG. 6 shows that the reduction in joint inflammation and absence of viremia upon CHIKV re-infection in vaccinated mice is mediated by CHIKV neutralizing antibody response. WT C57BL/6 mice were vaccinated subcutaneously with WT CHIKV or CHIKV nsP mutants (RH CHIKV, EV CHIKV and RHEV CHIKV) at the metatarsal region of the footpad. Re-infection with WT CHIKV infection was performed via the same route at 3 months post-infection.
The graph in (A) shows the severity of joint inflammation.
The graph in (B) shows viremia of the mice which were monitored over 2 weeks. The data are presented as mean±SD (n=6).
The graph in (C) shows presence of CHIKV-specific antibodies in the pooled sera of the re-infected mice.
The graph in (D) shows pooled sera from re-infected mice were neutralizing against CHIKV infection in an in vitro neutralization assay. Percentage infection was normalized to virus-only infection. All data are presented as mean±SD.

Figure 7:
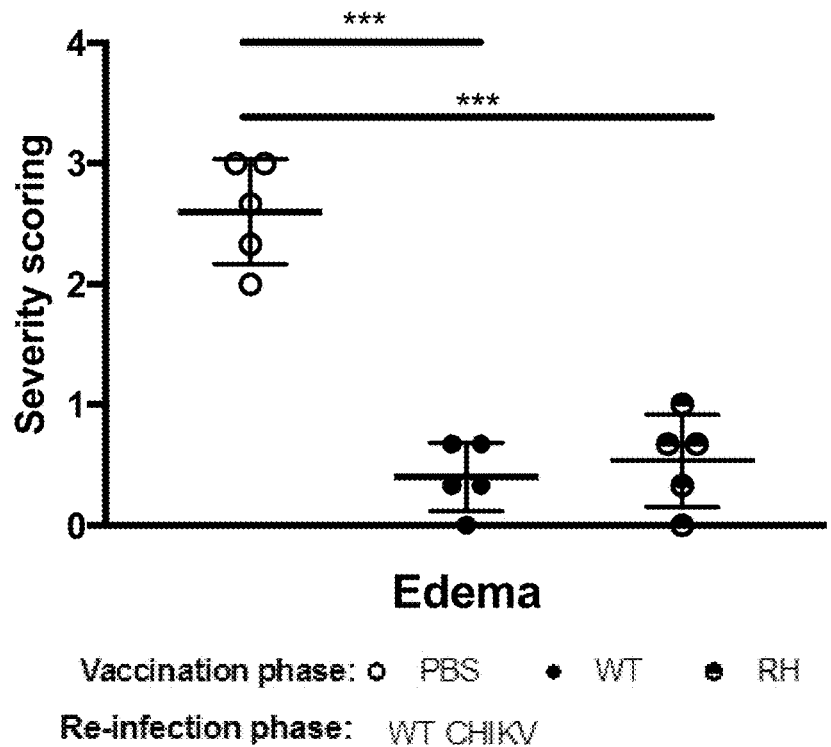
Figure 7:
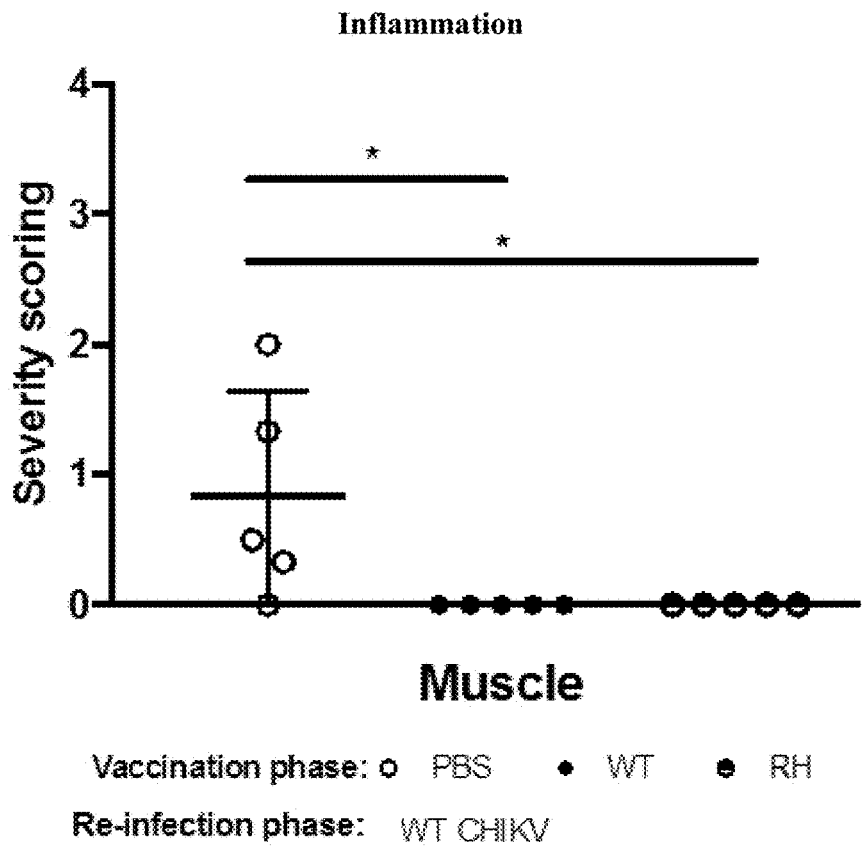

FIG. 7 shows vaccination with attenuated CHIKVs protect against CHIKV-induced joint pathology.
Panel (A) shows representative hematoxylin and eosin (H&E) images of inflamed joint footpad on 6 dpi. "Ed" marks region of edema; the arrow in the "Mock-vaccinated+ WT CHIKV" column marks synovitis; the arrow in the "WT CHIKV-vaccinated+WT CHIKV" column marks normal synovial membrane; the arrow in the "RH CHIKV-vaccinated+WT CHIKV" column marks mild synovial hyperplasia; "*" marks infiltration of mononuclear cells; "D" marks degeneration of muscle; "N" marks necrosis of muscle; and "R" marks regeneration of muscle.
Panel (B) shows the histopathological scoring of edema, inflammation in different regions of the joint footpad and muscle pathology of CHIKV infected animals (n=5 per group) on 6 dpi. Scoring was done on three sections from each joint footpad, and data were expressed as means±SD. All data were analysed by one-way ANOVA with Tukey post-test (*P<0.05, P<0.01, and *P<0.001).

Figure 8:
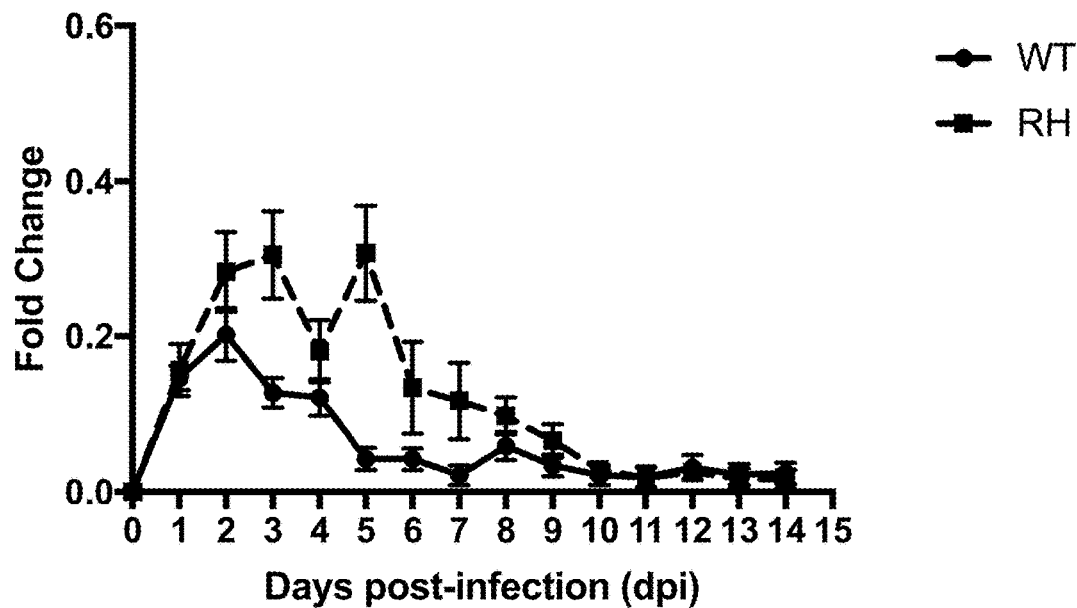
Figure 8:
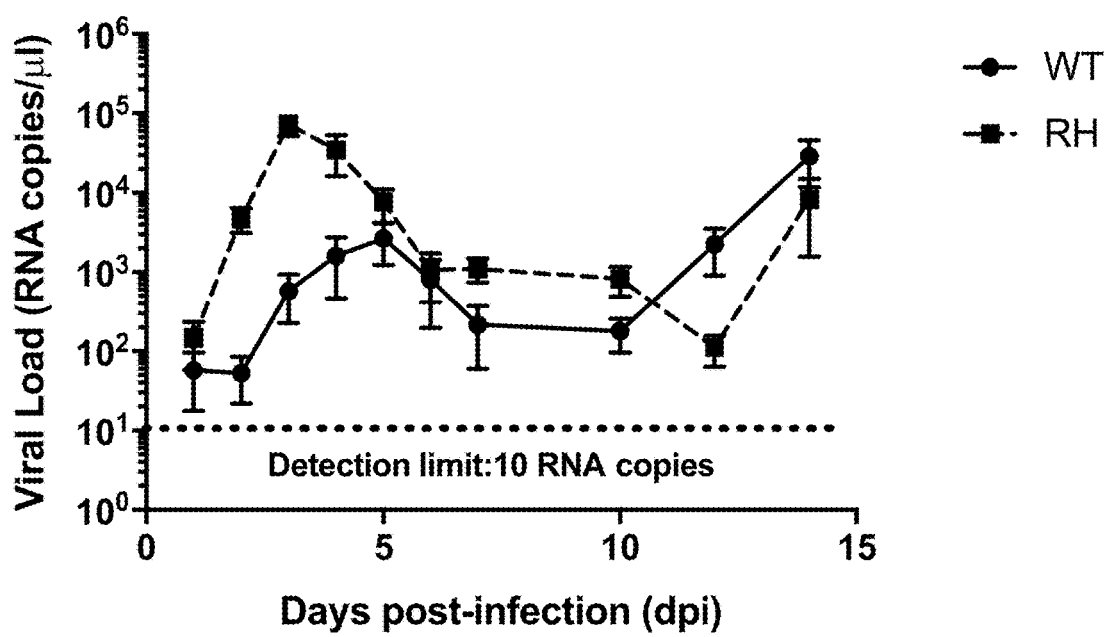
Figure 8:
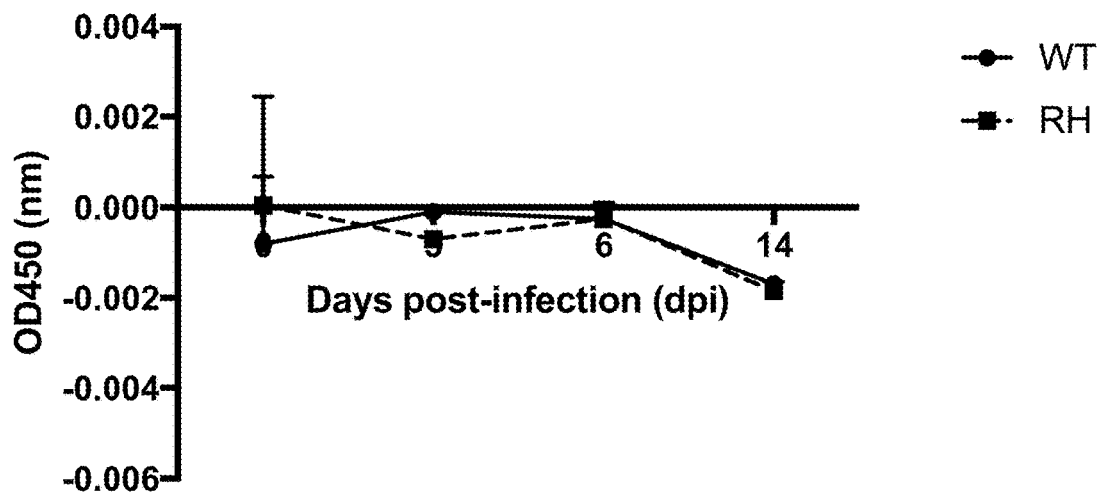
Figure 8:
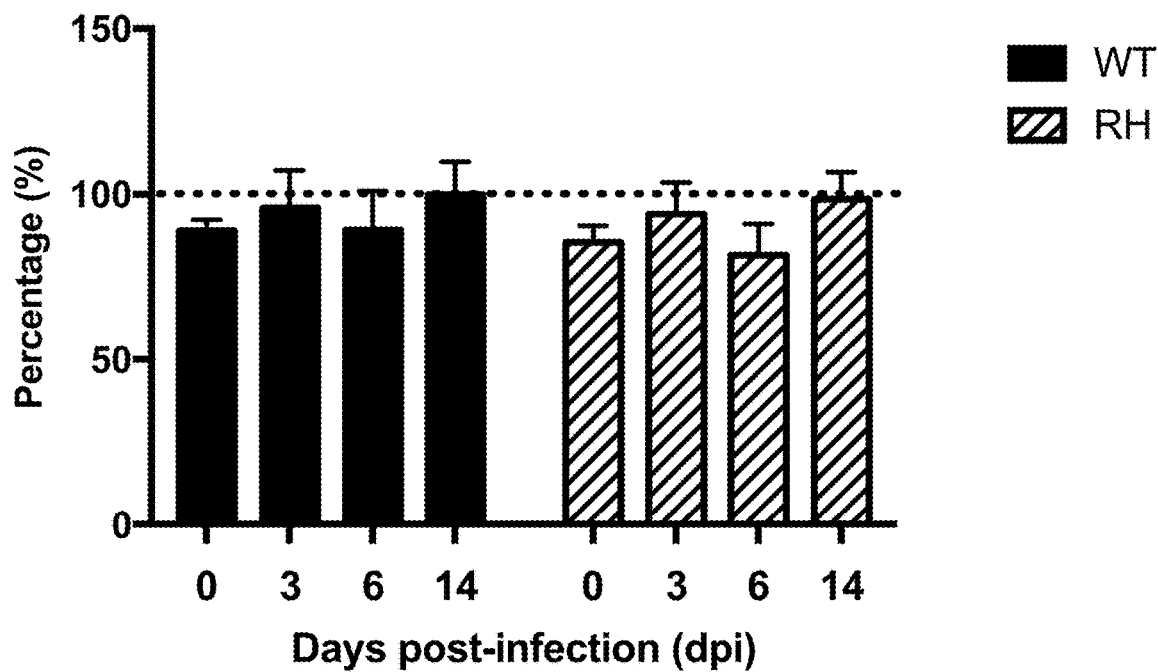

FIG. 8 shows vaccination with WT and attenuated CHIKV do not induce protective antibodies in pMT mice. pMT mice were vaccinated subcutaneously with WT CHIKV or attenuated CHIKV (RH CHIKV) at the metatarsal region of the footpad. Re-infection with WT CHIKV infection was performed via the same route at 3 months post-infection.
The graph in (A) shows joint inflammation of re-infected pMT mice.
The graph in (B) shows viremia quantification in mice.
The graph in (C) shows CHIKV-specific antibody IgG titer in pMT mice.
The graph in (D) shows the neutralization capacity of the antibodies in pMT peripheral blood determined using neutralization assay as described above.
Data are presented in mean±standard error of the mean (SEM) and are representative of 2 independent experiments (n=8).

Figure 9:
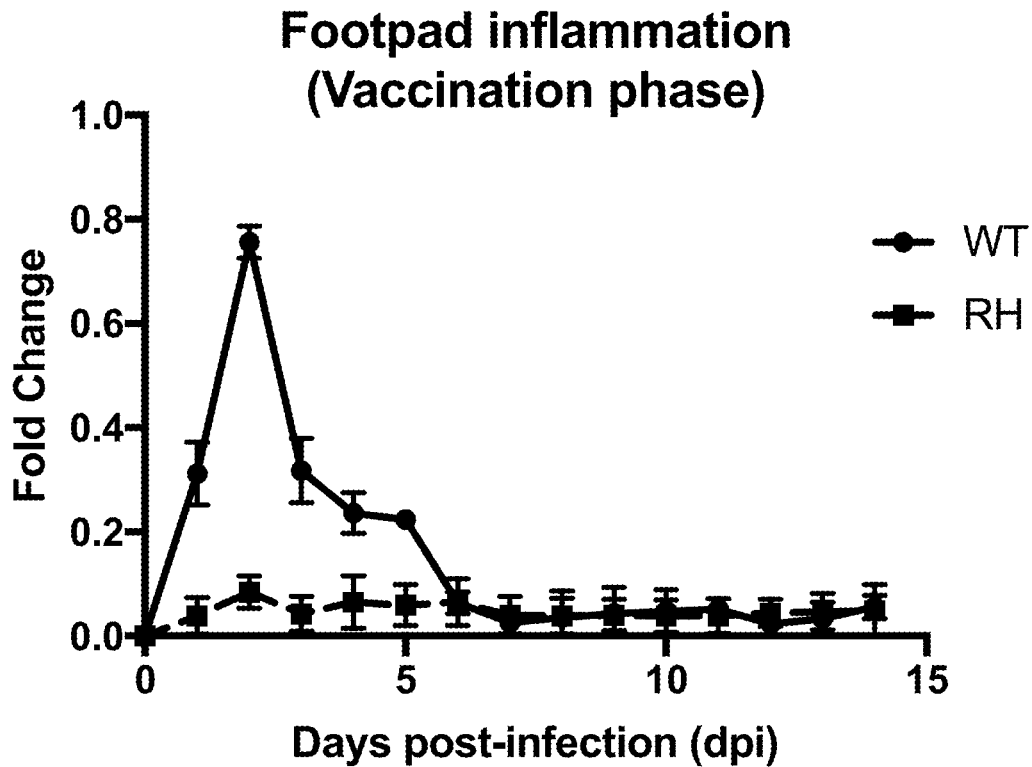
Figure 9:
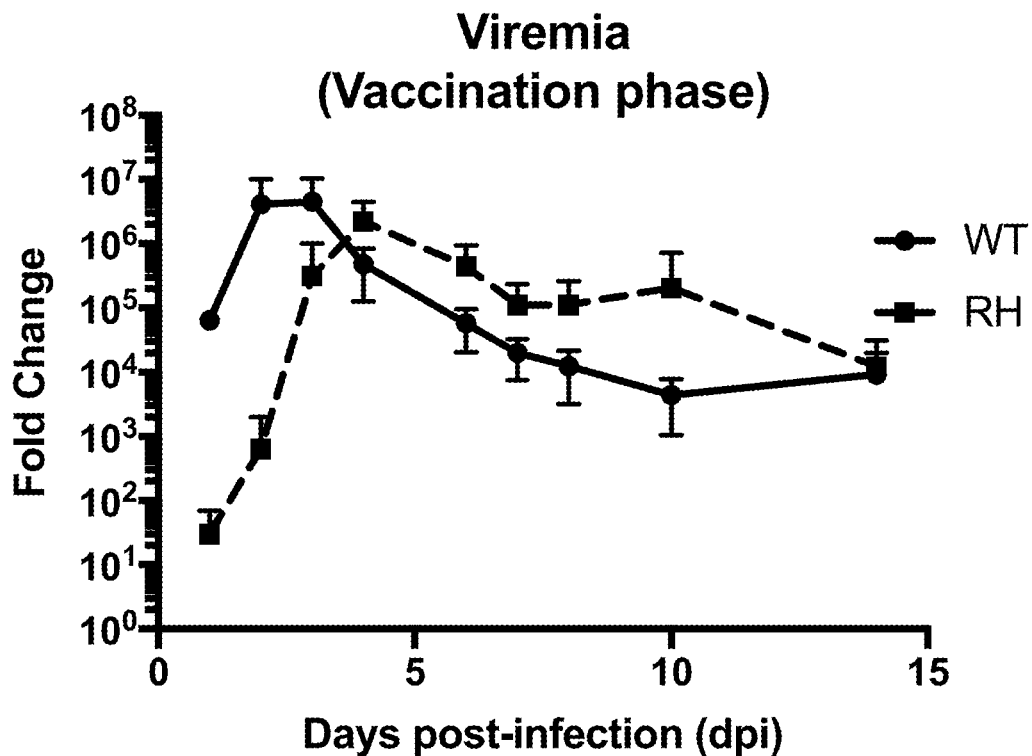
Figure 9:
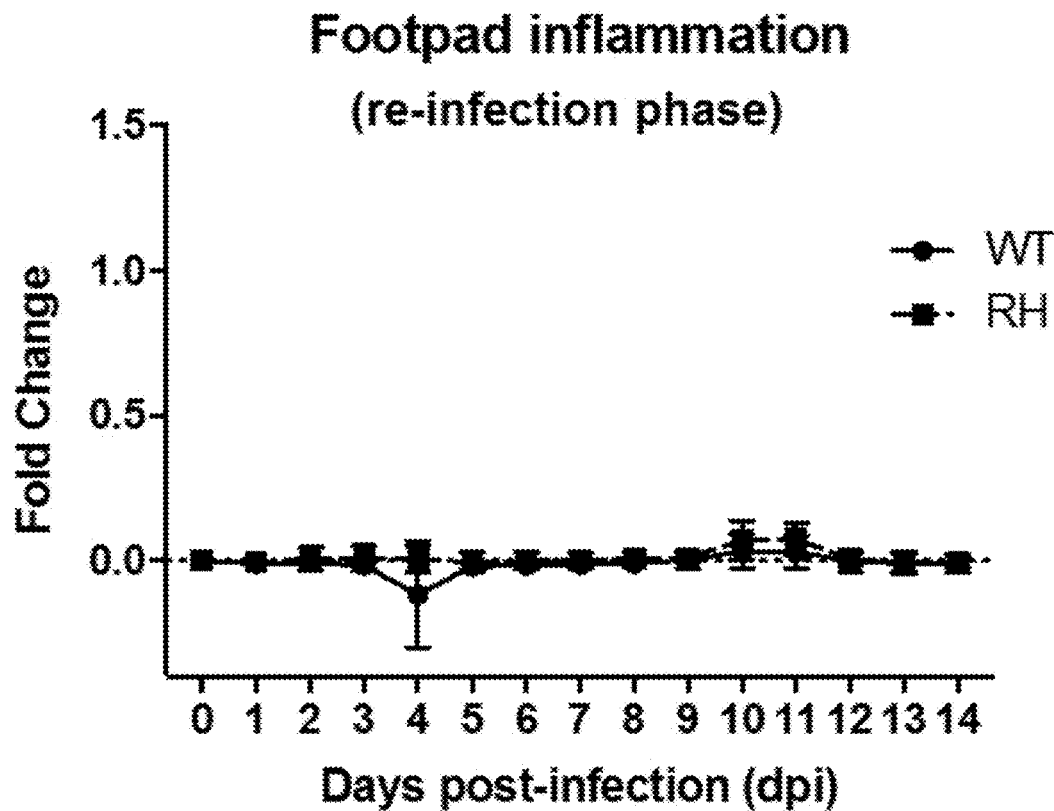
Figure 9:
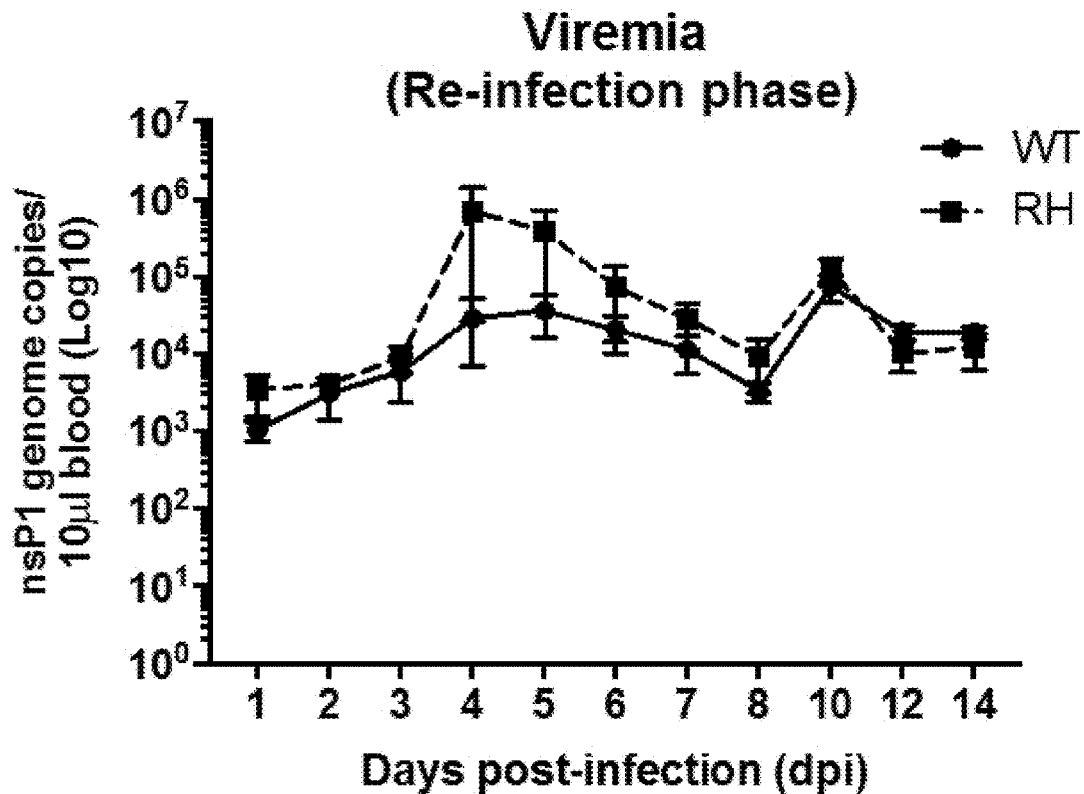

FIG. 9 shows high levels of viremia are detected in RAG-1$^{-/-}$ mice vaccinated with WT and RH CHIKV. RAG-1$^{-/-}$ mice were vaccinated subcutaneously with WT CHIKV or RH CHIKV at the metatarsal region of the footpad. Re-infection with WT CHIKV infection was performed via the same route at 3 months post-infection.
The graph in (A) shows joint inflammation of RAG-1$^{-/-}$ and (B) viremia quantification in RAG-1$^{-/-}$ mice upon vaccination.
The graph in (C) shows joint inflammation of RAG-1$^{-/-}$ and (D) viremia quantification in RAG-1$^{-/-}$ mice upon re-infection with WT CHIKV.
Data are presented in mean±standard deviation (SD) (n=5).

Figure 10:
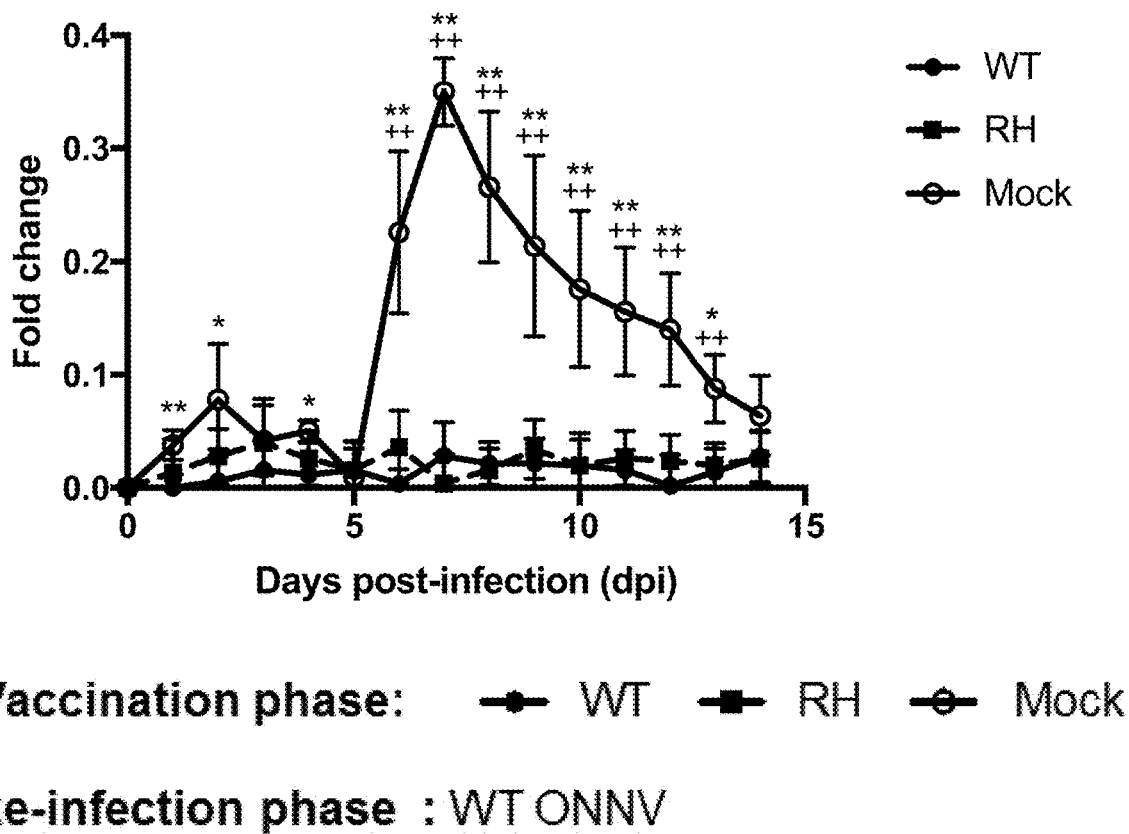

FIG. 10 shows vaccination with RH CHIKV protects mice against WT ONNV infection. WT C57BL/6 mice were vaccinated subcutaneously with WT CHIKV or RH CHIKV at the metatarsal region of the footpad. Re-infection with WT ONNV was performed via the same route at 3 months post-infection.
The graph in (A) shows the severity of joint inflammation and (B) viremia of the mice monitored over 2 weeks. The data are presented as mean±SD (n=5). All data are presented as mean±SD. Data were analysed by Mann-Whitney U two-tailed analysis (*P<0.05, **P<0.01).

Figure 11:
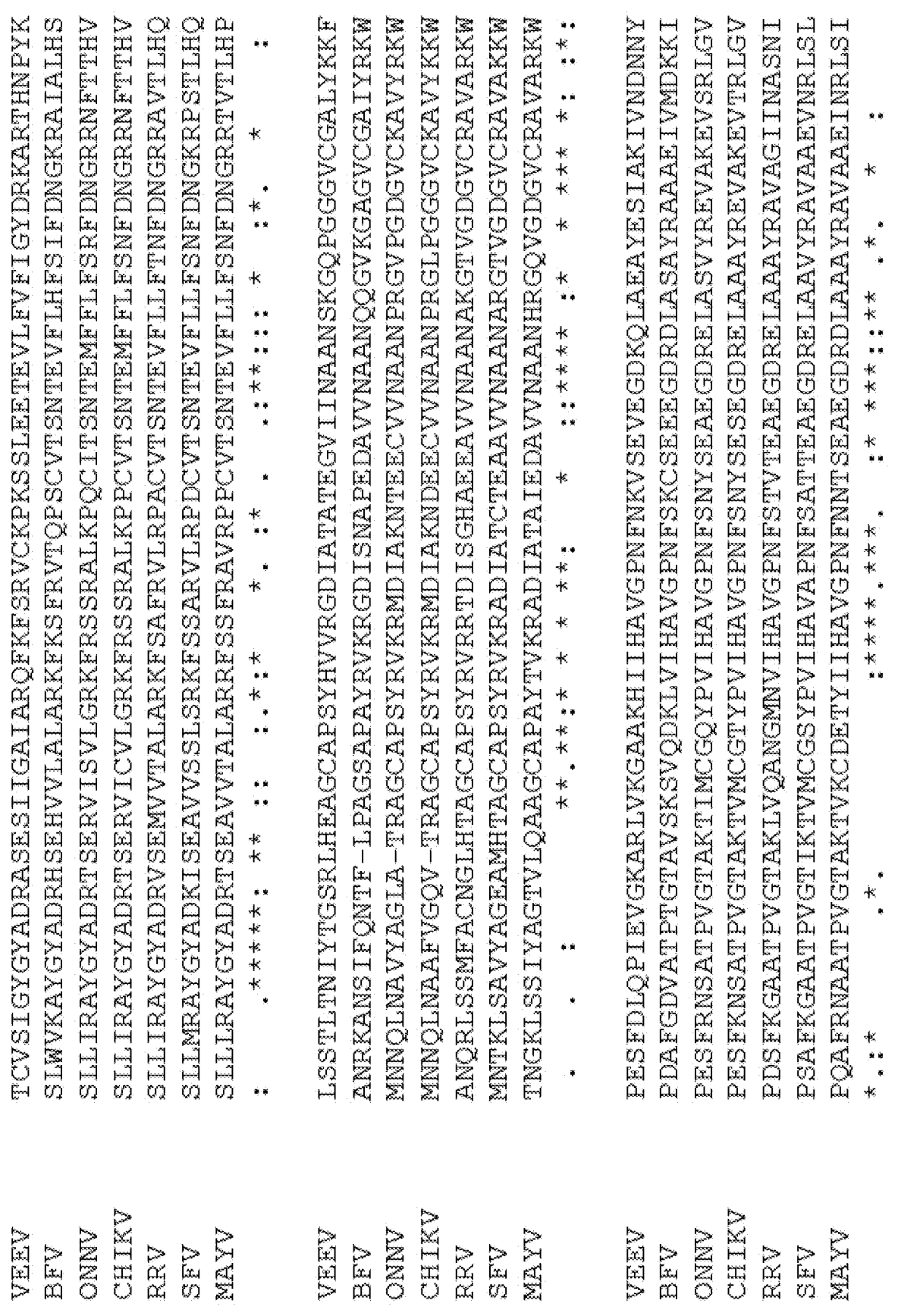
Figure 11:
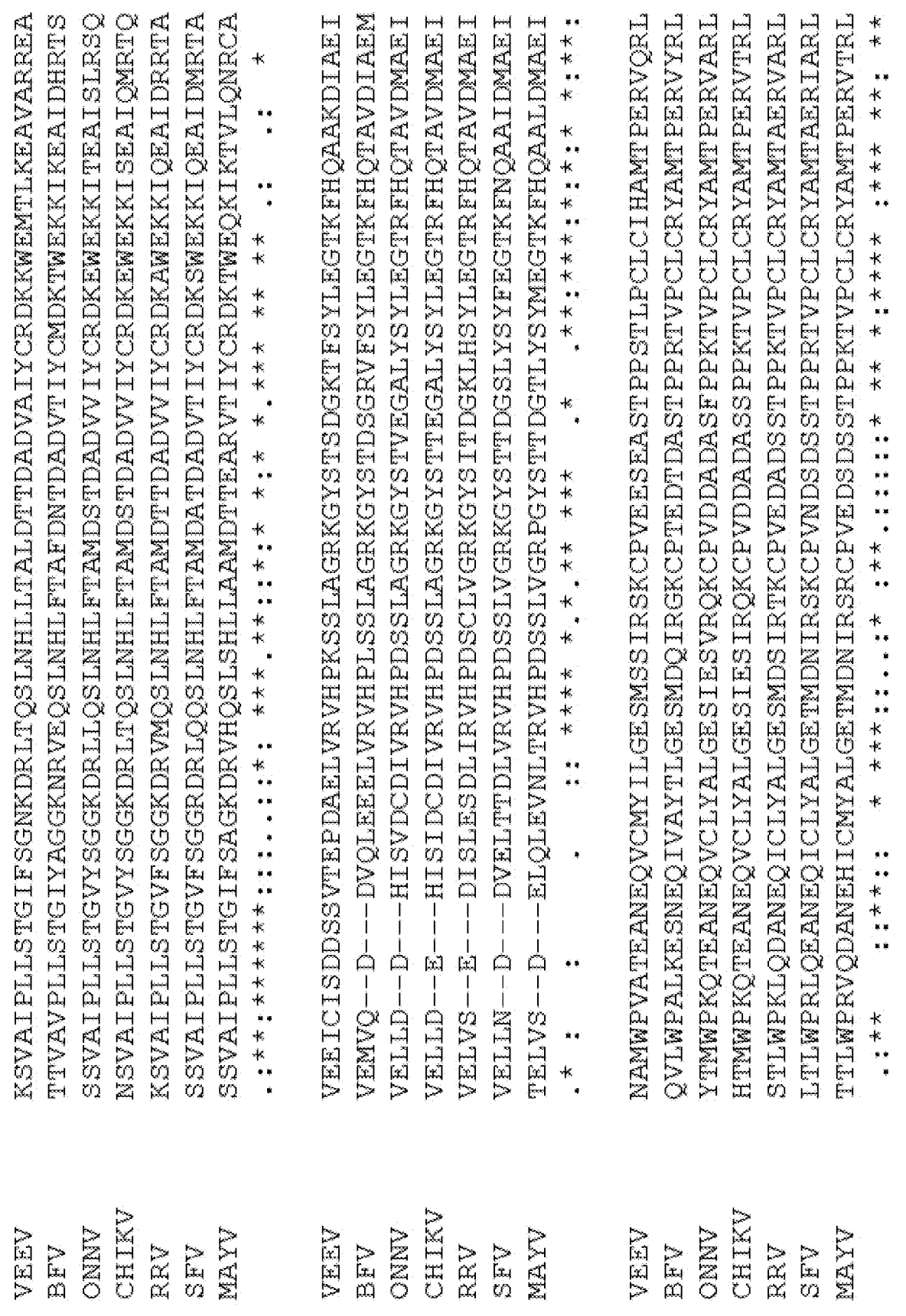

FIG. 11 shows the alignment of P1234 polyproteins of seven alphaviruses using multiple sequence alignment. "VEEV" indicates Venezuelan equine encephalitis virus (SEQ ID NO: 8); "BFV" indicates Barmah Forest virus (SEQ ID NO: 9); "ONNV" indicates O'nyong'nyong virus (SEQ ID NO: 10); "CHIKV" indicates Chikungunya virus (SEQ ID NO: 1); "RRV" indicates Ross River virus (SEQ ID NO: 11); "SFV" indicates Semliki Forest virus (SEQ ID NO: 12); and "MAYV" indicates Mayaro virus (SEQ ID NO: 13). An "*" (asterisk) indicates positions which have a single, fully conserved residue. A ":" (colon) indicates conservation between groups of strongly similar properties—scoring >0.5 in the Gonnet PAM 250 matrix. A "." (period) indicates conservation between groups of weakly similar properties—scoring=<0.5 in the Gonnet PAM 250 matrix. The amino acid residues with grey background indicate the amino acid residues at a position equivalent to position 532 of SEQ ID NO.: 1. The amino acids residues which are in bold, underlined and with grey background indicate the amino acid residues at a position equivalent to position 1050 of SEQ ID NO.: 1.

TABLE 1

List of polypeptide sequences of the disclosure.

| Polypeptide | Sequence |
|---|---|
| SEQ ID NO: 1<br>Polypeptide sequence of wild-type CHIKV LR2006 OPY1 non-structural polyprotein.<br>The amino acid residues at positions 532 (R) and 1050 (E) are underlined and in bold. | MDPVYVDIDADSAFLKALQRAYPMFEVEPRQVTPNDHANA<br>RAFSHLAIKLIEQEIDPDSTILDIGSAPARRMMSDRKYHCVCP<br>MRSAEDPERLANYARKLASAAGKVLDRNISGKIGDLQAVMA<br>VPDTETPTFCLHTDVSCRQRADVAIYQDVYAVHAPTSLYHQ<br>AIKGVRVAYWVGFDTTPFMYNAMAGAYPSYSTNWADEQVL<br>KAKNIGLCSTDLTEGRRGKLSIMRGKKLKPCDRVLFSVGSTL<br>YPESRKLLKSWHLPSVFHLKGKLSFTCRCDTVVSCEGYVVK<br>RITMSPGLYGKTTGYAVTHHADGFLMCKTTDTVDGERMSF<br>SVCTYVPATICDQMTGILATEVTPEDAQKLLVGLNQRIVVNG<br>RTQRNTNTMKNYLLPVVAQAFSKWAKECRKDMEDEKLLGV<br>RERTLTCCCLWAFKKQKTHTVYKRPDTQSIQKVQAEFDSFV<br>VPSLWSSGLSIPLRTRIKWLLSKVPKTDLIPYSGDAREARDA<br>EKEAEEEREAELTREALPPLQAAQEDVQVEIDVEQLEDRAG<br>AGIIETPRGAIKVTAQPTDHVVGEYLVLSPQTVLRSQKLSLIH<br>ALAEQVKTCTHNGRAGRYAVEAYDGRVLVPSGYAISPEDF<br>QSLSESATMVYNEREFVNRKLHHIAMHGPALNTDEESYELV<br>RAERTEHEYVYDVDQRRCCKKEEAAGLVLVGDLTNPPYHE<br>FAYEGLKIRPACPYKIAVIGVFGVPGSGKSAIIKNLVTRQDLV<br>TSGKKENCQEITTDVMRQRGLEISARTVDSLLLNGCNRPVD<br>VLYVDEAFACHSGTLLALIALVRPRQKVVLCGDPKQCGFFN<br>MMQMKVNYNHNICTQVYHKSISRRCTLPVTAIVSSLHYEGK<br>MRTTNEYNKPIVVDTTGSTKPDPGDLVLTCFRGWVKQLQID<br>YRGYEVMTAAASQGLTRKGVYAVRQKVNENPLYASTSEHV<br>NVLLTRTEGKLVWKTLSGDPWIKTLQNPPKGNFKATIKEWE<br>VEHASIMAGICSHQMTFDTFQNKANVCWAKSLVPILETAGIK<br>LNDRQWSQIIQAFKEDKAYSPEVALNEICTRMYGVDLDSGL<br>FSKPLVSVYYADNHWDNRPGGKMFGFNPEAASILERKYPF<br>TKGKWNINKQICVTTRRIEDFNPTTNIIPANRRLPHSLVAEHR<br>PVKGERMEWLVNKINGHHVLLVSGYNLALPTKRVTWVAPL<br>GVRGADYTYNLELGLPATLGRYDLVVINIHTPFRIHHYQQCV<br>DHAMKLQMLGGDSLRLLKPGGSLLIRAYGYADRTSERVICV<br>LGRKFRSSRALKPPCVTSNTEMFFLFSNFDNGRRNFTTHV<br>MNNQLNAAFVGQVTRAGCAPSYRVKRMDIAKNDEECVVNA<br>ANPRGLPGGGVCKAVYKKWPESFKNSATPVGTAKTVMCG<br>TYPVIHAVGPNFSNYSESEGDRELAAAYREVAKEVTRLGVN<br>SVAIPLLSTGVYSGGKDRLTQSLNHLFTAMDSTDADVVIYCR<br>DKEWEKKISEAIQMRTQVELLDEHISIDCDIVRVHPDSSLAG<br>RKGYSTTEGALYSYLEGTRFHQTAVDMAEIHTMWPKQTEA<br>NEQVCLYALGESIESIRQKCPVDDADASSPPKTVPCLCRYA<br>MTPERVTRLRMNHVTSIIVCSSFPLPKYKIEGVQKVKCSKVM<br>LFDHNVPSRVSPREYRSSQESAQEASTITSLTHSQFDLSVD<br>GEILPVPSDLDADAPALEPALDDGATHTLPSTTGNLAAVSD<br>WVMSTVPVAPPRRRRGRNLTVTCDEREGNITPMASVRFFR<br>AELCPVVQETAETRDTAMSLQAPPSTATEPNHPPISFGASS<br>ETFPITFGDFNEGEIESLSSELLTFGDFLPGEVDDLTDSDWS<br>TCSDTDDELRLDRAGGYIFSSDTGPGHLQQKSVRQSVLPV<br>NTLEEVHEEKCYPPKLDEAKEQLLLKKLQESASMANRSRYQ<br>SRKVENMKAAIIQRLKRGCRLYLMSETPKVPTYRTTYPAPVY<br>SPPINVRLSNPESAVAACNEFLARNYPTVSSYQITDEYDAYL<br>DMVDGSESCLDRATFNPSKLRSYPKQHAYHAPSIRSAVPSP<br>FQNTLQNVLAAATKRNCNVTQMRELPTLDSAVFNVECFKKF<br>ACNQEYWEEFAASPIRITTENLATYVTKLKGPKAAALFAKTH<br>NLLPLQEVPMDRFTVDMKRDVKVTPGTKHTEERPKVQVIQA<br>AEPLATAYLCGIHRELVRRLNAVLLPNVHTLFDMSAEDFDAII<br>AAHFKPGDTVLETDIASFDKSQDDSLALTALMLLEDLGVDHS<br>LLDLIEAAFGEISSCHLPTGTRFKFGAMMKSGMFLTLFVNTL<br>LNITIASRVLEDRLTKSACAAFIGDDNIIHGVVSDELMAARCA<br>TWMNMEVKIIDAVVSLKAPYFCGGFILHDTVTGTACRVADPL<br>KRLFKLGKPLAAGDEQDEDRRRALADEVIRWQRTGLIDELE<br>KAVYSRYEVQGISVVVMSMATFASSRSNFEKLRGPVITLYG<br>GPK |
| SEQ ID NO: 2<br>Polypeptide sequence of CHIKV LR2006 OPY1 non-structural polyprotein with mutation at position 532.<br>The amino acid residue at | MDPVYVDIDADSAFLKALQRAYPMFEVEPRQVTPNDHANA<br>RAFSHLAIKLIEQEIDPDSTILDIGSAPARRMMSDRKYHCVCP<br>MRSAEDPERLANYARKLASAAGKVLDRNISGKIGDLQAVMA<br>VPDTETPTFCLHTDVSCRQRADVAIYQDVYAVHAPTSLYHQ<br>AIKGVRVAYWVGFDTTPFMYNAMAGAYPSYSTNWADEQVL<br>KAKNIGLCSTDLTEGRRGKLSIMRGKKLKPCDRVLFSVGSTL |

TABLE 1-continued

List of polypeptide sequences of the disclosure.

| Polypeptide | Sequence |
| --- | --- |
| position 532 (R mutated to H) is underlined and in bold. | YPESRKLLKSWHLPSVFHLKGKLSFTCRCDTVVSCEGYVVK<br>RITMSPGLYGKTTGYAVTHHADGFLMCKTTDTVDGERMSF<br>SVCTYVPATICDQMTGILATEVTPEDAQKLLVGLNQRIVVNG<br>RTQRNTNTMKNYLLPVVAQAFSKWAKECRKDMEDEKLLGV<br>RERTLTCCCLWAFKKQKTHTVYKRPDTQSIQKVQAEFDSFV<br>VPSLWSSGLSIPLRTRIKWLLSKVPKTDLIPYSGDAREARDA<br>EKEAEEEREAELTREALPPLQAAQEDVQVEIDVEQLEDHAG<br>AGIIETPRGAIKVTAQPTDHVVGEYLVLSPQTVLRSQKLSLIH<br>ALAEQVKTCTHNGRAGRYAVEAYDGRVLVPSGYAISPEDF<br>QSLSESATMVYNEREFVNRKLHHIAMHGPALNTDEESYELV<br>RAERTEHEYVYDVDQRRCCKKEEAAGLVLVGDLTNPPYHE<br>FAYEGLKIRPACPYKIAVIGVFGVPGSGKSAIIKNLVTRQDLV<br>TSGKKENCQEITTDVMRQRGLEISARTVDSLLLNGCNRPVD<br>VLYVDEAFACHSGTLLALIALVRPRQKVVLCGDPKQCGFFN<br>MMQMKVNYNHNICTQVYHKSISRRCTLPVTAIVSSLHYEGK<br>MRTTNEYNKPIVVDTTGSTKPDPGDLVLTCFRGWVKQLQID<br>YRGYEVMTAAASQGLTRKGVYAVRQKVNENPLYASTSEHV<br>NVLLTRTEGKLVWKTLSGDPWIKTLQNPPKGNFKATIKEWE<br>VEHASIMAGICSHQMTFDTFQNKANVCWAKSLVPILETAGIK<br>LNDROWSQIIQAFKEDKAYSPEVALNEICTRMYGVDLDSGL<br>FSKPLVSVYYADNHWDNRPGGKMFGFNPEAASILERKYPF<br>TKGKWNINKQICVTTRRIEDFNPTTNIIPANRRLPHSLVAEHR<br>PVKGERMEWLVNKINGHHVLLVSGYNLALPTKRVTWVAPL<br>GVRGADYTYNLELGLPATLGRYDLVVINIHTPFRIHHYQQCV<br>DHAMKLQMLGGDSLRLLKPGGSLLIRAYGYADRTSERVICV<br>LGRKFRSSRALKPPCVTSNTEMFFLFSNFDNGRRNFTTHV<br>MNNQLNAAFVGQVTRAGCAPSYRVKRMDIAKNDEECVVNA<br>ANPRGLPGGGVCKAVYKKWPESFKNSATPVGTAKTVMCG<br>TYPVIHAVGPNFSNYSESEGDRELAAAYREVAKEVTRLGVN<br>SVAIPLLSTGVYSGGKDRLTQSLNHLFTAMDSTDADVVIYCR<br>DKEWEKKISEAIQMRTQVELLDEHISIDCDIVRVHPDSSLAG<br>RKGYSTTEGALYSYLEGTRFHQTAVDMAEIHTMWPKQTEA<br>NEQVCLYALGESIESIRQKCPVDDADASSPPKTVPCLCRYA<br>MTPERVTRLRMNHVTSIIVCSSFPLPKYKIEGVQKVKCSKVM<br>LFDHNVPSRVSPREYRSSQESAQEASTITSLTHSQFDLSVD<br>GEILPVPSDLDADAPALEPALDDGATHTLPSTTGNLAAVSD<br>WVMSTVPVAPPRRRRGRNLTVTCDEREGNITPMASVRFFR<br>AELCPVVQETAETRDTAMSLQAPPSTATEPNHPPISFGASS<br>ETFPITFGDFNEGEIESLSSELLTFGDFLPGEVDDLTDSDWS<br>TCSDTDDELRLDRAGGYIFSSDTGPGHLQQKSVRQSVLPV<br>NTLEEVHEEKCYPPKLDEAKEQLLLKKLQESASMANRSRYQ<br>SRKVENMKAAIIQRLKRGCRLYLMSETPKVPTYRTTYPAPVY<br>SPPINVRLSNPESAVAACNEFLARNYPTVSSYQITDEYDAYL<br>DMVDGSESCLDRATFNPSKLRSYPKQHAYHAPSIRSAVPSP<br>FQNTLQNVLAAATKRNCNVTQMRELPTLDSAVFNVECFKKF<br>ACNQEYWEEFAASPIRITTENLATYVTKLKGPKAAALFAKTH<br>NLLPLQEVPMDRFTVDMKRDVKVTPGTKHTEERPKVQVIQA<br>AEPLATAYLCGIHRELVRRLNAVLLPNVHTLFDMSAEDFDAII<br>AAHFKPGDTVLETDIASFDKSQDDSLALTALMLLEDLGVDHS<br>LLDLIEAAFGEISSCHLPTGTRFKFGAMMKSGMFLTLFVNTL<br>LNITIASRVLEDRLTKSACAAFIGDDNIIHGVVSDELMAARCA<br>TWMNMEVKIIDAVVSLKAPYFCGGFILHDTVTGTACRVADPL<br>KRLFKLGKPLAAGDEQDEDRRRALADEVIRWQRTGLIDELE<br>KAVYSRYEVQGISVVVMSMATFASSRSNFEKLRGPVITLYG<br>GPK |
| SEQ ID NO: 3<br>Polypeptide sequence of CHIKV LR2006 OPY1 non-structural polyprotein with mutation at position 1050. The amino acid residue at position 1050 (E mutated to V) is underlined and in bold. | MDPVYVDIDADSAFLKALQRAYPMFEVEPRQVTPNDHANA<br>RAFSHLAIKLIEQEIDPDSTILDIGSAPARRMMSDRKYHCVCP<br>MRSAEDPERLANYARKLASAAGKVLDRNISGKIGDLQAVMA<br>VPDTETPTFCLHTDVSCRQRADVAIYQDVYAVHAPTSLYHQ<br>AIKGVRVAYWVGFDTTPFMYNAMAGAYPSYSTNWADEQVL<br>KAKNIGLCSTDLTEGRRGKLSIMRGKKLKPCDRVLFSVGSTL<br>YPESRKLLKSWHLPSVFHLKGKLSFTCRCDTVVSCEGYVVK<br>RITMSPGLYGKTTGYAVTHHADGFLMCKTTDTVDGERMSF<br>SVCTYVPATICDQMTGILATEVTPEDAQKLLVGLNQRIVVNG<br>RTQRNTNTMKNYLLPVVAQAFSKWAKECRKDMEDEKLLGV<br>RERTLTCCCLWAFKKQKTHTVYKRPDTQSIQKVQAEFDSFV<br>VPSLWSSGLSIPLRTRIKWLLSKVPKTDLIPYSGDAREARDA<br>EKEAEEEREAELTREALPPLQAAQEDVQVEIDVEQLEDRAG<br>AGIIETPRGAIKVTAQPTDHVVGEYLVLSPQTVLRSQKLSLIH<br>ALAEQVKTCTHNGRAGRYAVEAYDGRVLVPSGYAISPEDF<br>QSLSESATMVYNEREFVNRKLHHIAMHGPALNTDEESYELV<br>RAERTEHEYVYDVDQRRCCKKEEAAGLVLVGDLTNPPYHE<br>FAYEGLKIRPACPYKIAVIGVFGVPGSGKSAIIKNLVTRQDLV<br>TSGKKENCQEITTDVMRQRGLEISARTVDSLLLNGCNRPVD<br>VLYVDEAFACHSGTLLALIALVRPRQKVVLCGDPKQCGFFN |

TABLE 1-continued

List of polypeptide sequences of the disclosure.

| Polypeptide | Sequence |
|---|---|
| | MMQMKVNYNHNICTQVYHKSISRRCTLPVTAIVSSLHYEGK
MRTTNEYNKPIVVDTTGSTKPDPGDLVLTCFRGWVKQLQID
YRGYEVMTAAASQGLTRKGVYAVRQKVNENPLYASTSEHV
NVLLTRTEGKLVWKTLSGDPWIKTLQNPPKGNFKATIKEWE
VEHASIMAGICSHQMTFDTFQNKANVCWAKSLVPILETAGIK
LNDRQWSQ11QAFKEDKAYSPVVALNEICTRMYGVDLDSGL
FSKPLVSVYYADNHWDNRPGGKMFGFNPEAASILERKYPF
TKGKWNINKQICVTTRRIEDFNPTTNIIPANRRLPHSLVAEHR
PVKGERMEWLVNKINGHHVLLVSGYNLALPTKRVTWVAPL
GVRGADYTYNLELGLPATLGRYDLVVINIHTPFRIHHYQQCV
DHAMKLQMLGGDSLRLLKPGGSLLIRAYGYADRTSERVICV
LGRKFRSSRALKPPCVTSNTEMFFLFSNFDNGRRNFTTHV
MNNQLNAAFVGQVTRAGCAPSYRVKRMDIAKNDEECVVNA
ANPRGLPGGGVCKAVYKKWPESFKNSATPVGTAKTVMCG
TYPVIHAVGPNFSNYSESEGDRELAAAYREVAKEVTRLGVN
SVAIPLLSTGVYSGGKDRLTQSLNHLFTAMDSTDADVVIYCR
DKEWEKKISEAIQMRTQVELLDEHISIDCDIVRVHPDSSLAG
RKGYSTTEGALYSYLEGTRFHQTAVDMAEIHTMWPKQTEA
NEQVCLYALGESIESIRQKCPVDDADASSPPKTVPCLCRYA
MTPERVTRLRMNHVTSIIVCSSFPLPKYKIEGVQKVKCSKVM
LFDHNVPSRVSPREYRSSQESAQEASTITSLTHSQFDLSVD
GEILPVPSDLDADAPALEPALDDGATHTLPSTTGNLAAVSD
WVMSTVPVAPPRRRRGRNLTVTCDEREGNITPMASVRFFR
AELCPVVQETAETRDTAMSLQAPPSTATEPNHPPISFGASS
ETFPITFGDFNEGEIESLSSELLTFGDFLPGEVDDLTDSDWS
TCSDTDDELRLDRAGGYIFSSDTGPGHLQQKSVRQSVLPV
NTLEEVHEEKCYPPKLDEAKEQLLLKKLQESASMANRSRYQ
SRKVENMKAAIIQRLKRGCRLYLMSETPKVPTYRTTYPAPVY
SPPINVRLSNPESAVAACNEFLARNYPTVSSYQITDEYDAYL
DMVDGSESCLDRATFNPSKLRSYPKQHAYHAPSIRSAVPSP
FQNTLQNVLAAATKRNCNVTQMRELPTLDSAVFNVECFKKF
ACNQEYWEEFAASPIRITTENLATYVTKLKGPKAAALFAKTH
NLLPLQEVPMDRFTVDMKRDVKVTPGTKHTEERPKVQVIQA
AEPLATAYLCGIHRELVRRLNAVLLPNVHTLFDMSAEDFDAII
AAHFKPGDTVLETDIASFDKSQDDSLALTALMLLEDLGVDHS
LLDLIEAAFGEISSCHLPTGTRFKFGAMMKSGMFLTLFVNTL
LNITIASRVLEDRLTKSACAAFIGDDNIIHGVVSDELMAARCA
TWMNMEVKIIDAVVSLKAPYFCGGFILHDTVTGTACRVADPL
KRLFKLGKPLAAGDEQDEDRRRALADEVIRWQRTGLIDELE
KAVYSRYEVQGISVVVMSMATFASSRSNFEKLRGPVITLYG
GPK |
| SEQ ID NO: 4
Polypeptide sequence of
CHIKV LR2006 OPY1 non-
structural polyprotein with
mutations at 532 and 1050.
The amino acid residues at
positions 532 (R mutated to
H) and 1050 (E mutated to
V) are underlined and in
bold. | MDPVYVDIDADSAFLKALQRAYPMFEVEPRQVTPNDHANA
RAFSHLAIKLIEQEIDPDSTILDIGSAPARRMMSDRKYHCVCP
MRSAEDPERLANYARKLASAAGKVLDRNISGKIGDLQAVMA
VPDTETPTFCLHTDVSCRQRADVAIYQDVYAVHAPTSLYHQ
AIKGVRVAYWVGFDTTPFMYNAMAGAYPSYSTNWADEQVL
KAKNIGLCSTDLTEGRRGKLSIMRGKKLKPCDRVLFSVGSTL
YPESRKLLKSWHLPSVFHLKGKLSFTCRCDTVVSCEGYVVK
RITMSPGLYGKTTGYAVTHHADGFLMCKTTDTVDGERMSF
SVCTYVPATICDQMTGILATEVTPEDAQKLLVGLNQRIVVNG
RTQRNTNTMKNYLLPVVAQAFSKWAKECRKDMEDEKLLGV
RERTLTCCCLWAFKKQKTHTVYKRPDTQSIQKVQAEFDSFV
VPSLWSSGLSIPLRTRIKWLLSKVPKTDLIPYSGDAREARDA
EKEAEEEREAELTREALPPLQAAQEDVQVEIDVEQLEDHAG
AGIIETPRGAIKVTAQPTDHVVGEYLVLSPQTVLRSQKLSLIH
ALAEQVKTCTHNGRAGRYAVEAYDGRVLVPSGYAISPEDF
QSLSESATMVYNEREFVNRKLHHIAMHGPALNTDEESYELV
RAERTEHEYVYDVDQRRCCKKEEAAGLVLVGDLTNPPYHE
FAYEGLKIRPACPYKIAVIGVFGVPGSGKSAIIKNLVTRQDLV
TSGKKENCQEITTDVMRQRGLEISARTVDSLLLNGCNRPVD
VLYVDEAFACHSGTLLALIALVRPRQKVVLCGDPKQCGFFN
MMQMKVNYNHNICTQVYHKSISRRCTLPVTAIVSSLHYEGK
MRTTNEYNKPIVVDTTGSTKPDPGDLVLTCFRGWVKQLQID
YRGYEVMTAAASQGLTRKGVYAVRQKVNENPLYASTSEHV
NVLLTRTEGKLVWKTLSGDPWIKTLQNPPKGNFKATIKEWE
VEHASIMAGICSHQMTFDTFQNKANVCWAKSLVPILETAGIK
LNDRQWSQIIQAFKEDKAYSPVVALNEICTRMYGVDLDSGL
FSKPLVSVYYADNHWDNRPGGKMFGFNPEAASILERKYPF
TKGKWNINKQICVTTRRIEDFNPTTNIIPANRRLPHSLVAEHR
PVKGERMEWLVNKINGHHVLLVSGYNLALPTKRVTWVAPL
GVRGADYTYNLELGLPATLGRYDLVVINIHTPFRIHHYQQCV
DHAMKLQMLGGDSLRLLKPGGSLLIRAYGYADRTSERVICV
LGRKFRSSRALKPPCVTSNTEMFFLFSNFDNGRRNFTTHV
MNNQLNAAFVGQVTRAGCAPSYRVKRMDIAKNDEECVVNA
ANPRGLPGGGVCKAVYKKWPESFKNSATPVGTAKTVMCG |

TABLE 1-continued

List of polypeptide sequences of the disclosure.

| Polypeptide | Sequence |
|---|---|
| | TYPVIHAVGPNFSNYSESEGDRELAAAYREVAKEVTRLGVN
SVAIPLLSTGVYSGGKDRLTQSLNHLFTAMDSTDADVVIYCR
DKEWEKKISEAIQMRTQVELLDEHISIDCDIVRVHPDSSLAG
RKGYSTTEGALYSYLEGTRFHQTAVDMAEIHTMWPKQTEA
NEQVCLYALGESIESIRQKCPVDDADASSPPKTVPCLCRYA
MTPERVTRLRMNHVTSIIVCSSFPLPKYKIEGVQKVKCSKVM
LFDHNVPSRVSPREYRSSQESAQEASTITSLTHSQFDLSVD
GEILPVPSDLDADAPALEPALDDGATHTLPSTTGNLAAVSD
WVMSTVPVAPPRRRRGRNLTVTCDEREGNITPMASVRFFR
AELCPVVQETAETRDTAMSLQAPPSTATEPNHPPISFGASS
ETFPITFGDFNEGEIESLSSELLTFGDFLPGEVDDLTDSDWS
TCSDTDDELRLDRAGGYIFSSDTGPGHLQQKSVRQSVLPV
NTLEEVHEEKCYPPKLDEAKEQLLLKKLQESASMANRSRYQ
SRKVENMKAAIIQRLKRGCRLYLMSETPKVPTYRTTYPAPVY
SPPINVRLSNPESAVAACNEFLARNYPTVSSYQITDEYDAYL
DMVDGSESCLDRATFNPSKLRSYPKQHAYHAPSIRSAVPSP
FQNTLQNVLAAATKRNCNVTQMRELPTLDSAVFNVECFKKF
ACNQEYWEEFAASPIRITTENLATYVTKLKGPKAAALFAKTH
NLLPLQEVPMDRFTVDMKRDVKVTPGTKHTEERPKVQVIQA
AEPLATAYLCGIHRELVRRLNAVLLPNVHTLFDMSAEDFDAII
AAHFKPGDTVLETDIASFDKSQDDSLALTALMLLEDLGVDHS
LLDLIEAAFGEISSCHLPTGTRFKFGAMMKSGMFLTLFVNTL
LNITIASRVLEDRLTKSACAAFIGDDNIIHGVVSDELMAARCA
TWMNMEVKIIDAVVSLKAPYFCGGFILHDTVTGTACRVADPL
KRLFKLGKPLAAGDEQDEDRRRALADEVIRWQRTGLIDELE
KAVYSRYEVQGISVVVMSMATFASSRSNFEKLRGPVITLYG
GPK |

TABLE 2

List of polynucleotide sequences of the disclosure.

| Polynucleotide | Sequence |
|---|---|
| SEQ ID NO: 5
Polynucleotide sequence of CH IKV LR2006 OPY1 non-structural polyprotein with mutation at position 532 (CHIKV-R532H).
The amino acid at position 532 is mutated from R to H via mutagenesis of nucleotide sequences from AGA to CAC (underlined and in bold). | ATGGCTGCGTGAGACACACGTAGCCTACCAGTTTCTTA
CTGCTCTACTCTGCAAAGCAAGAGATTAATAACCCATCA
TGGATCCTGTGTACGTGGACATAGACGCTGACAGCGCC
TTTTTGAAGGCCCTGCAACGTGCGTACCCCATGTTTGAG
GTGGAACCAAGGCAGGTCACACCGAATGACCATGCTAA
TGCTAGAGCGTTCTCGCATCTAGCTATAAAACTAATAGA
GCAGGAAATTGACCCCGACTCAACCATCCTGGATATCG
GCAGTGCGCCAGCAAGGAGGATGATGTCGGACAGGAA
GTACCACTGCGTCTGCCCGATGCGCAGTGCGGAAGATC
CCGAGAGACTCGCCAATTATGCGAGAAAGCTAGCATCT
GCCGCAGGAAAAGTCCTGGACAGAAACATCTCTGGAAA
GATCGGGGACTTACAAGCAGTAATGGCCGTGCCAGACA
CGGAGACGCCAACATTCTGCTTACACACAGACGTCTCA
TGTAGACAGAGAGCAGACGTCGCTATATACCAAGACGT
CTATGCTGTACACGCACCCACGTCGCTATACCACCAGG
CGATTAAAGGGGTCCGAGTGGCGTACTGGGTTGGGTTC
GACACAACCCCGTTCATGTACAATGCCATGGCGGGTGC
CTACCCCTCATACTCGACAAACTGGGCAGATGAGCAGG
TACTGAAGGCTAAGAACATAGGATTATGTTCAACAGACC
TGACGGAAGGTAGACGAGGCAAGTTGTCTATTATGAGA
GGGAAAAAGCTAAAACCGTGCGACCGTGTGCTGTTCTC
AGTAGGGTCAACGCTCTACCCGGAAAGCCGCAAGCTAC
TTAAGAGCTGGCACCTGCCATCGGTGTTCCATTTAAAGG
GCAAACTCAGCTTCACATGCCGCTGTGATACAGTGGTTT
CGTGTGAGGGCTACGTCGTTAAGAGAATAACGATGAGC
CCAGGCCTTTATGGAAAAACCACAGGGTATGCGGTAAC
CCACCACGCAGACGGATTCCTGATGTGCAAGACTACCG
ACACGGTTGACGGCGAAAGAATGTCATTCTCGGTGTGC
ACATACGTGCCGGCGACCATTTGTGATCAAATGACCGG
CATCCTTGCTACAGAAGTCACGCCGGAGGATGCACAGA
AGCTGTTGGTGGGGCTGAACCAGAGAATAGTGGTTAAC
GGCAGAACGCAACGGAATACGAACACCATGAAAAATTA
TCTGCTTCCCGTGGTCGCCCAAGCCTTCAGTAAGTGGG
CAAAGGAGTGCCGGAAAGACATGGAAGATGAAAAACTC
CTGGGGGTCAGAGAAAGAACACTGACCTGCTGCTGTCT
ATGGGCATTCAAGAAGCAGAAAACACACACGGTCTACA
AGAGGCCTGATACCCAGTCAATTCAGAAGGTTCAGGCC
GAGTTTGACAGCTTTGTGGTACCGAGTCTGTGGTCGTC
CGGGTTGTCAATCCCTTTGAGGACTAGAATCAAATGGTT |

TABLE 2-continued

List of polynucleotide sequences of the disclosure.

| Polynucleotide | Sequence |
|---|---|
| | GTTAAGCAAGGTGCCAAAAACCGACCTGATCCCATACA |
| | GCGGAGACGCCCGAGAAGCCCGGGACGCAGAAAAAGA |
| | AGCAGAGGAAGAACGAGAAGCAGAACTGACTCGCGAA |
| | GCCCTACCACCTCTACAGGCAGCACAGGAAGATGTTCA |
| | GGTCGAAATCGACGTGGAACAGCTTGAGGACCACGCG |
| | GGCGCAGGAATAATAGAGACTCCGAGAGGAGCTATCAA |
| | AGTTACTGCCCAACCAACAGACCACGTCGTGGGAGAGT |
| | ACCTGGTACTCTCCCCGCAGACCGTACTACGTAGCCAG |
| | AAGCTCAGTCTGATTCACGCTTTGGCGGAGCAAGTGAA |
| | GACGTGCACGCACAACGGACGAGCAGGGAGGTATGCG |
| | GTCGAAGCGTACGACGGCCGAGTCCTAGTGCCCTCAG |
| | GCTATGCAATCTCGCCTGAAGACTTCCAGAGTCTAAGC |
| | GAAAGCGCAACGATGGTGTATAACGAAAGAGAGTTCGT |
| | AAACAGAAAGCTACACCATATTGCGATGCACGGACCAG |
| | CCCTGAACACCGACGAAGAGTCGTATGAGCTGGTGAGG |
| | GCAGAGAGGACAGAACACGAGTACGTCTACGACGTGGA |
| | TCAGAGAAGATGCTGTAAGAAGGAAGAAGCCGCAGGAC |
| | TGGTACTGGTGGGCGACTTGACTAATCCGCCCTACCAC |
| | GAATTCGCATATGAAGGGCTAAAAATCCGCCCTGCCTG |
| | CCCATACAAAATTGCAGTCATAGGAGTCTTCGGAGTACC |
| | GGGATCTGGCAAGTCAGCTATTATCAAGAACCTAGTTAC |
| | CAGGCAGGACCTGGTGACTAGCGGAAAGAAAGAAAACT |
| | GCCAAGAAATCACCACCGACGTGATGAGACAGAGAGGT |
| | CTAGAGATATCTGCACGTACGGTTGACTCGCTGCTCTTG |
| | AATGGATGCAACAGACCAGTCGACGTGTTGTACGTAGA |
| | CGAGGCGTTTGCGTGCCACTCTGGAACGCTACTTGCTT |
| | TGATCGCCTTGGTGAGACCAAGGCAGAAAGTTGTACTTT |
| | GTGGTGACCCGAAGCAGTGCGGCTTCTTCAATATGATG |
| | CAGATGAAAGTCAACTATAATCACAACATCTGCACCCAA |
| | GTGTACCACAAAAGTATCTCCAGGCGGTGTACACTGCC |
| | TGTGACCGCCATTGTGTCATCGTTGCATTACGAAGGCAA |
| | AATGCGCACTACGAATGAGTACAACAAGCCGATTGTAGT |
| | GGACACTACAGGCTCAACAAAACCTGACCCTGGAGACC |
| | TCGTGTTAACGTGCTTCAGAGGGTGGGTTAAACAACTG |
| | CAAATTGACTATCGTGGATACGAGGTCATGACAGCAGC |
| | CGCATCCCAAGGGTTAACCAGAAAAGGAGTTTACGCAG |
| | TTAGACAAAAAGTTAATGAAAACCCGCTCTATGCATCAA |
| | CGTCAGAGCACGTCAACGTACTCCTAACGCGTACGGAA |
| | GGTAAACTGGTATGGAAGACACTTTCCGGCGACCCGTG |
| | GATAAAGACGCTGCAGAACCCACCGAAAGGAAACTTCA |
| | AAGCAACTATTAAGGAGTGGGAGGTGGAGCATGCATCA |
| | ATAATGGCGGGCATCTGCAGTCACCAAATGACCTTCGA |
| | TACATTCCAAAATAAAGCCAACGTTTGTTGGGCTAAGAG |
| | CTTGGTCCCTATCCTCGAAACAGCGGGGATAAAACTAAA |
| | TGATAGGCAGTGGTCTCAGATAATTCAAGCCTTCAAAGA |
| | AGACAAAGCATACTCACCTGAAGTAGCCCTGAATGAAAT |
| | ATGTACGCGCATGTATGGGGTGGATCTAGACAGCGGGC |
| | TATTTTCTAAACCGTTGGTGTCTGTGTATTACGCGGATA |
| | ACCACTGGGATAATAGGCCTGGAGGGAAAATGTTCGGA |
| | TTTAACCCCGAGGCAGCATCCATTCTAGAAAGAAAGTAT |
| | CCATTCACAAAAGGGAAGTGGAACATCAACAAGCAGAT |
| | CTGCGTGACTACCAGGAGGATAGAAGACTTTAACCCTA |
| | CCACCAACATCATACCGGCCAACAGGAGACTACCACAC |
| | TCATTAGTGGCCGAACACCGCCCAGTAAAAGGGGAAAG |
| | AATGGAATGGCTGGTTAACAAGATAAACGGCCACCACG |
| | TGCTCCTGGTCAGTGGCTATAACCTTGCACTGCCTACTA |
| | AGAGAGTCACTTGGGTAGCGCCGTTAGGTGTCCGCGGA |
| | GCGGACTACACATACAACCTAGAGTTGGGTCTGCCAGC |
| | AACGCTTGGTAGGTATGACCTAGTGGTCATAAACATCCA |
| | CACACCTTTTCGCATACACCATTACCAACAGTGCGTCGA |
| | CCACGCAATGAAACTGCAAATGCTCGGGGGTGACTCAT |
| | TGAGACTGCTCAAACCGGGCGGCTCTCTATTGATCAGA |
| | GCATATGGTTACGCAGATAGAACCAGTGAACGAGTCAT |
| | CTGCGTATTGGGACGCAAGTTTAGATCGTCTAGAGCGT |
| | TGAAACCACCATGTGTCACCAGCAACACTGAGATGTTTT |
| | TCCTATTCAGCAACTTTGACAATGGCAGAAGGAATTTCA |
| | CAACTCATGTCATGAACAATCAACTGAATGCAGCCTTCG |
| | TAGGACAGGTCACCCGAGCAGGATGTGCACCGTCGTAC |
| | CGGGTAAAACGCATGGACATCGCGAAGAACGATGAAGA |
| | GTGCGTAGTCAACGCCGCTAACCCTCGCGGGTTACCGG |
| | GTGGCGGTGTTTGCAAGGCAGTATACAAAAAATGGCCG |
| | GAGTCCTTTAAGAACAGTGCAACACCAGTGGGAACCGC |
| | AAAAACAGTTATGTGCGGTACGTATCCAGTAATCCACGC |
| | TGTTGGACCAAACTTCTCTAATTATTCGGAGTCTGAAGG |
| | GGACCGGGAATTGGCAGCTGCCTATCGAGAAGTCGCAA |
| | AGGAAGTAACTAGGCTGGGAGTAAATAGTGTAGCTATA |

TABLE 2-continued

List of polynucleotide sequences of the disclosure.

| Polynucleotide | Sequence |
|---|---|
| | CCTCTCCTCTCCACAGGTGTATACTCAGGAGGGAAAGA |
| | CAGGCTGACCCAGTCACTGAACCACCTCTTTACAGCCA |
| | TGGACTCGACGGATGCAGACGTGGTCATCTACTGCCGC |
| | GACAAAGAATGGGAGAAGAAAATATCTGAGGCCATACA |
| | GATGCGGACCCAAGTAGAGCTGCTGGATGAGCACATCT |
| | CCATAGACTGCGATATTGTTCGCGTGCACCCTGACAGC |
| | AGCTTGGCAGGCAGAAAAGGATACAGCACCACGGAAG |
| | GCGCACTGTACTCATATCTAGAAGGGACCCGTTTTCATC |
| | AGACGGCTGTGGATATGGCGGAGATACATACTATGTGG |
| | CCAAAGCAAACAGAGGCCAATGAGCAAGTCTGCCTATA |
| | TGCCCTGGGGGAAAGTATTGAATCGATCAGGCAGAAAT |
| | GCCCGGTGGATGATGCAGACGCATCATCTCCCCCCAAA |
| | ACTGTCCCGTGCCTTTGCCGTTACGCTATGACTCCAGAA |
| | CGCGTCACCCGGCTTCGCATGAACCACGTCACAAGCAT |
| | AATTGTGTGTTCTTCGTTTCCCCTCCCAAAGTACAAATA |
| | GAAGGAGTGCAAAAAGTCAAATGCTCTAAGGTAATGCTA |
| | TTTGACCACAACGTGCCATCGCGCGTAAGTCCAAGGGA |
| | ATATAGATCTTCCCAGGAGTCTGCACAGGAGGCGAGTA |
| | CAATCACGTCACTGACGCATAGTCAATTCGACCTAAGCG |
| | TTGATGGCGAGATACTGCCCGTCCCGTCAGACCTGGAT |
| | GCTGACGCCCCAGCCCTAGAACCAGCACTAGACGACG |
| | GGGCGACACACACGCTGCCATCCACAACCGGAAACCTT |
| | GCGGCCGTGTCTGATTGGGTAATGAGCACCGTACCTGT |
| | CGCGCCGCCCAGAAGAAGGCGAGGGAGAAACCTGACT |
| | GTGACATGTGACGAGAGAGAAGGGAATATAACACCCAT |
| | GGCTAGCGTCCGATTCTTTAGGGCAGAGCTGTGTCCGG |
| | TCGTACAAGAAACAGCGGAGACGCGTGACACAGCAATG |
| | TCTCTTCAGGCACCACCGAGTACCGCCACGGAACCGAA |
| | TCATCCGCCGATCTCCTTCGGAGCATCAAGCGAGACGT |
| | TCCCCATTACATTTGGGGACTTCAACGAAGGAGAAATCG |
| | AAAGCTTGTCTTCTGAGCTACTAACTTTCGGAGACTTCT |
| | TACCAGGAGAAGTGGATGACTTGACAGACAGCGACTGG |
| | TCCACGTGCTCAGACACGGACGACGAGTTAAGACTAGA |
| | CAGGGCAGGTGGGTATATATTCTCGTCGGACACCGGTC |
| | CAGGTCATTTACAACAGAAGTCAGTACGCCAGTCAGTG |
| | CTGCCGGTGAACACCCTGGAGGAAGTCCACGAGGAGA |
| | AGTGTTACCCACCTAAGCTGGATGAAGCAAAGGAGCAA |
| | CTATTACTTAAGAAACTCCAGGAGAGTGCATCCATGGCC |
| | AACAGAAGCAGGTATCAGTCGCGCAAAGTAGAAAACAT |
| | GAAAGCAGCAATCATCCAGAGACTAAAGAGAGGCTGTA |
| | GACTATACTTAATGTCAGAGACCCCAAAAGTCCCTACTT |
| | ACCGGACTACATATCCGGCGCCTGTGTACTCGCCTCCG |
| | ATCAACGTCCGATTGTCCAATCCCGAGTCCGCAGTGGC |
| | AGCATGCAATGAGTTCTTAGCTAGAAACTATCCAACTGT |
| | CTCATCATACCAAATTACCGACGAGTATGATGCATATCT |
| | AGACATGGTGGACGGGTCGGAGAGTTGCCTGGACCGA |
| | GCGACATTCAATCCGTCAAAACTCAGGAGCTACCCGAA |
| | ACAGCACGCTTACCACGCGCCCTCCATCAGAAGCGCTG |
| | TACCGTCCCCATTCCAGAACACACTACAGAATGTACTGG |
| | CAGCAGCCACGAAAAGAAACTGCAACGTCACACAGATG |
| | AGGGAATTACCCACTTTGGACTCAGCAGTATTCAACGTG |
| | GAGTGTTTCAAAAAATTCGCATGCAACCAAGAATACTGG |
| | GAAGAATTTGCTGCCAGCCCTATTAGGATAACAACTGAG |
| | AATTTAGCAACCTATGTTACTAAACTAAAAGGGCCAAAA |
| | GCAGCAGCGCTATTCGCAAAAACCCATAATCTACTGCCA |
| | CTACAGGAAGTACCAATGGATAGGTTCACAGTAGATATG |
| | AAAAGGGACGTAAAGGTGACTCCTGGTACAAAGCATAC |
| | AGAGGAAAGACCTAAGGTGCAGGTTATACAGGCGGCTG |
| | AACCCTTGGCGACAGCATACCTATGTGGGATTCACAGA |
| | GAGCTGGTTAGGAGGCTGAACGCCGTCCTCCTACCCAA |
| | TGTACATACACTATTTGACATGTCTGCCGAGGATTTCGA |
| | TGCCATCATAGCCGCACACTTTAAGCCAGGAGACACTG |
| | TTTTGGAAACGGACATAGCCTCCTTTGATAAGAGCCAAG |
| | ATGATTCACTTGCGCTTACTGCTTTGATGCTGTTAGAGG |
| | ATTTAGGGTGGATCACTCCCTGCTGGACTTGATAGAG |
| | GCTGCTTTCGGAGAGATTTCCAGCTGTCACCTACCGAC |
| | AGGTACGCGCTTCAAGTTCGGCGCCATGATGAAATCAG |
| | GTATGTTCCTAACTCTGTTCGTCAACACATTGTTAAACAT |
| | CACCATCGCCAGCCGAGTGCTGGAAGATCGTCTGACAA |
| | AATCCGCGTGCGCGGCCTTCATCGGCGACGACAACATA |
| | ATACATGGAGTCGTCTCCGATGAATTGATGGCAGCCAG |
| | ATGTGCCACTTGGATGAACATGGAAGTGAAGATCATAGA |
| | TGCAGTTGTATCCTTGAAAGCCCCTTACTTTTGTGGAGG |
| | GTTTATACTGCACGATACTGTGACAGGAACAGCTTGCAG |
| | AGTGGCAGACCCGCTAAAAAGGCTTTTTAAACTGGGCA |
| | AACCGCTAGCGGCAGGTGACGAACAAGATGAAGATAGA |

TABLE 2-continued

List of polynucleotide sequences of the disclosure.

| Polynucleotide | Sequence |
| --- | --- |
| | AGACGAGCGCTGGCTGACGAAGTGATCAGATGGCAAC |
| | GAACAGGGCTAATTGATGAGCTGGAGAAAGCGGTATAC |
| | TCTAGGTACGAAGTGCAGGGTATATCAGTTGTGGTAATG |
| | TCCATGGCCACCTTTGCAAGCTCCAGATCCAACTTCGA |
| | GAAGCTCAGAGGACCCGTCATAACTTTGTACGGCGGTC |
| | CTAAATAGGTACGCACTACAGCTACCTATTTTGCAGAAG |
| | CCGACAGCAAGTATCTAAACACTAATCAGCTACAATGGA |
| | GTTCATCCCAACCCAAACTTTTTACAATAGGAGGTACCA |
| | GCCTCGACCCTGGACTCCGCGCCCTACTATCCAAGTCA |
| | TCAGGCCCAGACCGCGCCCTCAGAGGCAAGCTGGGCA |
| | ACTTGCCCAGCTGATCTCAGCAGTTAATAAACTGACAAT |
| | GCGCGCGGTACCACAACAGAAGCCACGCAGGAATCGG |
| | AAGAATAAGAAGCAAAAGCAAAAACAACAGGCGCCACA |
| | AAACAACACAAATCAAAAGAAGCAGCCACCTAAAAAGAA |
| | ACCGGCTCAAAAGAAAAAGAAGCCGGGCCGCAGAGAG |
| | AGGATGTGCATGAAAATCGAAAATGATTGTATTTTCGAA |
| | GTCAAGCACGAAGGTAAGGTAACAGGTTACGCGTGCCT |
| | GGTGGGGGACAAAGTAATGAAACCAGCACACGTAAAGG |
| | GGACCATCGATAACGCGGACCTGGCCAAACTGGCCTTT |
| | AAGCGGTCATCTAAGTATGACCTTGAATGCGCGCAGAT |
| | ACCCGTGCACATGAAGTCCGACGCTTCGAAGTTCACCC |
| | ATGAGAAACCGGAGGGGTACTACAACTGGCACCACGGA |
| | GCAGTACAGTACTCAGGAGGCCGGTTCACCATCCCTAC |
| | AGGTGCTGGCAAACCAGGGGACAGCGGCAGACCGATC |
| | TTCGACAACAAGGGACGCGTGGTGGCCATAGTCTTAGG |
| | AGGAGCTAATGAAGGAGCCCGTACAGCCCTCTCGGTGG |
| | TGACCTGGAATAAAGACATTGTCACTAAAATCACCCCCG |
| | AGGGGGCCGAAGAGTGGAGTCTTGCCATCCCAGTTATG |
| | TGCCTGTTGGCAAACACCACGTTCCCCTGCTCCCAGCC |
| | CCCTTGCACGCCCTGCTGCTACGAAAAGGAACCGGAGG |
| | AAACCCTACGCATGCTTGAGGACAACGTCATGAGACCT |
| | GGGTACTATCAGCTGCTACAAGCATCCTTAACATGTTCT |
| | CCCCACCGCCAGCGACGCAGCACCAAGGACAACTTCAA |
| | TGTCTATAAAGCCACAAGACCATACTTAGCTCACTGTCC |
| | CGACTGTGGAGAAGGGCACTCGTGCCATAGTCCCGTAG |
| | CACTAGAACGCATCAGAAATGAAGCGACAGACGGGACG |
| | CTGAAAATCCAGGTCTCCTTGCAAATCGGAATAAAGACG |
| | GATGACAGCCACGATTGGACCAAGCTGCGTTATATGGA |
| | CAACCACATGCCAGCAGACGCAGAGAGGGCGGGGCTA |
| | TTTGTAAGAACATCAGCACCGTGTACGATTACTGGAACA |
| | ATGGGACACTTCATCCTGGCCCGATGTCCAAAAGGGGA |
| | AACTCTGACGGTGGGATTCACTGACAGTAGGAAGATTA |
| | GTCACTCATGTACGCACCCATTTCACCACGACCCTCCTG |
| | TGATAGGTCGGGAAAAATTCCATTCCCGACCGCAGCAC |
| | GGTAAAGAGCTACCTTGCAGCACGTACGTGCAGAGCAC |
| | CGCCGCAACTACCGAGGAGATAGAGGTACACATGCCCC |
| | CAGACACCCCTGATCGCACATTAATGTCACAACAGTCC |
| | GGCAACGTAAAGATCACAGTCAATGGCCAGACGGTGCG |
| | GTACAAGTGTAATTGCGGTGGCTCAAATGAAGGACTAA |
| | CAACTACAGACAAAGTGATTAATAACTGCAAGGTTGATC |
| | AATGTCATGCCGCGGTCACCAATCACAAAAAGTGGCAG |
| | TATAACTCCCCTCTGGTCCCGCGTAATGCTGAACTTGG |
| | GGACCGAAAAGGAAAAATTCACATCCCGTTTCCGCTGG |
| | CAAATGTAACATGCAGGGTGCCTAAAGCAAGGAACCCC |
| | ACCGTGACGTACGGGAAAAACCAAGTCATCATGCTACT |
| | GTATCCTGACCACCCAACACTCCTGTCCTACCGGAATAT |
| | GGGAGAAGAACCAAACTATCAAGAAGAGTGGGTGATGC |
| | ATAAGAAGGAAGTCGTGCTAACCGTGCCGACTGAAGGG |
| | CTCGAGGTCACGTGGGGCAACAACGAGCCGTATAAGTA |
| | TTGGCCGCAGTTATCTACAAACGGTACAGCCCATGGCC |
| | ACCCGCATGAGATAATTCTGTATTATTATGAGCTGTACC |
| | CCACTATGACTGTAGTAGTTGTGTCAGTGGCCACGTTCA |
| | TACTCCTGTCGATGGTGGGTATGGCAGCGGGGATGTGC |
| | ATGTGTGCACGACGCAGATGCATCACACCGTATGAACT |
| | GACACCAGGAGCTACCGTCCCTTTCCTGCTTAGCCTAAT |
| | ATGCTGCATCAGAACAGCTAAAGCGGCCACATACCAAG |
| | AGGCTGCGATATACCTGTGGAACGAGCAGCAACCTTTG |
| | TTTTGGCTACAAGCCCTTATTCCGCTGGCAGCCCTGATT |
| | GTTCTATGCAACTGTCTGAGACTCTTACCATGCTGCTGT |
| | AAAACGTTGGCTTTTTTAGCCGTAATGAGCGTCGGTGCC |
| | CACACTGTGAGCGCGTACGAACACGTAACAGTGATCCC |
| | GAACACGGTGGGAGTACCGTATAAGACTCTAGTCAATA |
| | GACCTGGCTACAGCCCCATGGTATTGGAGATGGAACTA |
| | CTGTCAGTCACTTTGGAGCCAACACTATCGCTTGATTAC |
| | ATCACGTGCGAGTACAAAACCGTCATCCCGTCTCCGTA |
| | CGTGAAGTGCTGCGGTACAGCAGAGTGCAAGGACAAAA |

TABLE 2-continued

List of polynucleotide sequences of the disclosure.

| Polynucleotide | Sequence |
|---|---|
| | ACCTACCTGACTACAGCTGTAAGGTCTTCACCGGCGTC<br>TACCCATTTATGTGGGGCGGCGCCTACTGCTTCTGCGA<br>CGCTGAAAACACGCAGTTGAGCGAAGCACACGTGGAGA<br>AGTCCGAATCATGCAAAACAGAATTTGCATCAGCATACA<br>GGGCTCATACCGCATCTGCATCAGCTAAGCTCCGCGTC<br>CTTTACCAAGGAAATAACATCACTGTAACTGCCTATGCA<br>AACGGCGACCATGCCGTCACAGTTAAGGACGCCAAATT<br>CATTGTGGGGCCAATGTCTTCAGCCTGGACACCTTTCG<br>ACAACAAAATTGTGGTGTACAAAGGTGACGTCTATAACA<br>TGGACTACCCGCCCTTTGGCGCAGGAAGACCAGGACAA<br>TTTGGCGATATCCAAAGTCGCACACCTGAGAGTAAAGA<br>CGTCTATGCTAATACACAACTGGTACTGCAGAGACCGG<br>CTGTGGGTACGGTACACGTGCCATACTCTCAGGCACCA<br>TCTGGCTTTAAGTATTGGCTAAAAGAACGCGGGGCGTC<br>GCTGCAGCACACAGCACCATTTGGCTGCCAAATAGCAA<br>CAAACCCGGTAAGAGCGGTGAACTGCGCCGTAGGGAA<br>CATGCCCATCTCCATCGACATACCGGAAGCGGCCTTCA<br>CTAGGGTCGTCGACGCGCCCTCTTTAACGGACATGTCG<br>TGCGAGGTACCAGCCTGCACCCATTCCTCAGACTTTGG<br>GGGCGTCGCCATTATTAAATATGCAGCCAGCAAGAAAG<br>GCAAGTGTGCGGTGCATTCGATGACTAACGCCGTCACT<br>ATTCGGGAAGCTGAGATAGAAGTTGAAGGGAATTCTCA<br>GCTGCAAATCTCTTTCTCGACGGCCTTAGCCAGCGCCG<br>AATTCCGCGTACAAGTCTGTTCTACACAAGTACACTGTG<br>CAGCCGAGTGCCACCCCCCGAAGGACCACATAGTCAAC<br>TACCCGGCGTCACATACCACCCTCGGGGTCCAGGACAT<br>CTCCGCTACGGCGATGTCATGGGTGCAGAAGATCACGG<br>GAGGTGTGGGACTGGTTGTTGCTGTTGCCGCACTGATT<br>CTAATCGTGGTGCTATGCGTGTCGTTCAGCAGGCACTA<br>ACTTGACAATTAAGTATGAAGGTATATGTGTCCCCTAAG<br>AGACACACTGTACATAGCAAATAATCTATAGATCAAAGG<br>GCTACGCAACCCCTGAATAGTAACAAAATACAAAATCAC<br>TAAAAATTATAAAAACAGAAAAATACATAAATAGGTATAC<br>GTGTCCCCTAAGAGACACATTGTATGTAGGTGATAAGTA<br>TAGATCAAAGGGCCGAATAACCCCTGAATAGTAACAAAA<br>TATGAAAATCAATAAAAATCATAAAATAGAAAAACCATAA<br>ACAGAAGTAGTTCAAAGGGCTATAAAACCCCTGAATAGT<br>AACAAAACATAAAATTAATAAAAATCAAATGAATACCATA<br>ATTGGCAAACGGAAGAGATGTAGGTACTTAAGCTTCCTA<br>AAAGCAGCCGAACTCACTTTGAGAAGTAGGCATAGCAT<br>ACCGAACTCTTCCACGATTCTCCGAACCCACAGGGACG<br>TAGGAGATGTTATTTGTTTTTAATATTTCAAAAAAAAAAAA<br>AAAAAAAAAAAAA |
| SEQ ID NO: 6<br>Polynucleotide sequence of CHIKV LR2006 OPY1 non-structural polyprotein with mutation at position 1050 (CHIKV-E1050V).<br>The amino acid at position 1050 is mutated from E to V via mutagenesis of nucleotide sequences from GAA to GTG (underlined and in bold). | ATGGCTGCGTGAGACACACGTAGCCTACCAGTTTCTTA<br>CTGCTCTACTCTGCAAAGCAAGAGATTAATAACCCATCA<br>TGGATCCTGTGTACGTGGACATAGACGCTGACAGCGCC<br>TTTTTGAAGGCCCTGCAACGTGCGTACCCCATGTTTGAG<br>GTGGAACCAAGGCAGGTCACACCGAATGACCATGCTAA<br>TGCTAGAGCGTTCTCGCATCTAGCTATAAAACTAATAGA<br>GCAGGAAATTGACCCCGACTCAACCATCCTGGATATCG<br>GCAGTGCGCCAGCAAGGAGGATGATGTCGGACAGGAA<br>GTACCACTGCGTCTGCCCGATGCGCAGTGCGGAAGATC<br>CCGAGAGACTCGCCAATTATGCGAGAAAGCTAGCATCT<br>GCCGCAGGAAAAGTCCTGGACAGAAACATCTCTGGAAA<br>GATCGGGGACTTACAAGCAGTAATGGCCGTGCCAGACA<br>CGGAGACGCCAACATTCTGCTTACACACAGACGTCTCA<br>TGTAGACAGAGAGCAGACGTCGCTATATACCAAGACGT<br>CTATGCTGTACACGCACCCACGTCGCTATACCACCAGG<br>CGATTAAAGGGGTCCGAGTGGCGTACTGGGTTGGGTTC<br>GACACAACCCCGTTCATGTACAATGCCATGGCGGGTGC<br>CTACCCCTCATACTCGACAAACTGGGCAGATGAGCAGG<br>TACTGAAGGCTAAGAACATAGGATTATGTTCAACAGACC<br>TGACGGAAGGTAGACGAGGCAAGTTGTCTATTATGAGA<br>GGGAAAAAGCTAAAACCGTGCGACCGTGTGCTGTTCTC<br>AGTAGGGTCAACGCTCTACCCGGAAAGCCGCAAGCTAC<br>TTAAGAGCTGGCACCTGCCATCGGTGTTCCATTTAAAGG<br>GCAAACTCAGCTTCACATGCCGCTGTGATACAGTGGTTT<br>CGTGTGAGGGCTACGTCGTTAAGAGAATAACGATGAGC<br>CCAGGCCTTTATGGAAAAACCACAGGGTATGCGGTAAC<br>CCACCACGCAGACGGATTCCTGATGTGCAAGACTACCG<br>ACACGGTTGACGGCGAAAGAATGTCATTCTCGGTGTGC<br>ACATACGTGCCGGCGACCATTTGTGATCAAATGACCGG<br>CATCCTTGCTACAGAAGTCACGCCGGAGGATGCACAGA<br>AGCTGTTGGTGGGGCTGAACCAGAGAATAGTGGTTAAC<br>GGCAGAACGCAACGGAATACGAACACCATGAAAAATTA |

TABLE 2-continued

List of polynucleotide sequences of the disclosure.

| Polynucleotide | Sequence |
| --- | --- |
| | TCTGCTTCCCGTGGTCGCCCAAGCCTTCAGTAAGTGGG |
| | CAAAGGAGTGCCGGAAAGACATGGAAGATGAAAAACTC |
| | CTGGGGGTCAGAGAAAGAACACTGACCTGCTGCTGTCT |
| | ATGGGCATTCAAGAAGCAGAAAACACACACGGTCTACA |
| | AGAGGCCTGATACCCAGTCAATTCAGAAGGTTCAGGCC |
| | GAGTTTGACAGCTTTGTGGTACCGAGTCTGTGGTCGTC |
| | CGGGTTGTCAATCCCTTTGAGGACTAGAATCAAATGGTT |
| | GTTAAGCAAGGTGCCAAAAACCGACCTGATCCCATACA |
| | GCGGAGACGCCCGAGAAGCCCGGGACGCAGAAAAAGA |
| | AGCAGAGGAAGAACGAGAAGCAGAACTGACTCGCGAA |
| | GCCCTACCACCTCTACAGGCAGCACAGGAAGATGTTCA |
| | GGTCGAAATCGACGTGGAACAGCTTGAGGACAGAGCG |
| | GGCGCAGGAATAATAGAGACTCCGAGAGGAGCTATCAA |
| | AGTTACTGCCCAACCAACAGACCACGTCGTGGGAGAGT |
| | ACCTGGTACTCTCCCCGCAGACCGTACTACGTAGCCAG |
| | AAGCTCAGTCTGATTCACGCTTTGGCGGAGCAAGTGAA |
| | GACGTGCACGCACAACGGACGAGCAGGGAGGTATGCG |
| | GTCGAAGCGTACGACGGCCGAGTCCTAGTGCCCTCAG |
| | GCTATGCAATCTCGCCTGAAGACTTCCAGAGTCTAAGC |
| | GAAAGCGCAACGATGGTGTATAACGAAAGAGAGTTCGT |
| | AAACAGAAAGCTACACCATATTGCGATGCACGGACCAG |
| | CCCTGAACACCGACGAAGAGTCGTATGAGCTGGTGAGG |
| | GCAGAGAGGACAGAACACGAGTACGTCTACGACGTGGA |
| | TCAGAGAAGATGCTGTAAGAAGGAAGAAGCCGCAGGAC |
| | TGGTACTGGTGGGCGACTTGACTAATCCGCCCTACCAC |
| | GAATTCGCATATGAAGGGCTAAAAATCCGCCCTGCCTG |
| | CCCATACAAAATTGCAGTCATAGGAGTCTTCGGAGTACC |
| | GGGATCTGGCAAGTCAGCTATTATCAAGAACCTAGTTAC |
| | CAGGCAGGACCTGGTGACTAGCGGAAAGAAAGAAAACT |
| | GCCAAGAAATCACCACCGACGTGATGAGACAGAGAGGT |
| | CTAGAGATATCTGCACGTACGGTTGACTCGCTGCTCTTG |
| | AATGGATGCAACAGACCAGTCGACGTGTTGTACGTAGA |
| | CGAGGCGTTTGCGTGCCACTCTGGAACGCTACTTGCTT |
| | TGATCGCCTTGGTGAGACCAAGGCAGAAGTTGTACTTT |
| | GTGGTGACCCGAAGCAGTGCGGCTTCTTCAATATGATG |
| | CAGATGAAAGTCAACTATAATCACAACATCTGCACCCAA |
| | GTGTACCACAAAAGTATCTCCAGGCGGTGTACACTGCC |
| | TGTGACCGCCATTGTGTCATCGTTGCATTACGAAGGCAA |
| | AATGCGCACTACGAATGAGTACAACAAGCCGATTGTAGT |
| | GGACACTACAGGCTCAACAAAACCTGACCCTGGAGACC |
| | TCGTGTTAACGTGCTTCAGAGGGTGGGTTAAACAACTG |
| | CAAATTGACTATCGTGGATACGAGGTCATGACAGCAGC |
| | CGCATCCCAAGGGTTAACCAGAAAAGGAGTTTACGCAG |
| | TTAGACAAAAAGTTAATGAAAACCCGCTCTATGCATCAA |
| | CGTCAGAGCACGTCAACGTACTCCTAACGCGTACGGAA |
| | GGTAAACTGGTATGGAAGACACTTTCCGGCGACCCGTG |
| | GATAAAGACGCTGCAGAACCCACCGAAAGGAAACTTCA |
| | AAGCAACTATTAAGGAGTGGGAGGTGGAGCATGCATCA |
| | ATAATGGCGGGCATCTGCAGTCACCAAATGACCTTCGA |
| | TACATTCCAAAATAAAGCCAACGTTTGTTGGGCTAAGAG |
| | CTTGGTCCCTATCCTCGAAACAGCGGGGATAAAACTAAA |
| | TGATAGGCAGTGGTCTCAGATAATTCAAGCCTTCAAGA |
| | AGACAAAGCATACTCACCTGTGGTAGCCCTGAATGAAAT |
| | ATGTACGCGCATGTATGGGGTGGATCTAGACAGCGGGC |
| | TATTTTCTAAACCGTTGGTGTCTGTGTATTACGCGGATA |
| | ACCACTGGGATAATAGGCCTGGAGGGAAAATGTTCGGA |
| | TTTAACCCCGAGGCAGCATCCATTCTAGAAAGAAAGTAT |
| | CCATTCACAAAAGGGAAGTGGAACATCAACAAGCAGAT |
| | CTGCGTGACTACCAGGAGGATAGAAGACTTTAACCCTA |
| | CCACCAACATCATACCGGCCAACAGGAGACTACCACAC |
| | TCATTAGTGGCCGAACACCGCCCAGTAAAGGGGAAAG |
| | AATGGAATGGCTGGTTAACAAGATAAACGGCCACCACG |
| | TGCTCCTGGTCAGTGCTATAACCTTGCACTGCCTACTA |
| | AGAGAGTCACTTGGGTAGCGCCGTTAGGTGTCCGCGGA |
| | GCGGACTACACATACAACCTAGAGTTGGGTCTGCCAGC |
| | AACGCTTGGTAGGTATGACCTAGTGGTCATAAACATCCA |
| | CACACCTTTTCGCATACACCATTACCAACAGTGCGTCGA |
| | CCACGCAATGAAACTGCAAATGCTCGGGGGTGACTCAT |
| | TGAGACTGCTCAAACCGGGCGGCTCTCTATTGATCAGA |
| | GCATATGGTTACGCAGATAGAACCAGTGAACGAGTCAT |
| | CTGCGTATTGGGACGCAAGTTTAGATCGTCTAGAGCGT |
| | TGAAACCACCATGTGTCACCAGCAACACTGAGATGTTTT |
| | TCCTATTCAGCAACTTTGACAATGGCAGAAGGAATTTCA |
| | CAACTCATGTCATGAACAATCAACTGAATGCAGCCTTCG |
| | TAGGACAGGTCACCCGAGCAGGATGTGCACCGTCGTAC |
| | CGGGTAAAACGCATGGACATCGCGAAGAACGATGAAGA |

TABLE 2-continued

List of polynucleotide sequences of the disclosure.

| Polynucleotide | Sequence |
|---|---|
| | GTGCGTAGTCAACGCCGCTAACCCTCGCGGGTTACCGG
GTGGCGGTGTTTGCAAGGCAGTATACAAAAAATGGCCG
GAGTCCTTTAAGAACAGTGCAACACCAGTGGGAACCGC
AAAAACAGTTATGTGCGGTACGTATCCAGTAATCCACGC
TGTTGGACCAAACTTCTCTAATTATTCGGAGTCTGAAGG
GGACCGGGAATTGGCAGCTGCCTATCGAGAAGTCGCAA
AGGAAGTAACTAGGCTGGGAGTAAATAGTGTAGCTATA
CCTCTCCTCTCCACAGGTGTATACTCAGGAGGGAAAGA
CAGGCTGACCCAGTCACTGAACCACCTCTTTACAGCCA
TGGACTCGACGGATGCAGACGTGGTCATCTACTGCCGC
GACAAAGAATGGGAGAAGAAAATATCTGAGGCCATACA
GATGCGGACCCAAGTAGAGCTGCTGGATGAGCACATCT
CCATAGACTGCGATATTGTTCGCGTGCACCCTGACAGC
AGCTTGGCAGGCAGAAAAGGATACAGCACCACGGAAG
GCGCACTGTACTCATATCTAGAAGGGACCCGTTTTCATC
AGACGGCTGTGGATATGGCGGAGATACATACTATGTGG
CCAAAGCAAACAGAGGCCAATGAGCAAGTCTGCCTATA
TGCCCTGGGGGAAAGTATTGAATCGATCAGGCAGAAAT
GCCCGGTGGATGATGCAGACGCATCATCTCCCCCCAAA
ACTGTCCCGTGCCTTTGCCGTTACGCTATGACTCCAGAA
CGCGTCACCCGGCTTCGCATGAACCACGTCACAAGCAT
AATTGTGTGTTCTTCGTTTCCCCTCCCAAAGTACAAAATA
GAAGGAGTGCAAAAAGTCAAATGCTCTAAGGTAATGCTA
TTTGACCACAACGTGCCATCGCGCGTAAGTCCAAGGGA
ATATAGATCTTCCCAGGAGTCTGCACAGGAGGCGAGTA
CAATCACGTCACTGACGCATAGTCAATTCGACCTAAGCG
TTGATGGCGAGATACTGCCCGTCCCGTCAGACCTGGAT
GCTGACGCCCCAGCCCTAGAACCAGCACTAGACGACG
GGGCGACACACACGCTGCCATCCACAACCGGAAACCTT
GCGGCCGTGTCTGATTGGGTAATGAGCACCGTACCTGT
CGCGCCGCCCAGAAGAAGGCGAGGGAGAAACCTGACT
GTGACATGTGACGAGAGAGAAGGGAATATAACACCCAT
GGCTAGCGTCCGATTCTTTAGGGCAGAGCTGTGTCCGG
TCGTACAAGAAACAGCGGAGACGCGTGACACAGCAATG
TCTCTTCAGGCACCACCGAGTACCGCCACGGAACCGAA
TCATCCGCCGATCTCCTTCGGAGCATCAAGCGAGACGT
TCCCCATTACATTTGGGGACTTCAACGAAGGAGAAATCG
AAAGCTTGTCTTCTGAGCTACTAACTTTCGGAGACTTCT
TACCAGGAGAAGTGGATGACTTGACAGACAGCGACTGG
TCCACGTGCTCAGACACGGACGACGAGTTAAGACTAGA
CAGGGCAGGTGGGTATATATTCTCGTCGGACACCGGTC
CAGGTCATTTACAACAGAAGTCAGTACGCCAGTCAGTG
CTGCCGGTGAACACCCTGGAGGAAGTCCACGAGGAGA
AGTGTTACCCACCTAAGCTGGATGAAGCAAAGGAGCAA
CTATTACTTAAGAAACTCCAGGAGAGTGCATCCATGGCC
AACAGAAGCAGGTATCAGTCGCGCAAAGTAGAAAACAT
GAAAGCAGCAATCATCCAGAGACTAAAGAGAGGCTGTA
GACTATACTTAATGTCAGAGACCCCAAAAGTCCCTACTT
ACCGGACTACATATCCGGCGCCTGTGTACTCGCCTCCG
ATCAACGTCCGATTGTCCAATCCCGAGTCCGCAGTGGC
AGCATGCAATGAGTTCTTAGCTAGAAACTATCCAACTGT
CTCATCATACCAAATTACCGACGAGTATGATGCATATCT
AGACATGGTGGACGGGTCGGAGAGTTGCCTGGACCGA
GCGACATTCAATCCGTCAAAACTCAGGAGCTACCCGAA
ACAGCACGCTTACCACGCGCCCTCCATCAGAAGCGCTG
TACCGTCCCCATTCCAGAACACACTACAGAATGTACTGG
CAGCAGCCACGAAAAGAAACTGCAACGTCACACAGATG
AGGGAATTACCCACTTTGGACTCAGCAGTATTCAACGTG
GAGTGTTTCAAAAAATTCGCATGCAACCAAGAATACTGG
GAAGAATTTGCTGCCAGCCCTATTAGGATAACAACTGAG
AATTTAGCAACCTATGTTACTAAACTAAAAGGGCAAAA
GCAGCAGCGCTATTCGCAAAAACCCATAATCTACTGCCA
CTACAGGAAGTACCAATGGATAGGTTCACAGTAGATATG
AAAAGGGACGTAAAGGTGACTCCTGGTACAAAGCATAC
AGAGGAAAGACCTAAGGTGCAGGTTATACAGGCGGCTG
AACCCTTGGCGACAGCATACCTATGTGGGATTCACAGA
GAGCTGGTTAGGAGGCTGAACGCCGTCCTCCTACCCAA
TGTACATACACTATTTGACATGTCTGCCGAGGATTTCGA
TGCCATCATAGCCGCACACTTTAAGCCAGGAGACACTG
TTTTGGAAACGGACATAGCCTCCTTTGATAAGAGCCAAG
ATGATTCACTTGCGCTTACTGCTTTGATGCTGTTAGAGG
ATTTAGGGGTGGATCACTCCCTGCTGGACTTGATAGAG
GCTGCTTTCGGAGAGATTTCCAGCTGTCACCTACCGAC
AGGTACGCGCTTCAAGTTCGGCGCCATGATGAAATCAG
GTATGTTCCTAACTCTGTTCGTCAACACATTGTTAAACAT
CACCCATCGCCAGCCGAGTGCTGGAAGATCGTCTGACAA |

TABLE 2-continued

List of polynucleotide sequences of the disclosure.

| Polynucleotide | Sequence |
|---|---|
| | AATCCGCGTGCGCGGCCTTCATCGGCGACGACAACATA |
| | ATACATGGAGTCGTCTCCGATGAATTGATGGCAGCCAG |
| | ATGTGCCACTTGGATGAACATGGAAGTGAAGATCATGA |
| | TGCAGTTGTATCCTTGAAAGCCCCTTACTTTTGTGGAGG |
| | GTTTATACTGCACGATACTGTGACAGGAACAGCTTGCAG |
| | AGTGGCAGACCCGCTAAAAAGGCTTTTTAAACTGGGCA |
| | AACCGCTAGCGGCAGGTGACGAACAAGATGAAGATAGA |
| | AGACGAGCGCTGGCTGACGAAGTGATCAGATGGCAAC |
| | GAACAGGGCTAATTGATGAGCTGGAGAAAGCGGTATAC |
| | TCTAGGTACGAAGTGCAGGGTATATCAGTTGTGGTAATG |
| | TCCATGGCCACCTTTGCAAGCTCCAGATCCAACTTCGA |
| | GAAGCTCAGAGGACCCGTCATAACTTTGTACGGCGGTC |
| | CTAAATAGGTACGCACTACAGCTACCTATTTTGCAGAAG |
| | CCGACAGCAAGTATCTAAACACTAATCAGCTACAATGGA |
| | GTTCATCCCAACCCAAACTTTTTACAATAGGAGGTACCA |
| | GCCTCGACCCTGGACTCCGCGCCCTACTATCCAAGTCA |
| | TCAGGCCCAGACCGCGCCCTCAGAGGCAAGCTGGGCA |
| | ACTTGCCCAGCTGATCTCAGCAGTTAATAAACTGACAAT |
| | GCGCGCGGTACCACAACAGAAGCCACGCAGGAATCGG |
| | AAGAATAAGAAGCAAAAGCAAAAACAACAGGCGCCACA |
| | AAACAACACAAATCAAAAGAAGCAGCCACCTAAAAAGAA |
| | ACCGGCTCAAAAGAAAAAGAAGCCGGGCCGCAGAGAG |
| | AGGATGTGCATGAAAATCGAAAATGATTGTATTTTCGAA |
| | GTCAAGCACGAAGGTAAGGTAACAGGTTACGCGTGCCT |
| | GGTGGGGGACAAAGTAATGAAACCAGCACACGTAAAGG |
| | GGACCATCGATAACGCGGACCTGGCCAAACTGGCCTTT |
| | AAGCGGTCATCTAAGTATGACCTTGAATGCGCGCAGAT |
| | ACCCGTGCACATGAAGTCCGACGCTTCGAAGTTCACCC |
| | ATGAGAAACCGGAGGGGTACTACAACTGGCACCACGGA |
| | GCAGTACAGTACTCAGGAGGCCGGTTCACCATCCCTAC |
| | AGGTGCTGGCAAACCAGGGGACAGCGGCAGACCGATC |
| | TTCGACAACAAGGGACGCGTGGTGGCCATAGTCTTAGG |
| | AGGAGCTAATGAAGGAGCCCGTACAGCCCTCTCGGTGG |
| | TGACCTGGAATAAAGACATTGTCACTAAAATCACCCCCG |
| | AGGGGGCCGAAGAGTGGAGTCTTGCCATCCCAGTTATG |
| | TGCCTGTTGGCAAACACCACGTTCCCCTGCTCCCAGCC |
| | CCCTTGCACGCCCTGCTGCTACGAAAAGGAACCGGAGG |
| | AAACCCTACGCATGCTTGAGGACAACGTCATGAGACCT |
| | GGGTACTATCAGCTGCTACAAGCATCCTTAACATGTTCT |
| | CCCCACCGCCAGCGACGCAGCACCAAGGACAACTTCAA |
| | TGTCTATAAAGCCACAAGACCATACTTAGCTCACTGTCC |
| | CGACTGTGGAGAAGGGCACTCGTGCCATAGTCCCGTAG |
| | CACTAGAACGCATCAGAAATGAAGCGACAGACGGGACG |
| | CTGAAAATCCAGGTCTCCTTGCAAATCGGAATAAAGACG |
| | GATGACAGCCACGATTGGACCAAGCTGCGTTATATGGA |
| | CAACCACATGCCAGCAGACGCAGAGAGGGCGGGGCTA |
| | TTTGTAAGAACATCAGCACCGTGTACGATTACTGGAACA |
| | ATGGGACACTTCATCCTGGCCCGATGTCCAAAAGGGGA |
| | AACTCTGACGGTGGGATTCACTGACAGTAGGAAGATTA |
| | GTCACTCATGTACGCACCCATTTCACCACGACCCTCCTG |
| | TGATAGGTCGGGAAAAATTCCATTCCCGACCGCAGCAC |
| | GGTAAAGAGCTACCTTGCAGCACGTACGTGCAGAGCAC |
| | CGCCGCAACTACCGAGGAGATAGAGGTACACATGCCCC |
| | CAGACACCCCTGATCGCACATTAATGTCACAACAGTCC |
| | GGCAACGTAAAGATCACAGTCAATGGCCAGACGGTGCG |
| | GTACAAGTGTAATTGCGGTGGCTCAAATGAAGGACTAA |
| | CAACTACAGACAAAGTGATTAATAACTGCAAGGTTGATC |
| | AATGTCATGCCGCGGTCACCAATCACAAAAAGTGGCAG |
| | TATAACTCCCCTCTGGTCCCGCGTAATGCTGAACTTGG |
| | GGACCGAAAAGGAAAAATTCACATCCCGTTTCCGCTGG |
| | CAAATGTAACATGCAGGGTGCCTAAAGCAAGGAACCCC |
| | ACCGTGACGTACGGGAAAAACCAAGTCATCATGCTACT |
| | GTATCCTGACCACCCAACACTCCTGTCCTACCGGAATAT |
| | GGGAGAAGAACCAAACTATCAAGAAGAGTGGGTGATGC |
| | ATAAGAAGGAAGTCGTGCTAACCGTGCCGACTGAAGGG |
| | CTCGAGGTCACGTGGGGCAACAACGAGCCGTATAAGTA |
| | TTGGCCGCAGTTATCTACAAACGGTACAGCCCATGGCC |
| | ACCCGCATGAGATAATTCTGTATTATTATGAGCTGTACC |
| | CCACTATGACTGTAGTAGTTGTGTCAGTGGCCACGTTCA |
| | TACTCCTGTCGATGGTGGGTATGGCAGCGGGGATGTGC |
| | ATGTGTGCACGACGCAGATGCATCACACCGTATGAACT |
| | GACACCAGGAGCTACCGTCCCTTTCCTGCTTAGCCTAAT |
| | ATGCTGCATCAGAACAGCTAAAGCGGCCACATACCAAG |
| | AGGCTGCGATATACCTGTGGAACGAGCAGCAACCTTTG |
| | TTTTGGCTACAAGCCCTTATTCCGCTGGCAGCCCTGATT |
| | GTTCTATGCAACTGTCTGAGACTCTTACCATGCTGCTGT |

TABLE 2-continued

List of polynucleotide sequences of the disclosure.

| Polynucleotide | Sequence |
|---|---|
| | AAAACGTTGGCTTTTTTAGCCGTAATGAGCGTCGGTGCC<br>CACACTGTGAGCGCGTACGAACACGTAACAGTGATCCC<br>GAACACGGTGGGAGTACCGTATAAGACTCTAGTCAATA<br>GACCTGGCTACAGCCCCATGGTATTGGAGATGGAACTA<br>CTGTCAGTCACTTTGGAGCCAACACTATCGCTTGATTAC<br>ATCACGTGCGAGTACAAAACCGTCATCCCGTCTCCGTA<br>CGTGAAGTGCTGCGGTACAGCAGAGTGCAAGGACAAAA<br>ACCTACCTGACTACAGCTGTAAGGTCTTCACCGGCGTC<br>TACCCATTTATGTGGGCGGCGCCTACTGCTTCTGCGA<br>CGCTGAAAACACGCAGTTGAGCGAAGCACACGTGGAGA<br>AGTCCGAATCATGCAAAACAGAATTTGCATCAGCATACA<br>GGGCTCATACCGCATCTGCATCAGCTAAGCTCCGCGTC<br>CTTTACCAAGGAAATAACATCACTGTAACTGCCTATGCA<br>AACGGCGACCATGCCGTCACAGTTAAGGACGCCAAATT<br>CATTGTGGGGCCAATGTCTTCAGCCTGGACACCTTTCG<br>ACAACAAAATTGTGGTGTACAAAGGTGACGTCTATAACA<br>TGGACTACCCGCCCTTTGGCGCAGGAAGACCAGGACAA<br>TTTGGCGATATCCAAAGTCGCACACCTGAGAGTAAAGA<br>CGTCTATGCTAATACACAACTGGTACTGCAGAGACCGG<br>CTGTGGGTACGGTACACGTGCCATACTCTCAGGCACCA<br>TCTGGCTTTAAGTATTGGCTAAAAGAACGCGGGGCGTC<br>GCTGCAGCACACAGCACCATTTGGCTGCCAAATAGCAA<br>CAAACCCGGTAAGAGCGGTGAACTGCGCCGTAGGGAA<br>CATGCCCATCTCCATCGACATACCGGAAGCGGCCTTCA<br>CTAGGGTCGTCGACGCGCCCTCTTTAACGGACATGTCG<br>TGCGAGGTACCAGCCTGCACCCATTCCTCAGACTTTGG<br>GGGCGTCGCCATTATTAAATATGCAGCCAGCAAGAAAG<br>GCAAGTGTGCGGTGCATTCGATGACTAACGCCGTCACT<br>ATTCGGGAAGCTGAGATAGAAGTTGAAGGGAATTCTCA<br>GCTGCAAATCTCTTTCTCGACGGCCTTAGCCAGCGCCG<br>AATTCCGCGTACAAGTCTGTTCTACACAAGTACACTGTG<br>CAGCCGAGTGCCACCCCCCGAAGGACCACATAGTCAAC<br>TACCCGGCGTCACATACCACCCTCGGGGTCCAGGACAT<br>CTCCGCTACGGCGATGTCATGGGTGCAGAAGATCACGG<br>GAGGTGTGGGACTGGTTGTTGCTGTTGCCGCACTGATT<br>CTAATCGTGGTGCTATGCGTGTCGTTCAGCAGGCACTA<br>ACTTGACAATTAAGTATGAAGGTATATGTGTCCCCTAAG<br>AGACACACTGTACATAGCAAATAATCTATAGATCAAAGG<br>GCTACGCAACCCCTGAATAGTAACAAAATACAAAATCAC<br>TAAAAATTATAAAAACAGAAAAATACATAAATAGGTATAC<br>GTGTCCCCTAAGAGACACATTGTATGTAGGTGATAAGTA<br>TAGATCAAAGGGCCGAATAACCCCTGAATAGTAACAAAA<br>TATGAAAATCAATAAAAATCATAAAATAGAAAAACCATAA<br>ACAGAAGTAGTTCAAAGGGCTATAAAACCCCTGAATAGT<br>AACAAAACATAAAATTAATAAAAATCAAATGAATACCATA<br>ATTGGCAAACGGAAGAGATGTAGGTACTTAAGCTTCCTA<br>AAAGCAGCCGAACTCACTTTGAGAAGTAGGCATAGCAT<br>ACCGAACTCTTCCACGATTCTCCGAACCCACAGGGACG<br>TAGGAGATGTTATTTTGTTTTTAATATTTCAAAAAAAAAA<br>AAAAAAAAAAAA |
| SEQ ID NO: 7<br>Polynucleotide sequence of CHIKV LR2006 OPY1 non-structural polyprotein with mutations at 532 and 1050 (CHIKV-R532H + E1050V). The amino acids at positions 532 and 1050 are mutated from R to H and E to V, respectively, via mutagenesis of nucleotide sequences from AGA to CAC (underlined and in bold) and GAA to GTG (underlined and in bold), respectively. | ATGGCTGCGTGAGACACACGTAGCCTACCAGTTTCTTA<br>CTGCTCTACTCTGCAAAGCAAGAGATTAATAACCCATCA<br>TGGATCCTGTGTACGTGACATAGACGCTGACAGCGCC<br>TTTTTGAAGGCCCTGCAACGTGCGTACCCCATGTTTGAG<br>GTGGAACCAAGGCAGGTCACACCGAATGACCATGCTAA<br>TGCTAGAGCGTTCTCGCATCTAGCTATAAAACTAATAGA<br>GCAGGAAATTGACCCCGACTCAACCATCCTGGATATCG<br>GCAGTGCGCCAGCAAGGAGGATGATGTCGGACAGGAA<br>GTACCACTGCGTCTGCCCGATGCGCAGTGCGGAAGATC<br>CCGAGAGACTCGCCAATTATGCGAGAAAGCTAGCATCT<br>GCCGCAGGAAAAGTCCTGGACAGAAACATCTCTGGAAA<br>GATCGGGGACTTACAAGCAGTAATGGCCGTGCCAGACA<br>CGGAGACGCCAACATTCTGCTTACACACAGACGTCTCA<br>TGTAGACAGAGAGCAGACGTCGCTATATACCAAGACGT<br>CTATGCTGTACACGCACCCACGTCGCTATACCACCAGG<br>CGATTAAAGGGTCCGAGTGGCGTACTGGGTTGGGTTC<br>GACACAACCCCGTTCATGTACAATGCCATGGCGGGTGC<br>CTACCCCTCATACTCGACAAACTGGGCAGATGAGCAGG<br>TACTGAAGGCTAAGAACATAGGATTATGTTCAACAGACC<br>TGACGGAAGGTAGACGAGGCAAGTTGTCTATTATGAGA<br>GGGAAAAAGCTAAAACCGTGCGACCGTGTGCTGTTCTC<br>AGTAGGGTCAACGCTCTACCCGGAAAGCCGCAAGCTAC<br>TTAAGAGCTGGCACCTGCCATCGGTGTTCCATTTAAAGG<br>GCAAACTCAGCTTCACATGCCGCTGTGATACAGTGGTTT<br>CGTGTGAGGGCTACGTCGTTAAGAGAATAACGATGAGC |

TABLE 2-continued

List of polynucleotide sequences of the disclosure.

| Polynucleotide | Sequence |
|---|---|
| | CCAGGCCTTTATGGAAAAACCACAGGGTATGCGGTAAC |
| | CCACCACGCAGACGGATTCCTGATGTGCAAGACTACCG |
| | ACACGGTTGACGGCGAAAGAATGTCATTCTCGGTGTGC |
| | ACATACGTGCCGGCGACCATTTGTGATCAAATGACCGG |
| | CATCCTTGCTACAGAAGTCACGCCGGAGGATGCACAGA |
| | AGCTGTTGGTGGGGCTGAACCAGAGAATAGTGGTTAAC |
| | GGCAGAACGCAACGGAATACGAACACCATGAAAAATTA |
| | TCTGCTTCCCGTGGTCGCCCAAGCCTTCAGTAAGTGGG |
| | CAAAGGAGTGCCGGAAAGACATGGAAGATGAAAAACTC |
| | CTGGGGGTCAGAGAAAGAACACTGACCTGCTGCTGTCT |
| | ATGGGCATTCAAGAAGCAGAAAACACACACGGTCTACA |
| | AGAGGCCTGATACCCAGTCAATTCAGAAGGTTCAGGCC |
| | GAGTTTGACAGCTTTGTGGTACCGAGTCTGTGGTCGTC |
| | CGGGTTGTCAATCCCTTTGAGGACTAGAATCAAATGGTT |
| | GTTAAGCAAGGTGCCAAAAACCGACCTGATCCCATACA |
| | GCGGAGACGCCCGAGAAGCCCGGGACGCAGAAAAAGA |
| | AGCAGAGGAAGAACGAGAAGCAGAACTGACTCGCGAA |
| | GCCCTACCACCTCTACAGGCAGCACAGGAAGATGTTCA |
| | GGTCGAAATCGACGTGGAACAGCTTGAGGACACGCG |
| | GGCGCAGGAATAATAGAGACTCCGAGAGGAGCTATCAA |
| | AGTTACTGCCCAACCAACAGACCACGTCGTGGGAGAGT |
| | ACCTGGTACTCTCCCCGCAGACCGTACTACGTAGCCAG |
| | AAGCTCAGTCTGATTCACGCTTTGGCGGAGCAAGTGAA |
| | GACGTGCACGCACAACGGACGAGCAGGGAGGTATGCG |
| | GTCGAAGCGTACGACGGCCGAGTCCTAGTGCCCTCAG |
| | GCTATGCAATCTCGCCTGAAGACTTCCAGAGTCTAAGC |
| | GAAAGCGCAACGATGGTGTATAACGAAAGAGAGTTCGT |
| | AAACAGAAAGCTACACCATATTGCGATGCACGGACCAG |
| | CCCTGAACACCGACGAAGAGTCGTATGAGCTGGTGAGG |
| | GCAGAGAGGACAGAACACGAGTACGTCTACGACGTGGA |
| | TCAGAGAAGATGCTGTAAGAAGGAAGAAGCCGCAGGAC |
| | TGGTACTGGTGGGCGACTTGACTAATCCGCCCTACCAC |
| | GAATTCGCATATGAAGGGCTAAAAATCCGCCCTGCCTG |
| | CCCATACAAAATTGCAGTCATAGGAGTCTTCGGAGTACC |
| | GGGATCTGGCAAGTCAGCTATTATCAAGAACCTAGTTAC |
| | CAGGCAGGACCTGGTGACTAGCGGAAAGAAAGAAAACT |
| | GCCAAGAAATCACCACCGACGTGATGAGACAGAGAGGT |
| | CTAGAGATATCTGCACGTACGGTTGACTCGCTGCTCTTG |
| | AATGGATGCAACAGACCAGTCGACGTGTTGTACGTAGA |
| | CGAGGCGTTTGCGTGCCACTCTGGAACGCTACTTGCTT |
| | TGATCGCCTTGGTGAGACCAAGGCAGAAAGTTGTACTTT |
| | GTGGTGACCCGAAGCAGTGCGGCTTCTTCAATATGATG |
| | CAGATGAAAGTCAACTATAATCACAACATCTGCACCCAA |
| | GTGTACCACAAAAGTATCTCCAGGCGGTGTACACTGCC |
| | TGTGACCGCCATTGTGTCATCGTTGCATTACGAAGGCAA |
| | AATGCGCACTACGAATGAGTACAACAAGCCGATTGTAGT |
| | GGACACTACAGGCTCAACAAAACCTGACCCTGGAGACC |
| | TCGTGTTAACGTGCTTCAGAGGGTGGGTTAAACAACTG |
| | CAAATTGACTATCGTGGATACGAGGTCATGACAGCAGC |
| | CGCATCCCAAGGGTTAACCAGAAAAGGAGTTTACGCAG |
| | TTAGACAAAAAGTTAATGAAAACCCGCTCTATGCATCAA |
| | CGTCAGAGCACGTCAACGTACTCCTAACGCGTACGGAA |
| | GGTAAACTGGTATGGAAGACACTTTCCGGCGACCCGTG |
| | GATAAAGACGCTGCAGAACCCACCGAAAGGAAACTTCA |
| | AAGCAACTATTAAGGAGTGGGAGGTGGAGCATGCATCA |
| | ATAATGGCGGGCATCTGCAGTCACCAAATGACCTTCGA |
| | TACATTCCAAAATAAAGCCAACGTTTGTTGGGCTAAGAG |
| | CTTGGTCCCTATCCTCGAAACAGCGGGGATAAAACTAAA |
| | TGATAGGCAGTGGTCTCAGATAATTCAAGCCTTCAAAGA |
| | AGACAAAGCATACTCACCTGTGGTAGCCCTGAATGAAAT |
| | ATGTACGCGCATGTATGGGGTGGATCTAGACAGCGGGC |
| | TATTTTCTAAACCGTTGGTGTCTGTGTATTACGCGGATA |
| | ACCACTGGGATAATAGGCCTGGAGGGAAAATGTTCGGA |
| | TTTAACCCCGAGGCAGCATCCATTCTAGAAAGAAAGTAT |
| | CCATTCACAAAAGGGAAGTGGAACATCAACAAGCAGAT |
| | CTGCGTGACTACCAGGAGGATAGAAGACTTTAACCCTA |
| | CCACCAACATCATACCGGCCAACAGGAGACTACCACAC |
| | TCATTAGTGGCCGAACACCGCCCAGTAAAAGGGGAAAG |
| | AATGGAATGGCTGGTTAACAAGATAAACGGCCACCACG |
| | TGCTCCTGGTCAGTGGCTATAACCTTGCACTGCCTACTA |
| | AGAGAGTCACTTGGGTAGCGCCGTTAGGTGTCCGCGGA |
| | GCGGACTACACATACAACCTAGAGTTGGGTCTGCCAGC |
| | AACGCTTGGTAGGTATGACCTAGTGGTCATAAACATCCA |
| | CACACCTTTTCGCATACACCATTACCAACAGTGCGTCGA |
| | CCACGCAATGAAACTGCAAATGCTCGGGGGTGACTCAT |
| | TGAGACTGCTCAAACCGGGCGGCTCTCTATTGATCAGA |

TABLE 2-continued

List of polynucleotide sequences of the disclosure.

| Polynucleotide | Sequence |
|---|---|
| | GCATATGGTTACGCAGATAGAACCAGTGAACGAGTCAT |
| | CTGCGTATTGGGACGCAAGTTTAGATCGTCTAGAGCGT |
| | TGAAACCACCATGTGTCACCAGCAACACTGAGATGTTTT |
| | TCCTATTCAGCAACTTTGACAATGGCAGAAGGAATTTCA |
| | CAACTCATGTCATGAACAATCAACTGAATGCAGCCTTCG |
| | TAGGACAGGTCACCCGAGCAGGATGTGCACCGTCGTAC |
| | CGGGTAAAACGCATGGACATCGCGAAGAACGATGAAGA |
| | GTGCGTAGTCAACGCCGCTAACCCTCGCGGGTTACCGG |
| | GTGGCGGTGTTTGCAAGGCAGTATACAAAAAATGGCCG |
| | GAGTCCTTTAAGAACAGTGCAACACCAGTGGGAACCGC |
| | AAAAACAGTTATGTGCGGTACGTATCCAGTAATCCACGC |
| | TGTTGGACCAAACTTCTCTAATTATTCGGAGTCTGAAGG |
| | GGACCGGGAATTGGCAGCTGCCTATCGAGAAGTCGCAA |
| | AGGAAGTAACTAGGCTGGGAGTAAATAGTGTAGCTATA |
| | CCTCTCCTCTCCACAGGTGTATACTCAGGAGGGAAAGA |
| | CAGGCTGACCCAGTCACTGAACCACCTCTTTACAGCCA |
| | TGGACTCGACGGATGCAGACGTGGTCATCTACTGCCGC |
| | GACAAAGAATGGGAGAAGAAAATATCTGAGGCCATACA |
| | GATGCGGACCCAAGTAGAGCTGCTGGATGAGCACATCT |
| | CCATAGACTGCGATATTGTTCGCGTGCACCCTGACAGC |
| | AGCTTGGCAGGCAGAAAAGGATACAGCACCACGGAAG |
| | GCGCACTGTACTCATATCTAGAAGGGACCCGTTTTCATC |
| | AGACGGCTGTGGATATGGCGGAGATACATACTATGTGG |
| | CCAAAGCAAACAGAGGCCAATGAGCAAGTCTGCCTATA |
| | TGCCCTGGGGGAAAGTATTGAATCGATCAGGCAGAAAT |
| | GCCCGGTGGATGATGCAGACGCATCATCTCCCCCCAAA |
| | ACTGTCCCGTGCCTTTGCCGTTACGCTATGACTCCAGAA |
| | CGCGTCACCCGGCTTCGCATGAACCACGTCACAAGCAT |
| | AATTGTGTGTTCTTCGTTTCCCCTCCCAAAGTACAAAATA |
| | GAAGGAGTGCAAAAAGTCAAATGCTCTAAGGTAATGCTA |
| | TTTGACCACAACGTGCCATCGCGCGTAAGTCCAAGGGA |
| | ATATAGATCTTCCCAGGAGTCTGCACAGGAGGCGAGTA |
| | CAATCACGTCACTGACGCATAGTCAATTCGACCTAAGCG |
| | TTGATGGCGAGATACTGCCCGTCCCGTCAGACCTGGAT |
| | GCTGACGCCCCAGCCCTAGAACCAGCACTAGACGACG |
| | GGGCGACACACACGCTGCCATCCACAACCGGAAACCTT |
| | GCGGCCGTGTCTGATTGGGTAATGAGCACCGTACCTGT |
| | CGCGCCGCCCAGAAGAAGGCGAGGGAGAAACCTGACT |
| | GTGACATGTGACGAGAGAGAAGGGAATATAACACCCAT |
| | GGCTAGCGTCCGATTCTTTAGGGCAGAGCTGTGTCCGG |
| | TCGTACAAGAAACAGCGGAGACGCGTGACACAGCAATG |
| | TCTCTTCAGGCACCACCGAGTACCGCCACGGAACCGAA |
| | TCATCCGCCGATCTCCTTCGGAGCATCAAGCGAGACGT |
| | TCCCCATTACATTTGGGGACTTCAACGAAGGAGAAATCG |
| | AAAGCTTGTCTTCTGAGCTACTAACTTTCGGAGACTTCT |
| | TACCAGGAGAAGTGGATGACTTGACAGACAGCGACTGG |
| | TCCACGTGCTCAGACACGGACGACGAGTTAAGACTAGA |
| | CAGGGCAGGTGGGTATATATTCTCGTCGGACACCGGTC |
| | CAGGTCATTTACAACAGAAGTCAGTACGCCAGTCAGTG |
| | CTGCCGGTGAACACCCTGGAGGAAGTCCACGAGGAGA |
| | AGTGTTACCCACCTAAGCTGGATGAAGCAAAGGAGCAA |
| | CTATTACTTAAGAAACTCCAGGAGAGTGCATCCATGGCC |
| | AACAGAAGCAGGTATCAGTCGCGCAAAGTAGAAAACAT |
| | GAAAGCAGCAATCATCCAGAGACTAAAGAGAGGCTGTA |
| | GACTATACTTAATGTCAGAGACCCCAAAAGTCCCTACTT |
| | ACCGGACTACATATCCGGCGCCTGTGTACTCGCCTCCG |
| | ATCAACGTCCGATTGTCCAATCCCGAGTCCGCAGTGGC |
| | AGCATGCAATGAGTTCTTAGCTAGAAACTATCCAACTGT |
| | CTCATCATACCAAATTACCGACGAGTATGATGCATATCT |
| | AGACATGGTGGACGGGTCGGAGAGTTGCCTGGACCGA |
| | GCGACATTCAATCCGTCAAAACTCAGGAGCTACCCGAA |
| | ACAGCACGCTTACCACGCGCCCTCCATCAGAAGCGCTG |
| | TACCGTCCCCATTCCAGAACACACTACAGAATGTACTGG |
| | CAGCAGCCACGAAAAGAAACTGCAACGTCACACAGATG |
| | AGGGAATTACCCACTTTGGACTCAGCAGTATTCAACGTG |
| | GAGTGTTTCAAAAAATTCGCATGCAACCAAGAATACTGG |
| | GAAGAATTTGCTGCCAGCCCTATTAGGATAACAACTGAG |
| | AATTTAGCAACCTATGTTACTAAACTAAAAGGGCCAAAA |
| | GCAGCAGCGCTATTCGCAAAAACCCATAATCTACTGCCA |
| | CTACAGGAAGTACCAATGGATAGGTTCACAGTAGATATG |
| | AAAAGGGACGTAAAGGTGACTCCTGGTACAAAGCATAC |
| | AGAGGAAAGACCTAAGGTGCAGGTTATACAGGCGGCTG |
| | AACCCTTGGCGACAGCATACCTATGTGGGATTCACAGA |
| | GAGCTGGTTAGGAGGCTGAACGCCGTCCTCCTACCCAA |
| | TGTACATACACTATTTGACATGTCTGCCGAGGATTTCGA |
| | TGCCATCATAGCCGCACACTTTAAGCCAGGAGACACTG |

TABLE 2-continued

List of polynucleotide sequences of the disclosure.

| Polynucleotide | Sequence |
|---|---|
| | TTTTGGAAACGGACATAGCCTCCTTTGATAAGAGCCAAG |
| | ATGATTCACTTGCGCTTACTGCTTTGATGCTGTTAGAGG |
| | ATTTAGGGGTGGATCACTCCCTGCTGGACTTGATAGAG |
| | GCTGCTTTCGGAGAGATTTCCAGCTGTCACCTACCGAC |
| | AGGTACGCGCTTCAAGTTCGGCGCCATGATGAAATCAG |
| | GTATGTTCCTAACTCTGTTCGTCAACACATTGTTAAACAT |
| | CACCATCGCCAGCCGAGTGCTGGAAGATCGTCTGACAA |
| | AATCCGCGTGCGCGGCCTTCATCGGCGACGACAACATA |
| | ATACATGGAGTCGTCTCCGATGAATTGATGGCAGCCAG |
| | ATGTGCCACTTGGATGAACATGGAAGTGAAGATCATAGA |
| | TGCAGTTGTATCCTTGAAAGCCCCTTACTTTTGTGGAGG |
| | GTTTATACTGCACGATACTGTGACAGGAACAGCTTGCAG |
| | AGTGGCAGACCCGCTAAAAAGGCTTTTTAAACTGGGCA |
| | AACCGCTAGCGGCAGGTGACGAACAAGATGAAGATAGA |
| | AGACGAGCGCTGGCTGACGAAGTGATCAGATGGCAAC |
| | GAACAGGGCTAATTGATGAGCTGGAGAAAGCGGTATAC |
| | TCTAGGTACGAAGTGCAGGGTATATCAGTTGTGGTAATG |
| | TCCATGGCCACCTTTGCAAGCTCCAGATCCAACTTCGA |
| | GAAGCTCAGAGGACCCGTCATAACTTTGTACGGCGGTC |
| | CTAAATAGGTACGCACTACAGCTACCTATTTTGCAGAAG |
| | CCGACAGCAAGTATCTAAACACTAATCAGCTACAATGGA |
| | GTTCATCCCAACCCAAACTTTTTACAATAGGAGGTACCA |
| | GCCTCGACCCTGGACTCCGCGCCCTACTATCCAAGTCA |
| | TCAGGCCCAGACCGCGCCCTCAGAGGCAAGCTGGGCA |
| | ACTTGCCCAGCTGATCTCAGCAGTTAATAAACTGACAAT |
| | GCGCGCGGTACCACAACAGAAGCCACGCAGGAATCGG |
| | AAGAATAAGAAGCAAAAGCAAAAACAACAGGCGCCACA |
| | AAACAACACAAATCAAAAGAAGCAGCCACCTAAAAAGAA |
| | ACCGGCTCAAAAGAAAAAGAAGCCGGGCCGCAGAGAG |
| | AGGATGTGCATGAAAATCGAAATGATTGTATTTTCGAA |
| | GTCAAGCACGAAGGTAAGGTAACAGGTTACGCGTGCCT |
| | GGTGGGGGACAAAGTAATGAAACCAGCACACGTAAAGG |
| | GGACCATCGATAACGCGGACCTGGCCAAACTGGCCTTT |
| | AAGCGGTCATCTAAGTATGACCTTGAATGCGCGCAGAT |
| | ACCCGTGCACATGAAGTCCGACGCTTCGAAGTTCACCC |
| | ATGAGAAACCGGAGGGGTACTACAACTGGCACCACGGA |
| | GCAGTACAGTACTCAGGAGGCCGGTTCACCATCCCTAC |
| | AGGTGCTGGCAAACCAGGGGACAGCGGCAGACCGATC |
| | TTCGACAACAAGGGACGCGTGGTGGCCATAGTCTTAGG |
| | AGGAGCTAATGAAGGAGCCCGTACAGCCCTCTCGGTGG |
| | TGACCTGGAATAAAGACATTGTCACTAAAATCACCCCCG |
| | AGGGGGCCGAAGAGTGGAGTCTTGCCATCCCAGTTATG |
| | TGCCTGTTGGCAAACACCACGTTCCCCTGCTCCCAGCC |
| | CCCTTGCACGCCCTGCTGCTACGAAAAGGAACCGGAGG |
| | AAACCCTACGCATGCTTGAGGACAACGTCATGAGACCT |
| | GGGTACTATCAGCTGCTACAAGCATCCTTAACATGTTCT |
| | CCCCACCGCCAGCGACGCAGCACCAAGGACAACTTCAA |
| | TGTCTATAAAGCCACAAGACCATACTTAGCTCACTGTCC |
| | CGACTGTGGAGAAGGGCACTCGTGCCATAGTCCCGTAG |
| | CACTAGAACGCATCAGAAATGAAGCGACAGACGGGACG |
| | CTGAAAATCCAGGTCTCCTTGCAAATCGGAATAAAGACG |
| | GATGACAGCCACGATTGGACCAAGCTGCGTTATATGGA |
| | CAACCACATGCCAGCAGACGCAGAGAGGGCGGGGCTA |
| | TTTGTAAGAACATCAGCACCGTGTACGATTACTGGAACA |
| | ATGGGACACTTCATCCTGGCCCGATGTCCAAAAGGGGA |
| | AACTCTGACGGTGGGATTCACTGACAGTAGGAAGATTA |
| | GTCACTCATGTACGCACCCATTTCACCACGACCCTCCTG |
| | TGATAGGTCGGGAAAAATTCCATTCCCGACCGCAGCAC |
| | GGTAAAGAGCTACCTTGCAGCACGTACGTGCAGAGCAC |
| | CGCCGCAACTACCGAGGAGATAGAGGTACACATGCCCC |
| | CAGACACCCCTGATCGCACATTAATGTCACAACAGTCC |
| | GGCAACGTAAAGATCACAGTCAATGGCCAGACGGTGCG |
| | GTACAAGTGTAATTGCGGTGGCTCAAATGAAGGACTAA |
| | CAACTACAGACAAAGTGATTAATAACTGCAAGGTTGATC |
| | AATGTCATGCCGCGGTCACCAATCACAAAAAGTGGCAG |
| | TATAACTCCCCTCTGGTCCCGCGTAATGCTGAACTTGG |
| | GGACCGAAAAGGAAAAATTCACATCCCGTTTCCGCTGG |
| | CAAATGTAACATGCAGGGTGCCTAAAGCAAGGAACCCC |
| | ACCGTGACGTACGGGAAAAACCAAGTCATCATGCTACT |
| | GTATCCTGACCACCCAACACTCCTGTCCTACCGGAATAT |
| | GGGAGAAGAACCAAACTATCAAGAAGAGTGGGTGATGC |
| | ATAAGAAGGAAGTCGTGCTAACCGTGCCGACTGAAGGG |
| | CTCGAGGTCACGTGGGCAACAACGAGCCGTATAAGTA |
| | TTGGCCGCAGTTATCTACAAACGGTACAGCCCATGGCC |
| | ACCCGCATGAGATAATTCTGTATTATTATGAGCTGTACC |
| | CCACTATGACTGTAGTAGTTGTGTCAGTGGCCACGTTCA |

TABLE 2-continued

List of polynucleotide sequences of the disclosure.

| Polynucleotide | Sequence |
|---|---|
| | TACTCCTGTCGATGGTGGGTATGGCAGCGGGGATGTGC |
| | ATGTGTGCACGACGCAGATGCATCACACCGTATGAACT |
| | GACACCAGGAGCTACCGTCCCTTTCCTGCTTAGCCTAAT |
| | ATGCTGCATCAGAACAGCTAAAGCGGCCACATACCAAG |
| | AGGCTGCGATATACCTGTGGAACGAGCAGCAACCTTTG |
| | TTTTGGCTACAAGCCCTTATTCCGCTGGCAGCCCTGATT |
| | GTTCTATGCAACTGTCTGAGACTCTTACCATGCTGCTGT |
| | AAAACGTTGGCTTTTTTAGCCGTAATGAGCGTCGGTGCC |
| | CACACTGTGAGCGCGTACGAACACGTAACAGTGATCCC |
| | GAACACGGTGGGAGTACCGTATAAGACTCTAGTCAATA |
| | GACCTGGCTACAGCCCCATGGTATTGGAGATGGAACTA |
| | CTGTCAGTCACTTTGGAGCCAACACTATCGCTTGATTAC |
| | ATCACGTGCGAGTACAAAACCGTCATCCCGTCTCCGTA |
| | CGTGAAGTGCTGCGGTACAGCAGAGTGCAAGGACAAAA |
| | ACCTACCTGACTACAGCTGTAAGGTCTTCACCGGCGTC |
| | TACCCATTTATGTGGGCGGCGCCTACTGCTTCTGCGA |
| | CGCTGAAAACACGCAGTTGAGCGAAGCACACGTGGAGA |
| | AGTCCGAATCATGCAAAACAGAATTTGCATCAGCATACA |
| | GGGCTCATACCGCATCTGCATCAGCTAAGCTCCGCGTC |
| | CTTTACCAAGGAAATAACATCACTGTAACTGCCTATGCA |
| | AACGGCGACCATGCCGTCACAGTTAAGGACGCCAAATT |
| | CATTGTGGGGCCAATGTCTTCAGCCTGGACACCTTTCG |
| | ACAACAAAATTGTGGTGTACAAAGGTGACGTCTATAACA |
| | TGGACTACCCGCCCTTTGGCGCAGGAAGACCAGGACAA |
| | TTTGGCGATATCCAAAGTCGCACACCTGAGAGTAAAGA |
| | CGTCTATGCTAATACACAACTGGTACTGCAGAGACCGG |
| | CTGTGGGTACGGTACACGTGCCATACTCTCAGGCACCA |
| | TCTGGCTTTAAGTATTGGCTAAAAGAACGCGGGGCGTC |
| | GCTGCAGCACACAGCACCATTTGGCTGCCAAATAGCAA |
| | CAAACCCGGTAAGAGCGGTGAACTGCGCCGTAGGGAA |
| | CATGCCCATCTCCATCGACATACCGGAAGCGGCCTTCA |
| | CTAGGGTCGTCGACGCGCCCTCTTTAACGGACATGTCG |
| | TGCGAGGTACCAGCCTGCACCCATTCCTCAGACTTTGG |
| | GGGCGTCGCCATTATTAAATATGCAGCCAGCAAGAAAG |
| | GCAAGTGTGCGGTGCATTCGATGACTAACGCCGTCACT |
| | ATTCGGGAAGCTGAGATAGAAGTTGAAGGGAATTCTCA |
| | GCTGCAAATCTCTTTCTCGACGGCCTTAGCCAGCGCCG |
| | AATTCCGCGTACAAGTCTGTTCTACACAAGTACACTGTG |
| | CAGCCGAGTGCCACCCCCCGAAGGACCACATAGTCAAC |
| | TACCCGGCGTCACATACCACCCTCGGGGTCCAGGACAT |
| | CTCCGCTACGGCGATGTCATGGGTGCAGAAGATCACGG |
| | GAGGTGTGGGACTGGTTGTTGCTGTTGCCGCACTGATT |
| | CTAATCGTGGTGCTATGCGTGTCGTTCAGCAGGCACTA |
| | ACTTGACAATTAAGTATGAAGGTATATGTGTCCCCTAAG |
| | AGACACACTGTACATAGCAAATAATCTATAGATCAAAGG |
| | GCTACGCAACCCCTGAATAGTAACAAAATACAAAATCAC |
| | TAAAAATTATAAAAACAGAAAAATACATAAATAGGTATAC |
| | GTGTCCCCTAAGAGACACATTGTATGTAGGTGATAAGTA |
| | TAGATCAAAGGGCCGAATAACCCCTGAATAGTAACAAAA |
| | TATGAAAATCAATAAAAATCATAAAATAGAAAAACCATAA |
| | ACAGAAGTAGTTCAAAGGGCTATAAAACCCCTGAATAGT |
| | AACAAAACATAAAATTAATAAAAATCAAATGAATACCATA |
| | ATTGGCAAACGGAAGAGATGTAGGTACTTAAGCTTCCTA |
| | AAAGCAGCCGAACTCACTTTGAGAAGTAGGCATAGCAT |
| | ACCGAACTCTTCCACGATTCTCCGAACCCACAGGGACG |
| | TAGGAGATGTTATTTTGTTTTAATATTTCAAAAAAAAAAA |
| | AAAAAAAAAAAA |

EXAMPLES

Example 1: Materials and Methods

Cell Lines and Cell Culture Method

The cell lines used are African green monkey kidney epithelial cells (Vero-E6) and mouse tail fibroblasts (MTFs) were maintained in Dulbecco's Modified Eagle Medium (DMEM) (Gibco) supplemented with 10% Fetal Bovine Serum (FBS) (Gibco). *Aedes albopictus* monolayer (C6/36) cells were cultured in Leibovitz's medium (L-15) (Gibco) supplemented with 10% FBS. All cultures were incubated at 37° C. with 5% $CO_2$ supplied with the exception of C6/36 which was incubated at 28° C. with no $CO_2$ supplied. All media and reagents were tested negative for endotoxins.

Virus Strains

The virus strain used is the LR2006 OPY1 strain.

Method for Generating Mutations in CHIKV

PCR-based site directed mutagenesis and subcloning were performed using the Polymerase Incomplete Primer Extension (PIPE) cloning method to generate the mutations at amino acid positions 532 and 1050 in CHIKV. The method is adapted from Saul, et al. (2015).

Method for Determining Viral Infectivity and Replicative Potential in MTFs

Primary MTFs were first isolated from C57BL/6 mice. The isolated MTFs were then infected with ZsGreen (ZsG)- tagged WT CHIKV, CHIKV with R to H amino acid substitution (RH) and CHIKV with both R to H and E to V amino acid mutations (RHEV). Flow cytometry was used for subsequent analysis of infected MTF populations.

Respective Zs-Green tagged CHIKV mutants were used to infect mouse tail fibroblasts ($2\times10^6$ cells per infection) for 1.5 h in a 37° C. incubator, with atmosphere of 5% (v/v) C02. Virus overlay was removed and cells were washed once with appropriate serum-free medium before they were re-suspended in appropriate complete medium. Cells were further incubated at 37° C., with atmosphere of 5% (v/v) $CO_2$, before being harvested at indicated time points. During harvesting, 140 µl of infected cell suspension was aliquoted for viral RNA extraction. Cells were acquired using either BD FACS Calibur or BD FACS Canto II (BD Biosciences) to detect for ZsGreen signal in the FITC channel, to measure infectivity. Software used include BD FACSDiva software (for FACSCanto II) (BD Biosciences). A total of 30,000-50,000 cells were acquired and results were analyzed with FlowJo (version 10) (Tree Star).

Method for Determining Concentration of Type 1 IFN in MTFs

CHIKV-infected MTFs were harvested at 12 hours post infection (hpi), and the concentration of Type 1 IFN were measured using the Luminex® screening assay kit according to the manufacturer's protocol which may be found on https-colon-slash-slash-www.thermofisher.com/order/catalog/product/EPX020-22187-901. Three independent experiments were performed and the data were presented as mean±SD.

Method for Determining Viremia

Ten microliters of blood was obtained from the tail vein and re-suspended in 120 µl of DPBS and 10 µl of citrate-phosphate-dextrose solution (Sigma-Aldrich). Purification of viral RNA from the blood samples was performed with QIAamp Viral RNA Kit (QIAGEN) following the manufacturer's instructions. Viral copies were quantified by quantitative Real-time polymerase chain reaction (qRT-PCR) using a QuantiTect Probe RT-PCR Kit (QIAGEN), with primers and probe specific for CHIKV nsP 1, and extrapolated from a standard curve generated using serial dilutions of CHIKV negative-sense nsP 1 RNA transcripts Method for Infecting Mouse to Induce Joint Inflammation Mice were inoculated subcutaneously in the ventral side of the right hind footpad with $1\times10^6$ plaque forming units (PFU) of the respective virus in 30 µl of Dulbecco's Phosphate-Buffered Saline (DPBS). Level of viremia was monitored daily from 1 day post-infection (dpi) until 8 dpi, and subsequently every alternate day until 14 dpi. Joint swelling of the virus-inoculated foot was measured daily from 0 dpi to 14 dpi. Height (thickness) and breadth measurements were done for the metatarsal region of the foot, and quantified as (height×breadth). The disease score was expressed as the relative fold change in foot size compared with pre-infected foot (0 dpi), using the following formula: [(x–day 0)/day 0×100], where x is the quantified joint inflammation for each respective day.

Method for Isolation of Leukocyte and Measurement of the Levels of Subsets of Leukocytes For the hind feet joint cell analysis, mice were sacrificed, and footpads and ankles were removed at 6 dpi, deskinned, and placed immediately in 4 ml digestion medium containing dispase (2 U/ml; Invitrogen), Collagenase IV (20 µg/ml; Sigma-Aldrich), and DNase I mix (50 µg/ml; Roche Applied Science) in complete RPMI medium. Tissues were incubated in digestion medium for 4 h at 37° C., 5% $CO_2$ on a shaker. Digested tissues and digestion medium were deposited onto a 40-µm cell strainer, and 3 ml fresh complete RPMI medium was added. Digested tissues were ground against the cell strainer with a 1-ml syringe plunger, using a circular motion to release a maximum number of cells into the medium. Cells were centrifuged at 500×g, and RBCs were lysed in buffered ammonium chloride solution. Cells were washed once in complete RPMI medium, resuspended in 10 ml complete RPMI medium, and overlaid onto 10 ml 35% v/v Percoll/RPMI 1640 medium (Sigma-Aldrich). Cells were centrifuged at 2400 rpm for 20 min, resuspended, and washed once more with complete medium before being counted.

Appropriate number of cells was transferred into 96-well v-bottom plates (Greiner Bio-one, Germany) staining in preparation for flow cytometry acquisition. Cells were first incubated with 50 µl of LIVE/DEAD Fixable Aqua Dead Cell Stain Kit (Life Technologies, USA) at room temperature for 30 minutes, followed by washing with 100 µl of DPBS. Cells were then incubated with 1% rat and mouse serum blocking buffer (Sigma Aldrich, St. Louis, Mo., USA) to prevent non-specific binding for 20 minutes. Antibodies were used at 1:200 dilutions for each sample. The cells were then incubated with the respective antibody master mix for 20 minutes, before washing with DPBS. The cells were then fixed with 150 µl of IC Fixation Buffer (eBioscience, USA) for 5 minutes. The cells were washed with DPBS, and subsequently re-suspended in 150 µl of DPBS. Samples were then acquired with BD LSRII™ 5 lasers flow cytometer using the FACSDiva™ software, and analyzed with FlowJo version 10.0.7.

Method for Detecting CHIKV Antibody and Antibody Neutralization Assay

ELISA

Antibody (Ab) titers were assessed by a virion-based ELISA. CHIKV-coated ($10^6$ virions/well in 50 µl dPBS) polystyrene 96-well MaxiSorp plates (Nunc) were blocked with PBS containing 0.05% Tween 20 (PBST) and 5% w/v nonfat milk for 1.5 hours at 37° C. Sera from normal and infected groups of animals were heat inactivated and serially diluted in Ab diluent (0.05% PBST+2.5% w/v nonfat milk). One hundred microliters of diluted sera was added into each well and incubated for 1 hour at 37° C. HRP-conjugated goat anti-mouse IgG, IgG1, IgG2b, IgG2c, IgG3, and IgM Abs were used. Total IgG and IgM quantification assays were performed using sera from individual animals diluted at 1:2000 and 1:100, respectively. Pooled sera were used for antibody isotyping. All HRP-conjugated Abs were from Santa Cruz, except for IgG3 (Southern Biotech). ELISA assays were developed using TMB substrate (Sigma-Aldrich), and terminated by Stop reagent (Sigma-Aldrich). Absorbance was measured at 450 nm. CHIKV-specific Ab isotype Ab titers are defined as the lowest dilution required for a detectable signal above control naïve pooled sera.

Neutralization Assay

Neutralizing activity of antibodies was tested using an immunofluorescence-based cell infection assay in HEK293T cells. WT CHIKV LR2006 OPY1 infectious clone expressing sub-genomic ZsGreen protein was incubated with heat-inactivated mouse sera, diluted with complete media, for 1 hour at 37° C. with gentle rocking (160 rpm). Virus-Ab mixtures were added at multiplicity of infection (MOI) 5 to HEK293T cells seeded in a 96-well plate ($3\times10^4$ cells/well) and incubated for 18 hrs. Subsequently, cells were harvested and fixed with 4% paraformaldehyde, followed by acquisition using the MACSQuant Analyzer (Miltenyi Biotec). Infected cells expressing ZsGreen were quantified with FlowJo v10.0.7 software (FlowJo, LLC). Percentage of infectivity was calculated according to this equation: % Infectivity=100×(% infection from neutralization group/% infection from virus infection group).

Histological Analysis

Mice were euthanized on 6 dpi, and perfused with 10% neutral buffered formalin (NBF). The virus-inoculated joints were harvested from the respective mice, and fixed in 10% NBF for 24 hours at room temperature. The joints then underwent decalcification in 5% formic acid, and sectioned to three parts at 5 mm interval. Sectioned tissues were routinely processed, stained with hematoxylin and eosin (H&E), and embedded in paraffin wax, before being sliced into 5-km films. Tissues were viewed under the Olympus BX53 upright microscope (Olympus Life Science) and images were taken with Olympus DP71 digital color camera using Olympus DP controller and DP manager software.

Histological assessments were performed by histo-pathologists in a blinded fashion, with pathological changes evaluated using a scoring method in each individual animal, based on the presence of edema, inflammation, muscle necrosis, tendonitis, and synovitis. Severity grades were assigned to the following scale: 0—no finding; 1—minimal; 2—mild; 3—moderate; 4—marked; 5—severe.

Example 2: Mutations in the CHIKV nsPs Reduce Viral Infectivity and Replicative Potential in Mouse Tail Fibroblasts To investigate if mutation in the CHIKV nsPs reduces the infectivity and replicative potential of CHIKV, primary MTFs were first isolated from C57BL/6 mice. The MTFs were then infected with ZsGreen (ZsG)-tagged WT CHIKV, CHIKV with R to H amino acid substitution (RH CHIKV), CHIKV with E to V amino acid substitution (EV CHIKV) and CHIKV with both R to H and E to V amino acid mutations (RHEV CHIKV) as described above. Flow cytometry was then used for subsequent analysis of infected MTF populations.

Figure 1:
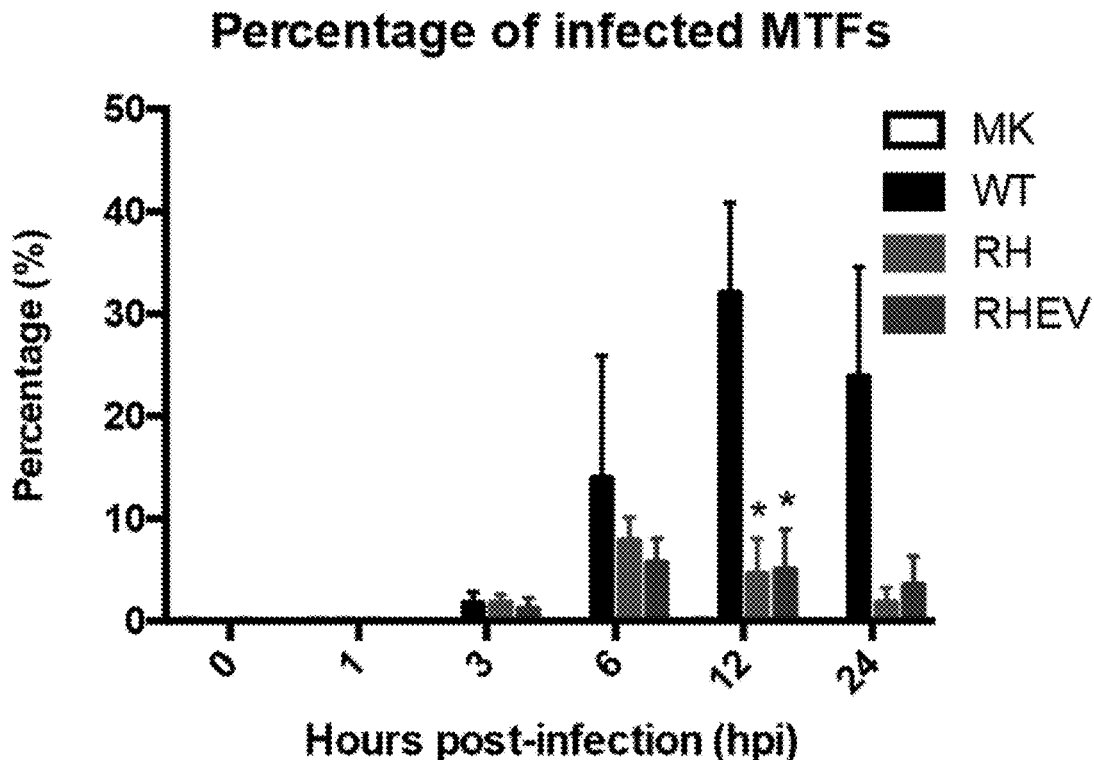
FIG. 1 shows that mutations in the CHIKV nsPs reduce viral infectivity and replicative potential in mouse tail fibroblasts (MTFs). Primary MTFs were isolated from C57BL/6 mice. MTFs were infected with ZsGreen (ZsG)-tagged wild-type (WT) CHIKV, CHIKV with R to H amino acid substitution (RH) at position 532, CHIKV with E to V amino acid substitution (EV) at position 1050 and CHIKV with both R to H and E to V amino acid mutations (RHEV) at both positions 532 and 1050, respectively. Subsequent analysis of infected MTF population was done by flow cytometry.
Figure 1:
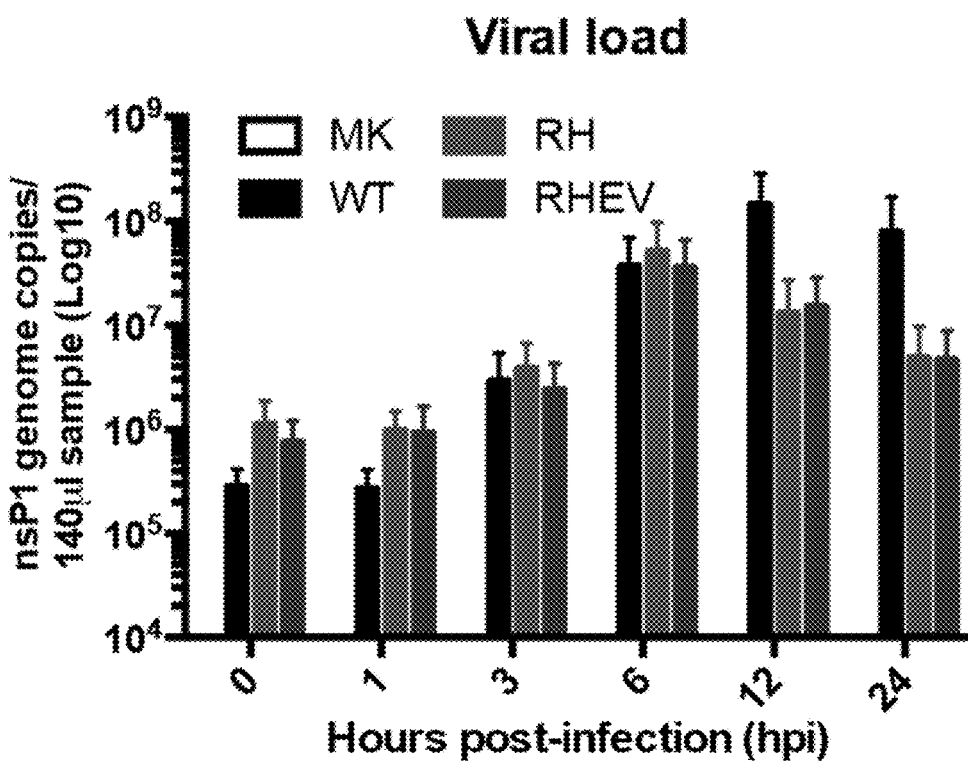
Figure 1:
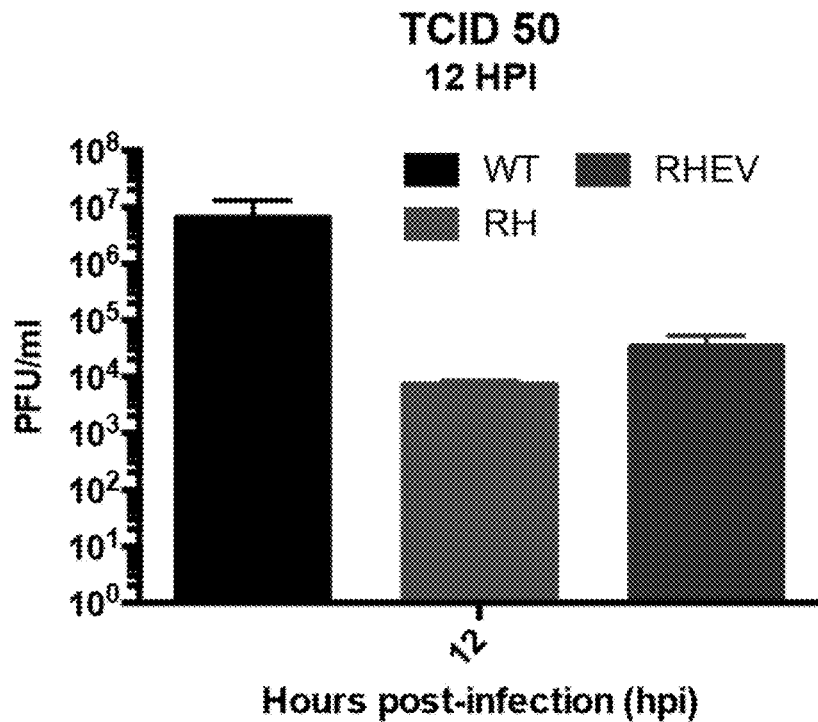
Figure 1:
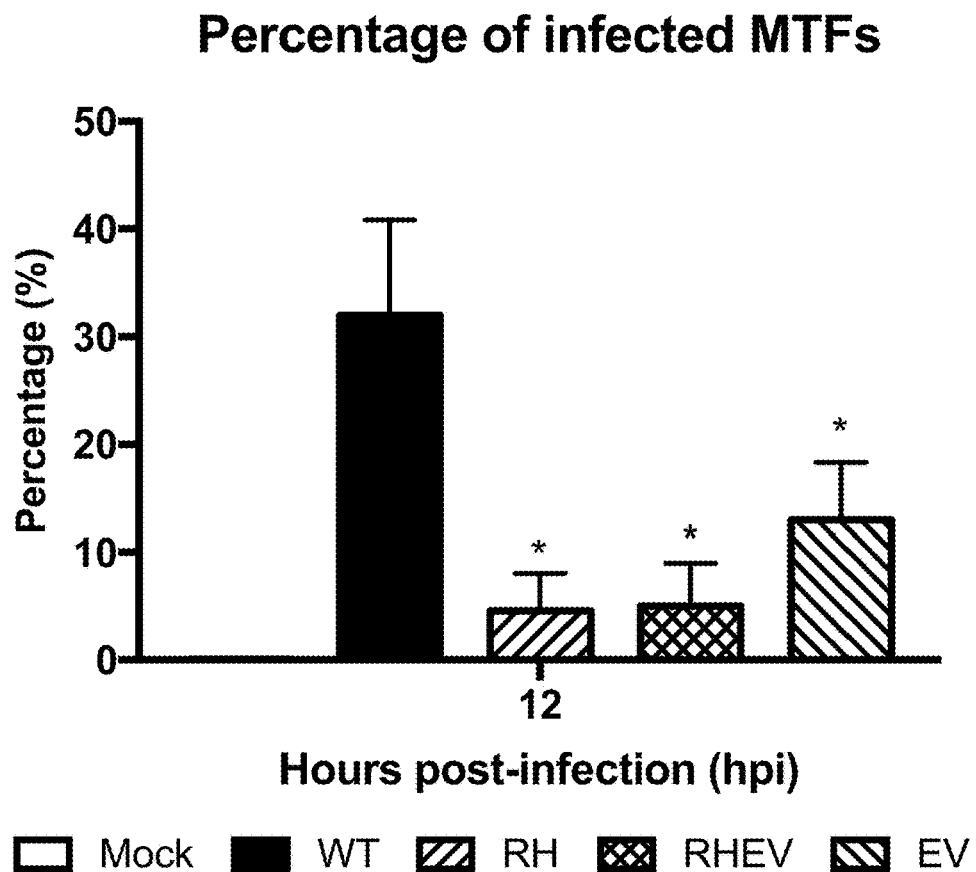
Figure 1:
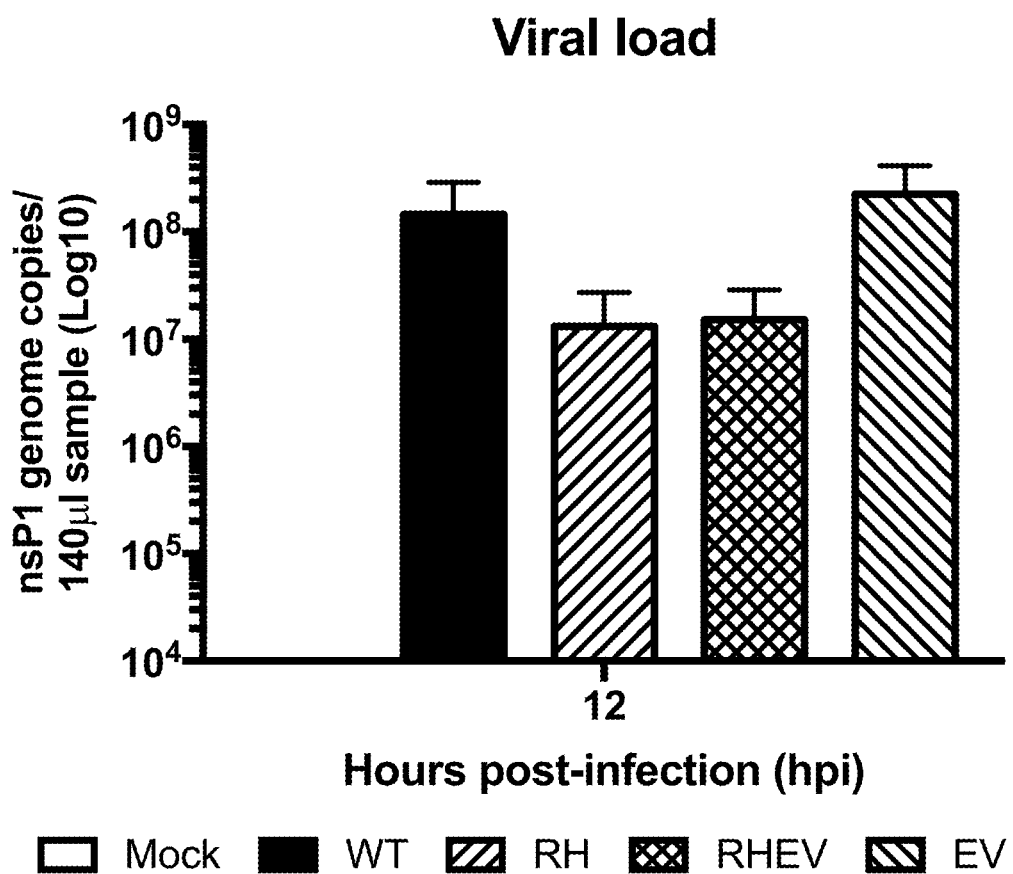

Lower percentage of CHIKV-infected MTFs were observed from day 6 to day 24 when infection was performed using CHIKV with the RH mutation at position 532 and RHEV mutations at positions 532 and 1050, compared to the WT CHIKV (FIG. 1A). Therefore, RH and RHEV mutations resulted in reduced CHIKV infectivity. Lower percentage of EV CHIKV-infected MTFs were observed at 12 hpi (FIG. 1D). Therefore, EV mutation resulted also in reduced CHIKV infectivity. Mock groups ("MK" in FIGS. 1A and 1B) are negative controls for the experiments. During the infection step of the experiments, the mock groups are treated with serum free DMEM media, which is the same media that the virus is re-suspended in.

To investigate if mutation in the CHIKV nsPs affects the replicative potential of CHIKV, the viral load in MTFs infected using the RH and RHEV CHIKV were determined using the method described above. FIG. 1B shows that the viral loads in MTFs infected with RH and RHEV CHIKV mutants reduced from 12 hours post infection and extended at least up to 24 hours post infection compared to wild-type infected cells. However, FIG. 1E shows no significant change to the viral load in MTFs infected with EV CHIKV-infected MTFs at 12 hpi compared to MTFs infected with ST CHIKV. Virus quantification was also performed at 12 hours post infection using the TCID$_{50}$ assay. FIG. 1C shows that at the 12 hour post infection time point, the infectious virus titre for RH CHIKV and RHEV CHIKV were significantly lower than the wild-type. Therefore, RH and RHEV mutations resulted in reduced replicative potential of CHIKV in MTFs as observed in the viral load and TCID$_{50}$ assays.

Example 3: Mutations in the CHIKV nsPs Result in More Robust Type 1 IFN Response To investigate if mutation in the CHIKV nsP affects the Type 1 IFN response, the MTFs infected with the CHIKV constructs were harvested at 12 hours post infection. The concentrations of the Type 1 IFN were then analysed using the Luminex® screening assay as described above.

FIG. 2A shows that infection with the RH CHIKV nsP mutant increased the concentration of IFN-α. Similarly, infection with RH CHIKV nsP mutant also increased the concentration of IFN-β (FIG. 2B). RHEV CHIKV nsP mutant resulted in further increase in the concentrations of both IFN-α and IFN-β compared to WT CHIKV and the RH CHIKV nsP mutant (FIGS. 2A and 2B). Therefore, mutation in the CHIKV nsP results in increased Type 1 IFN response in infected MTF cells. Furthermore, it was shown that simultaneous RHEV CHIKV nsP mutant induced a more robust IFN response in MTF cells. However, EV CHIKV mutants did not increase the concentrations of IFN-α or IFN-β compared to WT CHKV, RH CHIKV and RHEV CHIKV (FIGS. 2A and 2B).

Example 4: Mutations in the CHIKV nsPs Result in Faster Clearance of Viremia and Less Severe Virus-Induced Joint Inflammation To investigate if the mutations in the CHIKV nsPs affect the clearance of the CHIKV from the bloodstream or viremia, WT C57BL/6 mice were infected with ZsG-tagged WT CHIKV, RH CHIKV, EV CHIKV and RHEV CHIKV nsP mutants at the metatarsal region of the footpad as described above.

The progression of viremia in the virus-infected mice was monitored over the course of two weeks as shown in FIG. 3A. Both the RH CHIKV and RHEV CHIKV nsP mutants displayed faster clearance of viremia compared to the WT CHIKV, with the RHEV CHIKV nsP mutant showing the faster clearance rate among the four CHIKV tested. However, EV CHIKV displayed the highest viremia and slowest clearance rate among the CHIKV tested.

To investigate the severity of the joint inflammation induced by the different nsP mutants, the joint inflammation of mice infected with the WT CHIKV, RH CHIKV, EV CHIKV and the RHEV CHIKV nsP mutant were measured over the course of two weeks. FIG. 3B shows that the mice infected with the CHIKV nsP mutants also displayed less severe joint inflammation compared to the WT CHIKV. However, the joint inflammation of mice infected with EV CHIKV was not reduced compared to the WT CHIKV.

Example 5: Mutations in the CHIKV nsPs Result in Lower Infectivity at the Site of Inflammation To investigate if mutation in the CHIKV nsPs affects viral infectivity at the site of inflammation, WT C57BL/6 mice were infected subcutaneously with ZsG-tagged WT CHIKV, RH CHIKV, EV CHIKV and RHEV CHIKV nsP mutant at the metatarsal region of the footpad. Leukocytes were then isolated from the footpad at 3 and 6 days post infection. Infections in CD45+ leukocytes and various leukocyte subsets (specifically the monocytes and macrophages, neutrophils, NK cells, CD4+ T cells and CD8+ T cells) were assessed using flow cytometry as explained above. FIG. 4G shows the leukocytes isolated for each treatment as analysed using flow cytometry.

FIG. 4A shows the RH, EV and RHEV mutations were able to reduce the viral infectivity of the CHIKV nsP mutants on CD45+ leukocytes.

FIG. 4B-4F shows that both the RH and RHEV mutations were able to reduce the viral infectivity of the CHIKV nsP mutants on various subsets of leukocytes. It was also found that the RH mutation in the CHIKV drastically reduced the viral infectivity in these cells.

Example 6: Mice Infected with CHIKV nsP Mutants are Protected from Virus Infection To investigate if infection with the RH and RHEV CHIKV nsP mutants results in protection of the infected mice from subsequent virus infection, WT C57BL/6 mice were re-infected at the metatarsal region of the footpad with WT CHIKV, RH CHIKV and RHEV CHIKV nsP mutants at 90 days after the first infection. Joint inflammation of the re-infected mice was monitored over 2 weeks.

FIGS. 5A, 5C and 5D show that the relative fold increase in footpad size in mice infected with RH CHIKV and RHEV CHIKV nsP mutants were significantly decreased. Therefore, RH CHIKV and RHEV CHIKV nsP mutants are protected from subsequent WT CHIKV virus infection.

Example 7: Antibody Response to CHIKV nsP Mutant Infection

FIG. 6A shows that there was no joint inflammation observed in the re-infection phase using WT CHIKV after the initial infection with RH CHIKV, EV CHIKV and the RHEV CHIKV. Therefore, vaccinated mice did not suffer from joint swelling upon WT CHIKV infection. Viremia was also not detected in any of the mice vaccinated with RH CHIKV, EV CHIKV and the RHEV CHIKV when re-infected with WT CHIKV (FIG. 6B). Infection with WT CHIKV did not provide such protection against foot pad inflammation or viremia when re-infected with WT CHIKV.

To investigate the antibody response of mice during the re-infection phase, presence of CHIKV-specific antibodies were measured as described above. FIG. 6C shows the production of anti-CHIKV IgG antibody in the sera of re-infected mice is more robust in vaccinated mice compared to non-vaccinated mice.

The neutralization capacities of the CHIKV-specific antibodies (that are present in the sera) produced by re-infected mice were also investigated using the neutralisation assay described above. FIG. 6D shows that the sera elicited during the re-infection phase had higher virus neutralizing capacity.

Example 8: Protection from CHIKV-Induced Edema Formation and Tissue Damage

Histological assays were also performed as described above to visually observe if vaccination with the nsP mutants provide protection against CHIKV-induced edema formation and tissue damage. FIGS. 7A and 7B shows that vaccination with WT CHIKV and RH CHIKV protects mice from CHIKV-induced edema formation and tissue damage.

Example 9: Anti-CHIKV Antibody Production is Important Protection Against Joint Inflammation and Viremia To investigate if antibodies are important for protection against joint inflammation and viremia, pMT mice (mice which lack antibodies) were first vaccinated with WT CHIKV or RH CHIKV. The mice were then re-infected with WT CHIKV 3 months post-infection. Vaccination of pMT mice did not protect the mice from the re-infection (FIG. 8A). High level of viremia was also observed in the re-infected pMT mice (FIG. 8B). Virion-based ELISA, performed as described above, did not detect CHIKV-specific antibodies in the pMT mice (FIG. 8C). Similarly, the sera from the pMT mice did not show neutralizing activity against CHIKV in a human cell-line in vitro infection model (FIG. 8D). Thus, mature B lymphocytes and antibodies are important for protection against joint inflammation and viremia in the vaccinated mice. Without the mature B lymphocytes and antibodies, vaccinated pMT mice stay unprotected against CHIKV infection. Therefore, anti-CHIKV antibody production is important protection against joint inflammation and viremia.

Example 10: B and T Lymphocytes are Important for Clearing Viremia During Vaccination and Re-Infection To investigate if mature B and T lymphocytes are important for protection against joint inflammation and viremia, RAG-1$^{-/-}$ mice (which lack mature B and T lymphocytes) are first vaccinated with WT CHIKV or RH CHIKV. Reinfection with WT CHIKV did not result in joint inflammation (FIG. 9C) even though joint inflammation was observed in the vaccination phase (FIG. 9A). However, it was found that viremia was not cleared during the vaccination phase with RH CHIKV (FIG. 9B). After 3 months from the vaccination, the mice were re-infected with WT-CHIKV. Vaccination of RAG-1$^{-/-}$ mice did not stop the replication of CHIKV in the host cell (FIG. 9D). However, no joint swelling were observed during the re-infected with WT-CHIKV (FIG. 9D). Thus, mature B and T lymphocytes are important for protection against joint inflammation and viremia in the vaccinated mice. Without the mature B and T lymphocytes, vaccinated RAG-1$^{-/-}$ mice stay unprotected against CHIKV infection. Therefore, B and T lymphocytes are important for clearing viremia during vaccination and re-infection.

Example 11: CHIKV nsP Mutant Protects Against Joint Swelling from ONNV Infection To investigate if vaccination with CHIKV nsP mutants provides protection against WT ONNV infection, WT C57BL/6 mice were vaccinated subcutaneously with WT CHIKV or RH CHIKV at the metatarsal region of the footpad. The mice were then re-infected with WT ONNV 3 months post-infection with the CHIKV nsP mutants. Vaccinated mice did not suffer from joint swelling upon ONNV infection (FIG. 10A). Low levels of viremia could be detected in the blood of both vaccinated and naïve mice infected with ONNV (FIG. 10B). Therefore, vaccination with RH CHIKV did provide protection against joint swelling, but only a lower level of protection against viremia when infected with ONNV.

REFERENCES

Saul S, Ferguson M, Cordonin C, et al. Differences in Processing Determinants of Nonstructural Polyprotein and in the Sequence of Nonstructural Protein 3 Affect Neurovirulence of Semliki Forest Virus. Diamond Miss., ed. Journal of Virology. 2015; 89(21):11030-11045. doi: 10.1128/JVI.01186-15.

The invention claimed is:

1. A recombinant polypeptide comprising the amino acid sequence set forth in SEQ ID NO: 1 or a variant thereof comprising at least 80% identity to the amino acid sequence set forth in SEQ ID NO: 1, wherein said polypeptide comprises one or more mutations selected from the group consisting of:
   a substitution of R with H at a position equivalent to amino acid position 532 of SEQ ID NO: 1, and
   a substitution of E with V at a position equivalent to amino acid position 1050 of SEQ ID NO: 1,
   wherein the mutations are attenuating mutations.

2. The recombinant polypeptide of claim 1, wherein the amino acid sequence set forth in SEQ ID NO: 1 is derived from a Chikungunya virus strain LR2006 OPY1.

3. The recombinant polypeptide of claim 1 comprising an amino acid sequence selected from the group consisting of SEQ ID NO: 2, SEQ ID NO: 3, and SEQ ID NO: 4.

4. A recombinant virus particle comprising the polypeptide of claim 1.

5. The recombinant virus particle of claim 4, wherein the virus is one or more of the following: (a) the virus is an alphavirus; (b) the virus is an alphavirus derived from a Chikungunya virus strain; (c) the virus is an Alphavirus derived from a Chikungunya virus strain LR2006 OPY1; and (d) the virus is a live attenuated virus.

6. A method of eliciting an immune response against alphavirus infection in a subject comprising administering an immunogenic composition to the subject, the immunogenic composition comprising an infectious clone comprising a polynucleotide sequence encoding the polypeptide of claim 1.

7. The method of claim 6, wherein the subject is a human or non-human primate at risk of Chikungunya virus infection.

8. The method of claim 6, wherein the subject is a human or non-human primate at risk of O'nyong'nyong virus infection.

9. The method of claim 6 wherein the immunogenic composition is to be administered by a route selected from the group consisting of intramuscular, intradermal, subcutaneous, intravenous, oral, and intranasal administration.

10. The method of claim 6, wherein the polynucleotide is one or more of the following:
    (a) the polynucleotide is DNA or RNA; and
    (b) the polynucleotide comprises a nucleotide sequence selected from the group consisting of SEQ ID NO: 5, SEQ ID NO:6, and SEQ ID NO: 7, or a variant thereof comprising a nucleotide sequence comprising at least 80% identity to SEQ ID NO: 5, SEQ ID NO:6, or SEQ ID NO: 7.

11. The method of claim 10, wherein the polynucleotide comprises the nucleotide sequence of SEQ ID NO: 5, SEQ ID NO:6 or SEQ ID NO: 7.

12. The method of claim 6, wherein the immunogenic composition is one or more of the following:
    (a) an immunogenic composition wherein the recombinant virus is a live attenuated Chikungunya virus;
    (b) an immunogenic composition further comprising an adjuvant, a preservative, a stabilizer and/or a pharmaceutically acceptable carrier; and
    (c) an immunogenic composition further comprising an expression vector comprising a polynucleotide sequence encoding the polypeptide of claim 1.

13. The method of claim 12, wherein the adjuvant is selected from the group consisting of (a) aluminum hydroxide, (b) aluminum phosphate, (c) gamma inulin, (d) algammulin, (e) cholecalciferol in oil, (f) OWEM1, (g) OWEM2, and (h) OWEM3.

14. The method of claim 6, wherein the immunogenic composition is encapsulated in liposomes.

15. A method of eliciting an immune response against alphavirus infection in a subject comprising administering an immunogenic composition to the subject, the immunogenic composition comprising the recombinant virus particle of claim 4.

16. The method of claim 15, wherein the recombinant virus particle is one or more of the following:
    (a) a recombinant virus particle wherein the virus is an alphavirus;
    (b) a recombinant virus particle wherein the virus is an alphavirus derived from a Chikungunya virus strain;
    (c) a recombinant virus particle wherein the virus is an alphavirus derived from a Chikungunya virus strain LR2006 OPY1; and
    (d) a recombinant virus particle wherein the virus is a live attenuated virus.

17. A method of eliciting an immune response against alphavirus infection in a subject comprising administering an immunogenic composition to the subject, the immunogenic composition comprising a recombinant virus particle comprising a polynucleotide encoding the polypeptide of claim 1.

18. A method of eliciting an immune response against alphavirus infection in a subject comprising administering an immunogenic composition to the subject, the immunogenic composition comprising a polynucleotide sequence encoding the polypeptide of claim 1.

* * * * *

SEQUENCE LISTING

<160> NUMBER OF SEQ ID NOS: 13

<210> SEQ ID NO 1
<211> LENGTH: 2474
<212> TYPE: PRT
<213> ORGANISM: Artificial sequence
<220> FEATURE:
<223> OTHER INFORMATION: Polypeptide sequence of wild-type CHIKV LR2006
      OPY -continued Glu Asp Ala Gln Lys Leu Leu Val Gly Leu Asn Gln Arg Ile Val Val
           355                 360                 365

Asn Gly Arg Thr Gln Arg Asn Thr Asn Thr Met Lys Asn Tyr Leu Leu
370                 375                 380

Pro Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Gln Lys Thr His Thr Val Tyr
            420                 425                 430

Lys Arg Pro Asp Thr Gln Ser Ile Gln Lys Val Gln Ala Glu Phe Asp
            435                 440                 445

Ser Phe Val Val Pro Ser Leu Trp Ser Ser Gly Leu Ser Ile Pro Leu
        450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Arg Glu Ala Glu Leu Thr Arg Glu Ala Leu Pro Pro
            500                 505                 510

Leu Gln Ala Ala Gln Glu Asp Val Gln Val Glu Ile Asp Val Glu Gln
        515                 520                 525

Leu Glu Asp Arg Ala Gly Ala Gly Ile Ile Glu Thr Pro Arg Gly Ala
        530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
            595                 600                 605

Gly Tyr Ala Ile Ser Pro Glu Asp Phe Gln Ser Leu Ser Glu Ser Ala
        610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Glu Ala Ala Gly Leu Val Leu Val
            675                 680                 685

Gly Asp Leu Thr Asn Pro Pro Tyr His Glu Phe Ala Tyr Glu Gly Leu
690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
            755                 760                 765

Val Asp Ser Leu Leu Leu Asn Gly Cys Asn Arg Pro Val Asp Val Leu

-continued

```
                770             775             780
Tyr Val Asp Glu Ala Phe Ala Cys His Ser Gly Thr Leu Leu Ala Leu
785             790             795             800

Ile Ala Leu Val Arg Pro Arg Gln Lys Val Val Leu Cys Gly Asp Pro
            805             810             815

Lys Gln Cys Gly Phe Phe Asn Met Met Gln Met Lys Val Asn Tyr Asn
            820             825             830

His Asn Ile Cys Thr Gln Val Tyr His Lys Ser Ile Ser Arg Arg Cys
            835             840             845

Thr Leu Pro Val Thr Ala Ile Val Ser Ser Leu His Tyr Glu Gly Lys
        850             855             860

Met Arg Thr Thr Asn Glu Tyr Asn Lys Pro Ile Val Val Asp Thr Thr
865             870             875             880

Gly Ser Thr Lys Pro Asp Pro Gly Asp Leu Val Leu Thr Cys Phe Arg
            885             890             895

Gly Trp Val Lys Gln Leu Gln Ile Asp Tyr Arg Gly Tyr Glu Val Met
            900             905             910

Thr Ala Ala Ala Ser Gln Gly Leu Thr Arg Lys Gly Val Tyr Ala Val
        915             920             925

Arg Gln Lys Val Asn Glu Asn Pro Leu Tyr Ala Ser Thr Ser Glu His
    930             935             940

Val Asn Val Leu Leu Thr Arg Thr Glu Gly Lys Leu Val Trp Lys Thr
945             950             955             960

Leu Ser Gly Asp Pro Trp Ile Lys Thr Leu Gln Asn Pro Pro Lys Gly
            965             970             975

Asn Phe Lys Ala Thr Ile Lys Glu Trp Glu Val Glu His Ala Ser Ile
            980             985             990

Met Ala Gly Ile Cys Ser His Gln Met Thr Phe Asp Thr Phe Gln Asn
            995             1000            1005

Lys Ala Asn Val Cys Trp Ala Lys Ser Leu Val Pro Ile Leu Glu
    1010            1015            1020

Thr Ala Gly Ile Lys Leu Asn Asp Arg Gln Trp Ser Gln Ile Ile
    1025            1030            1035

Gln Ala Phe Lys Glu Asp Lys Ala Tyr Ser Pro Glu Val Ala Leu
    1040            1045            1050

Asn Glu Ile Cys Thr Arg Met Tyr Gly Val Asp Leu Asp Ser Gly
    1055            1060            1065

Leu Phe Ser Lys Pro Leu Val Ser Val Tyr Tyr Ala Asp Asn His
    1070            1075            1080

Trp Asp Asn Arg Pro Gly Gly Lys Met Phe Gly Phe Asn Pro Glu
    1085            1090            1095

Ala Ala Ser Ile Leu Glu Arg Lys Tyr Pro Phe Thr Lys Gly Lys
    1100            1105            1110

Trp Asn Ile Asn Lys Gln Ile Cys Val Thr Thr Arg Arg Ile Glu
    1115            1120            1125

Asp Phe Asn Pro Thr Thr Asn Ile Ile Pro Ala Asn Arg Arg Leu
    1130            1135            1140

Pro His Ser Leu Val Ala Glu His Arg Pro Val Lys Gly Glu Arg
    1145            1150            1155

Met Glu Trp Leu Val Asn Lys Ile Asn Gly His His Val Leu Leu
    1160            1165            1170

Val Ser Gly Tyr Asn Leu Ala Leu Pro Thr Lys Arg Val Thr Trp
    1175            1180            1185
```

-continued

Val Ala Pro Leu Gly Val Arg Gly Ala Asp Tyr Thr Tyr Asn Leu
1190            1195              1200

Glu Leu Gly Leu Pro Ala Thr Leu Gly Arg Tyr Asp Leu Val Val
1205            1210              1215

Ile Asn Ile His Thr Pro Phe Arg Ile His His Tyr Gln Gln Cys
1220            1225              1230

Val Asp His Ala Met Lys Leu Gln Met Leu Gly Gly Asp Ser Leu
1235            1240              1245

Arg Leu Leu Lys Pro Gly Gly Ser Leu Leu Ile Arg Ala Tyr Gly
1250            1255              1260

Tyr Ala Asp Arg Thr Ser Glu Arg Val Ile Cys Val Leu Gly Arg
1265            1270              1275

Lys Phe Arg Ser Ser Arg Ala Leu Lys Pro Pro Cys Val Thr Ser
1280            1285              1290

Asn Thr Glu Met Phe Phe Leu Phe Ser Asn Phe Asp Asn Gly Arg
1295            1300              1305

Arg Asn Phe Thr Thr His Val Met Asn Asn Gln Leu Asn Ala Ala
1310            1315              1320

Phe Val Gly Gln Val Thr Arg Ala Gly Cys Ala Pro Ser Tyr Arg
1325            1330              1335

Val Lys Arg Met Asp Ile Ala Lys Asn Asp Glu Glu Cys Val Val
1340            1345              1350

Asn Ala Ala Asn Pro Arg Gly Leu Pro Gly Gly Gly Val Cys Lys
1355            1360              1365

Ala Val Tyr Lys Lys Trp Pro Glu Ser Phe Lys Asn Ser Ala Thr
1370            1375              1380

Pro Val Gly Thr Ala Lys Thr Val Met Cys Gly Thr Tyr Pro Val
1385            1390              1395

Ile His Ala Val Gly Pro Asn Phe Ser Asn Tyr Ser Glu Ser Glu
1400            1405              1410

Gly Asp Arg Glu Leu Ala Ala Ala Tyr Arg Glu Val Ala Lys Glu
1415            1420              1425

Val Thr Arg Leu Gly Val Asn Ser Val Ala Ile Pro Leu Leu Ser
1430            1435              1440

Thr Gly Val Tyr Ser Gly Gly Lys Asp Arg Leu Thr Gln Ser Leu
1445            1450              1455

Asn His Leu Phe Thr Ala Met Asp Ser Thr Asp Ala Asp Val Val
1460            1465              1470

Ile Tyr Cys Arg Asp Lys Glu Trp Glu Lys Lys Ile Ser Glu Ala
1475            1480              1485

Ile Gln Met Arg Thr Gln Val Glu Leu Leu Asp Glu His Ile Ser
1490            1495              1500

Ile Asp Cys Asp Ile Val Arg Val His Pro Asp Ser Ser Leu Ala
1505            1510              1515

Gly Arg Lys Gly Tyr Ser Thr Thr Glu Gly Ala Leu Tyr Ser Tyr
1520            1525              1530

Leu Glu Gly Thr Arg Phe His Gln Thr Ala Val Asp Met Ala Glu
1535            1540              1545

Ile His Thr Met Trp Pro Lys Gln Thr Glu Ala Asn Glu Gln Val
1550            1555              1560

Cys Leu Tyr Ala Leu Gly Glu Ser Ile Glu Ser Ile Arg Gln Lys
1565            1570              1575

```
Cys Pro Val Asp Asp Ala Asp Ala Ser Ser Pro Pro Lys Thr Val
    1580            1585                1590

Pro Cys Leu Cys Arg Tyr Ala Met Thr Pro Glu Arg Val Thr Arg
    1595            1600                1605

Leu Arg Met Asn His Val Thr Ser Ile Ile Val Cys Ser Ser Phe
    1610            1615                1620

Pro Leu Pro Lys Tyr Lys Ile Glu Gly Val Gln Lys Val Lys Cys
    1625            1630                1635

Ser Lys Val Met Leu Phe Asp His Asn Val Pro Ser Arg Val Ser
    1640            1645                1650

Pro Arg Glu Tyr Arg Ser Ser Gln Glu Ser Ala Gln Glu Ala Ser
    1655            1660                1665

Thr Ile Thr Ser Leu Thr His Ser Gln Phe Asp Leu Ser Val Asp
    1670            1675                1680

Gly Glu Ile Leu Pro Val Pro Ser Asp Leu Asp Ala Asp Ala Pro
    1685            1690                1695

Ala Leu Glu Pro Ala Leu Asp Asp Gly Ala Thr His Thr Leu Pro
    1700            1705                1710

Ser Thr Thr Gly Asn Leu Ala Ala Val Ser Asp Trp Val Met Ser
    1715            1720                1725

Thr Val Pro Val Ala Pro Pro Arg Arg Arg Gly Arg Asn Leu
    1730            1735                1740

Thr Val Thr Cys Asp Glu Arg Glu Gly Asn Ile Thr Pro Met Ala
    1745            1750                1755

Ser Val Arg Phe Phe Arg Ala Glu Leu Cys Pro Val Val Gln Glu
    1760            1765                1770

Thr Ala Glu Thr Arg Asp Thr Ala Met Ser Leu Gln Ala Pro Pro
    1775            1780                1785

Ser Thr Ala Thr Glu Pro Asn His Pro Pro Ile Ser Phe Gly Ala
    1790            1795                1800

Ser Ser Glu Thr Phe Pro Ile Thr Phe Gly Asp Phe Asn Glu Gly
    1805            1810                1815

Glu Ile Glu Ser Leu Ser Ser Glu Leu Leu Thr Phe Gly Asp Phe
    1820            1825                1830

Leu Pro Gly Glu Val Asp Asp Leu Thr Asp Ser Asp Trp Ser Thr
    1835            1840                1845

Cys Ser Asp Thr Asp Asp Glu Leu Arg Leu Asp Arg Ala Gly Gly
    1850            1855                1860

Tyr Ile Phe Ser Ser Asp Thr Gly Pro Gly His Leu Gln Gln Lys
    1865            1870                1875

Ser Val Arg Gln Ser Val Leu Pro Val Asn Thr Leu Glu Glu Val
    1880            1885                1890

His Glu Glu Lys Cys Tyr Pro Pro Lys Leu Asp Glu Ala Lys Glu
    1895            1900                1905

Gln Leu Leu Leu Lys Lys Leu Gln Glu Ser Ala Ser Met Ala Asn
    1910            1915                1920

Arg Ser Arg Tyr Gln Ser Arg Lys Val Glu Asn Met Lys Ala Ala
    1925            1930                1935

Ile Ile Gln Arg Leu Lys Arg Gly Cys Arg Leu Tyr Leu Met Ser
    1940            1945                1950

Glu Thr Pro Lys Val Pro Thr Tyr Arg Thr Thr Tyr Pro Ala Pro
    1955            1960                1965

Val Tyr Ser Pro Pro Ile Asn Val Arg Leu Ser Asn Pro Glu Ser
```

```
                  1970              1975              1980
    Ala Val Ala Ala Cys Asn Glu Phe Leu Ala Arg Asn Tyr Pro Thr
                  1985              1990              1995
    Val Ser Ser Tyr Gln Ile Thr Asp Glu Tyr Asp Ala Tyr Leu Asp
                  2000              2005              2010
    Met Val Asp Gly Ser Glu Ser Cys Leu Asp Arg Ala Thr Phe Asn
                  2015              2020              2025
    Pro Ser Lys Leu Arg Ser Tyr Pro Lys Gln His Ala Tyr His Ala
                  2030              2035              2040
    Pro Ser Ile Arg Ser Ala Val Pro Ser Pro Phe Gln Asn Thr Leu
                  2045              2050              2055
    Gln Asn Val Leu Ala Ala Ala Thr Lys Arg Asn Cys Asn Val Thr
                  2060              2065              2070
    Gln Met Arg Glu Leu Pro Thr Leu Asp Ser Ala Val Phe Asn Val
                  2075              2080              2085
    Glu Cys Phe Lys Lys Phe Ala Cys Asn Gln Glu Tyr Trp Glu Glu
                  2090              2095              2100
    Phe Ala Ala Ser Pro Ile Arg Ile Thr Thr Glu Asn Leu Ala Thr
                  2105              2110              2115
    Tyr Val Thr Lys Leu Lys Gly Pro Lys Ala Ala Leu Phe Ala
                  2120              2125              2130
    Lys Thr His Asn Leu Leu Pro Leu Gln Glu Val Pro Met Asp Arg
                  2135              2140              2145
    Phe Thr Val Asp Met Lys Arg Asp Val Lys Val Thr Pro Gly Thr
                  2150              2155              2160
    Lys His Thr Glu Glu Arg Pro Lys Val Gln Val Ile Gln Ala Ala
                  2165              2170              2175
    Glu Pro Leu Ala Thr Ala Tyr Leu Cys Gly Ile His Arg Glu Leu
                  2180              2185              2190
    Val Arg Arg Leu Asn Ala Val Leu Leu Pro Asn Val His Thr Leu
                  2195              2200              2205
    Phe Asp Met Ser Ala Glu Asp Phe Asp Ala Ile Ile Ala Ala His
                  2210              2215              2220
    Phe Lys Pro Gly Asp Thr Val Leu Glu Thr Asp Ile Ala Ser Phe
                  2225              2230              2235
    Asp Lys Ser Gln Asp Asp Ser Leu Ala Leu Thr Ala Leu Met Leu
                  2240              2245              2250
    Leu Glu Asp Leu Gly Val Asp His Ser Leu Leu Asp Leu Ile Glu
                  2255              2260              2265
    Ala Ala Phe Gly Glu Ile Ser Ser Cys His Leu Pro Thr Gly Thr
                  2270              2275              2280
    Arg Phe Lys Phe Gly Ala Met Met Lys Ser Gly Met Phe Leu Thr
                  2285              2290              2295
    Leu Phe Val Asn Thr Leu Leu Asn Ile Thr Ile Ala Ser Arg Val
                  2300              2305              2310
    Leu Glu Asp Arg Leu Thr Lys Ser Ala Cys Ala Ala Phe Ile Gly
                  2315              2320              2325
    Asp Asp Asn Ile Ile His Gly Val Val Ser Asp Glu Leu Met Ala
                  2330              2335              2340
    Ala Arg Cys Ala Thr Trp Met Asn Met Glu Val Lys Ile Ile Asp
                  2345              2350              2355
    Ala Val Val Ser Leu Lys Ala Pro Tyr Phe Cys Gly Gly Phe Ile
                  2360              2365              2370
```

```
Leu His  Asp Thr Val Thr Gly  Thr Ala Cys Arg Val  Ala Asp Pro
    2375                 2380                 2385

Leu Lys  Arg Leu Phe Lys Leu  Gly Lys Pro Leu Ala  Ala Gly Asp
    2390                 2395                 2400

Glu Gln  Asp Glu Asp Arg Arg  Arg Ala Leu Ala Asp  Glu Val Ile
    2405                 2410                 2415

Arg Trp  Gln Arg Thr Gly Leu  Ile Asp Glu Leu Glu  Lys Ala Val
    2420                 2425                 2430

Tyr Ser  Arg Tyr Glu Val Gln  Gly Ile Ser Val Val  Val Met Ser
    2435                 2440                 2445

Met Ala  Thr Phe Ala Ser Ser  Arg Ser Asn Phe Glu  Lys Leu Arg
    2450                 2455                 2460

Gly Pro  Val Ile Thr Leu Tyr  Gly Gly Pro Lys
    2465                 2470

<210> SEQ ID NO 2
<211> LENGTH: 2474
<212> TYPE: PRT
<213> ORGANISM: Artificial sequence
<220> FEATURE:
<223> OTHER INFORMATION: Polypeptide sequence of CHIKV LR2006 OPY1
      non-structural polyprotein with mutation at position 532 from
      arginine to histidine.

<400> SEQUENCE: 2

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Gly Lys Ile Gly Asp Leu Gln Ala Val Met Ala Val Pro Asp Thr
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

Leu Ser Ile Met Arg Gly Lys Lys Leu Lys Pro Cys Asp Arg Val Leu
225                 230                 235                 240
```

```
Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
        260                 265                 270

Thr Cys Arg Cys Asp Thr Val Ser Cys Glu Gly Tyr Val Val Lys
        275                 280                 285

Arg Ile Thr Met Ser Pro Gly Leu Tyr Gly Lys Thr Thr Gly Tyr Ala
        290                 295                 300

Val Thr His His Ala Asp Gly Phe Leu Met Cys Lys Thr Thr Asp Thr
305                 310                 315                 320

Val Asp Gly Glu Arg Met Ser Phe Ser Val Cys Thr Tyr Val Pro Ala
                325                 330                 335

Thr Ile Cys Asp Gln Met Thr Gly Ile Leu Ala Thr Glu Val Thr Pro
        340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
        370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
        420                 425                 430

Lys Arg Pro Asp Thr Gln Ser Ile Gln Lys Val Gln Ala Glu Phe Asp
        435                 440                 445

Ser Phe Val Val Pro Ser Leu Trp Ser Ser Gly Leu Ser Ile Pro Leu
        450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Arg Glu Ala Glu Leu Thr Arg Glu Ala Leu Pro Pro
        500                 505                 510

Leu Gln Ala Ala Gln Glu Asp Val Gln Val Glu Ile Asp Val Glu Gln
        515                 520                 525

Leu Glu Asp His Ala Gly Ala Gly Ile Ile Glu Thr Pro Arg Gly Ala
        530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
        580                 585                 590

Gly Arg Tyr Ala Val Glu Ala Tyr Asp Gly Arg Val Leu Val Pro Ser
        595                 600                 605

Gly Tyr Ala Ile Ser Pro Glu Asp Phe Gln Ser Leu Ser Glu Ser Ala
        610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
```

```
            660                 665                 670
Gln Arg Arg Cys Cys Lys Lys Glu Glu Ala Ala Gly Leu Val Leu Val
            675                 680                 685
Gly Asp Leu Thr Asn Pro Pro Tyr His Glu Phe Ala Tyr Glu Gly Leu
            690                 695                 700
Lys Ile Arg Pro Ala Cys Pro Tyr Lys Ile Ala Val Ile Gly Val Phe
705                 710                 715                 720
Gly Val Pro Gly Ser Gly Lys Ser Ala Ile Ile Lys Asn Leu Val Thr
                    725                 730                 735
Arg Gln Asp Leu Val Thr Ser Gly Lys Lys Glu Asn Cys Gln Glu Ile
                    740                 745                 750
Thr Thr Asp Val Met Arg Gln Arg Gly Leu Glu Ile Ser Ala Arg Thr
            755                 760                 765
Val Asp Ser Leu Leu Leu Asn Gly Cys Asn Arg Pro Val Asp Val Leu
            770                 775                 780
Tyr Val Asp Glu Ala Phe Ala Cys His Ser Gly Thr Leu Leu Ala Leu
785                 790                 795                 800
Ile Ala Leu Val Arg Pro Arg Gln Lys Val Val Leu Cys Gly Asp Pro
                    805                 810                 815
Lys Gln Cys Gly Phe Phe Asn Met Met Gln Met Lys Val Asn Tyr Asn
                    820                 825                 830
His Asn Ile Cys Thr Gln Val Tyr His Lys Ser Ile Ser Arg Arg Cys
                    835                 840                 845
Thr Leu Pro Val Thr Ala Ile Val Ser Ser Leu His Tyr Glu Gly Lys
            850                 855                 860
Met Arg Thr Thr Asn Glu Tyr Asn Lys Pro Ile Val Val Asp Thr Thr
865                 870                 875                 880
Gly Ser Thr Lys Pro Asp Pro Gly Asp Leu Val Leu Thr Cys Phe Arg
                    885                 890                 895
Gly Trp Val Lys Gln Leu Gln Ile Asp Tyr Arg Gly Tyr Glu Val Met
                    900                 905                 910
Thr Ala Ala Ala Ser Gln Gly Leu Thr Arg Lys Gly Val Tyr Ala Val
            915                 920                 925
Arg Gln Lys Val Asn Glu Asn Pro Leu Tyr Ala Ser Thr Ser Glu His
            930                 935                 940
Val Asn Val Leu Leu Thr Arg Thr Glu Gly Lys Leu Val Trp Lys Thr
945                 950                 955                 960
Leu Ser Gly Asp Pro Trp Ile Lys Thr Leu Gln Asn Pro Pro Lys Gly
                    965                 970                 975
Asn Phe Lys Ala Thr Ile Lys Glu Trp Glu Val Glu His Ala Ser Ile
                    980                 985                 990
Met Ala Gly Ile Cys Ser His Gln Met Thr Phe Asp Thr Phe Gln Asn
                    995                 1000                1005
Lys Ala Asn Val Cys Trp Ala Lys Ser Leu Val Pro Ile Leu Glu
            1010                1015                1020
Thr Ala Gly Ile Lys Leu Asn Asp Arg Gln Trp Ser Gln Ile Ile
            1025                1030                1035
Gln Ala Phe Lys Glu Asp Lys Ala Tyr Ser Pro Glu Val Ala Leu
            1040                1045                1050
Asn Glu Ile Cys Thr Arg Met Tyr Gly Val Asp Leu Asp Ser Gly
            1055                1060                1065
Leu Phe Ser Lys Pro Leu Val Ser Val Tyr Tyr Ala Asp Asn His
            1070                1075                1080
```

Trp Asp Asn Arg Pro Gly Gly Lys Met Phe Gly Phe Asn Pro Glu
1085             1090                 1095

Ala Ala Ser Ile Leu Glu Arg Lys Tyr Pro Phe Thr Lys Gly Lys
1100             1105                 1110

Trp Asn Ile Asn Lys Gln Ile Cys Val Thr Thr Arg Arg Ile Glu
1115             1120                 1125

Asp Phe Asn Pro Thr Thr Asn Ile Ile Pro Ala Asn Arg Arg Leu
1130             1135                 1140

Pro His Ser Leu Val Ala Glu His Arg Pro Val Lys Gly Glu Arg
1145             1150                 1155

Met Glu Trp Leu Val Asn Lys Ile Asn Gly His His Val Leu Leu
1160             1165                 1170

Val Ser Gly Tyr Asn Leu Ala Leu Pro Thr Lys Arg Val Thr Trp
1175             1180                 1185

Val Ala Pro Leu Gly Val Arg Gly Ala Asp Tyr Thr Tyr Asn Leu
1190             1195                 1200

Glu Leu Gly Leu Pro Ala Thr Leu Gly Arg Tyr Asp Leu Val Val
1205             1210                 1215

Ile Asn Ile His Thr Pro Phe Arg Ile His Tyr Gln Gln Cys
1220             1225                 1230

Val Asp His Ala Met Lys Leu Gln Met Leu Gly Gly Asp Ser Leu
1235             1240                 1245

Arg Leu Leu Lys Pro Gly Gly Ser Leu Leu Ile Arg Ala Tyr Gly
1250             1255                 1260

Tyr Ala Asp Arg Thr Ser Glu Arg Val Ile Cys Val Leu Gly Arg
1265             1270                 1275

Lys Phe Arg Ser Ser Arg Ala Leu Lys Pro Pro Cys Val Thr Ser
1280             1285                 1290

Asn Thr Glu Met Phe Phe Leu Phe Ser Asn Phe Asp Asn Gly Arg
1295             1300                 1305

Arg Asn Phe Thr Thr His Val Met Asn Asn Gln Leu Asn Ala Ala
1310             1315                 1320

Phe Val Gly Gln Val Thr Arg Ala Gly Cys Ala Pro Ser Tyr Arg
1325             1330                 1335

Val Lys Arg Met Asp Ile Ala Lys Asn Asp Glu Glu Cys Val Val
1340             1345                 1350

Asn Ala Ala Asn Pro Arg Gly Leu Pro Gly Gly Gly Val Cys Lys
1355             1360                 1365

Ala Val Tyr Lys Lys Trp Pro Glu Ser Phe Lys Asn Ser Ala Thr
1370             1375                 1380

Pro Val Gly Thr Ala Lys Thr Val Met Cys Gly Thr Tyr Pro Val
1385             1390                 1395

Ile His Ala Val Gly Pro Asn Phe Ser Asn Tyr Ser Glu Ser Glu
1400             1405                 1410

Gly Asp Arg Glu Leu Ala Ala Ala Tyr Arg Glu Val Ala Lys Glu
1415             1420                 1425

Val Thr Arg Leu Gly Val Asn Ser Val Ala Ile Pro Leu Leu Ser
1430             1435                 1440

Thr Gly Val Tyr Ser Gly Gly Lys Asp Arg Leu Thr Gln Ser Leu
1445             1450                 1455

Asn His Leu Phe Thr Ala Met Asp Ser Thr Asp Ala Asp Val Val
1460             1465                 1470

```
Ile Tyr Cys Arg Asp Lys Glu Trp Glu Lys Lys Ile Ser Glu Ala
1475                1480                1485

Ile Gln Met Arg Thr Gln Val Glu Leu Leu Asp Glu His Ile Ser
1490                1495                1500

Ile Asp Cys Asp Ile Val Arg Val His Pro Asp Ser Ser Leu Ala
1505                1510                1515

Gly Arg Lys Gly Tyr Ser Thr Thr Glu Gly Ala Leu Tyr Ser Tyr
1520                1525                1530

Leu Glu Gly Thr Arg Phe His Gln Thr Ala Val Asp Met Ala Glu
1535                1540                1545

Ile His Thr Met Trp Pro Lys Gln Thr Glu Ala Asn Glu Gln Val
1550                1555                1560

Cys Leu Tyr Ala Leu Gly Glu Ser Ile Glu Ser Ile Arg Gln Lys
1565                1570                1575

Cys Pro Val Asp Asp Ala Asp Ala Ser Ser Pro Pro Lys Thr Val
1580                1585                1590

Pro Cys Leu Cys Arg Tyr Ala Met Thr Pro Glu Arg Val Thr Arg
1595                1600                1605

Leu Arg Met Asn His Val Thr Ser Ile Ile Val Cys Ser Ser Phe
1610                1615                1620

Pro Leu Pro Lys Tyr Lys Ile Glu Gly Val Gln Lys Val Lys Cys
1625                1630                1635

Ser Lys Val Met Leu Phe Asp His Asn Val Pro Ser Arg Val Ser
1640                1645                1650

Pro Arg Glu Tyr Arg Ser Ser Gln Glu Ser Ala Gln Glu Ala Ser
1655                1660                1665

Thr Ile Thr Ser Leu Thr His Ser Gln Phe Asp Leu Ser Val Asp
1670                1675                1680

Gly Glu Ile Leu Pro Val Pro Ser Asp Leu Asp Ala Asp Ala Pro
1685                1690                1695

Ala Leu Glu Pro Ala Leu Asp Asp Gly Ala Thr His Thr Leu Pro
1700                1705                1710

Ser Thr Thr Gly Asn Leu Ala Ala Val Ser Asp Trp Val Met Ser
1715                1720                1725

Thr Val Pro Val Ala Pro Pro Arg Arg Arg Gly Arg Asn Leu
1730                1735                1740

Thr Val Thr Cys Asp Glu Arg Glu Gly Asn Ile Thr Pro Met Ala
1745                1750                1755

Ser Val Arg Phe Phe Arg Ala Glu Leu Cys Pro Val Val Gln Glu
1760                1765                1770

Thr Ala Glu Thr Arg Asp Thr Ala Met Ser Leu Gln Ala Pro Pro
1775                1780                1785

Ser Thr Ala Thr Glu Pro Asn His Pro Pro Ile Ser Phe Gly Ala
1790                1795                1800

Ser Ser Glu Thr Phe Pro Ile Thr Phe Gly Asp Phe Asn Glu Gly
1805                1810                1815

Glu Ile Glu Ser Leu Ser Ser Glu Leu Leu Thr Phe Gly Asp Phe
1820                1825                1830

Leu Pro Gly Glu Val Asp Asp Leu Thr Asp Ser Asp Trp Ser Thr
1835                1840                1845

Cys Ser Asp Thr Asp Asp Glu Leu Arg Leu Asp Arg Ala Gly Gly
1850                1855                1860

Tyr Ile Phe Ser Ser Asp Thr Gly Pro Gly His Leu Gln Gln Lys
```

-continued

```
            1865                1870                1875
Ser Val Arg Gln Ser Val Leu Pro Val Asn Thr Leu Glu Glu Val
            1880                1885                1890
His Glu Glu Lys Cys Tyr Pro Pro Lys Leu Asp Glu Ala Lys Glu
            1895                1900                1905
Gln Leu Leu Leu Lys Lys Leu Gln Glu Ser Ala Ser Met Ala Asn
            1910                1915                1920
Arg Ser Arg Tyr Gln Ser Arg Lys Val Glu Asn Met Lys Ala Ala
            1925                1930                1935
Ile Ile Gln Arg Leu Lys Arg Gly Cys Arg Leu Tyr Leu Met Ser
            1940                1945                1950
Glu Thr Pro Lys Val Pro Thr Tyr Arg Thr Thr Tyr Pro Ala Pro
            1955                1960                1965
Val Tyr Ser Pro Pro Ile Asn Val Arg Leu Ser Asn Pro Glu Ser
            1970                1975                1980
Ala Val Ala Ala Cys Asn Glu Phe Leu Ala Arg Asn Tyr Pro Thr
            1985                1990                1995
Val Ser Ser Tyr Gln Ile Thr Asp Glu Tyr Asp Ala Tyr Leu Asp
            2000                2005                2010
Met Val Asp Gly Ser Glu Ser Cys Leu Asp Arg Ala Thr Phe Asn
            2015                2020                2025
Pro Ser Lys Leu Arg Ser Tyr Pro Lys Gln His Ala Tyr His Ala
            2030                2035                2040
Pro Ser Ile Arg Ser Ala Val Pro Ser Pro Phe Gln Asn Thr Leu
            2045                2050                2055
Gln Asn Val Leu Ala Ala Ala Thr Lys Arg Asn Cys Asn Val Thr
            2060                2065                2070
Gln Met Arg Glu Leu Pro Thr Leu Asp Ser Ala Val Phe Asn Val
            2075                2080                2085
Glu Cys Phe Lys Lys Phe Ala Cys Asn Gln Glu Tyr Trp Glu Glu
            2090                2095                2100
Phe Ala Ala Ser Pro Ile Arg Ile Thr Thr Glu Asn Leu Ala Thr
            2105                2110                2115
Tyr Val Thr Lys Leu Lys Gly Pro Lys Ala Ala Ala Leu Phe Ala
            2120                2125                2130
Lys Thr His Asn Leu Leu Pro Leu Gln Glu Val Pro Met Asp Arg
            2135                2140                2145
Phe Thr Val Asp Met Lys Arg Asp Val Lys Val Thr Pro Gly Thr
            2150                2155                2160
Lys His Thr Glu Glu Arg Pro Lys Val Gln Val Ile Gln Ala Ala
            2165                2170                2175
Glu Pro Leu Ala Thr Ala Tyr Leu Cys Gly Ile His Arg Glu Leu
            2180                2185                2190
Val Arg Arg Leu Asn Ala Val Leu Leu Pro Asn Val His Thr Leu
            2195                2200                2205
Phe Asp Met Ser Ala Glu Asp Phe Asp Ala Ile Ile Ala Ala His
            2210                2215                2220
Phe Lys Pro Gly Asp Thr Val Leu Glu Thr Asp Ile Ala Ser Phe
            2225                2230                2235
Asp Lys Ser Gln Asp Asp Ser Leu Ala Leu Thr Ala Leu Met Leu
            2240                2245                2250
Leu Glu Asp Leu Gly Val Asp His Ser Leu Leu Asp Leu Ile Glu
            2255                2260                2265
```

```
Ala Ala Phe Gly Glu Ile Ser  Ser Cys His Leu Pro  Thr Gly Thr
        2270              2275              2280

Arg Phe Lys Phe Gly Ala Met  Met Lys Ser Gly Met  Phe Leu Thr
        2285              2290              2295

Leu Phe Val Asn Thr Leu Leu  Asn Ile Thr Ile Ala  Ser Arg Val
        2300              2305              2310

Leu Glu Asp Arg Leu Thr Lys  Ser Ala Cys Ala Ala  Phe Ile Gly
        2315              2320              2325

Asp Asp Asn Ile Ile His Gly  Val Val Ser Asp Glu  Leu Met Ala
        2330              2335              2340

Ala Arg Cys Ala Thr Trp Met  Asn Met Glu Val Lys  Ile Ile Asp
        2345              2350              2355

Ala Val Val Ser Leu Lys Ala  Pro Tyr Phe Cys Gly  Gly Phe Ile
        2360              2365              2370

Leu His Asp Thr Val Thr Gly  Thr Ala Cys Arg Val  Ala Asp Pro
        2375              2380              2385

Leu Lys Arg Leu Phe Lys Leu  Gly Lys Pro Leu Ala  Ala Gly Asp
        2390              2395              2400

Glu Gln Asp Glu Asp Arg Arg  Arg Ala Leu Ala Asp  Glu Val Ile
        2405              2410              2415

Arg Trp Gln Arg Thr Gly Leu  Ile Asp Glu Leu Glu  Lys Ala Val
        2420              2425              2430

Tyr Ser Arg Tyr Glu Val Gln  Gly Ile Ser Val Val  Val Met Ser
        2435              2440              2445

Met Ala Thr Phe Ala Ser Ser  Arg Ser Asn Phe Glu  Lys Leu Arg
        2450              2455              2460

Gly Pro Val Ile Thr Leu Tyr  Gly Gly Pro Lys
        2465              2470

<210> SEQ ID NO 3
<211> LENGTH: 2474
<212> TYPE: PRT
<213> ORGANISM: Artificial sequence
<220> FEATURE:
<223> OTHER INFORMATION: Polypeptide sequence of CHIKV LR2006 OPY1
      non-structural polyprotein with mutation at position 1050 from
      glutamic acid to valine.

<400> SEQUENCE: 3

Met Asp Pro Val Tyr Val Asp  Ile Asp Ala Asp Ser  Ala Phe Leu Lys
1                5                    10                   15

Ala Leu Gln Arg Ala Tyr Pro  Met Phe Glu Val Glu  Pro Arg Gln Val
            20                   25                   30

Thr Pro Asn Asp His Ala Asn  Ala Arg Ala Phe Ser  His Leu Ala Ile
            35                   40                   45

Lys Leu Ile Glu Gln Glu Ile  Asp Pro Asp Ser Thr  Ile Leu Asp Ile
        50                   55                   60

Gly Ser Ala Pro Ala Arg Arg  Met Met Ser Asp Arg  Lys Tyr His Cys
65                   70                   75                   80

Val Cys Pro Met Arg Ser Ala  Glu Asp Pro Glu Arg  Leu Ala Asn Tyr
            85                   90                   95

Ala Arg Lys Leu Ala Ser Ala  Ala Gly Lys Val Leu  Asp Arg Asn Ile
            100                  105                  110

Ser Gly Lys Ile Gly Asp Leu  Gln Ala Val Met Ala  Val Pro Asp Thr
            115                  120                  125
```

-continued

```
Glu Thr Pro Thr Phe Cys Leu His Thr Asp Val Ser Cys Arg Gln Arg
130                 135                 140
Ala Asp Val Ala Ile Tyr Gln Asp Val Tyr Ala Val His Ala Pro Thr
145                 150                 155                 160
Ser Leu Tyr His Gln Ala Ile Lys Gly Val Arg Val Ala Tyr Trp Val
                165                 170                 175
Gly Phe Asp Thr Thr Pro Phe Met Tyr Asn Ala Met Ala Gly Ala Tyr
            180                 185                 190
Pro Ser Tyr Ser Thr Asn Trp Ala Asp Glu Gln Val Leu Lys Ala Lys
        195                 200                 205
Asn Ile Gly Leu Cys Ser Thr Asp Leu Thr Glu Gly Arg Arg Gly Lys
210                 215                 220
Leu Ser Ile Met Arg Gly Lys Lys Leu Lys Pro Cys Asp Arg Val Leu
225                 230                 235                 240
Phe Ser Val Gly Ser Thr Leu Tyr Pro Glu Ser Arg Lys Leu Leu Lys
                245                 250                 255
Ser Trp His Leu Pro Ser Val Phe His Leu Lys Gly Lys Leu Ser Phe
            260                 265                 270
Thr Cys Arg Cys Asp Thr Val Val Ser Cys Glu Gly Tyr Val Val Lys
        275                 280                 285
Arg Ile Thr Met Ser Pro Gly Leu Tyr Gly Lys Thr Thr Gly Tyr Ala
290                 295                 300
Val Thr His His Ala Asp Gly Phe Leu Met Cys Lys Thr Thr Asp Thr
305                 310                 315                 320
Val Asp Gly Glu Arg Met Ser Phe Ser Val Cys Thr Tyr Val Pro Ala
                325                 330                 335
Thr Ile Cys Asp Gln Met Thr Gly Ile Leu Ala Thr Glu Val Thr Pro
            340                 345                 350
Glu Asp Ala Gln Lys Leu Leu Val Gly Leu Asn Gln Arg Ile Val Val
        355                 360                 365
Asn Gly Arg Thr Gln Arg Asn Thr Asn Thr Met Lys Asn Tyr Leu Leu
370                 375                 380
Pro Val Val Ala Gln Ala Phe Ser Lys Trp Ala Lys Glu Cys Arg Lys
385                 390                 395                 400
Asp Met Glu Asp Glu Lys Leu Leu Gly Val Arg Glu Arg Thr Leu Thr
                405                 410                 415
Cys Cys Cys Leu Trp Ala Phe Lys Lys Gln Lys Thr His Thr Val Tyr
            420                 425                 430
Lys Arg Pro Asp Thr Gln Ser Ile Gln Lys Val Gln Ala Glu Phe Asp
        435                 440                 445
Ser Phe Val Val Pro Ser Leu Trp Ser Ser Gly Leu Ser Ile Pro Leu
450                 455                 460
Arg Thr Arg Ile Lys Trp Leu Leu Ser Lys Val Pro Lys Thr Asp Leu
465                 470                 475                 480
Ile Pro Tyr Ser Gly Asp Ala Arg Glu Ala Arg Asp Ala Glu Lys Glu
                485                 490                 495
Ala Glu Glu Glu Arg Glu Ala Glu Leu Thr Arg Glu Ala Leu Pro Pro
            500                 505                 510
Leu Gln Ala Ala Gln Glu Asp Val Gln Val Glu Ile Asp Val Glu Gln
        515                 520                 525
Leu Glu Asp Arg Ala Gly Ala Gly Ile Ile Glu Thr Pro Arg Gly Ala
530                 535                 540
Ile Lys Val Thr Ala Gln Pro Thr Asp His Val Val Gly Glu Tyr Leu
```

-continued

```
            545                 550                 555                 560
        Val Leu Ser Pro Gln Thr Val Leu Arg Ser Gln Lys Leu Ser Leu Ile
                        565                 570                 575
        His Ala Leu Ala Glu Gln Val Lys Thr Cys Thr His Asn Gly Arg Ala
                        580                 585                 590
        Gly Arg Tyr Ala Val Glu Ala Tyr Asp Gly Arg Val Leu Val Pro Ser
                        595                 600                 605
        Gly Tyr Ala Ile Ser Pro Glu Asp Phe Gln Ser Leu Ser Glu Ser Ala
                        610                 615                 620
        Thr Met Val Tyr Asn Glu Arg Glu Phe Val Asn Arg Lys Leu His His
        625                 630                 635                 640
        Ile Ala Met His Gly Pro Ala Leu Asn Thr Asp Glu Glu Ser Tyr Glu
                        645                 650                 655
        Leu Val Arg Ala Glu Arg Thr Glu His Glu Tyr Val Tyr Asp Val Asp
                        660                 665                 670
        Gln Arg Arg Cys Cys Lys Lys Glu Ala Ala Gly Leu Val Leu Val
                        675                 680                 685
        Gly Asp Leu Thr Asn Pro Pro Tyr His Glu Phe Ala Tyr Glu Gly Leu
                        690                 695                 700
        Lys Ile Arg Pro Ala Cys Pro Tyr Lys Ile Ala Val Ile Gly Val Phe
        705                 710                 715                 720
        Gly Val Pro Gly Ser Gly Lys Ser Ala Ile Ile Lys Asn Leu Val Thr
                        725                 730                 735
        Arg Gln Asp Leu Val Thr Ser Gly Lys Lys Glu Asn Cys Gln Glu Ile
                        740                 745                 750
        Thr Thr Asp Val Met Arg Gln Arg Gly Leu Glu Ile Ser Ala Arg Thr
                        755                 760                 765
        Val Asp Ser Leu Leu Leu Asn Gly Cys Asn Arg Pro Val Asp Val Leu
                        770                 775                 780
        Tyr Val Asp Glu Ala Phe Ala Cys His Ser Gly Thr Leu Leu Ala Leu
        785                 790                 795                 800
        Ile Ala Leu Val Arg Pro Arg Gln Lys Val Val Leu Cys Gly Asp Pro
                        805                 810                 815
        Lys Gln Cys Gly Phe Phe Asn Met Met Gln Met Lys Val Asn Tyr Asn
                        820                 825                 830
        His Asn Ile Cys Thr Gln Val Tyr His Lys Ser Ile Ser Arg Arg Cys
                        835                 840                 845
        Thr Leu Pro Val Thr Ala Ile Val Ser Ser Leu His Tyr Glu Gly Lys
                        850                 855                 860
        Met Arg Thr Thr Asn Glu Tyr Asn Lys Pro Ile Val Val Asp Thr Thr
        865                 870                 875                 880
        Gly Ser Thr Lys Pro Asp Pro Gly Asp Leu Val Leu Thr Cys Phe Arg
                        885                 890                 895
        Gly Trp Val Lys Gln Leu Gln Ile Asp Tyr Arg Gly Tyr Glu Val Met
                        900                 905                 910
        Thr Ala Ala Ala Ser Gln Gly Leu Thr Arg Lys Gly Val Tyr Ala Val
                        915                 920                 925
        Arg Gln Lys Val Asn Glu Asn Pro Leu Tyr Ala Ser Thr Ser Glu His
                        930                 935                 940
        Val Asn Val Leu Leu Thr Arg Thr Glu Gly Lys Leu Val Trp Lys Thr
        945                 950                 955                 960
        Leu Ser Gly Asp Pro Trp Ile Lys Thr Leu Gln Asn Pro Pro Lys Gly
                        965                 970                 975
```

```
Asn Phe Lys Ala Thr Ile Lys Glu Trp Glu Val Glu His Ala Ser Ile
            980                 985                 990

Met Ala Gly Ile Cys Ser His Gln Met Thr Phe Asp Thr Phe Gln Asn
            995                 1000                1005

Lys Ala Asn Val Cys Trp Lys Ser Leu Val Pro Ile Leu Glu
            1010                1015                1020

Thr Ala Gly Ile Lys Leu Asn Asp Arg Gln Trp Ser Gln Ile Ile
            1025                1030                1035

Gln Ala Phe Lys Glu Asp Lys Ala Tyr Ser Pro Val Val Ala Leu
            1040                1045                1050

Asn Glu Ile Cys Thr Arg Met Tyr Gly Val Asp Leu Asp Ser Gly
            1055                1060                1065

Leu Phe Ser Lys Pro Leu Val Ser Val Tyr Tyr Ala Asp Asn His
            1070                1075                1080

Trp Asp Asn Arg Pro Gly Gly Lys Met Phe Gly Phe Asn Pro Glu
            1085                1090                1095

Ala Ala Ser Ile Leu Glu Arg Lys Tyr Pro Phe Thr Lys Gly Lys
            1100                1105                1110

Trp Asn Ile Asn Lys Gln Ile Cys Val Thr Thr Arg Arg Ile Glu
            1115                1120                1125

Asp Phe Asn Pro Thr Thr Asn Ile Ile Pro Ala Asn Arg Arg Leu
            1130                1135                1140

Pro His Ser Leu Val Ala Glu His Arg Pro Val Lys Gly Glu Arg
            1145                1150                1155

Met Glu Trp Leu Val Asn Lys Ile Asn Gly His His Val Leu Leu
            1160                1165                1170

Val Ser Gly Tyr Asn Leu Ala Leu Pro Thr Lys Arg Val Thr Trp
            1175                1180                1185

Val Ala Pro Leu Gly Val Arg Gly Ala Asp Tyr Thr Tyr Asn Leu
            1190                1195                1200

Glu Leu Gly Leu Pro Ala Thr Leu Gly Arg Tyr Asp Leu Val Val
            1205                1210                1215

Ile Asn Ile His Thr Pro Phe Arg Ile His His Tyr Gln Gln Cys
            1220                1225                1230

Val Asp His Ala Met Lys Leu Gln Met Leu Gly Gly Asp Ser Leu
            1235                1240                1245

Arg Leu Leu Lys Pro Gly Gly Ser Leu Leu Ile Arg Ala Tyr Gly
            1250                1255                1260

Tyr Ala Asp Arg Thr Ser Glu Arg Val Ile Cys Val Leu Gly Arg
            1265                1270                1275

Lys Phe Arg Ser Ser Arg Ala Leu Lys Pro Pro Cys Val Thr Ser
            1280                1285                1290

Asn Thr Glu Met Phe Phe Leu Phe Ser Asn Phe Asp Asn Gly Arg
            1295                1300                1305

Arg Asn Phe Thr Thr His Val Met Asn Asn Gln Leu Asn Ala Ala
            1310                1315                1320

Phe Val Gly Gln Val Thr Arg Ala Gly Cys Ala Pro Ser Tyr Arg
            1325                1330                1335

Val Lys Arg Met Asp Ile Ala Lys Asn Asp Glu Glu Cys Val Val
            1340                1345                1350

Asn Ala Ala Asn Pro Arg Gly Leu Pro Gly Gly Gly Val Cys Lys
            1355                1360                1365
```

-continued

Ala Val Tyr Lys Lys Trp Pro Glu Ser Phe Lys Asn Ser Ala Thr
1370              1375              1380

Pro Val Gly Thr Ala Lys Thr Val Met Cys Gly Thr Tyr Pro Val
1385              1390              1395

Ile His Ala Val Gly Pro Asn Phe Ser Asn Tyr Ser Glu Ser Glu
1400              1405              1410

Gly Asp Arg Glu Leu Ala Ala Ala Tyr Arg Glu Val Ala Lys Glu
1415              1420              1425

Val Thr Arg Leu Gly Val Asn Ser Val Ala Ile Pro Leu Leu Ser
1430              1435              1440

Thr Gly Val Tyr Ser Gly Gly Lys Asp Arg Leu Thr Gln Ser Leu
1445              1450              1455

Asn His Leu Phe Thr Ala Met Asp Ser Thr Asp Ala Asp Val Val
1460              1465              1470

Ile Tyr Cys Arg Asp Lys Glu Trp Glu Lys Lys Ile Ser Glu Ala
1475              1480              1485

Ile Gln Met Arg Thr Gln Val Glu Leu Leu Asp Glu His Ile Ser
1490              1495              1500

Ile Asp Cys Asp Ile Val Arg Val His Pro Asp Ser Ser Leu Ala
1505              1510              1515

Gly Arg Lys Gly Tyr Ser Thr Thr Glu Gly Ala Leu Tyr Ser Tyr
1520              1525              1530

Leu Glu Gly Thr Arg Phe His Gln Thr Ala Val Asp Met Ala Glu
1535              1540              1545

Ile His Thr Met Trp Pro Lys Gln Thr Glu Ala Asn Glu Gln Val
1550              1555              1560

Cys Leu Tyr Ala Leu Gly Glu Ser Ile Glu Ser Ile Arg Gln Lys
1565              1570              1575

Cys Pro Val Asp Asp Ala Asp Ala Ser Ser Pro Lys Thr Val
1580              1585              1590

Pro Cys Leu Cys Arg Tyr Ala Met Thr Pro Glu Arg Val Thr Arg
1595              1600              1605

Leu Arg Met Asn His Val Thr Ser Ile Ile Val Cys Ser Ser Phe
1610              1615              1620

Pro Leu Pro Lys Tyr Lys Ile Glu Gly Val Gln Lys Val Lys Cys
1625              1630              1635

Ser Lys Val Met Leu Phe Asp His Asn Val Pro Ser Arg Val Ser
1640              1645              1650

Pro Arg Glu Tyr Arg Ser Ser Gln Glu Ser Ala Gln Glu Ala Ser
1655              1660              1665

Thr Ile Thr Ser Leu Thr His Ser Gln Phe Asp Leu Ser Val Asp
1670              1675              1680

Gly Glu Ile Leu Pro Val Pro Ser Asp Leu Asp Ala Asp Ala Pro
1685              1690              1695

Ala Leu Glu Pro Ala Leu Asp Asp Gly Ala Thr His Thr Leu Pro
1700              1705              1710

Ser Thr Thr Gly Asn Leu Ala Ala Val Ser Asp Trp Val Met Ser
1715              1720              1725

Thr Val Pro Val Ala Pro Pro Arg Arg Arg Arg Gly Arg Asn Leu
1730              1735              1740

Thr Val Thr Cys Asp Glu Arg Glu Gly Asn Ile Thr Pro Met Ala
1745              1750              1755

Ser Val Arg Phe Phe Arg Ala Glu Leu Cys Pro Val Val Gln Glu

-continued

```
                1760                1765                1770
Thr Ala Glu Thr Arg Asp Thr Ala Met Ser Leu Gln Ala Pro Pro
        1775                1780                1785
Ser Thr Ala Thr Glu Pro Asn His Pro Pro Ile Ser Phe Gly Ala
        1790                1795                1800
Ser Ser Glu Thr Phe Pro Ile Thr Phe Gly Asp Phe Asn Glu Gly
        1805                1810                1815
Glu Ile Glu Ser Leu Ser Ser Glu Leu Leu Thr Phe Gly Asp Phe
        1820                1825                1830
Leu Pro Gly Glu Val Asp Asp Leu Thr Asp Ser Asp Trp Ser Thr
        1835                1840                1845
Cys Ser Asp Thr Asp Asp Glu Leu Arg Leu Asp Arg Ala Gly Gly
        1850                1855                1860
Tyr Ile Phe Ser Ser Asp Thr Gly Pro Gly His Leu Gln Gln Lys
        1865                1870                1875
Ser Val Arg Gln Ser Val Leu Pro Val Asn Thr Leu Glu Glu Val
        1880                1885                1890
His Glu Glu Lys Cys Tyr Pro Pro Lys Leu Asp Glu Ala Lys Glu
        1895                1900                1905
Gln Leu Leu Leu Lys Lys Leu Gln Glu Ser Ala Ser Met Ala Asn
        1910                1915                1920
Arg Ser Arg Tyr Gln Ser Arg Lys Val Glu Asn Met Lys Ala Ala
        1925                1930                1935
Ile Ile Gln Arg Leu Lys Arg Gly Cys Arg Leu Tyr Leu Met Ser
        1940                1945                1950
Glu Thr Pro Lys Val Pro Thr Tyr Arg Thr Thr Tyr Pro Ala Pro
        1955                1960                1965
Val Tyr Ser Pro Pro Ile Asn Val Arg Leu Ser Asn Pro Glu Ser
        1970                1975                1980
Ala Val Ala Ala Cys Asn Glu Phe Leu Ala Arg Asn Tyr Pro Thr
        1985                1990                1995
Val Ser Ser Tyr Gln Ile Thr Asp Glu Tyr Asp Ala Tyr Leu Asp
        2000                2005                2010
Met Val Asp Gly Ser Glu Ser Cys Leu Asp Arg Ala Thr Phe Asn
        2015                2020                2025
Pro Ser Lys Leu Arg Ser Tyr Pro Lys Gln His Ala Tyr His Ala
        2030                2035                2040
Pro Ser Ile Arg Ser Ala Val Pro Ser Pro Phe Gln Asn Thr Leu
        2045                2050                2055
Gln Asn Val Leu Ala Ala Ala Thr Lys Arg Asn Cys Asn Val Thr
        2060                2065                2070
Gln Met Arg Glu Leu Pro Thr Leu Asp Ser Ala Val Phe Asn Val
        2075                2080                2085
Glu Cys Phe Lys Lys Phe Ala Cys Asn Gln Glu Tyr Trp Glu Glu
        2090                2095                2100
Phe Ala Ala Ser Pro Ile Arg Ile Thr Thr Glu Asn Leu Ala Thr
        2105                2110                2115
Tyr Val Thr Lys Leu Lys Gly Pro Lys Ala Ala Ala Leu Phe Ala
        2120                2125                2130
Lys Thr His Asn Leu Leu Pro Leu Gln Glu Val Pro Met Asp Arg
        2135                2140                2145
Phe Thr Val Asp Met Lys Arg Asp Val Lys Val Thr Pro Gly Thr
        2150                2155                2160
```

Lys His Thr Glu Glu Arg Pro Lys Val Gln Val Ile Gln Ala Ala
             2165                2170                2175

Glu Pro Leu Ala Thr Ala Tyr Leu Cys Gly Ile His Arg Glu Leu
         2180                2185                2190

Val Arg Arg Leu Asn Ala Val Leu Leu Pro Asn Val His Thr Leu
     2195                2200                2205

Phe Asp Met Ser Ala Glu Asp Phe Asp Ala Ile Ile Ala Ala His
 2210                2215                2220

Phe Lys Pro Gly Asp Thr Val Leu Glu Thr Asp Ile Ala Ser Phe
         2225                2230                2235

Asp Lys Ser Gln Asp Ser Leu Ala Leu Thr Ala Leu Met Leu
     2240                2245                2250

Leu Glu Asp Leu Gly Val Asp His Ser Leu Leu Asp Leu Ile Glu
 2255                2260                2265

Ala Ala Phe Gly Glu Ile Ser Ser Cys His Leu Pro Thr Gly Thr
         2270                2275                2280

Arg Phe Lys Phe Gly Ala Met Met Lys Ser Gly Met Phe Leu Thr
     2285                2290                2295

Leu Phe Val Asn Thr Leu Leu Asn Ile Thr Ile Ala Ser Arg Val
 2300                2305                2310

Leu Glu Asp Arg Leu Thr Lys Ser Ala Cys Ala Ala Phe Ile Gly
         2315                2320                2325

Asp Asp Asn Ile Ile His Gly Val Val Ser Asp Glu Leu Met Ala
     2330                2335                2340

Ala Arg Cys Ala Thr Trp Met Asn Met Glu Val Lys Ile Ile Asp
 2345                2350                2355

Ala Val Val Ser Leu Lys Ala Pro Tyr Phe Cys Gly Gly Phe Ile
         2360                2365                2370

Leu His Asp Thr Val Thr Gly Thr Ala Cys Arg Val Ala Asp Pro
     2375                2380                2385

Leu Lys Arg Leu Phe Lys Leu Gly Lys Pro Leu Ala Ala Gly Asp
 2390                2395                2400

Glu Gln Asp Glu Asp Arg Arg Ala Leu Ala Asp Glu Val Ile
         2405                2410                2415

Arg Trp Gln Arg Thr Gly Leu Ile Asp Glu Leu Glu Lys Ala Val
     2420                2425                2430

Tyr Ser Arg Tyr Glu Val Gln Gly Ile Ser Val Val Val Met Ser
 2435                2440                2445

Met Ala Thr Phe Ala Ser Ser Arg Ser Asn Phe Glu Lys Leu Arg
         2450                2455                2460

Gly Pro Val Ile Thr Leu Tyr Gly Gly Pro Lys
     2465                2470

<210> SEQ ID NO 4
<211> LENGTH: 2474
<212> TYPE: PRT
<213> ORGANISM: artificial sequence
<220> FEATURE:
<223> OTHER INFORMATION: Polypeptide sequence of CHIKV LR2006 OPY1
      non-structural polyprotein with mutations at 532 from arginine to
      histidine and at 1050 from glutamic acid to valine.

<400> SEQUENCE: 4

Met Asp Pro Val Tyr Val Asp Ile Asp Ala Asp Ser Ala Phe Leu Lys
1               5                   10                  15

```
Ala Leu Gln Arg Ala Tyr Pro Met Phe Glu Val Glu Pro Arg Gln Val
             20                  25                  30

Thr Pro Asn Asp His Ala Asn Ala Arg Ala Phe Ser His Leu Ala Ile
         35                  40                  45

Lys Leu Ile Glu Gln Glu Ile Asp Pro Asp Ser Thr Ile Leu Asp Ile
 50                  55                  60

Gly Ser Ala Pro Ala Arg Arg Met Met Ser Asp Arg Lys Tyr His Cys
 65                  70                  75                  80

Val Cys Pro Met Arg Ser Ala Glu Asp Pro Glu Arg Leu Ala Asn Tyr
                 85                  90                  95

Ala Arg Lys Leu Ala Ser Ala Ala Gly Lys Val Leu Asp Arg Asn Ile
                100                 105                 110

Ser Gly Lys Ile Gly Asp Leu Gln Ala Val Met Ala Val Pro Asp Thr
                115                 120                 125

Glu Thr Pro Thr Phe Cys Leu His Thr Asp Val Ser Cys Arg Gln Arg
        130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Val
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Gly Arg Arg Gly Lys
210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Lys
                245                 250                 255

Ser Trp His Leu Pro Ser Val Phe His Leu Lys Gly Lys Leu Ser Phe
            260                 265                 270

Thr Cys Arg Cys Asp Thr Val Val Ser Cys Glu Gly Tyr Val Val Lys
        275                 280                 285

Arg Ile Thr Met Ser Pro Gly Leu Tyr Gly Lys Thr Thr Gly Tyr Ala
    290                 295                 300

Val Thr His His Ala Asp Gly Phe Leu Met Cys Lys Thr Thr Asp Thr
305                 310                 315                 320

Val Asp Gly Glu Arg Met Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Gln Ala Glu Phe Asp
```

-continued

```
                435                 440                 445
Ser Phe Val Pro Ser Leu Trp Ser Gly Leu Ser Ile Pro Leu
450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Arg Glu Ala Arg Asp Ala Glu Lys Glu
                485                 490                 495

Ala Glu Glu Arg Glu Ala Glu Leu Thr Arg Glu Ala Leu Pro Pro
                500                 505                 510

Leu Gln Ala Ala Gln Glu Asp Val Gln Val Glu Ile Asp Val Glu Gln
            515                 520                 525

Leu Glu Asp His Ala Gly Ala Gly Ile Ile Glu Thr Pro Arg Gly Ala
530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Asn Gly Arg Ala
            580                 585                 590

Gly Arg Tyr Ala Val Glu Ala Tyr Asp Gly Arg Val Leu Val Pro Ser
                595                 600                 605

Gly Tyr Ala Ile Ser Pro Glu Asp Phe Gln Ser Leu Ser Glu Ser Ala
610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
                660                 665                 670

Gln Arg Arg Cys Cys Lys Lys Glu Ala Ala Gly Leu Val Leu Val
            675                 680                 685

Gly Asp Leu Thr Asn Pro Pro Tyr His Glu Phe Ala Tyr Glu Gly Leu
690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
            755                 760                 765

Val Asp Ser Leu Leu Asn Gly Cys Asn Arg Pro Val Asp Val Leu
770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
            835                 840                 845

Thr Leu Pro Val Thr Ala Ile Val Ser Ser Leu His Tyr Glu Gly Lys
850                 855                 860
```

-continued

```
Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
            885                 890                 895

Gly Trp Val Lys Gln Leu Gln Ile Asp Tyr Arg Gly Tyr Glu Val Met
                900                 905                 910

Thr Ala Ala Ala Ser Gln Gly Leu Thr Arg Lys Gly Val Tyr Ala Val
                    915                 920                 925

Arg Gln Lys Val Asn Glu Asn Pro Leu Tyr Ala Ser Thr Ser Glu His
                        930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
                    980                 985                 990

Met Ala Gly Ile Cys Ser His Gln Met Thr Phe Asp Thr Phe Gln Asn
                    995                 1000                1005

Lys Ala Asn Val Cys Trp Ala Lys Ser Leu Val Pro Ile Leu Glu
    1010                1015                1020

Thr Ala Gly Ile Lys Leu Asn Asp Arg Gln Trp Ser Gln Ile Ile
    1025                1030                1035

Gln Ala Phe Lys Glu Asp Lys Ala Tyr Ser Pro Val Val Ala Leu
    1040                1045                1050

Asn Glu Ile Cys Thr Arg Met Tyr Gly Val Asp Leu Asp Ser Gly
    1055                1060                1065

Leu Phe Ser Lys Pro Leu Val Ser Val Tyr Tyr Ala Asp Asn His
    1070                1075                1080

Trp Asp Asn Arg Pro Gly Gly Lys Met Phe Gly Phe Asn Pro Glu
    1085                1090                1095

Ala Ala Ser Ile Leu Glu Arg Lys Tyr Pro Phe Thr Lys Gly Lys
    1100                1105                1110

Trp Asn Ile Asn Lys Gln Ile Cys Val Thr Thr Arg Arg Ile Glu
    1115                1120                1125

Asp Phe Asn Pro Thr Thr Asn Ile Ile Pro Ala Asn Arg Arg Leu
    1130                1135                1140

Pro His Ser Leu Val Ala Glu His Arg Pro Val Lys Gly Glu Arg
    1145                1150                1155

Met Glu Trp Leu Val Asn Lys Ile Asn Gly His His Val Leu Leu
    1160                1165                1170

Val Ser Gly Tyr Asn Leu Ala Leu Pro Thr Lys Arg Val Thr Trp
    1175                1180                1185

Val Ala Pro Leu Gly Val Arg Gly Ala Asp Tyr Thr Tyr Asn Leu
    1190                1195                1200

Glu Leu Gly Leu Pro Ala Thr Leu Gly Arg Tyr Asp Leu Val Val
    1205                1210                1215

Ile Asn Ile His Thr Pro Phe Arg Ile His His Tyr Gln Gln Cys
    1220                1225                1230

Val Asp His Ala Met Lys Leu Gln Met Leu Gly Gly Asp Ser Leu
    1235                1240                1245

Arg Leu Leu Lys Pro Gly Gly Ser Leu Leu Ile Arg Ala Tyr Gly
    1250                1255                1260
```

```
Tyr Ala Asp Arg Thr Ser Glu Arg Val Ile Cys Val Leu Gly Arg
    1265                1270                1275
Lys Phe Arg Ser Ser Arg Ala Leu Lys Pro Pro Cys Val Thr Ser
    1280                1285                1290
Asn Thr Glu Met Phe Phe Leu Phe Ser Asn Phe Asp Asn Gly Arg
    1295                1300                1305
Arg Asn Phe Thr Thr His Val Met Asn Asn Gln Leu Asn Ala Ala
    1310                1315                1320
Phe Val Gly Gln Val Thr Arg Ala Gly Cys Ala Pro Ser Tyr Arg
    1325                1330                1335
Val Lys Arg Met Asp Ile Ala Lys Asn Asp Glu Glu Cys Val Val
    1340                1345                1350
Asn Ala Ala Asn Pro Arg Gly Leu Pro Gly Gly Gly Val Cys Lys
    1355                1360                1365
Ala Val Tyr Lys Lys Trp Pro Glu Ser Phe Lys Asn Ser Ala Thr
    1370                1375                1380
Pro Val Gly Thr Ala Lys Thr Val Met Cys Gly Thr Tyr Pro Val
    1385                1390                1395
Ile His Ala Val Gly Pro Asn Phe Ser Asn Tyr Ser Glu Ser Glu
    1400                1405                1410
Gly Asp Arg Glu Leu Ala Ala Ala Tyr Arg Glu Val Ala Lys Glu
    1415                1420                1425
Val Thr Arg Leu Gly Val Asn Ser Val Ala Ile Pro Leu Leu Ser
    1430                1435                1440
Thr Gly Val Tyr Ser Gly Gly Lys Asp Arg Leu Thr Gln Ser Leu
    1445                1450                1455
Asn His Leu Phe Thr Ala Met Asp Ser Thr Asp Ala Asp Val Val
    1460                1465                1470
Ile Tyr Cys Arg Asp Lys Glu Trp Glu Lys Lys Ile Ser Glu Ala
    1475                1480                1485
Ile Gln Met Arg Thr Gln Val Glu Leu Leu Asp Glu His Ile Ser
    1490                1495                1500
Ile Asp Cys Asp Ile Val Arg Val His Pro Asp Ser Ser Leu Ala
    1505                1510                1515
Gly Arg Lys Gly Tyr Ser Thr Thr Glu Gly Ala Leu Tyr Ser Tyr
    1520                1525                1530
Leu Glu Gly Thr Arg Phe His Gln Thr Ala Val Asp Met Ala Glu
    1535                1540                1545
Ile His Thr Met Trp Pro Lys Gln Thr Glu Ala Asn Glu Gln Val
    1550                1555                1560
Cys Leu Tyr Ala Leu Gly Glu Ser Ile Glu Ser Ile Arg Gln Lys
    1565                1570                1575
Cys Pro Val Asp Asp Ala Asp Ala Ser Ser Pro Lys Thr Val
    1580                1585                1590
Pro Cys Leu Cys Arg Tyr Ala Met Thr Pro Glu Arg Val Thr Arg
    1595                1600                1605
Leu Arg Met Asn His Val Thr Ser Ile Ile Val Cys Ser Ser Phe
    1610                1615                1620
Pro Leu Pro Lys Tyr Lys Ile Glu Gly Val Gln Lys Val Lys Cys
    1625                1630                1635
Ser Lys Val Met Leu Phe Asp His Asn Val Pro Ser Arg Val Ser
    1640                1645                1650
Pro Arg Glu Tyr Arg Ser Ser Gln Glu Ser Ala Gln Glu Ala Ser
```

```
            1655                1660                1665
Thr Ile Thr Ser Leu Thr His Ser Gln Phe Asp Leu Ser Val Asp
    1670                1675                1680
Gly Glu Ile Leu Pro Val Pro Ser Asp Leu Asp Ala Asp Ala Pro
    1685                1690                1695
Ala Leu Glu Pro Ala Leu Asp Asp Gly Ala Thr His Thr Leu Pro
    1700                1705                1710
Ser Thr Thr Gly Asn Leu Ala Ala Val Ser Asp Trp Val Met Ser
    1715                1720                1725
Thr Val Pro Val Ala Pro Pro Arg Arg Arg Gly Arg Asn Leu
    1730                1735                1740
Thr Val Thr Cys Asp Glu Arg Glu Gly Asn Ile Thr Pro Met Ala
    1745                1750                1755
Ser Val Arg Phe Phe Arg Ala Glu Leu Cys Pro Val Val Gln Glu
    1760                1765                1770
Thr Ala Glu Thr Arg Asp Thr Ala Met Ser Leu Gln Ala Pro Pro
    1775                1780                1785
Ser Thr Ala Thr Glu Pro Asn His Pro Pro Ile Ser Phe Gly Ala
    1790                1795                1800
Ser Ser Glu Thr Phe Pro Ile Thr Phe Gly Asp Phe Asn Glu Gly
    1805                1810                1815
Glu Ile Glu Ser Leu Ser Ser Glu Leu Leu Thr Phe Gly Asp Phe
    1820                1825                1830
Leu Pro Gly Glu Val Asp Asp Leu Thr Asp Ser Asp Trp Ser Thr
    1835                1840                1845
Cys Ser Asp Thr Asp Asp Glu Leu Arg Leu Asp Arg Ala Gly Gly
    1850                1855                1860
Tyr Ile Phe Ser Ser Asp Thr Gly Pro Gly His Leu Gln Gln Lys
    1865                1870                1875
Ser Val Arg Gln Ser Val Leu Pro Val Asn Thr Leu Glu Glu Val
    1880                1885                1890
His Glu Glu Lys Cys Tyr Pro Pro Lys Leu Asp Glu Ala Lys Glu
    1895                1900                1905
Gln Leu Leu Leu Lys Lys Leu Gln Glu Ser Ala Ser Met Ala Asn
    1910                1915                1920
Arg Ser Arg Tyr Gln Ser Arg Lys Val Glu Asn Met Lys Ala Ala
    1925                1930                1935
Ile Ile Gln Arg Leu Lys Arg Gly Cys Arg Leu Tyr Leu Met Ser
    1940                1945                1950
Glu Thr Pro Lys Val Pro Thr Tyr Arg Thr Thr Tyr Pro Ala Pro
    1955                1960                1965
Val Tyr Ser Pro Pro Ile Asn Val Arg Leu Ser Asn Pro Glu Ser
    1970                1975                1980
Ala Val Ala Ala Cys Asn Glu Phe Leu Ala Arg Asn Tyr Pro Thr
    1985                1990                1995
Val Ser Ser Tyr Gln Ile Thr Asp Glu Tyr Asp Ala Tyr Leu Asp
    2000                2005                2010
Met Val Asp Gly Ser Glu Ser Cys Leu Asp Arg Ala Thr Phe Asn
    2015                2020                2025
Pro Ser Lys Leu Arg Ser Tyr Pro Lys Gln His Ala Tyr His Ala
    2030                2035                2040
Pro Ser Ile Arg Ser Ala Val Pro Ser Pro Phe Gln Asn Thr Leu
    2045                2050                2055
```

```
Gln Asn Val Leu Ala Ala Ala Thr Lys Arg Asn Cys Asn Val Thr
    2060                2065                2070

Gln Met Arg Glu Leu Pro Thr Leu Asp Ser Ala Val Phe Asn Val
    2075                2080                2085

Glu Cys Phe Lys Lys Phe Ala Cys Asn Gln Glu Tyr Trp Glu Glu
    2090                2095                2100

Phe Ala Ala Ser Pro Ile Arg Ile Thr Thr Glu Asn Leu Ala Thr
    2105                2110                2115

Tyr Val Thr Lys Leu Lys Gly Pro Lys Ala Ala Ala Leu Phe Ala
    2120                2125                2130

Lys Thr His Asn Leu Leu Pro Leu Gln Glu Val Pro Met Asp Arg
    2135                2140                2145

Phe Thr Val Asp Met Lys Arg Asp Val Lys Val Thr Pro Gly Thr
    2150                2155                2160

Lys His Thr Glu Glu Arg Pro Lys Val Gln Val Ile Gln Ala Ala
    2165                2170                2175

Glu Pro Leu Ala Thr Ala Tyr Leu Cys Gly Ile His Arg Glu Leu
    2180                2185                2190

Val Arg Arg Leu Asn Ala Val Leu Leu Pro Asn Val His Thr Leu
    2195                2200                2205

Phe Asp Met Ser Ala Glu Asp Phe Asp Ala Ile Ile Ala Ala His
    2210                2215                2220

Phe Lys Pro Gly Asp Thr Val Leu Glu Thr Asp Ile Ala Ser Phe
    2225                2230                2235

Asp Lys Ser Gln Asp Asp Ser Leu Ala Leu Thr Ala Leu Met Leu
    2240                2245                2250

Leu Glu Asp Leu Gly Val Asp His Ser Leu Leu Asp Leu Ile Glu
    2255                2260                2265

Ala Ala Phe Gly Glu Ile Ser Ser Cys His Leu Pro Thr Gly Thr
    2270                2275                2280

Arg Phe Lys Phe Gly Ala Met Met Lys Ser Gly Met Phe Leu Thr
    2285                2290                2295

Leu Phe Val Asn Thr Leu Leu Asn Ile Thr Ile Ala Ser Arg Val
    2300                2305                2310

Leu Glu Asp Arg Leu Thr Lys Ser Ala Cys Ala Ala Phe Ile Gly
    2315                2320                2325

Asp Asp Asn Ile Ile His Gly Val Val Ser Asp Glu Leu Met Ala
    2330                2335                2340

Ala Arg Cys Ala Thr Trp Met Asn Met Glu Val Lys Ile Ile Asp
    2345                2350                2355

Ala Val Val Ser Leu Lys Ala Pro Tyr Phe Cys Gly Gly Phe Ile
    2360                2365                2370

Leu His Asp Thr Val Thr Gly Thr Ala Cys Arg Val Ala Asp Pro
    2375                2380                2385

Leu Lys Arg Leu Phe Lys Leu Gly Lys Pro Leu Ala Ala Gly Asp
    2390                2395                2400

Glu Gln Asp Glu Asp Arg Arg Arg Ala Leu Ala Asp Glu Val Ile
    2405                2410                2415

Arg Trp Gln Arg Thr Gly Leu Ile Asp Glu Leu Glu Lys Ala Val
    2420                2425                2430

Tyr Ser Arg Tyr Glu Val Gln Gly Ile Ser Val Val Val Met Ser
    2435                2440                2445
```

```
Met Ala Thr Phe Ala Ser Ser Arg Ser Asn Phe Glu Lys Leu Arg
    2450                2455                2460

Gly Pro Val Ile Thr Leu Tyr Gly Gly Pro Lys
    2465                2470
```

<210> SEQ ID NO 5
<211> LENGTH: 11835
<212> TYPE: DNA
<213> ORGANISM: Artificial sequence
<220> FEATURE:
<223> OTHER INFORMATION: Polynucleotide sequence of CHIKV LR2006 OPY1
      non-structural polyprotein with mutation at position 532 (CHIKV-R532H).

<400> SEQUENCE: 5

```
atggctgcgt gagacacacg tagcctacca gtttcttact gctctactct gcaaagcaag     60
agattaataa cccatcatgg atcctgtgta cgtggacata gacgctgaca gcgccttttt    120
gaaggccctg caacgtgcgt accccatgtt tgaggtggaa ccaaggcagg tcacaccgaa    180
tgaccatgct aatgctagag cgttctcgca tctagctata aaactaatag agcaggaaat    240
tgaccccgac tcaaccatcc tggatatcgg cagtgcgcca gcaaggagga tgatgtcgga    300
caggaagtac cactgcgtct gcccgatgcg cagtgcggaa gatcccgaga gactcgccaa    360
ttatgcgaga aagctagcat ctgccgcagg aaaagtcctg gacagaaaca tctctggaaa    420
gatcggggac ttacaagcag taatggccgt gccagacacg gagacgccaa cattctgctt    480
acacacagac gtctcatgta gacagagagc agacgtcgct atataccaag acgtctatgc    540
tgtacacgca cccacgtcgc tataccacca ggcgattaaa ggggtccgag tggcgtactg    600
ggttgggttc gacacaaccc cgttcatgta caatgccatg gcgggtgcct acccctcata    660
ctcgacaaac tgggcagatg agcaggtact gaaggctaag aacataggat tatgttcaac    720
agacctgacg gaaggtagac gaggcaagtt gtctattatg agagggaaaa agctaaaacc    780
gtgcgaccgt gtgctgttct cagtagggtc aacgctctac ccggaaagcc gcaagctact    840
taagagctgg cacctgccat cggtgttcca tttaaagggc aaactcagct tcacatgccg    900
ctgtgataca gtggtttcgt gtgagggcta cgtcgttaag agaataacga tgagcccagg    960
cctttatgga aaaaccacag ggtatgcggt aacccaccac gcagacggat tcctgatgtg   1020
caagactacc gacacggttg acggcgaaag aatgtcattc tcggtgtgca catacgtgcc   1080
ggcgaccatt tgtgatcaaa tgaccggcat ccttgctaca gaagtcacgc cggaggatgc   1140
acagaagctg ttggtggggc tgaaccagag aatagtggtt aacggcagaa cgcaacggaa   1200
tacgaacacc atgaaaaatt atctgcttcc cgtggtcgcc caagccttca gtaagtgggc   1260
aaaggagtgc cggaaagaca tggaagatga aaaactcctg gggtcagag aaagaacact   1320 gacctgctgc tgtctatggg cattcaagaa gcagaaaaca cacacggtct acaagaggcc   1380
tgatacccag tcaattcaga aggttcaggc cgagtttgac agctttgtgg taccgagtct   1440
gtggtcgtcc gggttgtcaa tccctttgag gactagaatc aaatggttgt taagcaaggt   1500
gccaaaaacc gacctgatcc catacagcgg agacgcccga gaagcccggg acgcagaaaa   1560
agaagcagag gaagaacgag aagcagaact gactcgcgaa gccctaccac ctctacaggc   1620
agcacaggaa gatgttcagg tcgaaatcga cgtggaacag cttgaggacc acgcgggcgc   1680
aggaataata gagactccga gaggagctat caaagttact gcccaaccaa cagaccacgt   1740
cgtgggagag tacctggtac tctccccgca gaccgtacta cgtagccaga agctcagtct   1800
gattcacgct ttggcggagc aagtgaagac gtgcacgcac aacggacgag cagggaggta   1860
```

```
tgcggtcgaa gcgtacgacg gccgagtcct agtgccctca ggctatgcaa tctcgcctga   1920
agacttccag agtctaagcg aaagcgcaac gatggtgtat aacgaaagag agttcgtaaa   1980
cagaaagcta caccatattg cgatgcacgg accagccctg aacaccgacg aagagtcgta   2040
tgagctggtg agggcagaga ggacagaaca cgagtacgtc tacgacgtgg atcagagaag   2100
atgctgtaag aaggaagaag ccgcaggact ggtactggtg ggcgacttga ctaatccgcc   2160
ctaccacgaa ttcgcatatg aagggctaaa atccgccct gcctgccat acaaaattgc     2220 agtcatagga gtcttcggag taccgggatc tggcaagtca gctattatca agaacctagt   2280
taccaggcag gacctggtga ctagcggaaa gaaagaaaac tgccaagaaa tcaccaccga   2340
cgtgatgaga cagagaggtc tagagatatc tgcacgtacg gttgactcgc tgctcttgaa   2400
tggatgcaac agaccagtcg acgtgttgta cgtagacgag gcgtttgcgt gccactctgg   2460
aacgctactt gctttgatcg ccttggtgag accaaggcag aaagttgtac tttgtggtga   2520
cccgaagcag tgcggcttct tcaatatgat gcagatgaaa gtcaactata atcacaacat   2580
ctgcacccaa gtgtaccaca aaagtatctc caggcggtgt acactgcctg tgaccgccat   2640
tgtgtcatcg ttgcattacg aaggcaaaat gcgcactacg aatgagtaca caagccgat    2700 tgtagtggac actacaggct caacaaaacc tgaccctgga gacctcgtgt taacgtgctt   2760
cagagggtgg gttaaacaac tgcaaattga ctatcgtgga tacgaggtca tgacagcagc   2820
cgcatcccaa gggttaacca gaaaggagt ttacgcagtt agacaaaaag ttaatgaaaa     2880
cccgctctat gcatcaacgt cagagcacgt caacgtactc ctaacgcgta cggaaggtaa   2940
actggtatgg aagacactt ccggcgaccc gtggataaag acgctgcaga cccaccgaa      3000 aggaaacttc aaagcaacta ttaaggagtg gaggtggag catgcatcaa taatggcggg    3060
catctgcagt caccaaatga ccttcgatac attccaaaat aaagccaacg tttgttgggc   3120
taagagcttg gtccctatcc tcgaaacagc ggggataaaa ctaaatgata ggcagtggtc   3180
tcagataatt caagccttca agaagacaa agcatactca cctgaagtag ccctgaatga    3240
aatatgtacg cgcatgtatg gggtggatct agacagcggg ctatttcta aaccgttggt    3300 gtctgtgtat tacgcggata accactggga taataggcct ggagggaaaa tgttcggatt   3360
taaccccgag gcagcatcca ttctagaaag aaagtatcca ttcacaaag ggaagtggaa    3420 catcaacaag cagatctgcg tgactaccag gaggatagaa gactttaacc ctaccaccaa   3480
catcataccg gccaacagga gactaccaca ctcattagtg gccgaacacc gcccagtaaa   3540
aggggaaaga atggaatggc tggttaacaa gataaacggc caccacgtgc tcctggtcag   3600
tggctataac cttgcactgc ctactaagag agtcacttgg gtagcgccgt aggtgtccg    3660 cggagcggac tacacataca acctagagtt gggtctgcca gcaacgcttg gtaggtatga   3720
cctagtggtc ataaacatcc acacaccttt tcgcatacac cattaccaac agtgcgtcga   3780
ccacgcaatg aaactgcaaa tgctcggggg tgactcattg agactgctca accgggcgg    3840 ctctctattg atcagagcat atggttacgc agatagaacc agtgaacgag tcatctgcgt   3900
attgggacgc aagtttagat cgtctagagc gttgaaacca ccatgtgtca ccagcaacac   3960
tgagatgttt ttcctattca gcaactttga caatggcaga aggaatttca caactcatgt   4020
catgaacaat caactgaatg cagccttcgt aggacaggtc acccgagcag gatgtgcacc   4080 gtcgtaccg gtaaaacgca tggacatcgc gaagaacgat gaagagtgcg tagtcaacg    4140 cgctaaccct cgcggggttac cgggtggcgg tgtttgcaag gcagtataca aaaatggcc   4200
```

```
ggagtcctttt aagaacagtg caacaccagt gggaaccgca aaaacagtta tgtgcggtac    4260
gtatccagta atccacgctg ttggaccaaa cttctctaat tattcggagt ctgaagggga    4320
ccgggaattg gcagctgcct atcgagaagt cgcaaaggaa gtaactaggc tgggagtaaa    4380
tagtgtagct atacctctcc tctccacagg tgtatactca ggagggaaag acaggctgac    4440
ccagtcactg aaccacctct ttacagccat ggactcgacg gatgcagacg tggtcatcta    4500
ctgccgcgac aaagaatggg agaagaaaat atctgaggcc atacagatgc ggacccaagt    4560
agagctgctg gatgagcaca tctccataga ctgcgatatt gttcgcgtgc accctgacag    4620
cagcttggca ggcagaaaag gatacagcac cacggaaggc gcactgtact catatctaga    4680
agggacccgt tttcatcaga cggctgtgga tatggcggag atacatacta tgtggccaaa    4740
gcaaacagag gccaatgagc aagtctgcct atatgccctg ggggaaagta ttgaatcgat    4800
caggcagaaa tgcccggtgg atgatgcaga cgcatcatct ccccccaaaa ctgtcccgtg    4860
cctttgccgt tacgctatga ctccagaacg cgtcacccgg cttcgcatga accacgtcac    4920
aagcataatt gtgtgttctt cgtttccccct cccaaagtac aaaatagaag gagtgcaaaa    4980
agtcaaatgc tctaaggtaa tgctatttga ccacaacgtg ccatcgcgcg taagtccaag    5040
ggaatataga tcttcccagg agtctgcaca ggaggcgagt acaatcacgt cactgacgca    5100
tagtcaattc gacctaagcg ttgatggcga gatactgccc gtcccgtcag acctggatgc    5160
tgacgcccca gccctagaac cagcactaga cgacggggcg acacacacgc tgccatccac    5220
aaccggaaac cttgcggccg tgtctgattg ggtaatgagc accgtacctg tcgcgccgcc    5280
cagaagaagg cgagggagaa acctgactgt gacatgtgac gagagagaag ggaatataac    5340
acccatggct agcgtccgat tctttagggc agagctgtgt ccggtcgtac aagaaacagc    5400
ggagacgcgt gacacagcaa tgtctcttca ggcaccaccg agtaccgcca cggaaccgaa    5460
tcatccgccg atctccttcg gagcatcaag cgagacgttc cccattacat tggggactt    5520
caacgaagga gaaatcgaaa gcttgtcttc tgagctacta actttcggag acttcttacc    5580
aggagaagtg gatgacttga cagacagcga ctggtccacg tgctcagaca cggacgacga    5640
gttaagacta gacaggggcag gtgggtatat attctcgtcg acaccggtc caggtcattt    5700
acaacagaag tcagtacgcc agtcagtgct gccggtgaac accctggagg aagtccacga    5760
ggagaagtgt tacccaccta agctggatga agcaaaggag caactattac ttaagaaact    5820
ccaggagagt gcatccatgg ccaacagaag caggtatcag tcgcgcaaag tagaaaacat    5880
gaaagcagca atcatccaga gactaaagag aggctagtaga ctatacttaa tgtcagagac    5940
cccaaaagtc cctacttacc ggactacata tccggcgcct gtgtactcgc ctccgatcaa    6000
cgtccgattg tccaatcccg agtccgcagt ggcagcatgc aatgagttct tagctagaaa    6060
ctatccaact gtctcatcat accaaattac cgacgagtat gatgcatatc tagacatggt    6120
ggacgggtcg gagagttgcc tggaccgagc gacattcaat ccgtcaaaac tcaggagcta    6180
cccgaaacag cacgcttacc acgcgccctc catcagaagc gctgtaccgt ccccattcca    6240
gaacacacta cagaatgtac tggcagcagc cacgaaaaga aactgcaacg tcacacagat    6300
gagggaatta cccactttgg actcagcagt attcaacgtg gagtgtttca aaaaattcgc    6360
atgcaaccaa gaatactggg aagaatttgc tgccagccct attaggataa caactgagaa    6420
tttagcaacc tatgttacta aactaaaagg gccaaaagca gcagcgctat cgcaaaaaac    6480
ccataatcta ctgccactac aggaagtacc aatggatagg ttcacagtag atatgaaaag    6540
ggacgtaaag gtgactcctg gtacaaagca tacagaggaa agacctaagg tgcaggttat    6600
```

-continued

```
acaggcggct gaacccttgg cgacagcata cctatgtggg attcacagag agctggttag    6660
gaggctgaac gccgtcctcc tacccaatgt acatacacta tttgacatgt ctgccgagga    6720
tttcgatgcc atcatagccg cacactttaa gccaggagac actgttttgg aaacggacat    6780
agcctccttt gataagagcc aagatgattc acttgcgctt actgctttga tgctgttaga    6840
ggatttaggg gtggatcact ccctgctgga cttgatagag gctgctttcg gagagatttc    6900
cagctgtcac ctaccgacag gtacgcgctt caagttcggc gccatgatga aatcaggtat    6960
gttcctaact ctgttcgtca acacattgtt aaacatcacc atcgccagcc gagtgctgga    7020
agatcgtctg acaaaatccg cgtgcgcggc cttcatcggc gacgcaacaa taatacatgg    7080
agtcgtctcc gatgaattga tggcagccag atgtgccact tggatgaaca tggaagtgaa    7140
gatcatagat gcagttgtat ccttgaaagc cccttacttt tgtggagggt ttatactgca    7200
cgatactgtg acaggaacag cttgcagagt ggcagacccg ctaaaaaggc tttttaaact    7260
gggcaaaccg ctagcggcag gtgacgaaca agatgaagat agaagacgag cgctggctga    7320
cgaagtgatc agatggcaac gaacagggct aattgatgag ctggagaaag cggtatactc    7380
taggtacgaa gtgcagggta tatcagttgt ggtaatgtcc atggccacct ttgcaagctc    7440
cagatccaac ttcgagaagc tcagaggacc cgtcataact ttgtacggcg gtcctaaata    7500
ggtacgcact acagctacct attttgcaga agccgacagc aagtatctaa acactaatca    7560
gctacaatgg agttcatccc aacccaaact ttttacaata ggaggtacca gcctcgaccc    7620
tggactccgc gccctactat ccaagtcatc aggcccagac cgcgccctca gaggcaagct    7680
gggcaacttg cccagctgat ctcagcagtt aataaactga caatgcgcgc ggtaccacaa    7740
cagaagccac gcaggaatcg gaagaataag aagcaaaagc aaaaacaaca ggcgccacaa    7800
aacaacacaa atcaaaagaa gcagccacct aaaaagaaac cggctcaaaa gaaaaagaag    7860
ccgggccgca gagagaggat gtgcatgaaa atcgaaaatg attgtatttt cgaagtcaag    7920
cacgaaggta aggtaacagg ttacgcgtgc ctggtggggg acaaagtaat gaaaccagca    7980
cacgtaaagg ggaccatcga taacgcggac ctggccaaac tggcctttaa gcggtcatct    8040
aagtatgacc ttgaatgcgc gcagataccc gtgcacatga agtccgacgc ttcgaagttc    8100
acccatgaga aaccggaggg gtactacaac tggcaccacg gagcagtaca gtactcagga    8160
ggccggttca ccatccctac aggtgctggc aaaccagggg acagcggcag accgatcttc    8220
gacaacaagg gacgcgtggt ggccatagtc ttaggaggag ctaatgaagg agcccgtaca    8280
gccctctcgg tggtgacctg gaataaagac attgtcacta aaatcacccc cgagggggcc    8340
gaagagtgga gtcttgccat cccagttatg tgcctgttgg caaacaccac gttccctgc    8400 tcccagcccc cttgcacgcc ctgctgctac gaaaaggaac cggaggaaac cctacgcatg    8460
cttgaggaca acgtcatgag acctgggtac tatcagctgc tacaagcatc cttaacatgt    8520
tctccccacc gccagcgacg cagcaccaag gacaacttca atgtctataa agccacaaga    8580
ccatacttag ctcactgtcc cgactgtgga gaagggcact cgtgccatag tcccgtagca    8640
ctagaacgca tcagaaatga agcgacagac gggacgctga aaatccaggt ctccttgcaa    8700
atcggaataa agacggatga cagccacgat tggaccaagc tgcgttatat ggacaaccac    8760
atgccagcag acgcagagag ggcggggcta tttgtaagaa catcagcacc gtgtacgatt    8820
actggaacaa tgggacactt catcctggcc cgatgtccaa aaggggaaac tctgacggtg    8880
ggattcactg acagtaggaa gattagtcac tcatgtacgc acccatttca ccacgaccct    8940
```

```
cctgtgatag gtcgggaaaa attccattcc cgaccgcagc acggtaaaga gctaccttgc   9000
agcacgtacg tgcagagcac cgccgcaact accgaggaga tagaggtaca catgccccca   9060 gacaccctg  atcgcacatt aatgtcacaa cagtccggca acgtaaagat cacagtcaat    9120 ggccagacg  tgcggtacaa gtgtaattgc ggtggctcaa atgaaggact aacaactaca    9180
gacaaagtga ttaataactg caaggttgat caatgtcatg ccgcggtcac caatcacaaa   9240
aagtggcagt ataactcccc tctggtcccg cgtaatgctg aacttgggga ccgaaaagga   9300
aaaattcaca tcccgtttcc gctggcaaat gtaacatgca gggtgcctaa agcaaggaac   9360
cccaccgtga cgtacgggaa aaaccaagtc atcatgctac tgtatcctga ccacccaaca   9420
ctcctgtcct accggaatat gggagaagaa ccaaactatc aagaagagtg ggtgatgcat   9480
aagaaggaag tcgtgctaac cgtgccgact gaagggctcg aggtcacgtg gggcaacaac   9540
gagccgtata agtattggcc gcagttatct acaaacggta cagcccatgg ccacccgcat   9600
gagataattc tgtattatta tgagctgtac cccactatga ctgtagtagt tgtgtcagtg   9660
gccacgttca tactcctgtc gatggtgggt atggcagcgg ggatgtgcat gtgtgcacga   9720
cgcagatgca tcacaccgta tgaactgaca ccaggagcta ccgtcccttt cctgcttagc   9780
ctaatatgct gcatcagaac agctaaagcg gcccatacc  aagaggctgc gatatacctg   9840
tggaacgagc agcaaccttt gttttggcta caagccctta ttccgctggc agccctgatt   9900
gttctatgca actgtctgag actcttacca tgctgctgta aaacgttggc ttttttagcc   9960
gtaatgagcg tcggtgccca cactgtgagc gcgtacgaac acgtaacagt gatcccgaac  10020
acggtgggag taccgtataa gactctagtc aatagacctg gctacagccc catggtattg  10080
gagatggaac tactgtcagt cactttggag ccaacactat cgcttgatta catcacgtgc  10140
gagtacaaaa ccgtcatccc gtctccgtac gtgaagtgct gcggtacagc agagtgcaag  10200
gacaaaaacc tacctgacta cagctgtaag gtcttcaccg gcgtctaccc atttatgtgg  10260
ggcggcgcct actgcttctg cgacgctgaa aacacgcagt tgagcgaagc acacgtggag  10320
aagtccgaat catgcaaaac agaatttgca tcagcataca gggctcatac cgcatctgca  10380
tcagctaagc tccgcgtcct ttaccaagga aataacatca ctgtaactgc ctatgcaaac  10440
ggcgaccatg ccgtcacagt taaggacgcc aaattcattg tggggccaat gtcttcagcc  10500
tggacacctt tcgacaacaa aattgtggtg tacaaaggtg acgtctataa catggactac  10560 ccgcccttg  gcgcaggaag accaggacaa tttggcgata tccaaagtcg cacacctgag   10620
agtaaagacg tctatgctaa tacacaactg gtactgcaga gaccggctgt gggtacggta  10680
cacgtgccat actctcaggc accatctggc tttaagtatt ggctaaaaga acgcggggcg  10740
tcgctgcagc acacagcacc atttggctgc caaatagcaa caaacccggt aagagcggtg  10800
aactgcgccg tagggaacat gcccatctcc atcgacatac cggaagcggc cttcactagg  10860
gtcgtcgacg cgccctcttt aacgacatg  tcgtgcgagg taccagcctg cacccattcc   10920
tcagactttg ggggcgtcgc cattattaaa tatgcagcca gcaagaaagg caagtgtgcg  10980
gtgcattcga tgactaacgc cgtcactatt cgggaagctg agatagaagt tgaagggaat  11040
tctcagctgc aaatctcttt ctcgacggcc ttagccagcg ccgaattccg cgtacaagtc  11100
tgttctacac aagtacactg tgcagccgag tgccaccccc cgaaggacca catagtcaac  11160 tacccgcgt  cacataccac cctcgggtc  caggacatct ccgctacggc gatgtcatgg    11220
gtgcagaaga tcacgggagg tgtgggactg gttgttgctg ttgccgcact gattctaatc  11280
gtggtgctat gcgtgtcgtt cagcaggcac taacttgaca attaagtatg aaggtatatg  11340
```

```
tgtcccctaa gagacacact gtacatagca aataatctat agatcaaagg gctacgcaac    11400
ccctgaatag taacaaaata caaaatcact aaaaattata aaaacagaaa aatacataaa    11460
taggtatacg tgtcccctaa gagacacatt gtatgtaggt gataagtata gatcaaaggg    11520
ccgaataacc cctgaatagt aacaaaatat gaaaatcaat aaaaatcata aaatagaaaa    11580
accataaaca gaagtagttc aaagggctat aaaaccoctg aatagtaaca aaacataaaa    11640
ttaataaaaa tcaaatgaat accataattg gcaaacggaa gagatgtagg tacttaagct    11700
tcctaaaagc agccgaactc actttgagaa gtaggcatag cataccgaac tcttccacga    11760
ttctccgaac ccacagggac gtaggagatg ttattttgtt tttaatattt caaaaaaaaa    11820
aaaaaaaaaa aaaaa                                                    11835
```

<210> SEQ ID NO 6
<211> LENGTH: 11835
<212> TYPE: DNA
<213> ORGANISM: Artificial sequence
<220> FEATURE:
<223> OTHER INFORMATION: Polynucleotide sequence of CHIKV LR2006 OPY1
    non-structural polyprotein with mutation at position 1050
    (CHIKV-E1050V).

<400> SEQUENCE: 6

```
atggctgcgt gagacacacg tagcctacca gtttcttact gctctactct gcaaagcaag      60
agattaataa cccatcatgg atcctgtgta cgtggacata gacgctgaca gcgccttttt     120
gaaggccctg caacgtgcgt accccatgtt gaggtggaa ccaaggcagg tcacaccgaa      180
tgaccatgct aatgctagag cgttctcgca tctagctata aaactaatag agcaggaaat     240
tgaccccgac tcaaccatcc tggatatcgg cagtgcgcca gcaaggagga tgatgtcgga     300
caggaagtac cactgcgtct gcccgatgcg cagtgcggaa gatcccgaga gactcgccaa     360
ttatgcgaga aagctagcat ctgccgcagg aaaagtcctg gacagaaaca tctctggaaa     420
gatcggggac ttacaagcag taatggccgt gccagacacg gagacgccaa cattctgctt     480
acacacagac gtctcatgta gacagagagc agacgtcgct atataccaag acgtctatgc     540
tgtacacgca cccacgtcgc tataccacca ggcgattaaa ggggtccgag tggcgtactg     600
ggttgggttc gacacaaccc cgttcatgta caatgccatg gcgggtgcct accccctcata     660 ctcgacaaac tgggcagatg agcaggtact gaaggctaag aacataggat tatgttcaac     720
agacctgacg gaaggtagac gaggcaagtt gtctattatg agagggaaaa agctaaaacc     780
gtgcgaccgt gtgctgttct cagtagggtc aacgctctac ccggaaagcc gcaagctact     840
taagagctgg cacctgccat cggtgttcca tttaaagggc aaactcagct tcacatgccg     900
ctgtgataca gtggtttcgt gtgagggcta cgtcgttaag agaataacga tgagcccagg     960
cctttatgga aaaaccacag gtatgcggt aacccaccac gcagacggat tcctgatgtg    1020
caagactacc gacacggttg acggcgaaag aatgtcattc tcggtgtgca catacgtgcc    1080
ggcgaccatt tgtgatcaaa tgaccggcat ccttgctaca gaagtcacgc cggaggatgc    1140
acagaagctg ttggtgggc tgaaccagag aatagtggtt aacggcagaa cgcaacggaa    1200
tacgaacacc atgaaaaatt atctgcttcc cgtggtcgcc caagcttca gtaagtgggc    1260 aaaggagtgc cggaaagaca tggaagatga aaaactcctg ggggtcagag aagaacact    1320 gacctgctgc tgtctatggg cattcaagaa gcagaaaaca cacacggtct acaagaggcc    1380 tgataccccag tcaattcaga aggttcaggc cgagtttgac agctttgtgg taccgagtct    1440
```

-continued

```
gtggtcgtcc gggttgtcaa tcccttttgag gactagaatc aaatggttgt taagcaaggt  1500
gccaaaaacc gacctgatcc catacagcgg agacgcccga gaagcccggg acgcagaaaa  1560
agaagcagag gaagaacgag aagcagaact gactcgcgaa gccctaccac ctctacaggc  1620
agcacaggaa gatgttcagg tcgaaatcga cgtggaacag cttgaggaca gagcgggcgc  1680
aggaataata gagactccga gaggagctat caaagttact gcccaaccaa cagaccacgt  1740
cgtgggagag tacctggtac tctccccgca gaccgtacta cgtagccaga agctcagtct  1800
gattcacgct ttggcggagc aagtgaagac gtgcacgcac aacggacgag cagggaggta  1860
tgcggtcgaa gcgtacgacg gccgagtcct agtgccctca ggctatgcaa tctcgcctga  1920
agacttccag agtctaagcg aaagcgcaac gatggtgtat aacgaaagag agttcgtaaa  1980
cagaaagcta caccatattg cgatgcacgg accagccctg aacaccgacg aagagtcgta  2040
tgagctggtg agggcagaga ggacagaaca cgagtacgtc tacgacgtgg atcagagaag  2100
atgctgtaag aaggaagaag ccgcaggact ggtactggtg ggcgacttga ctaatccgcc  2160
ctaccacgaa ttcgcatatg aagggctaaa aatccgccct gcctgccat acaaaattgc   2220
agtcatagga gtcttcggag taccgggatc tggcaagtca gctattatca gaacctagt   2280
taccaggcag gacctggtga ctagcggaaa gaaagaaaac tgccaagaaa tcaccaccga  2340
cgtgatgaga cagagaggtc tagagatatc tgcacgtacg gttgactcgc tgctcttgaa  2400
tggatgcaac agaccagtcg acgtgttgta cgtagacgag gcgtttgcgt gccactctgg  2460
aacgctactt gctttgatcg ccttggtgag accaaggcag aaagttgtac tttgtggtga  2520
cccgaagcag tgcggcttct tcaatatgat gcagatgaaa gtcaactata atcacaacat  2580
ctgcacccaa gtgtaccaca aaagtatctc caggcggtgt acactgcctg tgaccgccat  2640
tgtgtcatcg ttgcattacg aaggcaaaat gcgcactacg aatgagtaca acaagccgat  2700
tgtagtggac actacaggct caacaaaacc tgaccctgga gacctcgtgt taacgtgctt  2760
cagagggtgg gttaaacaac tgcaaattga ctatcgtgga tacgaggtca tgacagcagc  2820
cgcatcccaa gggttaacca gaaaaggagt ttacgcagtt agacaaaaag ttaatgaaaa  2880
cccgctctat gcatcaacgt cagagcacgt caacgtactc ctaacgcgta cggaaggtaa  2940
actggtatgg aagacactttt ccggcgaccc gtggataaag acgctgcaga acccaccgaa  3000
aggaaacttc aaagcaacta ttaaggagtg ggaggtggag catgcatcaa taatggcggg  3060
catctgcagt caccaaatga ccttcgatac attccaaaat aaagccaacg tttgttgggc  3120
taagagcttg gtccctatcc tcgaaacagc ggggataaaa ctaaatgata ggcagtggtc  3180
tcagataatt caagccttca aagaagacaa agcatactca cctgtggtag ccctgaatga  3240
aatatgtacg cgcatgtatg gggtggatct agacagcggg ctattttcta aaccgttggt  3300
gtctgtgtat tacgcggata accactggga taataggcct ggagggaaaa tgttcggatt  3360
taacccccgag gcagcatcca ttctagaaag aaagtatcca ttcacaaaag ggaagtggaa  3420
catcaacaag cagatctgcg tgactaccag gaggatagaa gactttaacc ctaccaccaa  3480
catcataccg gccaacagga gactaccaca ctcattagtg gccgaacacc gcccagtaaa  3540
agggaaaga atggaatggc tggttaacaa gataaacggc caccacgtgc tcctggtcag  3600
tggctataac cttgcactgc ctactaagag agtcacttgg gtagcgccgt taggtgtccg  3660
cggagcggac tacacataca acctagagtt gggtctgcca gcaacgcttg gtaggtatga  3720
cctagtggtc ataaacatcc acacaccttt tcgcatacac cattaccaac agtgcgtcga  3780
ccacgcaatg aaactgcaaa tgctcgggg tgactcattg agactgctca aaccgggcgg  3840
```

```
ctctctattg atcagagcat atggttacgc agatagaacc agtgaacgag tcatctgcgt    3900
attgggacgc aagtttagat cgtctagagc gttgaaacca ccatgtgtca ccagcaacac    3960
tgagatgttt ttcctattca gcaactttga caatggcaga aggaatttca caactcatgt    4020
catgaacaat caactgaatg cagccttcgt aggacaggtc acccgagcag gatgtgcacc    4080
gtcgtaccgg gtaaaacgca tggacatcgc gaagaacgat gaagagtgcg tagtcaacgc    4140
cgctaaccct cgcgggttac cgggtggcgg tgtttgcaag gcagtataca aaaatggcc    4200 ggagtccttt aagaacagtg caacaccagt gggaaccgca aaaacagtta tgtgcggtac    4260
gtatccagta atccacgctg ttggaccaaa cttctctaat tattcggagt ctgaaggga    4320 ccgggaattg gcagctgcct atcgagaagt cgcaaaggaa gtaactaggc tgggagtaaa    4380
tagtgtagct atacctctcc tctccacagg tgtatactca ggagggaaag acaggctgac    4440
ccagtcactg aaccacctct ttacagccat ggactcgacg gatgcagacg tggtcatcta    4500
ctgccgcgac aaagaatggg agaagaaaat atctgaggcc atacagatgc ggacccaagt    4560
agagctgctg gatgagcaca tctccataga ctgcgatatt gttcgcgtgc accctgacag    4620
cagcttggca ggcagaaaag gatacagcac cacggaaggc gcactgtact catatctaga    4680
agggacccgt tttcatcaga cggctgtgga tatggcggag atacatacta tgtggccaaa    4740
gcaaacagag gccaatgagc aagtctgcct atatgccctg ggggaaagta ttgaatcgat    4800
caggcagaaa tgcccggtgg atgatgcaga cgcatcatct cccccccaaaa ctgtcccgtg    4860 cctttgccgt tacgctatga ctccagaacg cgtcacccgg cttcgcatga accacgtcac    4920
aagcataatt gtgtgttctt cgtttccct cccaaagtac aaaatagaag gagtgcaaaa    4980
agtcaaatgc tctaaggtaa tgctatttga ccacaacgtg ccatcgcgcg taagtccaag    5040
ggaatataga tcttcccagg agtctgcaca ggaggcgagt acaatcacgt cactgacgca    5100
tagtcaattc gacctaagcg ttgatggcga gatactgccc gtcccgtcag acctggatgc    5160
tgacgcccca gccctagaac cagcactaga cgacggggcg acacacacgc tgccatccac    5220
aaccggaaac cttgcggccg tgtctgattg ggtaatgagc accgtacctg tcgcgccgcc    5280
cagaagaagg cgagggagaa acctgactgt gacatgtgac gagagagaag ggaatataac    5340
acccatggct agcgtccgat tctttagggc agagctgtgt ccggtcgtac aagaaacagc    5400
ggagacgcgt gacacagcaa tgtctcttca ggcaccaccg agtaccgcca cggaaccgaa    5460
tcatccgccg atctccttcg gagcatcaag cgagacgttc cccattacat tggggactt    5520 caacgaagga gaaatcgaaa gcttgtcttc tgagctacta actttcggag acttcttacc    5580
aggagaagtg gatgacttga cagacagcga ctggtccacg tgctcagaca cggacgacga    5640
gttaagacta gacagggcag gtgggtatat attctcgtcg acaccggtc caggtcatt    5700 acaacagaag tcagtacgcc agtcagtgct gccggtgaac accctggagg aagtccacga    5760
ggagaagtgt acccaccta agctggatga agcaaaggag caactattac ttaagaaact    5820
ccaggagagt gcatccatgg ccaacagaag caggtatcag tcgcgcaaag tagaaaacat    5880
gaaagcagca atcatccaga gactaaagag aggctgtaga ctatacttaa tgtcagagac    5940
cccaaaagtc cctacttacc ggactacata tccggcgcct gtgtactcgc ctccgatcaa    6000
cgtccgattg tccaatcccg agtccgcagt ggcagcatgc aatgagttct agctagaaa    6060 ctatccaact gtctcatcat accaaattac cgacagagtat gatgcatatc tagacatggt    6120
ggacgggtcg gagagttgcc tggaccgagc gacattcaat ccgtcaaaac tcaggagcta    6180
```

```
cccgaaacag cacgcttacc acgcgccctc catcagaagc gctgtaccgt ccccattcca    6240
gaacacacta cagaatgtac tggcagcagc cacgaaaaga aactgcaacg tcacacagat    6300
gagggaatta cccactttgg actcagcagt attcaacgtg gagtgtttca aaaaattcgc    6360
atgcaaccaa gaatactggg aagaatttgc tgccagccct attaggataa caactgagaa    6420
tttagcaacc tatgttacta aactaaaagg gccaaaagca gcagcgctat tcgcaaaaac    6480
ccataatcta ctgccactac aggaagtacc aatggatagg ttcacagtag atatgaaaag    6540
ggacgtaaag gtgactcctg gtacaaagca tacagaggaa agacctaagg tgcaggttat    6600
acaggcggct gaacccttgg cgacagcata cctatgtggg attcacagag agctggttag    6660
gaggctgaac gccgtcctcc tacccaatgt acatacacta tttgacatgt ctgccgagga    6720
tttcgatgcc atcatagccg cacactttaa gccaggagac actgttttgg aaacggacat    6780
agcctccttt gataagagcc aagatgattc acttgcgctt actgctttga tgctgttaga    6840
ggatttaggg gtggatcact ccctgctgga cttgatagag gctgctttcg gagagatttc    6900
cagctgtcac ctaccgacag gtacgcgctt caagttcggc gccatgatga aatcaggtat    6960
gttcctaact ctgttcgtca acacattgtt aaacatcacc atcgccagcc gagtgctgga    7020
agatcgtctg acaaaatccg cgtgcgcggc cttcatcggc gacgacaaca taatacatgg    7080
agtcgtctcc gatgaattga tggcagccag atgtgccact tggatgaaca tggaagtgaa    7140
gatcatagat gcagttgtat ccttgaaagc cccttacttt tgtggagggt ttatactgca    7200
cgatactgtg acaggaacag cttgcagagt ggcagacccg ctaaaaaggc ttttttaaact   7260 gggcaaaccg ctagcggcag gtgacgaaca agatgaagat agaagacgag cgctggctga    7320
cgaagtgatc agatggcaac gaacagggct aattgatgag ctggagaaag cggtatactc    7380
taggtacgaa gtgcagggta tatcagttgt ggtaatgtcc atggccacct ttgcaagctc    7440
cagatccaac ttcgagaagc tcagaggacc cgtcataact ttgtacggcg gtcctaaata    7500
ggtacgcact acagctacct attttgcaga agccgacagc aagtatctaa acactaatca    7560
gctacaatgg agttcatccc aacccaaact ttttacaata ggaggtacca gcctcgaccc    7620
tggactccgc gccctactat ccaagtcatc aggcccagac cgcgccctca gaggcaagct    7680
gggcaacttg cccagctgat ctcagcagtt aataaactga caatgcgcgc ggtaccacaa    7740
cagaagccac gcaggaatcg gaagaataag aagcaaaagc aaaaacaaca ggcgccacaa    7800
aacaacacaa atcaaaagaa gcagccacct aaaagaaac cggctcaaaa gaaaaagaag    7860
ccgggccgca gagagaggat gtgcatgaaa atcgaaaatg attgtatttt cgaagtcaag    7920
cacgaaggta aggtaacagg ttacgcgtgc ctggtggggg acaaagtaat gaaaccagca    7980
cacgtaaagg ggaccatcga taacgcggac ctggccaaac tggcctttaa gcggtcatct    8040
aagtatgacc ttgaatgcgc gcagataccc gtgcacatga agtccgacgc ttcgaagttc    8100
acccatgaga aaccggaggg gtactacaac tggcaccacg gagcagtaca gtactcagga    8160
ggccggttca ccatccctac aggtgctggc aaaccagggg acagcggcag accgatcttc    8220
gacaacaagg gacgcgtggt ggccatagtc ttaggaggag ctaatgaagg agcccgtaca    8280
gccctctcgg tggtgacctg gaataaagac attgtcacta aaatcacccc cgagggggcc    8340
gaagagtgga gtcttgccat cccagttatg tgcctgttgg caaacaccac gttccctgc    8400 tcccagccc cttgcacgcc ctgctgctac gaaaaggaac cggaggaaac cctacgcatg    8460
cttgaggaca acgtcatgag acctgggtac tatcagctgc tacaagcatc cttaacatgt    8520
tctccccacc gccagcgacg cagcaccaag gacaacttca atgtctataa agccacaaga    8580
```

```
ccatacttag ctcactgtcc cgactgtgga gaagggcact cgtgccatag tcccgtagca   8640
ctagaacgca tcagaaatga agcgacagac gggacgctga aaatccaggt ctccttgcaa   8700
atcggaataa agacggatga cagccacgat tggaccaagc tgcgttatat ggacaaccac   8760
atgccagcag acgcagagag ggcggggcta tttgtaagaa catcagcacc gtgtacgatt   8820
actggaacaa tgggacactt catcctggcc cgatgtccaa aagggaaac tctgacggtg     8880 ggattcactg acagtaggaa gattagtcac tcatgtacgc acccatttca ccacgaccct   8940
cctgtgatag gtcgggaaaa attccattcc cgaccgcagc acggtaaaga gctaccttgc   9000
agcacgtacg tgcagagcac cgccgcaact accgaggaga tagaggtaca catgccccca   9060
gacacccctg atcgcacatt aatgtcacaa cagtccggca acgtaaagat cacagtcaat   9120
ggccagacgg tgcggtacaa gtgtaattgc ggtggctcaa atgaaggact aacaactaca   9180
gacaaagtga ttaataactg caaggttgat caatgtcatg ccgcggtcac caatcacaaa   9240
aagtggcagt ataactcccc tctggtcccg cgtaatgctg aacttgggga ccgaaaagga   9300
aaaattcaca tcccgtttcc gctggcaaat gtaacatgca gggtgcctaa agcaaggaac   9360
cccaccgtga cgtacgggaa aaaccaagtc atcatgctac tgtatcctga ccacccaaca   9420
ctcctgtcct accggaatat gggagaagaa ccaaactatc aagaagagtg ggtgatgcat   9480
aagaaggaag tcgtgctaac cgtgccgact gaagggctcg aggtcacgtg ggcaacaac    9540 gagccgtata agtattggcc gcagttatct acaaacggta cagcccatgg ccacccgcat   9600
gagataattc tgtattatta tgagctgtac cccactatga ctgtagtagt tgtgtcagtg   9660
gccacgttca tactcctgtc gatggtgggt atggcagcgg ggatgtgcat gtgtgcacga   9720
cgcagatgca tcacaccgta tgaactgaca ccaggagcta ccgtcccttt cctgcttagc   9780
ctaatatgct gcatcagaac agctaaagcg gccacatacc aagaggctgc gatatacctg   9840
tggaacgagc agcaaccttt gttttggcta caagcccctta ttccgctggc agccctgatt  9900
gttctatgca actgtctgag actcttacca tgctgctgta aaacgttggc ttttttagcc   9960
gtaatgagcg tcggtgccca cactgtgagc gcgtacgaac acgtaacagt gatcccgaac  10020
acggtgggag taccgtataa gactctagtc aatagacctg gctacagccc catggtattg  10080
gagatggaac tactgtcagt cactttggag ccaacactat cgcttgatta catcacgtgc  10140
gagtacaaaa ccgtcatccc gtctccgtac gtgaagtgct gcggtacagc agagtgcaag  10200
gacaaaaacc tacctgacta cagctgtaag gtcttcaccg gcgtctaccc atttatgtgg  10260
ggcggcgcct actgcttctg cgacgctgaa aacacgcagt tgagcgaagc acacgtggag  10320
aagtccgaat catgcaaaac agaatttgca tcagcataca gggctcatac cgcatctgca  10380
tcagctaagc tccgcgtcct ttaccaagga ataacatca ctgtaactgc ctatgcaaac    10440
ggcgaccatg ccgtcacagt taaggacgcc aaattcattg tggggccaat gtcttcagcc  10500
tggacacctt tcgacaacaa aattgtggtg tacaaaggtg acgtctataa catgactac    10560 ccgcccttg gcgcaggaag accaggacaa tttggcgata tccaaagtcg cacacctgag   10620
agtaaagacg tctatgctaa tacacaactg gtactgcaga gaccggctgt gggtacggta  10680
cacgtgccat actctcaggc accatctggc tttaagtatt ggctaaaaga acgcggggcg  10740
tcgctgcagc acacagcacc atttggctgc caaatagcaa caaacccggt aagagcggtg  10800
aactgcgccg tagggaacat gcccatctcc atcgacatac cggaagcggc cttcactagg  10860
gtcgtcgacg cgccctcttt aacggacatg tcgtgcgagg taccagcctg cacccattcc  10920
```

```
tcagactttg ggggcgtcgc cattattaaa tatgcagcca gcaagaaagg caagtgtgcg  10980
gtgcattcga tgactaacgc cgtcactatt cgggaagctg agatagaagt tgaagggaat  11040
tctcagctgc aaatctcttt ctcgacggcc ttagccagcg ccgaattccg cgtacaagtc  11100
tgttctacac aagtacactg tgcagccgag tgccaccccc cgaaggacca catagtcaac  11160
tacccggcgt cacataccac cctcggggtc caggacatct ccgctacggc gatgtcatgg  11220
gtgcagaaga tcacgggagg tgtgggactg gttgttgctg ttgccgcact gattctaatc  11280
gtggtgctat gcgtgtcgtt cagcaggcac taacttgaca attaagtatg aaggtatatg  11340
tgtcccctaa gagacacact gtacatagca aataatctat agatcaaagg gctacgcaac  11400
ccctgaatag taacaaaata caaaatcact aaaaattata aaaacagaaa aatacataaa  11460
taggtatacg tgtcccctaa gagacacatt gtatgtaggt gataagtata gatcaaaggg  11520
ccgaataacc cctgaatagt aacaaaatat gaaaatcaat aaaaatcata aaatagaaaa  11580
accataaaca gaagtagttc aaagggctat aaaacccctg aatagtaaca aaacataaaa  11640
ttaataaaaa tcaaatgaat accataattg gcaaacggaa gagatgtagg tacttaagct  11700
tcctaaaagc agccgaactc actttgagaa gtaggcatag cataccgaac tcttccacga  11760
ttctccgaac ccacagggac gtaggagatg ttattttgtt tttaatattt caaaaaaaaa  11820
aaaaaaaaaa aaaaa                                                   11835
```

```
<210> SEQ ID NO 7
<211> LENGTH: 11835
<212> TYPE: DNA
<213> ORGANISM: Artificial sequence
<220> FEATURE:
<223> OTHER INFORMATION: Polynucleotide sequence of CHIKV LR2006 OPY1
      non-structural polyprotein with mutations at 532 and 1050
      (CHIKV-R532H+E1050V).

<400> SEQUENCE: 7
```

```
atggctgcgt gagacacacg tagcctacca gtttcttact gctctactct gcaaagcaag     60
agattaataa cccatcatgg atcctgtgta cgtggacata gacgctgaca gcgccttttt    120
gaaggccctg caacgtgcgt accccatgtt tgaggtggaa ccaaggcagg tcacaccgaa    180
tgaccatgct aatgctagag cgttctcgca tctagctata aaactaatag agcaggaaat    240
tgaccccgac tcaaccatcc tggatatcgg cagtgcgcca gcaaggagga tgatgtcgga    300
caggaagtac cactgcgtct gcccgatgcg cagtgcggaa gatcccgaga gactcgccaa    360
ttatgcgaga aagctagcat ctgccgcagg aaaagtcctg gacagaaaca tctctggaaa    420
gatcggggac ttacaagcag taatggccgt gccagacacg gagacgccaa cattctgctt    480
acacacagac gtctcatgta gacagagagc agacgtcgct atataccaag acgtctatgc    540
tgtacacgca cccacgtcgc tataccacca ggcgattaaa ggggtccgag tggcgtactg    600
ggttgggttc gacacaaccc cgttcatgta caatgccatg gcgggtgcct acccctcata    660
ctcgacaaac tgggcagatg agcaggtact gaaggctaag aacataggat tatgttcaac    720
agacctgacg gaaggtagac gaggcaagtt gtctattatg agagggaaaa agctaaaacc    780
gtgcgaccgt gtgctgttct cagtagggtc aacgctctac ccggaaagcc gcaagctact    840
taagagctgg cacctgccat cggtgttcca tttaaagggc aaactcagct tcacatgccg    900
ctgtgataca gtggtttcgt gtgagggcta cgtcgttaag agaataacga tgagcccagg    960
cctttatgga aaaaccacag ggtatgcggt aacccaccac gcagacggat tcctgatgtg   1020
caagactacc gacacggttg acggcgaaag aatgtcattc tcggtgtgca catacgtgcc   1080
```

```
ggcgaccatt tgtgatcaaa tgaccggcat ccttgctaca gaagtcacgc cggaggatgc      1140
acagaagctg ttggtggggc tgaaccagag aatagtggtt aacggcagaa cgcaacggaa      1200
tacgaacacc atgaaaaatt atctgcttcc cgtggtcgcc caagccttca gtaagtgggc      1260
aaaggagtgc cggaaagaca tggaagatga aaaactcctg ggggtcagag aaagaacact      1320
gacctgctgc tgtctatggg cattcaagaa gcagaaaaca cacacggtct acaagaggcc      1380
tgatacccag tcaattcaga aggttcaggc cgagtttgac agctttgtgg taccgagtct      1440
gtggtcgtcc gggttgtcaa tcccttttgag gactagaatc aaatggttgt taagcaaggt     1500
gccaaaaacc gacctgatcc catacagcgg agacgcccga gaagcccggg acgcagaaaa      1560
agaagcagag gaagaacgag aagcagaact gactcgcgaa gccctaccac ctctacaggc      1620
agcacaggaa gatgttcagg tcgaaatcga cgtggaacag cttgaggacc acgcgggcgc      1680
aggaataata gagactccga gaggagctat caaagttact gcccaaccaa cagaccacgt      1740
cgtgggagag tacctggtac tctccccgca gaccgtacta cgtagccaga agctcagtct      1800
gattcacgct ttggcggagc aagtgaagac gtgcacgcac aacggacgag cagggaggta      1860
tgcggtcgaa gcgtacgacg gccgagtcct agtgccctca ggctatgcaa tctcgcctga      1920
agacttccag agtctaagcg aaagcgcaac gatggtgtat aacgaaagag agttcgtaaa      1980
cagaaagcta caccatattg cgatgcacgg accagccctg aacaccgacg aagagtcgta      2040
tgagctggtg agggcagaga ggacagaaca cgagtacgtc tacgacgtgg atcagagaag      2100
atgctgtaag aaggaagaag ccgcaggact ggtactggtg ggcgacttga ctaatccgcc      2160
ctaccacgaa ttcgcatatg aagggctaaa aatccgccct gcctgcccat acaaaattgc      2220
agtcatagga gtcttcggag taccgggatc tggcaagtca gctattatca gaacctagt      2280 taccaggcag gacctggtga ctagcggaaa gaaagaaaac tgccaagaaa tcaccaccga      2340
cgtgatgaga cagagaggtc tagagatatc tgcacgtacg gttgactcgc tgctcttgaa      2400
tggatgcaac agaccagtcg acgtgttgta cgtagacgag gcgtttgcgt gccactctgg      2460
aacgctactt gctttgatcg ccttggtgag accaaggcag aaagttgtac tttgtggtga      2520
cccgaagcag tgcggcttct tcaatatgat gcagatgaaa gtcaactata atcacaacat      2580
ctgcacccaa gtgtaccaca aaagtatctc caggcggtgt acactgcctg tgaccgccat      2640
tgtgtcatcg ttgcattacg aaggcaaaat gcgcactacg aatgagtaca caagccgat      2700 tgtagtggac actacaggct caacaaaacc tgaccctgga gacctcgtgt aacgtgctt      2760 cagagggtgg gttaaacaac tgcaaattga ctatcgtgga tacgaggtca tgacagcagc      2820
cgcatcccaa gggttaacca gaaaaggagt ttacgcagtt agacaaaaag ttaatgaaaa      2880
cccgctctat gcatcaacgt cagagcacgt caacgtactc ctaacgcgta cggaaggtaa      2940
actggtatgg aagacacttt ccggcgaccc gtggataaag acgctgcaga acccaccgaa      3000
aggaaacttc aaagcaacta ttaaggagtg ggaggtggag catgcatcaa taatggcggg      3060
catctgcagt caccaaatga ccttcgatac attccaaaat aaagccaacg tttgttgggc      3120
taagagcttg gtccctatcc tcgaaacagc ggggataaaa ctaaatgata ggcagtggtc      3180
tcagataatt caagccttca agaagacaa agcatactca cctgtggtag ccctgaatga      3240
aatatgtacg cgcatgtatg gggtggatct agacagcggg ctattttcta aaccgttggt      3300
gtctgtgtat tacgcggata accactggga taataggcct ggagggaaaa tgttcggatt      3360 taacccccgag gcagcatcca ttctagaaag aaagtatcca ttcacaaaag ggaagtggaa      3420
```

```
catcaacaag cagatctgcg tgactaccag gaggatagaa gactttaacc ctaccaccaa    3480
catcataccg gccaacagga gactaccaca ctcattagtg gccgaacacc gcccagtaaa    3540
aggggaaaga atggaatggc tggttaacaa gataaacggc caccacgtgc tcctggtcag    3600
tggctataac cttgcactgc ctactaagag agtcacttgg gtagcgccgt taggtgtccg    3660
cggagcggac tacacataca acctagagtt gggtctgcca gcaacgcttg gtaggtatga    3720
cctagtggtc ataaacatcc acacaccttt tcgcatacac cattaccaac agtgcgtcga    3780
ccacgcaatg aaactgcaaa tgctcggggg tgactcattg agactgctca aaccgggcgg    3840
ctctctattg atcagagcat atggttacgc agatagaacc agtgaacgag tcatctgcgt    3900
attgggacgc aagtttagat cgtctagagc gtttgaaacca ccatgtgtca ccagcaacac    3960
tgagatgttt ttcctattca gcaactttga caatggcaga aggaatttca caactcatgt    4020
catgaacaat caactgaatg cagccttcgt aggacaggtc acccgagcag gatgtgcacc    4080
gtcgtaccgg gtaaaacgca tggacatcgc gaagaacgat gaagagtgcg tagtcaacgc    4140
cgctaaccct cgcgggttac cgggtggcgg tgtttgcaag gcagtataca aaaatggcc    4200 ggagtccttt aagaacagtg caacaccagt gggaaccgca aaaacagtta tgtgcggtac    4260
gtatccagta atccacgctg ttggaccaaa cttctctaat tattcggagt ctgaagggga    4320
ccgggaattg gcagctgcct atcgagaagt cgcaaaggaa gtaactaggc tgggagtaaa    4380
tagtgtagct atacctctcc tctccacagg tgtatactca ggagggaaag acaggctgac    4440
ccagtcactg aaccacctct ttacagccat ggactcgacg gatgcagacg tggtcatcta    4500
ctgccgcgac aaagaatggg agaagaaaat atctgaggcc atacagatgc ggacccaagt    4560
agagctgctg gatgagcaca tctccataga ctgcgatatt gttcgcgtgc accctgacag    4620
cagcttggca ggcagaaaag gatacagcac cacggaaggc gcactgtact catatctaga    4680
agggacccgt tttcatcaga cggctgtgga tatggcggag atacatacta tgtggccaaa    4740
gcaaacagag gccaatgagc aagtctgcct atatgccctg ggggaaagta ttgaatcgat    4800
caggcagaaa tgcccggtgg atgatgcaga cgcatcatct ccccccaaaa ctgtcccgtg    4860
cctttgccgt tacgctatga ctccagaacg cgtcacccgg cttcgcatga accacgtcac    4920
aagcataatt gtgtgttctt cgtttcccct cccaaagtac aaaatagaag gagtgcaaaa    4980
agtcaaatgc tctaaggtaa tgctatttga ccacaacgtg ccatcgcgcg taagtccaag    5040
ggaatataga tcttcccagg agtctgcaca ggaggcgagt acaatcacgt cactgacgca    5100
tagtcaattc gacctaagcg ttgatggcga gatactgccc gtcccgtcag acctggatgc    5160
tgacgcccca gccctagaac cagcactaga cgacggggcg acacacacgc tgccatccac    5220
aaccggaaac cttgcggccg tgtctgattg ggtaatgagc accgtacctg tcgcgccgcc    5280
cagaagaagg cgagggagaa acctgactgt gacatgtgac gagagagaag ggaatataac    5340
acccatggct agcgtccgat tctttaggc agagctgtgt ccggtcgtac aagaaacagc    5400
ggagacgcgt gacacagcaa tgtctcttca ggcaccaccg agtaccgcca cggaaccgaa    5460
tcatccgccg atctccttcg gagcatcaag cgagacgttc cccattacat tggggacttt    5520
caacgaagga gaaatcgaaa gcttgtcttc tgagctacta actttcggag acttcttacc    5580
aggagaagtg gatgacttga cagacagcga ctggtccacg tgctcagaca cggacgacga    5640
gttaagacta gacaggggcag gtgggtatat attctcgtcg gacaccggtc caggtcattt    5700
acaacagaag tcagtacgcc agtcagtgct gccggtgaac acctggagg aagtccacga    5760 ggagaagtgt taccccaccta agctggatga agcaaaggag caactattac ttaagaaact    5820
```

```
ccaggagagt gcatccatgg ccaacagaag caggtatcag tcgcgcaaag tagaaaacat   5880
gaaagcagca atcatccaga gactaaagag aggctgtaga ctatacttaa tgtcagagac   5940
cccaaaagtc cctacttacc ggactacata tccggcgcct gtgtactcgc ctccgatcaa   6000
cgtccgattg tccaatcccg agtccgcagt ggcagcatgc aatgagttct tagctagaaa   6060
ctatccaact gtctcatcat accaaattac cgacgagtat gatgcatatc tagacatggt   6120
ggacgggtcg gagagttgcc tggaccgagc gacattcaat ccgtcaaaac tcaggagcta   6180
cccgaaacag cacgcttacc acgcgccctc catcagaagc gctgtaccgt ccccattcca   6240
gaacacacta cagaatgtac tggcagcagc cacgaaaaga aactgcaacg tcacacagat   6300
gagggaatta cccactttgg actcagcagt attcaacgtg gagtgtttca aaaaattcgc   6360
atgcaaccaa gaatactggg aagaatttgc tgccagccct attaggataa caactgagaa   6420
tttagcaacc tatgttacta aactaaaagg gccaaaagca gcagcgctat tcgcaaaaac   6480
ccataatcta ctgccactac aggaagtacc aatggatagg ttcacagtag atatgaaaag   6540
ggacgtaaag gtgactcctg gtacaaagca tacagaggaa agacctaagg tgcaggttat   6600
acaggcggct gaacccttgg cgacagcata cctatgtggg attcacagag agctggttag   6660
gaggctgaac gccgtcctcc tacccaatgt acatacacta tttgacatgt ctgccgagga   6720
tttcgatgcc atcatagccg cacactttaa gccaggagac actgttttgg aaacggacat   6780
agcctccttt gataagagcc aagatgattc acttgcgctt actgctttga tgctgttaga   6840
ggatttaggg gtggatcact ccctgctgga cttgatagag gctgctttcg gagagatttc   6900
cagctgtcac ctaccgacag gtacgcgctt caagttcggc gccatgatga aatcaggtat   6960
gttcctaact ctgttcgtca acacattgtt aaacatcacc atcgccagcc gagtgctgga   7020
agatcgtctg acaaaatccg cgtgcgcggc cttcatcggc gacgacaaca taatacatgg   7080
agtcgtctcc gatgaattga tggcagccag atgtgccact tggatgaaca tggaagtgaa   7140
gatcatagat gcagttgtat ccttgaaagc cccttacttt gtggagggt ttatactgca   7200 cgatactgtg acaggaacag cttgcagagt ggcagacccg ctaaaaaggc tttttaaact   7260
gggcaaaccg ctagcggcag gtgacgaaca agatgaagat agaagacgag cgctggctga   7320
cgaagtgatc agatggcaac gaacagggct aattgatgag ctggagaaag cggtatactc   7380
taggtacgaa gtgcagggta tatcagttgt ggtaatgtcc atggccacct ttgcaagctc   7440
cagatccaac ttcgagaagc tcagaggacc cgtcataact ttgtacggcg gtcctaaata   7500
ggtacgcact acagctacct attttgcaga agccgacagc aagtatctaa acactaatca   7560
gctacaatgg agttcatccc aacccaaact ttttacaata ggaggtacca gcctcgaccc   7620
tggactccgc gccctactat ccaagtcatc aggcccagac cgcgccctca gaggcaagct   7680
gggcaacttg cccagctgat ctcagcagtt aataaactga caatgcgcgc ggtaccacaa   7740
cagaagccac gcaggaatcg gaagaataag agcaaaagc aaaacaaca ggcgccacaa   7800 aacaacacaa atcaaaagaa gcagccacct aaaagaaac cggctcaaaa gaaaagaag   7860 ccggccgca gagagaggat gtgcatgaaa atcgaaaatg attgtatttt cgaagtcaag   7920
cacgaaggta aggtaacagg ttacgcgtgc ctggtggggg acaaagtaat gaaaccagca   7980
cacgtaaagg ggaccatcga taacgcggac ctggccaaac tggcctttaa gcggtcatct   8040
aagtatgacc ttgaatgcgc gcagataccc gtgcacatga gtccgacgc ttcgaagttc   8100 acccatgaga aaccggaggg gtactacaac tggcaccacg gagcagtaca gtactcagga   8160
```

```
ggccggttca ccatccctac aggtgctggc aaaccagggg acagcggcag accgatcttc   8220
gacaacaagg gacgcgtggt ggccatagtc ttaggaggag ctaatgaagg agcccgtaca   8280
gccctctcgg tggtgacctg aataaagac attgtcacta aaatcacccc cgagggggcc   8340
gaagagtgga gtcttgccat cccagttatg tgcctgttgg caaacaccac gttcccctgc   8400
tcccagcccc cttgcacgcc ctgctgctac gaaaaggaac cggaggaaac cctacgcatg   8460
cttgaggaca acgtcatgag acctgggtac tatcagctgc tacaagcatc cttaacatgt   8520
tctccccacc gccagcgacg cagcaccaag gacaacttca atgtctataa agccacaaga   8580
ccatacttag ctcactgtcc cgactgtgga agggcact cgtgccatag tcccgtagca    8640
ctagaacgca tcagaaatga agcgacagac gggacgctga aaatccaggt ctccttgcaa   8700
atcggaataa agacggatga cagccacgat tggaccaagc tgcgttatat ggacaaccac   8760
atgccagcag acgcagagag ggcggggcta tttgtaagaa catcagcacc gtgtacgatt   8820
actggaacaa tgggacactt catcctggcc cgatgtccaa aagggaaac tctgacggtg    8880 ggattcactg acagtaggaa gattagtcac tcatgtacgc acccatttca ccacgaccct   8940
cctgtgatag gtcgggaaaa attccattcc cgaccgcagc acggtaaaga gctaccttgc   9000
agcacgtacg tgcagagcac cgccgcaact accgaggaga tagaggtaca catgcccca    9060 gacacccctg atcgcacatt aatgtcacaa cagtccggca acgtaaagat cacagtcaat   9120
ggccagacgg tgcggtacaa gtgtaattgc ggtggctcaa atgaaggact aacaactaca   9180
gacaaagtga ttaataactg caaggttgat caatgtcatg ccgcggtcac caatcacaaa   9240
aagtggcagt ataactcccc tctggtcccg cgtaatgctg aacttgggga ccgaaaagga   9300
aaaattcaca tcccgtttcc gctggcaaat gtaacatgca gggtgcctaa agcaaggaac   9360
cccaccgtga cgtacgggaa aaaccaagtc atcatgctac tgtatcctga ccacccaaca   9420
ctcctgtcct accggaatat gggagaagaa ccaaactatc aagaagagtg ggtgatgcat   9480
aagaaggaag tcgtgctaac cgtgccgact gaagggctcg aggtcacgtg ggcaacaac   9540 gagccgtata agtattggcc gcagttatct acaaacggta cagcccatgg ccacccgcat   9600
gagataattc tgtattatta tgagctgtac cccactatga ctgtagtagt tgtgtcagtg   9660
gccacgttca ctactcctgtc gatggtgggt atggcagcgg ggatgtgcat gtgtgcacga   9720
cgcagatgca tcacaccgta tgaactgaca ccaggagcta ccgtcccttt cctgcttagc   9780
ctaatatgct gcatcagaac agctaaagcg gccacatacc aagaggctgc gatatacctg   9840
tggaacgagc agcaaccttt gttttggcta caagcccta ttccgctggc agccctgatt    9900
gttctatgca actgtctgag actcttacca tgctgctgta aaacgttggc tttttagcc    9960 gtaatgagcg tcggtgccca cactgtgagc gcgtacgaac acgtaacagt gatcccgaac  10020
acggtgggag taccgtataa gactctagtc aatagacctg gctacagccc catggtattg  10080
gagatggaac tactgtcagt cactttggag ccaacactat cgcttgatta catcacgtgc  10140
gagtacaaaa ccgtcatccc gtctccgtac gtgaagtgct cgcgtacagc agagtgcaag  10200
gacaaaaacc tacctgacta cagctgtaag gtcttcaccg gcgtctaccc atttatgtgg  10260
ggcggcgcct actgcttctg cgacgctgaa acacgcagt tgagcgaagc acacgtggag  10320
aagtccgaat catgcaaaac agaatttgca tcagcataca gggctcatac cgcatctgca  10380
tcagctaagc tccgcgtcct ttaccaagga aataacatca ctgtaactgc ctatgcaaac  10440
ggcgaccatg ccgtcacagt taaggacgcc aaattcattg tggggccaat gtcttcagcc  10500
tggacacctt tcgacaacaa aattgtggtg tacaaaggtg acgtctataa catggactac  10560
```

```
ccgccctttg gcgcaggaag accaggacaa tttggcgata tccaaagtcg cacacctgag   10620
agtaaagacg tctatgctaa tacacaactg gtactgcaga gaccggctgt gggtacggta   10680
cacgtgccat actctcaggc accatctggc tttaagtatt ggctaaaaga acgcggggcg   10740
tcgctgcagc acacagcacc atttggctgc caaatagcaa caaacccggt aagagcggtg   10800
aactgcgccg tagggaacat gcccatctcc atcgacatac cggaagcggc cttcactagg   10860
gtcgtcgacg cgccctcttt aacgacatg tcgtgcgagg taccagcctg cacccattcc   10920
tcagactttg ggggcgtcgc cattattaaa tatgcagcca gcaagaaagg caagtgtgcg   10980
gtgcattcga tgactaacgc cgtcactatt cgggaagctg agatagaagt tgaagggaat   11040
tctcagctgc aaatctcttt ctcgacggcc ttagccagcg ccgaattccg cgtacaagtc   11100
tgttctacac aagtacactg tgcagccgag tgccaccccc cgaaggacca catagtcaac   11160
tacccggcgt cacataccac cctcggggtc caggacatct ccgctacggc gatgtcatgg   11220
gtgcagaaga tcacggggag tgtgggactg gttgttgctg ttgccgcact gattctaatc   11280
gtggtgctat gcgtgtcgtt cagcaggcac taacttgaca attaagtatg aaggtatatg   11340
tgtcccctaa gagacacact gtacatagca aataatctat agatcaaagg gctacgcaac   11400
ccctgaatag taacaaaata caaaatcact aaaaattata aaaacagaaa aatacataaa   11460
taggtatacg tgtcccctaa gagacacatt gtatgtaggt gataagtata gatcaaaggg   11520
ccgaataacc cctgaatagt aacaaaatat gaaaatcaat aaaaatcata aatagaaaa    11580 accataaaca gaagtagttc aaagggctat aaaaccctg aatagtaaca aaacataaaa   11640
ttaataaaaa tcaaatgaat accataattg gcaaacggaa gagatgtagg tacttaagct   11700
tcctaaaagc agccgaactc actttgagaa gtaggcatag cataccgaac tcttccacga   11760
ttctccgaac ccacagggac gtaggagatg ttattttgtt tttaatattt caaaaaaaaa   11820
aaaaaaaaaa aaaaa                                                     11835
```

<210> SEQ ID NO 8
<211> LENGTH: 2493
<212> TYPE: PRT
<213> ORGANISM: Venezuelan equine encephalitis virus

<400> SEQUENCE: 8

```
Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140
```

```
Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
            165                 170                 175

Gly Phe Asp Thr Thr Pro Phe Met Phe Lys Asn Leu Ala Gly Ala Tyr
                180                 185                 190

Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
                275                 280                 285

Arg Ile Ala Ile Ser Pro Gly Leu Tyr Gly Lys Pro Ser Gly Tyr Ala
290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
                355                 360                 365

Asn Gly Arg Thr Gln Arg Asn Thr Asn Thr Met Lys Asn Tyr Leu Leu
370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
                435                 440                 445

Ser Phe Val Leu Pro Arg Ile Gly Ser Asn Thr Leu Glu Ile Gly Leu
            450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Leu Arg Ala Ala Leu Pro Pro
                500                 505                 510

Leu Ala Ala Asp Val Glu Glu Pro Thr Leu Glu Ala Asp Val Asp Leu
            515                 520                 525

Met Leu Gln Glu Ala Gly Ala Gly Ser Val Glu Thr Pro Arg Gly Leu
            530                 535                 540

Ile Lys Val Thr Ser Tyr Ala Gly Glu Asp Lys Ile Gly Ser Tyr Ala
545                 550                 555                 560
```

```
Val Leu Ser Pro Gln Ala Val Leu Lys Ser Glu Lys Leu Ser Cys Ile
            565                 570                 575

His Pro Leu Ala Glu Gln Val Ile Val Ile Thr His Ser Gly Arg Lys
        580                 585                 590

Gly Arg Tyr Ala Val Glu Pro Tyr His Gly Lys Val Val Pro Glu
    595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Lys Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
                965                 970                 975

Phe Thr Ala Thr Ile Glu Glu Trp Gln Ala Glu His Asp Ala Ile Met
```

-continued

```
                980             985             990
Arg His Ile Leu Glu Arg Pro Asp Pro Thr Asp Val Phe Gln Asn Lys
            995             1000            1005
Ala Asn Val Cys Trp Ala Lys Ala Leu Val Pro Val Leu Lys Thr
    1010            1015            1020
Ala Gly Ile Asp Met Thr Thr Glu Gln Trp Asn Thr Val Asp Tyr
    1025            1030            1035
Phe Glu Thr Asp Lys Ala His Ser Ala Glu Ile Val Leu Asn Gln
    1040            1045            1050
Leu Cys Val Arg Phe Phe Gly Leu Asp Leu Asp Ser Gly Leu Phe
    1055            1060            1065
Ser Ala Pro Thr Val Pro Leu Ser Ile Arg Asn Asn His Trp Asp
    1070            1075            1080
Asn Ser Pro Ser Pro Asn Met Tyr Gly Leu Asn Lys Glu Val Val
    1085            1090            1095
Arg Gln Leu Ser Arg Arg Tyr Pro Gln Leu Pro Arg Ala Val Ala
    1100            1105            1110
Thr Gly Arg Val Tyr Asp Met Asn Thr Gly Thr Leu Arg Asn Tyr
    1115            1120            1125
Asp Pro Arg Ile Asn Leu Val Pro Val Asn Arg Arg Leu Pro His
    1130            1135            1140
Ala Leu Val Leu His His Asn Glu His Pro Gln Ser Asp Phe Ser
    1145            1150            1155
Ser Phe Val Ser Lys Leu Lys Gly Arg Thr Val Leu Val Val Gly
    1160            1165            1170
Glu Lys Leu Ser Val Pro Gly Lys Met Val Asp Trp Leu Ser Asp
    1175            1180            1185
Arg Pro Glu Ala Thr Phe Arg Ala Arg Leu Asp Leu Gly Ile Pro
    1190            1195            1200
Gly Asp Val Pro Lys Tyr Asp Ile Ile Phe Val Asn Val Arg Thr
    1205            1210            1215
Pro Tyr Lys Tyr His His Tyr Gln Gln Cys Glu Asp His Ala Ile
    1220            1225            1230
Lys Leu Ser Met Leu Thr Lys Lys Ala Cys Leu His Leu Asn Pro
    1235            1240            1245
Gly Gly Thr Cys Val Ser Ile Gly Tyr Gly Tyr Ala Asp Arg Ala
    1250            1255            1260
Ser Glu Ser Ile Ile Gly Ala Ile Ala Arg Gln Phe Lys Phe Ser
    1265            1270            1275
Arg Val Cys Lys Pro Lys Ser Ser Leu Glu Glu Thr Glu Val Leu
    1280            1285            1290
Phe Val Phe Ile Gly Tyr Asp Arg Lys Ala Arg Thr His Asn Pro
    1295            1300            1305
Tyr Lys Leu Ser Ser Thr Leu Thr Asn Ile Tyr Thr Gly Ser Arg
    1310            1315            1320
Leu His Glu Ala Gly Cys Ala Pro Ser Tyr His Val Val Arg Gly
    1325            1330            1335
Asp Ile Ala Thr Ala Thr Glu Gly Val Ile Ile Asn Ala Ala Asn
    1340            1345            1350
Ser Lys Gly Gln Pro Gly Gly Gly Val Cys Gly Ala Leu Tyr Lys
    1355            1360            1365
Lys Phe Pro Glu Ser Phe Asp Leu Gln Pro Ile Glu Val Gly Lys
    1370            1375            1380
```

```
Ala Arg Leu Val Lys Gly Ala Lys His Ile Ile His Ala Val
1385             1390            1395

Gly Pro Asn Phe Asn Lys Val Ser Glu Val Glu Gly Asp Lys Gln
1400             1405            1410

Leu Ala Glu Ala Tyr Glu Ser Ile Ala Lys Ile Val Asn Asp Asn
1415             1420            1425

Asn Tyr Lys Ser Val Ala Ile Pro Leu Leu Ser Thr Gly Ile Phe
1430             1435            1440

Ser Gly Asn Lys Asp Arg Leu Thr Gln Ser Leu Asn His Leu Leu
1445             1450            1455

Thr Ala Leu Asp Thr Thr Asp Ala Asp Val Ala Ile Tyr Cys Arg
1460             1465            1470

Asp Lys Lys Trp Glu Met Thr Leu Lys Glu Ala Val Ala Arg Arg
1475             1480            1485

Glu Ala Val Glu Glu Ile Cys Ile Ser Asp Asp Ser Ser Val Thr
1490             1495            1500

Glu Pro Asp Ala Glu Leu Val Arg Val His Pro Lys Ser Ser Leu
1505             1510            1515

Ala Gly Arg Lys Gly Tyr Ser Thr Ser Asp Gly Lys Thr Phe Ser
1520             1525            1530

Tyr Leu Glu Gly Thr Lys Phe His Gln Ala Ala Lys Asp Ile Ala
1535             1540            1545

Glu Ile Asn Ala Met Trp Pro Val Ala Thr Glu Ala Asn Glu Gln
1550             1555            1560

Val Cys Met Tyr Ile Leu Gly Glu Ser Met Ser Ser Ile Arg Ser
1565             1570            1575

Lys Cys Pro Val Glu Glu Ser Glu Ala Ser Thr Pro Pro Ser Thr
1580             1585            1590

Leu Pro Cys Leu Cys Ile His Ala Met Thr Pro Glu Arg Val Gln
1595             1600            1605

Arg Leu Lys Ala Ser Arg Pro Glu Gln Ile Thr Val Cys Ser Ser
1610             1615            1620

Phe Pro Leu Pro Lys Tyr Arg Ile Thr Gly Val Gln Lys Ile Gln
1625             1630            1635

Cys Ser Gln Pro Ile Leu Phe Ser Pro Lys Val Pro Ala Tyr Ile
1640             1645            1650

His Pro Arg Lys Tyr Leu Val Glu Thr Pro Val Asp Glu Thr
1655             1660            1665

Pro Glu Pro Ser Ala Glu Asn Gln Ser Thr Glu Gly Thr Pro Glu
1670             1675            1680

Gln Pro Pro Leu Ile Thr Glu Asp Glu Thr Arg Thr Arg Thr Pro
1685             1690            1695

Glu Pro Ile Ile Ile Glu Glu Glu Glu Asp Ser Ile Ser Leu
1700             1705            1710

Leu Ser Asp Gly Pro Thr His Gln Val Leu Gln Val Glu Ala Asp
1715             1720            1725

Ile His Gly Pro Pro Ser Val Ser Ser Ser Ser Trp Ser Ile Pro
1730             1735            1740

His Ala Ser Asp Phe Asp Val Asp Ser Leu Ser Ile Leu Asp Thr
1745             1750            1755

Leu Glu Gly Ala Ser Val Thr Ser Gly Ala Thr Ser Ala Glu Thr
1760             1765            1770
```

```
Asn Ser Tyr Phe Ala Lys Ser Met Glu Phe Leu Ala Arg Pro Val
1775                1780                1785

Pro Ala Pro Arg Thr Val Phe Arg Asn Pro Pro His Pro Ala Pro
1790                1795                1800

Arg Thr Arg Thr Pro Ser Leu Ala Pro Ser Arg Ala Cys Ser Arg
1805                1810                1815

Thr Ser Leu Val Ser Thr Pro Pro Gly Val Asn Arg Val Ile Thr
1820                1825                1830

Arg Glu Glu Leu Glu Ala Leu Thr Pro Ser Arg Thr Pro Ser Arg
1835                1840                1845

Ser Val Ser Arg Thr Ser Leu Val Ser Asn Pro Pro Gly Val Asn
1850                1855                1860

Arg Val Ile Thr Arg Glu Glu Phe Glu Ala Phe Val Ala Gln Gln
1865                1870                1875

Gln Arg Arg Phe Asp Ala Gly Ala Tyr Ile Phe Ser Ser Asp Thr
1880                1885                1890

Gly Gln Gly His Leu Gln Gln Lys Ser Val Arg Gln Thr Val Leu
1895                1900                1905

Ser Glu Val Val Leu Glu Arg Thr Glu Leu Glu Ile Ser Tyr Ala
1910                1915                1920

Pro Arg Leu Asp Gln Glu Lys Glu Glu Leu Leu Arg Lys Lys Leu
1925                1930                1935

Gln Leu Asn Pro Thr Pro Ala Asn Arg Ser Arg Tyr Gln Ser Arg
1940                1945                1950

Lys Val Glu Asn Met Lys Ala Ile Thr Ala Arg Arg Ile Leu Gln
1955                1960                1965

Gly Leu Gly His Tyr Leu Lys Ala Glu Gly Lys Val Glu Cys Tyr
1970                1975                1980

Arg Thr Leu His Pro Val Pro Leu Tyr Ser Ser Ser Val Asn Arg
1985                1990                1995

Ala Phe Ser Ser Pro Lys Val Ala Val Glu Ala Cys Asn Ala Met
2000                2005                2010

Leu Lys Glu Asn Phe Pro Thr Val Ala Ser Tyr Cys Ile Ile Pro
2015                2020                2025

Glu Tyr Asp Ala Tyr Leu Asp Met Val Asp Gly Ala Ser Cys Cys
2030                2035                2040

Leu Asp Thr Ala Ser Phe Cys Pro Ala Lys Leu Arg Ser Phe Pro
2045                2050                2055

Lys Lys His Ser Tyr Leu Glu Pro Thr Ile Arg Ser Ala Val Pro
2060                2065                2070

Ser Ala Ile Gln Asn Thr Leu Gln Asn Val Leu Ala Ala Ala Thr
2075                2080                2085

Lys Arg Asn Cys Asn Val Thr Gln Met Arg Glu Leu Pro Val Leu
2090                2095                2100

Asp Ser Ala Ala Phe Asn Val Glu Cys Phe Lys Lys Tyr Ala Cys
2105                2110                2115

Asn Asn Glu Tyr Trp Glu Thr Phe Lys Glu Asn Pro Ile Arg Leu
2120                2125                2130

Thr Glu Glu Asn Val Val Asn Tyr Ile Thr Lys Leu Lys Gly Pro
2135                2140                2145

Lys Ala Ala Ala Leu Phe Ala Lys Thr His Asn Leu Asn Met Leu
2150                2155                2160

Gln Asp Ile Pro Met Asp Arg Phe Val Met Asp Leu Lys Arg Asp
```

Val Lys Val Thr Pro Gly Thr Lys His Thr Glu Glu Arg Pro Lys
        2180                2185                2190

Val Gln Val Ile Gln Ala Ala Asp Pro Leu Ala Thr Ala Tyr Leu
        2195                2200                2205

Cys Gly Ile His Arg Glu Leu Val Arg Arg Leu Asn Ala Val Leu
        2210                2215                2220

Leu Pro Asn Ile His Thr Leu Phe Asp Met Ser Ala Glu Asp Phe
        2225                2230                2235

Asp Ala Ile Ile Ala Glu His Phe Gln Pro Gly Asp Cys Val Leu
        2240                2245                2250

Glu Thr Asp Ile Ala Ser Phe Asp Lys Ser Glu Asp Asp Ala Met
        2255                2260                2265

Ala Leu Thr Ala Leu Met Ile Leu Glu Asp Leu Gly Val Asp Ala
        2270                2275                2280

Glu Leu Leu Thr Leu Ile Glu Ala Ala Phe Gly Glu Ile Ser Ser
        2285                2290                2295

Ile His Leu Pro Thr Lys Thr Lys Phe Lys Phe Gly Ala Met Met
        2300                2305                2310

Lys Ser Gly Met Phe Leu Thr Leu Phe Val Asn Thr Val Ile Asn
        2315                2320                2325

Ile Val Ile Ala Ser Arg Val Leu Arg Glu Arg Leu Thr Gly Ser
        2330                2335                2340

Pro Cys Ala Ala Phe Ile Gly Asp Asp Asn Ile Val Lys Gly Val
        2345                2350                2355

Lys Ser Asp Lys Leu Met Ala Asp Arg Cys Ala Thr Trp Leu Asn
        2360                2365                2370

Met Glu Val Lys Ile Ile Asp Ala Val Val Gly Glu Lys Ala Pro
        2375                2380                2385

Tyr Phe Cys Gly Gly Phe Ile Leu Cys Asp Ser Val Thr Gly Thr
        2390                2395                2400

Ala Cys Arg Val Ala Asp Pro Leu Lys Arg Leu Phe Lys Leu Gly
        2405                2410                2415

Lys Pro Leu Ala Ala Asp Asp Glu His Asp Asp Asp Arg Arg Arg
        2420                2425                2430

Ala Leu His Glu Glu Ser Thr Arg Trp Asn Arg Val Gly Ile Leu
        2435                2440                2445

Ser Glu Leu Cys Lys Ala Val Glu Ser Arg Tyr Glu Thr Val Gly
        2450                2455                2460

Thr Ser Ile Ile Val Met Ala Met Thr Thr Leu Ala Ser Ser Val
        2465                2470                2475

Lys Ser Phe Ser Tyr Leu Arg Gly Ala Pro Ile Thr Leu Tyr Gly
        2480                2485                2490

<210> SEQ ID NO 9
<211> LENGTH: 2411
<212> TYPE: PRT
<213> ORGANISM: Barmah Forest virus

<400> SEQUENCE: 9

Met Ala Lys Pro Val Val Lys Ile Asp Val Glu Pro Glu Ser His Phe
1               5                   10                  15

Ala Lys Gln Val Gln Ser Cys Phe Pro Gln Phe Glu Ile Glu Ala Val
                20                  25                  30

```
Gln Thr Thr Pro Asn Asp His Ala His Ala Arg Ala Phe Ser His Leu
         35                  40                  45

Ala Thr Lys Leu Ile Glu Met Glu Thr Ala Lys Asp Gln Ile Ile Leu
 50                  55                  60

Asp Ile Gly Ser Ala Pro Ala Arg Arg Leu Tyr Ser Glu His Lys Tyr
 65                  70                  75                  80

His Cys Val Cys Pro Met Lys Cys Thr Glu Asp Pro Glu Arg Met Leu
                 85                  90                  95

Gly Tyr Ala Arg Lys Leu Ile Ala Gly Ser Ala Lys Gly Lys Ala Glu
             100                 105                 110

Lys Leu Arg Asp Leu Arg Asp Val Leu Ala Thr Pro Asp Ile Glu Thr
             115                 120                 125

Gln Ser Leu Cys Leu His Thr Asp Ala Ser Cys Arg Tyr Arg Gly Asp
 130                 135                 140

Val Ala Val Tyr Gln Asp Val Tyr Ala Ile Asp Ala Pro Thr Thr Leu
145                 150                 155                 160

Tyr His Gln Ala Leu Lys Gly Val Arg Thr Ala Tyr Trp Ile Gly Phe
                 165                 170                 175

Asp Thr Thr Pro Phe Met Tyr Asp Ala Leu Ala Gly Ala Tyr Pro Leu
             180                 185                 190

Tyr Ser Thr Asn Trp Ala Asp Glu Gln Val Leu Glu Ser Arg Asn Ile
             195                 200                 205

Gly Leu Cys Ser Asp Lys Val Ser Glu Gly Gly Lys Lys Gly Arg Ser
             210                 215                 220

Ile Leu Arg Lys Lys Phe Leu Lys Gln Ser Asp Arg Val Met Phe Ser
225                 230                 235                 240

Val Gly Ser Thr Leu Tyr Thr Glu Ser Arg Lys Leu Leu Gln Ser Trp
                 245                 250                 255

His Leu Pro Ser Thr Phe His Leu Lys Gly Lys Ser Ser Phe Thr Cys
             260                 265                 270

Arg Cys Asp Thr Ile Val Ser Cys Glu Gly Tyr Val Leu Lys Lys Ile
             275                 280                 285

Thr Met Cys Pro Gly Val Thr Gly Lys Pro Ile Gly Tyr Ala Val Thr
             290                 295                 300

His His Lys Glu Gly Phe Val Val Gly Lys Val Thr Asp Thr Ile Arg
305                 310                 315                 320

Gly Glu Arg Val Ser Phe Ala Val Cys Thr Tyr Val Pro Thr Thr Leu
                 325                 330                 335

Cys Asp Gln Met Thr Gly Ile Leu Ala Thr Glu Val Thr Ala Asp Asp
             340                 345                 350

Ala Gln Lys Leu Leu Val Gly Leu Asn Gln Arg Ile Val Val Asn Gly
             355                 360                 365

Arg Thr Gln Arg Asn Thr Asn Thr Met Lys Asn Tyr Leu Leu Pro Leu
             370                 375                 380

Val Ala Gln Ala Leu Ala Lys Trp Ala Lys Glu Ala Lys Gln Asp Met
385                 390                 395                 400

Glu Asp Glu Arg Pro Leu Asn Glu Arg Gln Arg Thr Leu Thr Cys Leu
                 405                 410                 415

Cys Cys Trp Ala Phe Lys Arg Asn Lys Arg His Ala Ile Tyr Lys Arg
             420                 425                 430

Pro Asp Thr Gln Ser Ile Val Lys Val Pro Cys Glu Phe Thr Ser Phe
             435                 440                 445

Pro Leu Val Ser Leu Trp Ser Ala Gly Met Ser Ile Ser Leu Arg Gln
```

-continued

```
            450                 455                 460
Lys Leu Lys Met Met Leu Gln Ala Arg Gln Pro Thr Gln Ile Ala Ala
465                 470                 475                 480

Val Thr Glu Glu Leu Ile Gln Glu Ala Ala Val Glu Gln Glu Ala
                485                 490                 495

Val Asp Thr Ala Asn Ala Glu Leu Asp His Ala Ala Trp Pro Ser Ile
                500                 505                 510

Val Asp Thr Thr Glu Arg His Val Glu Val Val Glu Glu Leu Asp
                515                 520                 525

Gln Arg Ala Gly Glu Gly Val Val Thr Pro Arg Asn Ser Ile Lys
                530                 535                 540

Val Ser Thr Gln Ile Gly Asp Ala Leu Ile Gly Ser Tyr Leu Ile Leu
545                 550                 555                 560

Ser Pro Gln Ala Val Leu Arg Ser Glu Lys Leu Ala Cys Ile His Asp
                565                 570                 575

Leu Ala Glu Gln Val Lys Leu Val Thr His Ser Gly Arg Ser Gly Arg
                580                 585                 590

Tyr Ala Val Asp Lys Tyr Asp Gly Arg Val Leu Val Pro Thr Gly Val
                595                 600                 605

Ala Ile Asp Ile Gln Ser Phe Gln Ala Leu Ser Glu Ser Ala Thr Leu
610                 615                 620

Val Tyr Asn Glu Arg Glu Phe Val Asn Arg Lys Leu Trp His Ile Ala
625                 630                 635                 640

Val Tyr Gly Ala Ala Leu Asn Thr Asp Glu Glu Gly Tyr Glu Lys Val
                645                 650                 655

Pro Val Glu Arg Ala Glu Ser Asp Tyr Val Phe Asp Val Asp Gln Lys
                660                 665                 670

Met Cys Leu Lys Lys Glu Gln Ala Ser Gly Trp Val Leu Cys Gly Glu
                675                 680                 685

Leu Val Asn Pro Pro Phe His Glu Phe Ala Tyr Glu Gly Leu Arg Thr
                690                 695                 700

Arg Pro Ser Ala Pro Tyr Lys Val His Thr Val Gly Val Tyr Gly Val
705                 710                 715                 720

Pro Gly Ser Gly Lys Ser Ala Ile Ile Lys Asn Thr Val Thr Met Ser
                725                 730                 735

Asp Leu Val Leu Ser Gly Lys Lys Glu Asn Cys Leu Glu Ile Met Asn
                740                 745                 750

Asp Val Leu Lys His Arg Ala Leu Arg Ile Thr Ala Lys Thr Val Asp
                755                 760                 765

Ser Val Leu Leu Asn Gly Val Lys His Thr Pro Asn Ile Leu Tyr Ile
770                 775                 780

Asp Glu Ala Phe Ser Cys His Ala Gly Thr Leu Leu Ala Thr Ile Ala
785                 790                 795                 800

Ile Val Arg Pro Lys Gln Lys Val Val Leu Cys Gly Asp Pro Lys Gln
                805                 810                 815

Cys Gly Phe Phe Asn Met Met Gln Leu Lys Val Asn Tyr Asn His Asp
                820                 825                 830

Ile Cys Ser Glu Val Phe His Lys Ser Ile Ser Arg Arg Cys Thr Gln
                835                 840                 845

Asp Ile Thr Ala Ile Val Ser Lys Leu His Tyr Gln Asp Arg Met Arg
                850                 855                 860

Thr Thr Asn Pro Arg Lys Gly Asp Ile Ile Ile Asp Thr Thr Gly Thr
865                 870                 875                 880
```

```
Thr Lys Pro Ala Lys Thr Asp Leu Ile Leu Thr Cys Phe Arg Gly Trp
            885                 890                 895
Val Lys Gln Leu Gln Gln Asp Tyr Arg Gly Asn Glu Val Met Thr Ala
            900                 905                 910
Ala Ala Ser Gln Gly Leu Thr Arg Ala Ser Val Tyr Ala Val Arg Thr
            915                 920                 925
Lys Val Asn Glu Asn Pro Leu Tyr Ala Gln Thr Ser Glu His Val Asn
            930                 935                 940
Val Leu Leu Thr Arg Thr Glu Asn Lys Leu Val Trp Lys Thr Leu Ser
945                 950                 955                 960
Thr Asp Pro Trp Ile Lys Thr Leu Thr Asn Pro Pro Arg Gly His Tyr
            965                 970                 975
Thr Ala Thr Ile Ala Glu Trp Glu Ala Glu His Gln Gly Ile Met Lys
            980                 985                 990
Ala Ile Gln Gly Tyr Ala Pro Pro Val Asn Thr Phe Met Asn Lys Val
            995                 1000                1005
Asn Val Cys Trp Ala Lys Thr Leu Thr Pro Val Leu Glu Thr Ala
            1010                1015                1020
Gly Ile Ser Leu Ser Ala Glu Asp Trp Ser Glu Leu Leu Pro Pro
            1025                1030                1035
Phe Ala Gln Asp Val Ala Tyr Ser Pro Glu Val Ala Leu Asn Ile
            1040                1045                1050
Ile Cys Thr Lys Met Tyr Gly Phe Asp Leu Asp Thr Gly Leu Phe
            1055                1060                1065
Ser Arg Pro Ser Val Pro Met Thr Tyr Thr Lys Asp His Trp Asp
            1070                1075                1080
Asn Arg Val Gly Gly Lys Met Tyr Gly Phe Ser Gln Gln Ala Tyr
            1085                1090                1095
Asp Gln Leu Ala Arg Arg His Pro Tyr Leu Arg Gly Arg Glu Lys
            1100                1105                1110
Ser Gly Met Gln Ile Val Val Thr Glu Met Arg Ile Gln Arg Pro
            1115                1120                1125
Arg Ser Asp Ala Asn Ile Ile Pro Ile Asn Arg Arg Leu Pro His
            1130                1135                1140
Ser Leu Val Ala Thr His Glu Tyr Arg Arg Ala Ala Arg Ala Glu
            1145                1150                1155
Glu Phe Phe Thr Thr Thr Arg Gly Tyr Thr Met Leu Leu Val Ser
            1160                1165                1170
Glu Tyr Asn Met Asn Leu Pro Asn Lys Lys Ile Thr Trp Leu Ala
            1175                1180                1185
Pro Ile Gly Thr Gln Gly Ala His His Thr Ala Asn Leu Asn Leu
            1190                1195                1200
Gly Ile Pro Pro Leu Leu Gly Ser Phe Asp Ala Val Val Val Asn
            1205                1210                1215
Met Pro Thr Pro Phe Arg Asn His His Tyr Gln Gln Cys Glu Asp
            1220                1225                1230
His Ala Met Lys Leu Gln Met Leu Ala Gly Asp Ala Leu Arg His
            1235                1240                1245
Ile Lys Pro Gly Gly Ser Leu Trp Val Lys Ala Tyr Gly Tyr Ala
            1250                1255                1260
Asp Arg His Ser Glu His Val Val Leu Ala Leu Ala Arg Lys Phe
            1265                1270                1275
```

| | | | | | | | | | | | |
|---|---|---|---|---|---|---|---|---|---|---|---|
|Lys|Ser|Phe|Arg|Val|Thr|Gln|Pro|Ser|Cys|Val|Thr|
| |1280| | | |1285| | | |1290| | |
|Ser|Asn|Thr| | | | | | | | | |
|Glu|Val|Phe|Leu|His|Phe|Ser|Ile|Phe|Asp|Asn|Gly|
| |1295| | | |1300| | | |1305| | |
|Lys|Arg|Ala| | | | | | | | | |
|Ile|Ala|Leu|His|Ser|Ala|Asn|Arg|Lys|Ala|Asn|Ser|
| |1310| | | |1315| | | |1320| | |
|Ile|Phe|Gln| | | | | | | | | |
|Asn|Thr|Phe|Leu|Pro|Ala|Gly|Ser|Ala|Pro|Ala|Tyr|
| |1325| | | |1330| | | |1335| | |
|Arg|Val|Lys| | | | | | | | | |
|Arg|Gly|Asp|Ile|Ser|Asn|Ala|Pro|Glu|Asp|Ala|Val|
| |1340| | | |1345| | | |1350| | |
|Val|Asn|Ala| | | | | | | | | |
|Ala|Asn|Gln|Gln|Gly|Val|Lys|Gly|Ala|Gly|Val|Cys|
| |1355| | | |1360| | | |1365| | |
|Gly|Ala|Ile| | | | | | | | | |
|Tyr|Arg|Lys|Trp|Pro|Asp|Ala|Phe|Gly|Asp|Val|Ala|
| |1370| | | |1375| | | |1380| | |
|Thr|Pro|Thr| | | | | | | | | |
|Gly|Thr|Ala|Val|Ser|Lys|Ser|Val|Gln|Asp|Lys|Leu|
| |1385| | | |1390| | | |1395| | |
|Val|Ile|His| | | | | | | | | |
|Ala|Val|Gly|Pro|Asn|Phe|Ser|Lys|Cys|Ser|Glu|Glu|
| |1400| | | |1405| | | |1410| | |
|Glu|Gly|Asp| | | | | | | | | |
|Arg|Asp|Leu|Ala|Ser|Ala|Tyr|Arg|Ala|Ala|Ala|Glu|
| |1415| | | |1420| | | |1425| | |
|Ile|Val|Met| | | | | | | | | |
|Asp|Lys|Lys|Ile|Thr|Thr|Val|Ala|Val|Pro|Leu|Leu|
| |1430| | | |1435| | | |1440| | |
|Ser|Thr|Gly| | | | | | | | | |
|Ile|Tyr|Ala|Gly|Gly|Lys|Asn|Arg|Val|Glu|Gln|Ser|
| |1445| | | |1450| | | |1455| | |
|Leu|Asn|His| | | | | | | | | |
|Leu|Phe|Thr|Ala|Phe|Asp|Asn|Thr|Asp|Ala|Asp|Val|
| |1460| | | |1465| | | |1470| | |
|Thr|Ile|Tyr| | | | | | | | | |
|Cys|Met|Asp|Lys|Thr|Trp|Glu|Lys|Lys|Ile|Lys|Glu|
| |1475| | | |1480| | | |1485| | |
|Ala|Ile|Asp| | | | | | | | | |
|His|Arg|Thr|Ser|Val|Glu|Met|Val|Gln|Asp|Asp|Val|
| |1490| | | |1495| | | |1500| | |
|Gln|Leu|Glu| | | | | | | | | |
|Glu|Glu|Leu|Val|Arg|Val|His|Pro|Leu|Ser|Ser|Leu|
| |1505| | | |1510| | | |1515| | |
|Ala|Gly|Arg| | | | | | | | | |
|Lys|Gly|Tyr|Ser|Thr|Asp|Ser|Gly|Arg|Val|Phe|Ser|
| |1520| | | |1525| | | |1530| | |
|Tyr|Leu|Glu| | | | | | | | | |
|Gly|Thr|Lys|Phe|His|Gln|Thr|Ala|Val|Asp|Ile|Ala|
| |1535| | | |1540| | | |1545| | |
|Glu|Met|Gln| | | | | | | | | |
|Val|Leu|Trp|Pro|Ala|Leu|Lys|Glu|Ser|Asn|Glu|Gln|
| |1550| | | |1555| | | |1560| | |
|Ile|Val|Ala| | | | | | | | | |
|Tyr|Thr|Leu|Gly|Glu|Ser|Met|Asp|Gln|Ile|Arg|Gly|
| |1565| | | |1570| | | |1575| | |
|Lys|Cys|Pro| | | | | | | | | |
|Thr|Glu|Asp|Thr|Asp|Ala|Ser|Thr|Pro|Pro|Arg|Thr|
| |1580| | | |1585| | | |1590| | |
|Val|Pro|Cys| | | | | | | | | |
|Leu|Cys|Arg|Tyr|Ala|Met|Thr|Pro|Glu|Arg|Val|Tyr|
| |1595| | | |1600| | | |1605| | |
|Arg|Leu|Lys| | | | | | | | | |
|Cys|Thr|Asn|Thr|Thr|Gln|Phe|Thr|Val|Cys|Ser|Ser|
| |1610| | | |1615| | | |1620| | |
|Phe|Glu|Leu| | | | | | | | | |
|Pro|Lys|Tyr|His|Ile|Gln|Gly|Val|Gln|Arg|Val|Lys|
| |1625| | | |1630| | | |1635| | |
|Cys|Glu|Arg| | | | | | | | | |
|Ile|Ile|Ile|Leu|Asp|Pro|Thr|Val|Pro|Thr|Tyr|Lys|
| |1640| | | |1645| | | |1650| | |
|Arg|Pro| | | | | | | | | | |
|Cys|Ile|Arg|Arg|Tyr|Pro|Ser|Thr|Ile|Ser|Cys|Asn|
| |1655| | | |1660| | | |1665| | |
|Ser|Ser|Glu| | | | | | | | | |
|Asp|Ser|Arg|Ser|Leu|Ser|Thr|Phe|Ser|Val|Ser|Ser|
|Asp|Ser|Ser| | | | | | | | | |

```
            1670                1675                1680

Ile Gly Ser Leu Pro Val Gly Asp Thr Arg Pro Ile Pro Ala Pro
            1685                1690                1695

Arg Thr Ile Phe Arg Pro Val Pro Ala Pro Arg Ala Pro Val Leu
            1700                1705                1710

Arg Thr Thr Pro Pro Pro Lys Pro Pro Arg Thr Phe Thr Val Arg
            1715                1720                1725

Ala Glu Val His Gln Ala Pro Pro Thr Pro Val Pro Pro Pro Arg
            1730                1735                1740

Pro Lys Arg Ala Ala Lys Leu Ala Arg Glu Met His Pro Gly Phe
            1745                1750                1755

Thr Phe Gly Asp Phe Gly Glu His Glu Val Glu Glu Leu Thr Ala
            1760                1765                1770

Ser Pro Leu Thr Phe Gly Asp Phe Ala Glu Gly Glu Ile Gln Gly
            1775                1780                1785

Met Gly Val Glu Phe Glu Arg Leu Gly Arg Ala Gly Gly Tyr Ile
            1790                1795                1800

Phe Ser Ser Asp Thr Gly Pro Gly His Leu Gln Gln Arg Ser Val
            1805                1810                1815

Leu Gln Asn Cys Thr Ala Glu Cys Ile Tyr Glu Pro Ala Lys Leu
            1820                1825                1830

Glu Lys Ile His Ala Pro Lys Leu Asp Lys Thr Lys Glu Asp Ile
            1835                1840                1845

Leu Arg Ser Lys Tyr Gln Met Lys Pro Ser Glu Ala Asn Lys Ser
            1850                1855                1860

Arg Tyr Gln Ser Arg Lys Val Glu Asn Met Lys Ala Glu Ile Val
            1865                1870                1875

Gly Arg Leu Leu Asp Gly Leu Gly Glu Tyr Leu Gly Thr Glu His
            1880                1885                1890

Pro Val Glu Cys Tyr Arg Ile Thr Tyr Pro Val Pro Ile Tyr Ser
            1895                1900                1905

Thr Ser Val Leu Arg Gly Leu Ser Ser Ala Lys Thr Ala Val Arg
            1910                1915                1920

Ala Cys Asn Ala Phe Leu Glu Ala Asn Phe Pro Ser Val Thr Ser
            1925                1930                1935

Tyr Lys Ile Thr Asp Glu Tyr Asp Ala Tyr Leu Asp Met Val Asp
            1940                1945                1950

Gly Ser Glu Ser Cys Leu Asp Arg Ser Ser Phe Ser Pro Ser Arg
            1955                1960                1965

Leu Arg Ser Phe Pro Lys Thr His Ser Tyr Leu Asp Pro Gln Ile
            1970                1975                1980

Asn Ser Ala Val Pro Ser Pro Phe Gln Asn Thr Leu Gln Asn Val
            1985                1990                1995

Leu Ala Ala Thr Lys Arg Asn Cys Asn Val Thr Gln Met Arg
            2000                2005                2010

Glu Leu Pro Thr Tyr Asp Ser Ala Val Leu Asn Val Glu Ala Phe
            2015                2020                2025

Arg Lys Tyr Ala Cys Lys Pro Asp Val Trp Asp Glu Tyr Arg Asp
            2030                2035                2040

Asn Pro Ile Cys Ile Thr Thr Glu Asn Val Thr Thr Tyr Val Ala
            2045                2050                2055

Lys Leu Lys Gly Pro Lys Ala Ala Ala Leu Phe Ala Lys Thr His
            2060                2065                2070
```

Asn Leu Ile Pro Leu His Gln Val Pro Met Asp Lys Phe Thr Val
2075                2080                2085

Asp Met Lys Arg Asp Val Lys Val Thr Pro Gly Thr Lys His Thr
2090                2095                2100

Glu Glu Arg Pro Lys Val Gln Val Ile Gln Ala Ala Glu Pro Leu
2105                2110                2115

Ala Thr Ala Tyr Leu Cys Gly Ile His Arg Glu Leu Val Arg Arg
2120                2125                2130

Leu Asn Asn Ala Leu Phe Pro Asn Ile His Thr Leu Phe Asp Met
2135                2140                2145

Ser Ala Glu Asp Phe Asp Ala Ile Ile Ala Glu His Phe Lys His
2150                2155                2160

Gly Asp His Val Leu Glu Thr Asp Ile Ala Ser Phe Asp Lys Ser
2165                2170                2175

Gln Asp Asp Ser Met Ala Leu Thr Ala Leu Met Ile Leu Glu Asp
2180                2185                2190

Leu Gly Val Asp Gln Asn Leu Met Asn Leu Ile Glu Ala Ala Phe
2195                2200                2205

Gly Glu Ile Val Ser Thr His Leu Pro Thr Gly Thr Arg Phe Lys
2210                2215                2220

Phe Gly Ala Met Met Lys Ser Gly Met Phe Leu Thr Leu Phe Val
2225                2230                2235

Asn Thr Ile Leu Asn Val Val Ile Ala Cys Arg Val Leu Glu Asp
2240                2245                2250

Gln Leu Ala Gln Ser Pro Cys Ala Ala Phe Ile Gly Asp Asp Asn
2255                2260                2265

Ile Ile His Gly Ile Ile Ser Asp Lys Leu Met Ala Asp Arg Cys
2270                2275                2280

Ala Thr Trp Met Asn Met Glu Val Lys Ile Leu Asp Ser Ile Val
2285                2290                2295

Gly Ile Arg Pro Pro Tyr Phe Cys Gly Gly Phe Ile Val Cys Asp
2300                2305                2310

Asp Val Thr Gly Thr Ala Cys Arg Val Ala Asp Pro Leu Lys Arg
2315                2320                2325

Leu Phe Lys Leu Gly Lys Pro Leu Pro Leu Asp Asp Gly Gln Asp
2330                2335                2340

Glu Asp Arg Arg Arg Ala Leu His Asp Glu Val Lys Thr Trp Ser
2345                2350                2355

Arg Val Gly Leu Arg His Arg Val Cys Glu Ala Ile Glu Asp Arg
2360                2365                2370

Tyr Ala Val His Ser Ser Glu Leu Val Leu Leu Ala Leu Thr Thr
2375                2380                2385

Leu Ser Lys Asn Leu Lys Ser Phe Arg Asn Ile Arg Gly Lys Pro
2390                2395                2400

Ile His Leu Tyr Gly Gly Pro Lys
2405                2410

<210> SEQ ID NO 10
<211> LENGTH: 2513
<212> TYPE: PRT
<213> ORGANISM: O'nyong'nyong virus

<400> SEQUENCE: 10

Met Asp Ser Val Tyr Val Asp Ile Asp Ala Asp Ser Ala Phe Leu Lys

```
 1               5                    10                       15
Ala Leu Gln Arg Ala Tyr Pro Met Phe Glu Val Glu Pro Lys Gln Val
                20                  25                  30

Thr Pro Asn Asp His Ala Asn Ala Arg Ala Phe Ser His Leu Ala Ile
                35                  40                  45

Lys Leu Ile Glu Gln Glu Ile Asp Pro Asp Ser Thr Ile Leu Asp Ile
                50                  55                  60

Gly Pro Ala Pro Ala Arg Arg Met Met Ser Asp Arg Lys Tyr His Cys
 65                 70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Thr Asp Lys Asn Ile
               100                 105                 110

Ser Gly Lys Ile Asn Asp Leu Gln Ala Val Met Ala Val Pro Asn Met
               115                 120                 125

Glu Thr Ser Thr Phe Cys Leu His Thr Asp Ala Thr Cys Lys Gln Arg
               130                 135                 140

Gly Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Ile
               165                 170                 175

Gly Phe Asp Thr Thr Pro Phe Met Tyr Asn Ala Met Ala Gly Ala Tyr
               180                 185                 190

Pro Ser Tyr Ser Thr Asn Trp Ala Asp Glu Gln Val Leu Lys Ala Lys
               195                 200                 205

Asn Ile Gly Leu Cys Ser Thr Asp Leu Ser Glu Gly Arg Arg Gly Lys
               210                 215                 220

Leu Ser Ile Met Arg Gly Lys Lys Leu Lys Pro Cys Asp Arg Val Leu
225                 230                 235                 240

Phe Ser Val Gly Ser Thr Leu Tyr Pro Glu Ser Arg Lys Leu Leu Gln
               245                 250                 255

Ser Trp His Leu Pro Ser Val Phe His Leu Lys Gly Lys Leu Ser Phe
               260                 265                 270

Thr Cys Arg Cys Asp Thr Ile Val Ser Cys Glu Gly Tyr Val Val Lys
               275                 280                 285

Arg Val Thr Met Ser Pro Gly Ile Tyr Gly Lys Thr Ser Gly Tyr Ala
               290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
               325                 330                 335

Thr Ile Cys Asp Gln Met Thr Gly Ile Leu Ala Thr Glu Val Thr Pro
               340                 345                 350

Glu Asp Ala Gln Lys Leu Leu Val Gly Leu Asn Gln Arg Ile Val Val
               355                 360                 365

Asn Gly Arg Thr Gln Arg Asn Thr Asn Thr Met Lys Asn Tyr Leu Leu
               370                 375                 380

Pro Ile Val Ala Gln Ala Phe Ser Lys Trp Ala Lys Glu Cys Arg Lys
385                 390                 395                 400

Asp Met Glu Asp Glu Lys Leu Leu Gly Val Arg Glu Arg Thr Leu Thr
               405                 410                 415

Cys Cys Cys Leu Trp Ala Phe Arg Lys His Lys Thr His Thr Val Tyr
               420                 425                 430
```

```
Lys Arg Pro Asp Thr Gln Ser Ile Gln Lys Val Pro Ala Glu Phe Asp
        435                 440                 445

Ser Phe Val Ile Pro Ser Leu Trp Ser Ser Gly Leu Ser Ile Pro Leu
450                 455                 460

Arg Thr Arg Ile Lys Trp Leu Leu Ser Lys Ala Pro Lys His Glu Gln
465                 470                 475                 480

Leu Pro His Ser Gly Asn Ala Glu Glu Ala Gln Ala Glu Met Asp
            485                 490                 495

Ala Ala Glu Glu Arg Glu Ala Glu Leu Thr Arg Glu Ala Met Pro Pro
                500                 505                 510

Leu Gln Ala Thr Gln Asp Val Gln Val Glu Ile Asp Val Glu Gln
            515                 520                 525

Leu Glu Asp Arg Ala Gly Ala Gly Ile Val Thr Pro Arg Gly Ala
530                 535                 540

Ile Lys Val Thr Ala Gln Pro Ser Asp Arg Val Val Gly Glu Tyr Leu
545                 550                 555                 560

Val Leu Thr Pro Gln Ala Val Leu Arg Ser Gln Lys Leu Ser Leu Ile
                565                 570                 575

His Ala Leu Ala Glu Gln Val Lys Thr Cys Thr His Ser Gly Arg Ala
            580                 585                 590

Gly Arg Tyr Ala Val Glu Ala Tyr Asp Gly Arg Val Leu Val Pro Ser
        595                 600                 605

Gly Tyr Ala Ile Pro Gln Glu Asp Phe Gln Ser Leu Ser Glu Ser Ala
        610                 615                 620

Thr Met Val Phe Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
            645                 650                 655

Leu Val Arg Val Glu Lys Thr Glu His Glu Tyr Val Tyr Asp Val Asp
        660                 665                 670

Gln Lys Lys Cys Cys Lys Arg Glu Glu Ala Thr Gly Leu Val Leu Val
        675                 680                 685

Gly Asp Leu Thr Ser Pro Tyr His Glu Phe Ala Tyr Glu Gly Leu
        690                 695                 700

Lys Ile Arg Pro Ala Cys Pro Tyr Lys Thr Ala Val Ile Gly Val Phe
705                 710                 715                 720

Gly Val Pro Gly Ser Gly Lys Ser Ala Ile Ile Lys Asn Leu Val Thr
            725                 730                 735

Arg Gln Asp Leu Val Thr Ser Gly Lys Lys Glu Asn Cys Gln Glu Ile
            740                 745                 750

Ser Asn Asp Val Met Arg Gln Arg Lys Leu Glu Ile Ser Ala Arg Thr
        755                 760                 765

Val Asp Ser Leu Leu Leu Asn Gly Cys Asn Lys Pro Val Glu Val Leu
770                 775                 780

Tyr Val Asp Glu Ala Phe Ala Cys His Ser Gly Thr Leu Leu Ala Leu
785                 790                 795                 800

Ile Ala Met Val Arg Pro Arg Gln Lys Val Val Leu Cys Gly Asp Pro
            805                 810                 815

Lys Gln Cys Gly Phe Phe Asn Met Met Gln Met Lys Val Asn Tyr Asn
                820                 825                 830

His Asn Ile Cys Thr Gln Val Tyr His Lys Ser Ile Ser Arg Arg Cys
            835                 840                 845
```

-continued

Thr Leu Pro Val Thr Ala Ile Val Ser Ser Leu His Tyr Glu Ser Lys
              850              855              860

Met Arg Thr Thr Asn Glu Tyr Asn Gln Pro Ile Val Val Asp Thr Thr
865              870              875              880

Gly Ile Thr Lys Pro Glu Pro Gly Asp Leu Val Leu Thr Cys Phe Arg
              885              890              895

Gly Trp Val Lys Gln Leu Gln Ile Asp Tyr Arg Gly Asn Glu Val Met
              900              905              910

Thr Ala Ala Ser Gln Gly Leu Thr Arg Lys Gly Val Tyr Ala Val
              915              920              925

Arg Gln Lys Val Asn Glu Asn Pro Leu Tyr Ala Ser Thr Ser Glu His
              930              935              940

Val Asn Val Leu Leu Thr Arg Thr Glu Gly Lys Leu Ile Trp Lys Thr
945              950              955              960

Leu Ser Gly Asp Pro Trp Ile Lys Ile Leu Gln Asn Pro Pro Lys Gly
              965              970              975

Asn Phe Lys Ala Thr Ile Lys Glu Trp Glu Ala Glu His Ala Ser Ile
              980              985              990

Met Ala Gly Ile Cys Asn His Gln Met Ala Phe Asp Thr Phe Gln Asn
              995              1000             1005

Lys Ala Asn Val Cys Trp Ala Lys Cys Leu Val Pro Ile Leu Asp
      1010             1015             1020

Thr Ala Gly Ile Lys Leu Ser Asp Arg Gln Trp Ser Gln Ile Val
      1025             1030             1035

Gln Ala Phe Lys Glu Asp Arg Ala Tyr Ser Pro Glu Val Ala Leu
      1040             1045             1050

Asn Glu Ile Cys Thr Arg Ile Tyr Gly Val Asp Leu Asp Ser Gly
      1055             1060             1065

Leu Phe Ser Lys Pro Leu Ile Ser Val Tyr Tyr Ala Asp Asn His
      1070             1075             1080

Trp Asp Asn Arg Pro Gly Gly Lys Met Phe Gly Phe Asn Pro Glu
      1085             1090             1095

Val Ala Leu Met Leu Glu Lys Lys Tyr Pro Phe Thr Lys Gly Lys
      1100             1105             1110

Trp Asn Ile Asn Lys Gln Ile Cys Ile Thr Thr Arg Lys Val Asp
      1115             1120             1125

Glu Phe Asn Pro Glu Thr Asn Ile Ile Pro Ala Asn Arg Arg Leu
      1130             1135             1140

Pro His Ser Leu Val Ala Glu His His Thr Val Arg Gly Glu Arg
      1145             1150             1155

Met Glu Trp Leu Val Asn Lys Ile Asn Gly His His Met Leu Leu
      1160             1165             1170

Val Ser Gly Tyr Asn Leu Ile Leu Pro Thr Lys Arg Val Thr Trp
      1175             1180             1185

Val Ala Pro Leu Gly Thr Arg Gly Ala Asp Tyr Thr Tyr Asn Leu
      1190             1195             1200

Glu Leu Gly Leu Pro Ala Thr Leu Gly Arg Tyr Asp Leu Val Val
      1205             1210             1215

Ile Asn Ile His Thr Pro Phe Arg Ile His His Tyr Gln Gln Cys
      1220             1225             1230

Val Asp His Ala Met Lys Leu Gln Met Leu Gly Gly Asp Ser Leu
      1235             1240             1245

Arg Leu Leu Lys Pro Gly Gly Ser Leu Leu Ile Arg Ala Tyr Gly

```
            1250                1255                1260
Tyr Ala Asp Arg Thr Ser Glu Arg Val Ile Ser Val Leu Gly Arg
            1265                1270                1275
Lys Phe Arg Ser Ser Arg Ala Leu Lys Pro Gln Cys Ile Thr Ser
            1280                1285                1290
Asn Thr Glu Met Phe Phe Leu Phe Ser Arg Phe Asp Asn Gly Arg
            1295                1300                1305
Arg Asn Phe Thr Thr His Val Met Asn Asn Gln Leu Asn Ala Val
            1310                1315                1320
Tyr Ala Gly Leu Ala Thr Arg Ala Gly Cys Ala Pro Ser Tyr Arg
            1325                1330                1335
Val Lys Arg Met Asp Ile Ala Lys Asn Thr Glu Glu Cys Val Val
            1340                1345                1350
Asn Ala Ala Asn Pro Arg Gly Val Pro Gly Asp Gly Val Cys Lys
            1355                1360                1365
Ala Val Tyr Arg Lys Trp Pro Glu Ser Phe Arg Asn Ser Ala Thr
            1370                1375                1380
Pro Val Gly Thr Ala Lys Thr Ile Met Cys Gly Gln Tyr Pro Val
            1385                1390                1395
Ile His Ala Val Gly Pro Asn Phe Ser Asn Tyr Ser Glu Ala Glu
            1400                1405                1410
Gly Asp Arg Glu Leu Ala Ser Val Tyr Arg Glu Val Ala Lys Glu
            1415                1420                1425
Val Ser Arg Leu Gly Val Ser Ser Val Ala Ile Pro Leu Leu Ser
            1430                1435                1440
Thr Gly Val Tyr Ser Gly Gly Lys Asp Arg Leu Leu Gln Ser Leu
            1445                1450                1455
Asn His Leu Phe Thr Ala Met Asp Ser Thr Asp Ala Asp Val Val
            1460                1465                1470
Ile Tyr Cys Arg Asp Lys Glu Trp Glu Lys Lys Ile Thr Glu Ala
            1475                1480                1485
Ile Ser Leu Arg Ser Gln Val Glu Leu Leu Asp Asp His Ile Ser
            1490                1495                1500
Val Asp Cys Asp Ile Val Arg Val His Pro Asp Ser Ser Leu Ala
            1505                1510                1515
Gly Arg Lys Gly Tyr Ser Thr Val Glu Gly Ala Leu Tyr Ser Tyr
            1520                1525                1530
Leu Glu Gly Thr Arg Phe His Gln Thr Ala Val Asp Met Ala Glu
            1535                1540                1545
Ile Tyr Thr Met Trp Pro Lys Gln Thr Glu Ala Asn Glu Gln Val
            1550                1555                1560
Cys Leu Tyr Ala Leu Gly Glu Ser Ile Glu Ser Val Arg Gln Lys
            1565                1570                1575
Cys Pro Val Asp Asp Ala Asp Ala Ser Phe Pro Lys Thr Val
            1580                1585                1590
Pro Cys Leu Cys Arg Tyr Ala Met Thr Pro Glu Arg Val Ala Arg
            1595                1600                1605
Leu Arg Met Asn His Thr Thr Ser Ile Ile Val Cys Ser Ser Phe
            1610                1615                1620
Pro Leu Pro Lys Tyr Lys Ile Glu Gly Val Gln Lys Val Lys Cys
            1625                1630                1635
Ser Lys Ala Leu Leu Phe Asp His Asn Val Pro Ser Arg Val Ser
            1640                1645                1650
```

-continued

```
Pro Arg Thr Tyr Arg Pro Ala Asp Glu Ile Ile Gln Thr Pro Gln
1655                1660                1665

Ile Pro Thr Glu Ala Cys Gln Asp Ala Gln Phe Val Gln Ser Ile
    1670                1675                1680

Thr Asp Glu Ala Val Pro Val Pro Ser Asp Leu Glu Ala Cys Asp
1685                1690                1695

Ala Thr Met Asp Trp Pro Ser Ile Asp Ile Val Pro Thr Arg Gln
1700                1705                1710

Arg Ser Asp Ser Phe Asp Ser Glu Tyr Ser Ser Arg Ser Asn Ile
    1715                1720                1725

Gln Leu Val Thr Ala Asp Val His Ala Pro Met Tyr Ala Asn Ser
1730                1735                1740

Leu Ala Ser Ser Gly Gly Ser Val Leu Ser Leu Ser Ser Glu Gln
1745                1750                1755

Ala Gln Asn Gly Ile Met Ile Leu Pro Asp Ser Glu Asp Thr Asp
1760                1765                1770

Ser Ile Ser Arg Val Ser Thr Pro Ile Ala Pro Pro Arg Arg Arg
1775                1780                1785

Leu Gly Arg Thr Ile Asn Val Thr Cys Asp Glu Arg Glu Gly Lys
1790                1795                1800

Ile Leu Pro Met Ala Ser Asp Arg Leu Phe Thr Ala Lys Pro Tyr
1805                1810                1815

Thr Val Ala Leu Gly Val Ser Thr Ala Asp Ile Thr Ala Tyr Pro
1820                1825                1830

Ile Gln Ala Pro Leu Gly Ser Thr Gln Pro Pro Ala Leu Glu Gln
1835                1840                1845

Ile Thr Phe Gly Asp Phe Ala Glu Gly Glu Ile Asp Asn Leu Leu
1850                1855                1860

Thr Gly Ala Leu Thr Phe Gly Asp Phe Glu Pro Gly Glu Val Glu
1865                1870                1875

Glu Leu Thr Asp Ser Glu Trp Ser Thr Cys Ser Asp Thr Asp Glu
1880                1885                1890

Glu Leu Arg Leu Asp Arg Ala Gly Gly Tyr Ile Phe Ser Ser Asp
1895                1900                1905

Thr Gly Gln Gly His Leu Gln Gln Lys Ser Val Arg Gln Thr Thr
1910                1915                1920

Leu Pro Val Asn Ile Val Glu Val His Glu Glu Lys Cys Tyr
1925                1930                1935

Pro Pro Lys Leu Asp Glu Ile Lys Glu Gln Leu Leu Leu Lys Arg
1940                1945                1950

Leu Gln Glu Ser Ala Ser Thr Ala Asn Arg Ser Arg Tyr Gln Ser
1955                1960                1965

Arg Lys Val Glu Asn Met Lys Ala Thr Ile Ile His Arg Leu Lys
1970                1975                1980

Glu Gly Cys Arg Leu Tyr Leu Ala Ser Asp Thr Pro Arg Val Pro
1985                1990                1995

Ser Tyr Arg Ile Thr Tyr Pro Ala Pro Val Tyr Ser Pro Ser Ile
2000                2005                2010

Ser Ile Lys Leu Asn Asn Pro Glu Thr Ala Val Ala Val Cys Asn
2015                2020                2025

Glu Phe Leu Ala Arg Asn Tyr Pro Thr Val Ala Ser Tyr Gln Val
2030                2035                2040
```

-continued

Thr Asp Glu Tyr Asp Ala Tyr Leu Asp Met Val Asp Gly Ser Glu
2045                2050                2055

Ser Cys Leu Asp Arg Ala Thr Phe Asn Pro Ser Lys Leu Arg Ser
2060                2065                2070

Tyr Pro Lys Gln His Ser Tyr His Ala Pro Thr Ile Arg Ser Ala
2075                2080                2085

Val Pro Ser Pro Phe Gln Asn Thr Leu Gln Asn Val Leu Ala Ala
2090                2095                2100

Ala Thr Lys Arg Asn Cys Asn Val Thr Gln Met Arg Glu Leu Pro
2105                2110                2115

Thr Met Asp Ser Ala Val Phe Asn Val Glu Cys Phe Lys Lys Tyr
2120                2125                2130

Ala Cys Asn Gln Glu Tyr Trp Arg Glu Phe Ala Ser Ser Pro Ile
2135                2140                2145

Arg Val Thr Thr Glu Asn Leu Thr Met Tyr Val Thr Lys Leu Lys
2150                2155                2160

Gly Pro Lys Ala Ala Leu Phe Ala Lys Thr His Asn Leu Leu
2165                2170                2175

Pro Leu Gln Glu Val Pro Met Asp Arg Phe Thr Met Asp Met Lys
2180                2185                2190

Arg Asp Val Lys Val Thr Pro Gly Thr Lys His Thr Glu Glu Arg
2195                2200                2205

Pro Lys Val Gln Val Ile Gln Ala Ala Glu Pro Leu Ala Thr Ala
2210                2215                2220

Tyr Leu Cys Gly Ile His Arg Glu Leu Val Arg Arg Leu Asn Ala
2225                2230                2235

Val Leu Leu Pro Asn Val His Thr Leu Phe Asp Met Ser Ala Glu
2240                2245                2250

Asp Phe Asp Ala Ile Ile Ser Thr His Phe Lys Pro Gly Asp Ala
2255                2260                2265

Val Leu Glu Thr Asp Ile Ala Ser Phe Asp Lys Ser Gln Asp Asp
2270                2275                2280

Ser Leu Ala Leu Thr Ala Met Met Leu Leu Glu Asp Leu Gly Val
2285                2290                2295

Asp Gln Pro Ile Leu Asp Leu Ile Glu Ala Ala Phe Gly Glu Ile
2300                2305                2310

Ser Ser Cys His Leu Pro Thr Gly Thr Arg Phe Lys Phe Gly Ala
2315                2320                2325

Met Met Lys Ser Gly Met Phe Leu Thr Leu Phe Val Asn Thr Leu
2330                2335                2340

Leu Asn Ile Thr Ile Ala Ser Arg Val Leu Glu Glu Arg Leu Thr
2345                2350                2355

Thr Ser Ala Cys Ala Ala Phe Ile Gly Asp Asp Asn Ile Ile His
2360                2365                2370

Gly Val Val Ser Asp Ala Leu Met Ala Ala Arg Cys Ala Thr Trp
2375                2380                2385

Met Asn Met Glu Val Lys Ile Ile Asp Ala Val Val Ser Glu Lys
2390                2395                2400

Ala Pro Tyr Phe Cys Gly Gly Phe Ile Leu His Asp Thr Val Thr
2405                2410                2415

Gly Thr Ser Cys Arg Val Ala Asp Pro Leu Lys Arg Leu Phe Lys
2420                2425                2430

Leu Gly Lys Pro Leu Ala Ala Gly Asp Glu Gln Asp Glu Asp Arg

-continued

```
                2435                2440                2445

Arg Arg Ala Leu Ala Asp Glu Val Thr Arg Trp Gln Arg Thr Gly
    2450                2455                2460

Leu Ile Thr Glu Leu Glu Lys Ala Val Tyr Ser Arg Tyr Glu Val
2465                2470                2475

Gln Gly Ile Thr Ala Val Ile Thr Ser Met Ala Thr Phe Ala Ser
    2480                2485                2490

Ser Lys Glu Asn Phe Lys Lys Leu Arg Gly Pro Val Val Thr Leu
2495                2500                2505

Tyr Gly Gly Pro Lys
    2510

<210> SEQ ID NO 11
<211> LENGTH: 2481
<212> TYPE: PRT
<213> ORGANISM: Ross River Virus
<220> FEATURE:
<221> NAME/KEY: misc_feature
<222> LOCATION: (1864)..(1864)
<223> OTHER INFORMATION: Xaa can be any naturally occurring amino acid

<400> SEQUENCE: 11

Met Lys Val Thr Val Asp Val Glu Ala Asp Ser Pro Phe Leu Lys Ala
1               5                   10                  15

Leu Gln Lys Ala Phe Pro Ala Phe Glu Val Glu Ser Gln Gln Val Thr
                20                  25                  30

Pro Asn Asp His Ala Asn Ala Arg Ala Phe Ser His Leu Ala Thr Lys
            35                  40                  45

Leu Ile Glu Gln Glu Val Pro Thr Asn Ile Thr Ile Leu Asp Val Gly
50                  55                  60

Ser Ala Pro Ala Arg Arg Leu Met Ser Asp His Ser Tyr His Cys Ile
65                  70                  75                  80

Cys Pro Met Lys Ser Ala Glu Asp Pro Glu Arg Leu Ala Asn Tyr Ala
                85                  90                  95

Arg Lys Leu Ala Lys Ala Ala Gly Glu Val Leu Asp Lys Asn Val Ser
            100                 105                 110

Gly Lys Ile Thr Asp Leu Gln Asp Val Met Ala Thr Pro Asp Leu Glu
        115                 120                 125

Ser Pro Thr Phe Cys Leu His Thr Asp Glu Thr Cys Arg Thr Arg Ala
    130                 135                 140

Glu Val Ala Val Tyr Gln Asp Val Tyr Ala Val His Ala Pro Thr Ser
145                 150                 155                 160

Leu Tyr His Gln Ala Met Lys Gly Val Arg Thr Val Tyr Trp Ile Gly
                165                 170                 175

Phe Asp Thr Thr Pro Phe Met Phe Glu Val Leu Ala Gly Ala Tyr Pro
            180                 185                 190

Thr Tyr Ser Thr Asn Trp Ala Asp Glu Gln Val Leu Gln Ala Arg Asn
        195                 200                 205

Ile Gly Leu Cys Ala Thr Ser Leu Ser Glu Gly His Arg Gly Lys Leu
    210                 215                 220

Ser Ile Met Arg Lys Lys Arg Leu Arg Pro Ser Asp Arg Val Met Phe
225                 230                 235                 240

Ser Val Gly Ser Thr Leu Tyr Ile Glu Ser Arg Arg Leu Leu Lys Ser
                245                 250                 255

Trp His Leu Pro Ser Val Phe His Leu Lys Gly Lys Asn Ser Phe Thr
            260                 265                 270
```

```
Cys Arg Cys Asp Thr Ile Val Ser Cys Glu Gly Tyr Val Lys Lys
            275                 280                 285
Ile Thr Met Ser Pro Gly Thr Tyr Gly Lys Thr Val Gly Tyr Ala Val
    290                 295                 300
Thr His His Ala Glu Gly Phe Leu Met Cys Lys Val Thr Asp Thr Val
305                 310                 315                 320
Arg Gly Glu Arg Val Ser Phe Pro Val Cys Thr Tyr Val Pro Ala Thr
                325                 330                 335
Ile Cys Asp Gln Met Thr Gly Ile Leu Ala Thr Asp Val Thr Pro Glu
            340                 345                 350
Asp Ala Gln Lys Leu Leu Val Gly Leu Asn Gln Arg Ile Val Val Asn
            355                 360                 365
Gly Arg Thr Gln Arg Asn Thr Asn Thr Met Lys Asn Tyr Leu Leu Pro
    370                 375                 380
Val Val Ala Gln Ala Phe Ser Lys Trp Ala Arg Glu Ala Lys Ala Asp
385                 390                 395                 400
Met Glu Asp Glu Lys Pro Leu Gly Thr Arg Glu Arg Thr Leu Thr Cys
                405                 410                 415
Cys Cys Leu Trp Ala Phe Lys Ser His Lys Thr His Thr Met Tyr Lys
            420                 425                 430
Arg Pro Asp Thr Gln Thr Ile Val Lys Val Pro Ser Thr Phe Asp Ser
            435                 440                 445
Phe Val Ile Pro Ser Leu Trp Ser Ser Ser Leu Ser Ile Gly Leu Arg
450                 455                 460
Gln Arg Ile Lys Leu Leu Leu Gly Pro Lys Leu Ser Arg Asp Leu Pro
465                 470                 475                 480
Tyr Ser Gly Asp Arg Asn Glu Ala Arg Glu Ala Glu Lys Glu Ala Glu
                485                 490                 495
Glu Thr Lys Glu Ala Glu Leu Thr Arg Glu Ala Leu Pro Pro Leu Val
            500                 505                 510
Gly Ser Asn Cys Ala Asp Asp Val Asp Arg Val Asp Val Glu Glu Leu
            515                 520                 525
Thr Tyr Arg Ala Gly Ala Gly Val Val Glu Thr Pro Arg Asn Ala Leu
    530                 535                 540
Arg Val Thr Pro Gln Glu Arg Asp Gln Leu Ile Gly Ala Tyr Leu Ile
545                 550                 555                 560
Leu Ser Pro Gln Ala Val Leu Lys Ser Glu Lys Leu Thr Pro Ile His
                565                 570                 575
Pro Leu Ala Glu Gln Val Thr Ile Met Thr His Ser Gly Arg Ser Gly
            580                 585                 590
Arg Tyr Pro Val Asp Arg Tyr Asp Gly Arg Val Leu Val Pro Thr Gly
            595                 600                 605
Ala Ala Ile Pro Val Ser Glu Phe Gln Ala Leu Ser Glu Ser Ala Thr
    610                 615                 620
Met Val Tyr Asn Glu Arg Glu Phe Ile Asn Arg Lys Leu His His Ile
625                 630                 635                 640
Ala Leu Tyr Gly Pro Ala Leu Asn Thr Glu Glu Glu Asn Tyr Glu Lys
                645                 650                 655
Val Arg Ala Glu Arg Ala Glu Ala Glu Tyr Val Phe Asp Val Asp Lys
            660                 665                 670
Arg Met Cys Val Lys Arg Glu Glu Ala Ser Gly Leu Val Leu Val Gly
            675                 680                 685
```

```
Asp Leu Ile Asn Pro Pro Phe His Glu Phe Ala Tyr Glu Gly Leu Lys
690                 695                 700

Ile Arg Pro Ala Thr Pro Phe Gln Thr Thr Val Ile Gly Val Phe Gly
705                 710                 715                 720

Val Pro Gly Ser Gly Lys Ser Ala Ile Ile Lys Ser Val Val Thr Thr
            725                 730                 735

Arg Asp Leu Val Ala Ser Gly Lys Lys Glu Asn Cys Gln Glu Ile Val
                740                 745                 750

Asn Asp Val Lys Lys Gln Arg Gly Leu Asp Val Thr Ala Arg Thr Val
            755                 760                 765

Asp Ser Ile Leu Leu Asn Gly Cys Arg Arg Gly Val Glu Asn Leu Tyr
770                 775                 780

Val Asp Glu Ala Phe Ala Cys His Ser Gly Thr Leu Leu Ala Leu Ile
785                 790                 795                 800

Ala Met Val Lys Pro Thr Gly Lys Val Ile Leu Cys Gly Asp Pro Lys
                805                 810                 815

Gln Cys Gly Phe Phe Asn Leu Met Gln Leu Lys Val Asn Phe Asn His
            820                 825                 830

Asp Ile Cys Thr Gln Val Leu His Lys Ser Ile Ser Arg Arg Cys Thr
            835                 840                 845

Leu Pro Ile Thr Ala Ile Val Ser Thr Leu His Tyr Gln Gly Lys Met
850                 855                 860

Arg Thr Thr Asn Leu Cys Ser Ala Pro Ile Gln Ile Asp Thr Thr Gly
865                 870                 875                 880

Thr Thr Lys Pro Ala Lys Gly Asp Ile Val Leu Thr Cys Phe Arg Gly
                885                 890                 895

Trp Val Lys Gln Leu Gln Ile Asp Tyr Arg Gly His Glu Val Met Thr
            900                 905                 910

Ala Ala Ala Ser Gln Gly Leu Thr Arg Lys Gly Val Tyr Ala Val Arg
            915                 920                 925

Gln Lys Val Asn Glu Asn Pro Leu Tyr Ala Pro Ser Ser Glu His Val
930                 935                 940

Asn Val Leu Leu Thr Arg Thr Glu Asn Arg Leu Val Trp Lys Thr Leu
945                 950                 955                 960

Ser Gly Asp Pro Trp Ile Lys Val Leu Thr Asn Ile Pro Lys Gly Asp
                965                 970                 975

Phe Ser Ala Thr Leu Glu Glu Trp Gln Glu His Asp Asn Ile Met
            980                 985                 990

Asn Ala Leu Arg Glu Arg Ser Thr Ala Val Asp Pro Phe Gln Asn Lys
            995                 1000                1005

Ala Lys Val Cys Trp Ala Lys Cys Leu Val Gln Val Leu Glu Thr
    1010                1015                1020

Ala Gly Ile Arg Met Thr Ala Glu Glu Trp Asp Thr Val Leu Ala
    1025                1030                1035

Phe Arg Glu Asp Arg Ala Tyr Ser Pro Glu Val Ala Leu Asn Glu
    1040                1045                1050

Ile Cys Thr Lys Tyr Tyr Gly Val Asp Leu Asp Ser Gly Leu Phe
    1055                1060                1065

Ser Ala Gln Ser Val Ser Leu Tyr Tyr Glu Asn Asn His Trp Asp
    1070                1075                1080

Asn Arg Pro Gly Gly Arg Met Tyr Gly Phe Asn Arg Glu Val Ala
    1085                1090                1095

Arg Lys Phe Glu Gln Arg Tyr Pro Phe Leu Arg Gly Lys Met Asp
```

```
                  1100                1105                1110
Ser  Gly  Leu  Gln  Val  Asn  Val  Pro  Glu  Arg  Lys  Val  Gln  Pro  Phe
     1115                1120                1125

Asn  Ala  Glu  Cys  Asn  Ile  Leu  Pro  Ser  Asn  Arg  Arg  Leu  Pro  His
     1130                1135                1140

Ala  Leu  Val  Thr  Ser  Tyr  Gln  Gln  Cys  Gln  Gly  Glu  Arg  Val  Glu
     1145                1150                1155

Trp  Leu  Leu  Lys  Lys  Leu  Pro  Gly  Tyr  His  Leu  Leu  Val  Ser
     1160                1165                1170

Glu  Tyr  Asn  Leu  Ala  Leu  Pro  His  Lys  Arg  Val  Phe  Trp  Ile  Ala
     1175                1180                1185

Pro  Pro  His  Val  Ser  Gly  Ala  Asp  Arg  Ile  Tyr  Asp  Leu  Asp  Leu
     1190                1195                1200

Gly  Leu  Pro  Leu  Asn  Ala  Gly  Arg  Tyr  Asp  Leu  Val  Phe  Val  Asn
     1205                1210                1215

Ile  His  Thr  Glu  Tyr  Arg  Thr  His  His  Tyr  Gln  Gln  Cys  Val  Asp
     1220                1225                1230

His  Ser  Met  Lys  Leu  Gln  Met  Leu  Gly  Gly  Asp  Ser  Leu  His  Leu
     1235                1240                1245

Leu  Lys  Pro  Gly  Gly  Ser  Leu  Leu  Ile  Arg  Ala  Tyr  Gly  Tyr  Ala
     1250                1255                1260

Asp  Arg  Val  Ser  Glu  Met  Val  Val  Thr  Ala  Leu  Ala  Arg  Lys  Phe
     1265                1270                1275

Ser  Ala  Phe  Arg  Val  Leu  Arg  Pro  Ala  Cys  Val  Thr  Ser  Asn  Thr
     1280                1285                1290

Glu  Val  Phe  Leu  Leu  Phe  Thr  Asn  Phe  Asp  Asn  Gly  Arg  Arg  Ala
     1295                1300                1305

Val  Thr  Leu  His  Gln  Ala  Asn  Gln  Arg  Leu  Ser  Ser  Met  Phe  Ala
     1310                1315                1320

Cys  Asn  Gly  Leu  His  Thr  Ala  Gly  Cys  Ala  Pro  Ser  Tyr  Arg  Val
     1325                1330                1335

Arg  Arg  Thr  Asp  Ile  Ser  Gly  His  Ala  Glu  Glu  Ala  Val  Val  Asn
     1340                1345                1350

Ala  Ala  Asn  Ala  Lys  Gly  Thr  Val  Gly  Asp  Gly  Val  Cys  Arg  Ala
     1355                1360                1365

Val  Ala  Arg  Lys  Trp  Pro  Asp  Ser  Phe  Lys  Gly  Ala  Ala  Thr  Pro
     1370                1375                1380

Val  Gly  Thr  Ala  Lys  Leu  Val  Gln  Ala  Asn  Gly  Met  Asn  Val  Ile
     1385                1390                1395

His  Ala  Val  Gly  Pro  Asn  Phe  Ser  Thr  Val  Thr  Glu  Ala  Glu  Gly
     1400                1405                1410

Asp  Arg  Glu  Leu  Ala  Ala  Ala  Tyr  Arg  Ala  Val  Ala  Gly  Ile  Ile
     1415                1420                1425

Asn  Ala  Ser  Asn  Ile  Lys  Ser  Val  Ala  Ile  Pro  Leu  Leu  Ser  Thr
     1430                1435                1440

Gly  Val  Phe  Ser  Gly  Gly  Lys  Asp  Arg  Val  Met  Gln  Ser  Leu  Asn
     1445                1450                1455

His  Leu  Phe  Thr  Ala  Met  Asp  Thr  Thr  Asp  Ala  Asp  Val  Val  Ile
     1460                1465                1470

Tyr  Cys  Arg  Asp  Lys  Ala  Trp  Glu  Lys  Lys  Ile  Gln  Glu  Ala  Ile
     1475                1480                1485

Asp  Arg  Arg  Thr  Ala  Val  Glu  Leu  Val  Ser  Glu  Asp  Ile  Ser  Leu
     1490                1495                1500
```

```
Glu  Ser  Asp  Leu  Ile  Arg  Val  His  Pro  Asp  Ser  Cys  Leu  Val  Gly
     1505                1510                1515

Arg  Lys  Gly  Tyr  Ser  Ile  Thr  Asp  Gly  Lys  Leu  His  Ser  Tyr  Leu
     1520                1525                1530

Glu  Gly  Thr  Arg  Phe  His  Gln  Thr  Ala  Val  Asp  Met  Ala  Glu  Ile
     1535                1540                1545

Ser  Thr  Leu  Trp  Pro  Lys  Leu  Gln  Asp  Ala  Asn  Glu  Gln  Ile  Cys
     1550                1555                1560

Leu  Tyr  Ala  Leu  Gly  Glu  Ser  Met  Asp  Ser  Ile  Arg  Thr  Lys  Cys
     1565                1570                1575

Pro  Val  Glu  Asp  Ala  Asp  Ser  Ser  Thr  Pro  Pro  Lys  Thr  Val  Pro
     1580                1585                1590

Cys  Leu  Cys  Arg  Tyr  Ala  Met  Thr  Ala  Glu  Arg  Val  Ala  Arg  Leu
     1595                1600                1605

Arg  Met  Asn  Asn  Thr  Lys  Ala  Ile  Ile  Val  Cys  Ser  Ser  Phe  Pro
     1610                1615                1620

Leu  Pro  Lys  Tyr  Arg  Ile  Glu  Gly  Val  Gln  Lys  Val  Lys  Cys  Asp
     1625                1630                1635

Arg  Val  Leu  Ile  Phe  Asp  Gln  Thr  Val  Pro  Ser  Leu  Val  Ser  Pro
     1640                1645                1650

Arg  Lys  Tyr  Ile  Pro  Ala  Ala  Ala  Ser  Thr  His  Ala  Asp  Thr  Val
     1655                1660                1665

Ser  Leu  Asp  Ser  Thr  Val  Ser  Thr  Gly  Ser  Ala  Trp  Ser  Phe  Pro
     1670                1675                1680

Ser  Glu  Ala  Thr  Tyr  Glu  Thr  Met  Glu  Val  Val  Ala  Glu  Val  His
     1685                1690                1695

His  Ser  Glu  Pro  Pro  Val  Pro  Pro  Arg  Arg  Arg  Arg  Ala  Gln
     1700                1705                1710

Val  Thr  Met  His  His  Gln  Glu  Leu  Leu  Glu  Val  Ser  Asp  Met  His
     1715                1720                1725

Thr  Pro  Ile  Ala  Ala  Arg  Val  Glu  Ile  Pro  Val  Tyr  Asp  Thr  Ala
     1730                1735                1740

Val  Val  Val  Glu  Arg  Val  Ala  Ile  Pro  Cys  Thr  Ser  Glu  Tyr  Ala
     1745                1750                1755

Lys  Pro  Ile  Pro  Ala  Pro  Arg  Ala  Ala  Arg  Val  Val  Pro  Val  Pro
     1760                1765                1770

Ala  Pro  Arg  Ile  Gln  Arg  Ala  Ser  Thr  Tyr  Arg  Val  Ser  Pro  Thr
     1775                1780                1785

Pro  Thr  Pro  Arg  Val  Leu  Arg  Ala  Ser  Val  Cys  Ser  Val  Thr  Thr
     1790                1795                1800

Ser  Ala  Gly  Val  Glu  Phe  Pro  Trp  Ala  Pro  Glu  Asp  Leu  Glu  Val
     1805                1810                1815

Leu  Thr  Glu  Pro  Val  His  Cys  Lys  Met  Arg  Glu  Pro  Val  Glu  Leu
     1820                1825                1830

Pro  Trp  Glu  Pro  Glu  Asp  Val  Asp  Ile  Gln  Phe  Gly  Asp  Phe  Glu
     1835                1840                1845

Thr  Ser  Asp  Lys  Ile  Gln  Phe  Gly  Asp  Ile  Asp  Phe  Asp  Gln  Phe
     1850                1855                1860

Xaa  Leu  Gly  Arg  Ala  Gly  Ala  Tyr  Ile  Phe  Ser  Ser  Asp  Thr  Gly
     1865                1870                1875

Pro  Gly  His  Leu  Gln  Gln  Lys  Ser  Val  Arg  Gln  His  Ala  Leu  Pro
     1880                1885                1890
```

-continued

Cys Glu Met Leu Tyr Val His Glu Glu Glu Arg Thr Tyr Pro Pro
1895                    1900                1905

Ala Leu Asp Glu Ala Arg Glu Lys Leu Leu Gln Ala Lys Met Gln
1910                    1915                1920

Met Ala Pro Thr Glu Ala Asn Lys Ser Arg Tyr Gln Ser Arg Lys
1925                    1930                1935

Val Glu Asn Met Lys Ala Val Ile Ile Asp Arg Leu Lys Asp Gly
1940                    1945                1950

Ala Arg Thr Tyr Leu Thr Glu Gln Ser Glu Lys Ile Pro Thr Tyr
1955                    1960                1965

Val Ser Lys Tyr Pro Arg Pro Val Tyr Ser Pro Ser Val Glu Asp
1970                    1975                1980

Ser Leu Gln Asn Pro Glu Val Ala Val Ala Ala Cys Asn Ala Phe
1985                    1990                1995

Leu Glu Ala Asn Tyr Pro Thr Val Ala Ser Tyr Gln Ile Thr Asp
2000                    2005                2010

Glu Tyr Asp Ala Tyr Leu Asp Met Val Asp Gly Ser Glu Ser Cys
2015                    2020                2025

Leu Asp Arg Ala Thr Phe Cys Pro Ala Lys Leu Arg Cys Tyr Pro
2030                    2035                2040

Lys His His Ala Tyr His Gln Pro Gln Val Arg Ser Ala Val Pro
2045                    2050                2055

Ser Pro Phe Gln Asn Thr Leu Gln Asn Val Leu Ala Ala Ala Thr
2060                    2065                2070

Lys Arg Asn Cys Asn Val Thr Gln Met Arg Glu Leu Pro Thr Leu
2075                    2080                2085

Asp Ser Ala Val Leu Asn Val Glu Cys Phe Lys Lys Phe Ala Cys
2090                    2095                2100

Asn Gly Glu Tyr Trp Gln Glu Phe Lys Asp Asn Pro Ile Arg Ile
2105                    2110                2115

Thr Thr Glu Asn Ile Thr Thr Tyr Val Thr Arg Leu Lys Gly Pro
2120                    2125                2130

Lys Ala Ala Ala Leu Phe Ala Lys Thr His Asn Leu Val Pro Leu
2135                    2140                2145

Gln Glu Val Pro Met Asp Arg Phe Val Val Asp Met Lys Arg Asp
2150                    2155                2160

Val Lys Val Thr Pro Gly Thr Lys His Thr Glu Glu Arg Pro Lys
2165                    2170                2175

Val Gln Val Ile Gln Ala Ala Glu Pro Leu Ala Thr Ala Tyr Leu
2180                    2185                2190

Cys Gly Ile His Arg Glu Leu Val Arg Arg Leu Lys Ala Val Leu
2195                    2200                2205

Ala Pro Asn Ile His Thr Leu Phe Asp Met Ser Ala Glu Asp Phe
2210                    2215                2220

Asp Ala Ile Ile Ala Ala His Phe Gln Pro Gly Asp Ala Val Leu
2225                    2230                2235

Glu Thr Asp Ile Ala Ser Phe Asp Lys Ser Gln Asp Asp Ser Leu
2240                    2245                2250

Ala Leu Thr Ala Leu Met Leu Leu Glu Asp Leu Gly Val Asp Gln
2255                    2260                2265

Glu Leu Leu Asp Leu Ile Glu Ala Ala Phe Gly Glu Ile Thr Ser
2270                    2275                2280

Val His Leu Pro Thr Gly Thr Arg Phe Lys Phe Gly Ala Met Met

```
                2285                2290                2295
Lys Ser Gly Met Phe Leu Thr Leu Phe Val Asn Thr Leu Leu Asn
            2300                2305                2310

Ile Val Ile Ala Cys Arg Val Leu Arg Glu Lys Leu Thr Asn Ser
            2315                2320                2325

Val Cys Ala Ala Phe Ile Gly Asp Asp Asn Ile Val His Gly Val
            2330                2335                2340

Arg Ser Asp Pro Leu Met Ala Glu Arg Cys Ala Ser Trp Val Asn
            2345                2350                2355

Met Glu Val Lys Ile Ile Asp Ala Thr Met Cys Glu Lys Pro Pro
            2360                2365                2370

Tyr Phe Cys Gly Gly Phe Ile Leu Tyr Asp Lys Val Thr Gly Ser
            2375                2380                2385

Ala Cys Arg Val Ala Asp Pro Leu Lys Arg Leu Phe Lys Leu Gly
            2390                2395                2400

Lys Pro Leu Pro Ala Gly Asp Thr Gln Asp Glu Asp Arg Arg Arg
            2405                2410                2415

Ala Leu Lys Asp Glu Thr Asp Arg Trp Ala Arg Val Gly Leu Lys
            2420                2425                2430

Ser Glu Leu Glu Ile Ala Leu Ser Ser Arg Tyr Glu Val Asn Gly
            2435                2440                2445

Thr Gly Asn Ile Val Arg Ala Met Ala Thr Leu Ala Lys Ser Leu
            2450                2455                2460

Lys Asn Phe Lys Lys Leu Arg Gly Pro Ile Val His Leu Tyr Gly
            2465                2470                2475

Gly Pro Lys
    2480

<210> SEQ ID NO 12
<211> LENGTH: 2432
<212> TYPE: PRT
<213> ORGANISM: Semliki Forest Virus

<400> SEQUENCE: 12

Met Ala Ala Lys Val His Val Asp Ile Glu Ala Asp Ser Pro Phe Ile
1               5                   10                  15

Lys Ser Leu Gln Lys Ala Phe Pro Ser Phe Glu Val Glu Ser Leu Gln
            20                  25                  30

Val Thr Pro Asn Asp His Ala Asn Ala Arg Ala Phe Ser His Leu Ala
        35                  40                  45

Thr Lys Leu Ile Glu Gln Glu Thr Asp Lys Asp Thr Leu Ile Leu Asp
    50                  55                  60

Ile Gly Ser Ala Pro Ser Arg Arg Met Met Ser Thr His Lys Tyr His
65                  70                  75                  80

Cys Val Cys Pro Met Arg Ser Ala Glu Asp Pro Glu Arg Leu Val Cys
                85                  90                  95

Tyr Ala Lys Lys Leu Ala Ala Ala Ser Gly Lys Val Leu Asp Arg Glu
            100                 105                 110

Ile Ala Gly Lys Ile Thr Asp Leu Gln Thr Val Met Ala Thr Pro Asp
        115                 120                 125

Ala Glu Ser Pro Thr Phe Cys Leu His Thr Asp Val Thr Cys Arg Thr
    130                 135                 140

Ala Ala Glu Val Ala Val Tyr Gln Asp Val Tyr Ala Val His Ala Pro
145                 150                 155                 160
```

-continued

```
Thr Ser Leu Tyr His Gln Ala Met Lys Gly Val Arg Thr Ala Tyr Trp
                165                 170                 175
Ile Gly Phe Asp Thr Thr Pro Phe Met Phe Asp Ala Leu Ala Gly Ala
            180                 185                 190
Tyr Pro Thr Tyr Ala Thr Asn Trp Ala Asp Glu Gln Val Leu Gln Ala
        195                 200                 205
Arg Asn Ile Gly Leu Cys Ala Ala Ser Leu Thr Glu Gly Arg Leu Gly
    210                 215                 220
Lys Leu Ser Ile Leu Arg Lys Lys Gln Leu Lys Pro Cys Asp Thr Val
225                 230                 235                 240
Met Phe Ser Val Gly Ser Thr Leu Tyr Thr Glu Ser Arg Lys Leu Leu
                245                 250                 255
Arg Ser Trp His Leu Pro Ser Val Phe His Leu Lys Gly Lys Gln Ser
            260                 265                 270
Phe Thr Cys Arg Cys Asp Thr Ile Val Ser Cys Glu Gly Tyr Val Val
        275                 280                 285
Lys Lys Ile Thr Met Cys Pro Gly Leu Tyr Gly Lys Thr Val Gly Tyr
    290                 295                 300
Ala Val Thr Tyr His Ala Glu Gly Phe Leu Val Cys Lys Thr Thr Asp
305                 310                 315                 320
Thr Val Lys Gly Glu Arg Val Ser Phe Pro Val Cys Thr Tyr Val Pro
                325                 330                 335
Ser Thr Ile Cys Asp Gln Met Thr Gly Ile Leu Ala Thr Asp Val Thr
            340                 345                 350
Pro Glu Asp Ala Gln Lys Leu Leu Val Gly Leu Asn Gln Arg Ile Val
        355                 360                 365
Val Asn Gly Arg Thr Gln Arg Asn Thr Asn Thr Met Lys Asn Tyr Leu
    370                 375                 380
Leu Pro Ile Val Ala Val Ala Phe Ser Lys Trp Ala Arg Glu Tyr Lys
385                 390                 395                 400
Ala Asp Leu Asp Asp Glu Lys Pro Leu Gly Val Arg Glu Arg Ser Leu
                405                 410                 415
Thr Cys Cys Cys Leu Trp Ala Phe Lys Thr Arg Lys Met His Thr Met
            420                 425                 430
Tyr Lys Lys Pro Asp Thr Gln Thr Ile Val Lys Val Pro Ser Glu Phe
        435                 440                 445
Asn Ser Phe Val Ile Pro Ser Leu Trp Ser Thr Gly Leu Ala Ile Pro
    450                 455                 460
Val Arg Ser Arg Ile Lys Met Leu Leu Ala Lys Lys Thr Lys Arg Glu
465                 470                 475                 480
Leu Ile Pro Val Leu Asp Ala Ser Ser Ala Arg Asp Ala Glu Gln Glu
                485                 490                 495
Glu Lys Glu Arg Leu Glu Ala Glu Leu Thr Arg Glu Ala Leu Pro Pro
            500                 505                 510
Leu Val Pro Ile Ala Pro Ala Glu Thr Gly Val Val Asp Val Asp Val
        515                 520                 525
Glu Glu Leu Glu Tyr His Ala Gly Ala Gly Val Val Glu Thr Pro Arg
    530                 535                 540
Ser Ala Leu Lys Val Thr Ala Gln Pro Asn Asp Val Leu Leu Gly Asn
545                 550                 555                 560
Tyr Val Val Leu Ser Pro Gln Thr Val Leu Lys Ser Ser Lys Leu Ala
                565                 570                 575
Pro Val His Pro Leu Ala Glu Gln Val Lys Ile Ile Thr His Asn Gly
```

```
            580                 585                 590
Arg Ala Gly Arg Tyr Gln Val Asp Gly Tyr Asp Gly Arg Val Leu Leu
            595                 600                 605

Pro Cys Gly Ser Ala Ile Pro Val Pro Glu Phe Gln Ala Leu Ser Glu
            610                 615                 620

Ser Ala Thr Met Val Tyr Asn Glu Arg Glu Phe Val Asn Arg Lys Leu
625                 630                 635                 640

Tyr His Ile Ala Val His Gly Pro Ser Leu Asn Thr Asp Glu Glu Asn
            645                 650                 655

Tyr Glu Lys Val Arg Ala Glu Arg Thr Asp Ala Glu Tyr Val Phe Asp
            660                 665                 670

Val Asp Lys Lys Cys Cys Val Lys Arg Glu Glu Ala Ser Gly Leu Val
            675                 680                 685

Leu Val Gly Glu Leu Thr Asn Pro Pro Phe His Glu Phe Ala Tyr Glu
            690                 695                 700

Gly Leu Lys Ile Arg Pro Ser Ala Pro Tyr Lys Thr Thr Val Val Gly
705                 710                 715                 720

Val Phe Gly Val Pro Gly Ser Gly Lys Ser Ala Ile Ile Lys Ser Leu
            725                 730                 735

Val Thr Lys His Asp Leu Val Thr Ser Gly Lys Lys Glu Asn Cys Gln
            740                 745                 750

Glu Ile Val Asn Asp Val Lys Lys His Arg Gly Leu Asp Ile Gln Ala
            755                 760                 765

Lys Thr Val Asp Ser Ile Leu Leu Asn Gly Cys Arg Arg Ala Val Asp
            770                 775                 780

Ile Leu Tyr Val Asp Glu Ala Phe Ala Cys His Ser Gly Thr Leu Leu
785                 790                 795                 800

Ala Leu Ile Ala Leu Val Lys Pro Arg Ser Lys Val Val Leu Cys Gly
            805                 810                 815

Asp Pro Lys Gln Cys Gly Phe Phe Asn Met Met Gln Leu Lys Val Asn
            820                 825                 830

Phe Asn His Asn Ile Cys Thr Glu Val Cys His Lys Ser Ile Ser Arg
            835                 840                 845

Arg Cys Thr Arg Pro Val Thr Ala Ile Val Ser Thr Leu His Tyr Gly
            850                 855                 860

Gly Lys Met Arg Thr Thr Asn Pro Cys Asn Lys Pro Ile Ile Ile Asp
865                 870                 875                 880

Thr Thr Gly Gln Thr Lys Pro Lys Pro Gly Asp Ile Val Leu Thr Cys
            885                 890                 895

Phe Arg Gly Trp Val Lys Gln Leu Gln Leu Asp Tyr Arg Gly His Glu
            900                 905                 910

Val Met Thr Ala Ala Ser Gln Gly Leu Thr Arg Lys Gly Val Tyr
            915                 920                 925

Ala Val Arg Gln Lys Val Asn Glu Asn Pro Leu Tyr Ala Pro Ala Ser
            930                 935                 940

Glu His Val Asn Val Leu Leu Thr Arg Thr Glu Asp Arg Leu Val Trp
945                 950                 955                 960

Lys Thr Leu Ala Gly Asp Pro Trp Ile Lys Val Leu Ser Asn Ile Pro
            965                 970                 975

Gln Gly Asn Phe Thr Ala Thr Leu Glu Glu Trp Gln Glu Glu His Asp
            980                 985                 990

Lys Ile Met Lys Val Ile Glu Gly Pro Ala Ala Pro Val Asp Ala Phe
            995                 1000                1005
```

```
Gln Asn Lys Ala Asn Val Cys Trp Ala Lys Ser Leu Val Pro Val
    1010                1015                1020

Leu Asp Thr Ala Gly Ile Arg Leu Thr Ala Glu Glu Trp Ser Thr
    1025                1030                1035

Ile Ile Thr Ala Phe Lys Glu Asp Arg Ala Tyr Ser Pro Val Val
    1040                1045                1050

Ala Leu Asn Glu Ile Cys Thr Lys Tyr Tyr Gly Val Asp Leu Asp
    1055                1060                1065

Ser Gly Leu Phe Ser Ala Pro Lys Val Ser Leu Tyr Tyr Glu Asn
    1070                1075                1080

Asn His Trp Asp Asn Arg Pro Gly Gly Arg Met Tyr Gly Phe Asn
    1085                1090                1095

Ala Ala Thr Ala Ala Arg Leu Glu Ala Arg His Thr Phe Leu Lys
    1100                1105                1110

Gly Gln Trp His Thr Gly Lys Gln Ala Val Ile Ala Glu Arg Lys
    1115                1120                1125

Ile Gln Pro Leu Ser Val Leu Asp Asn Val Ile Pro Ile Asn Arg
    1130                1135                1140

Arg Leu Pro His Ala Leu Val Ala Glu Tyr Lys Thr Val Lys Gly
    1145                1150                1155

Ser Arg Val Glu Trp Leu Val Asn Lys Val Arg Gly Tyr His Val
    1160                1165                1170

Leu Leu Val Ser Glu Tyr Asn Leu Ala Leu Pro Arg Arg Arg Val
    1175                1180                1185

Thr Trp Leu Ser Pro Leu Asn Val Thr Gly Ala Asp Arg Cys Tyr
    1190                1195                1200

Asp Leu Ser Leu Gly Leu Pro Ala Asp Ala Gly Arg Phe Asp Leu
    1205                1210                1215

Val Phe Val Asn Ile His Thr Glu Phe Arg Ile His His Tyr Gln
    1220                1225                1230

Gln Cys Val Asp His Ala Met Lys Leu Gln Met Leu Gly Gly Asp
    1235                1240                1245

Ala Leu Arg Leu Leu Lys Pro Gly Gly Ser Leu Leu Met Arg Ala
    1250                1255                1260

Tyr Gly Tyr Ala Asp Lys Ile Ser Glu Ala Val Val Ser Ser Leu
    1265                1270                1275

Ser Arg Lys Phe Ser Ser Ala Arg Val Leu Arg Pro Asp Cys Val
    1280                1285                1290

Thr Ser Asn Thr Glu Val Phe Leu Leu Phe Ser Asn Phe Asp Asn
    1295                1300                1305

Gly Lys Arg Pro Ser Thr Leu His Gln Met Asn Thr Lys Leu Ser
    1310                1315                1320

Ala Val Tyr Ala Gly Glu Ala Met His Thr Ala Gly Cys Ala Pro
    1325                1330                1335

Ser Tyr Arg Val Lys Arg Ala Asp Ile Ala Thr Cys Thr Glu Ala
    1340                1345                1350

Ala Val Val Asn Ala Ala Asn Ala Arg Gly Thr Val Gly Asp Gly
    1355                1360                1365

Val Cys Arg Ala Val Ala Lys Lys Trp Pro Ser Ala Phe Lys Gly
    1370                1375                1380

Ala Ala Thr Pro Val Gly Thr Ile Lys Thr Val Met Cys Gly Ser
    1385                1390                1395
```

```
Tyr Pro Val Ile His Ala Val Ala Pro Asn Phe Ser Ala Thr Thr
    1400                1405                1410

Glu Ala Glu Gly Asp Arg Glu Leu Ala Ala Val Tyr Arg Ala Val
    1415                1420                1425

Ala Ala Glu Val Asn Arg Leu Ser Leu Ser Ser Val Ala Ile Pro
    1430                1435                1440

Leu Leu Ser Thr Gly Val Phe Ser Gly Gly Arg Asp Arg Leu Gln
    1445                1450                1455

Gln Ser Leu Asn His Leu Phe Thr Ala Met Asp Ala Thr Asp Ala
    1460                1465                1470

Asp Val Thr Ile Tyr Cys Arg Asp Lys Ser Trp Glu Lys Lys Ile
    1475                1480                1485

Gln Glu Ala Ile Asp Met Arg Thr Ala Val Glu Leu Leu Asn Asp
    1490                1495                1500

Asp Val Glu Leu Thr Thr Asp Leu Val Arg Val His Pro Asp Ser
    1505                1510                1515

Ser Leu Val Gly Arg Lys Gly Tyr Ser Thr Thr Asp Gly Ser Leu
    1520                1525                1530

Tyr Ser Tyr Phe Glu Gly Thr Lys Phe Asn Gln Ala Ala Ile Asp
    1535                1540                1545

Met Ala Glu Ile Leu Thr Leu Trp Pro Arg Leu Gln Glu Ala Asn
    1550                1555                1560

Glu Gln Ile Cys Leu Tyr Ala Leu Gly Glu Thr Met Asp Asn Ile
    1565                1570                1575

Arg Ser Lys Cys Pro Val Asn Asp Ser Asp Ser Ser Thr Pro Pro
    1580                1585                1590

Arg Thr Val Pro Cys Leu Cys Arg Tyr Ala Met Thr Ala Glu Arg
    1595                1600                1605

Ile Ala Arg Leu Arg Ser His Gln Val Lys Ser Met Val Val Cys
    1610                1615                1620

Ser Ser Phe Pro Leu Pro Lys Tyr His Val Asp Gly Val Gln Lys
    1625                1630                1635

Val Lys Cys Glu Lys Val Leu Leu Phe Asp Pro Thr Val Pro Ser
    1640                1645                1650

Val Val Ser Pro Arg Lys Tyr Ala Ala Ser Thr Thr Asp His Ser
    1655                1660                1665

Asp Arg Ser Leu Arg Gly Phe Asp Leu Asp Trp Thr Thr Asp Ser
    1670                1675                1680

Ser Ser Thr Ala Ser Asp Thr Met Ser Leu Pro Ser Leu Gln Ser
    1685                1690                1695

Cys Asp Ile Asp Ser Ile Tyr Glu Pro Met Ala Pro Ile Val Val
    1700                1705                1710

Thr Ala Asp Val His Pro Glu Pro Ala Gly Ile Ala Asp Leu Ala
    1715                1720                1725

Ala Asp Val His Pro Glu Pro Ala Asp His Val Asp Leu Glu Asn
    1730                1735                1740

Pro Ile Pro Pro Pro Arg Pro Lys Arg Ala Ala Tyr Leu Ala Ser
    1745                1750                1755

Arg Ala Ala Glu Arg Pro Val Pro Ala Pro Arg Lys Pro Thr Pro
    1760                1765                1770

Ala Pro Arg Thr Ala Phe Arg Asn Lys Leu Pro Leu Thr Phe Gly
    1775                1780                1785

Asp Phe Asp Glu His Glu Val Asp Ala Leu Ala Ser Gly Ile Thr
```

-continued

```
            1790                1795                1800
Phe Gly Asp Phe Asp Asp Val Leu Arg Leu Gly Arg Ala Gly Ala
    1805                1810                1815
Tyr Ile Phe Ser Ser Asp Thr Gly Ser Gly His Leu Gln Gln Lys
    1820                1825                1830
Ser Val Arg Gln His Asn Leu Gln Cys Ala Gln Leu Asp Ala Val
    1835                1840                1845
Glu Glu Glu Lys Met Tyr Pro Pro Lys Leu Asp Thr Glu Arg Glu
    1850                1855                1860
Lys Leu Leu Leu Leu Lys Met Gln Met His Pro Ser Glu Ala Asn
    1865                1870                1875
Lys Ser Arg Tyr Gln Ser Arg Lys Val Glu Asn Met Lys Ala Thr
    1880                1885                1890
Val Val Asp Arg Leu Thr Ser Gly Ala Arg Leu Tyr Thr Gly Ala
    1895                1900                1905
Asp Val Gly Arg Ile Pro Thr Tyr Ala Val Arg Tyr Pro Arg Pro
    1910                1915                1920
Val Tyr Ser Pro Thr Val Ile Glu Arg Phe Ser Ser Pro Asp Val
    1925                1930                1935
Ala Ile Ala Ala Cys Asn Glu Tyr Leu Ser Arg Asn Tyr Pro Thr
    1940                1945                1950
Val Ala Ser Tyr Gln Ile Thr Asp Glu Tyr Asp Ala Tyr Leu Asp
    1955                1960                1965
Met Val Asp Gly Ser Asp Ser Cys Leu Asp Arg Ala Thr Phe Cys
    1970                1975                1980
Pro Ala Lys Leu Arg Cys Tyr Pro Lys His His Ala Tyr His Gln
    1985                1990                1995
Pro Thr Val Arg Ser Ala Val Pro Ser Pro Phe Gln Asn Thr Leu
    2000                2005                2010
Gln Asn Val Leu Ala Ala Ala Thr Lys Arg Asn Cys Asn Val Thr
    2015                2020                2025
Gln Met Arg Glu Leu Pro Thr Met Asp Ser Ala Val Phe Asn Val
    2030                2035                2040
Glu Cys Phe Lys Arg Tyr Ala Cys Ser Gly Glu Tyr Trp Glu Glu
    2045                2050                2055
Tyr Ala Lys Gln Pro Ile Arg Ile Thr Thr Glu Asn Ile Thr Thr
    2060                2065                2070
Tyr Val Thr Lys Leu Lys Gly Pro Lys Ala Ala Ala Leu Phe Ala
    2075                2080                2085
Lys Thr His Asn Leu Val Pro Leu Gln Glu Val Pro Met Asp Arg
    2090                2095                2100
Phe Thr Val Asp Met Lys Arg Asp Val Lys Val Thr Pro Gly Thr
    2105                2110                2115
Lys His Thr Glu Glu Arg Pro Lys Val Gln Val Ile Gln Ala Ala
    2120                2125                2130
Glu Pro Leu Ala Thr Ala Tyr Leu Cys Gly Ile His Arg Glu Leu
    2135                2140                2145
Val Arg Arg Leu Asn Ala Val Leu Arg Pro Asn Val His Thr Leu
    2150                2155                2160
Phe Asp Met Ser Ala Glu Asp Phe Asp Ala Ile Ile Ala Ser His
    2165                2170                2175
Phe His Pro Gly Asp Pro Val Leu Glu Thr Asp Ile Ala Ser Phe
    2180                2185                2190
```

Asp Lys Ser Gln Asp Asp Ser Leu Ala Leu Thr Gly Leu Met Ile
    2195                2200                2205

Leu Glu Asp Leu Gly Val Asp Gln Tyr Leu Leu Asp Leu Ile Glu
    2210                2215                2220

Ala Ala Phe Gly Glu Ile Ser Ser Cys His Leu Pro Thr Gly Thr
    2225                2230                2235

Arg Phe Lys Phe Gly Ala Met Met Lys Ser Gly Met Phe Leu Thr
    2240                2245                2250

Leu Phe Ile Asn Thr Val Leu Asn Ile Thr Ile Ala Ser Arg Val
    2255                2260                2265

Leu Glu Gln Arg Leu Thr Asp Ser Ala Cys Ala Ala Phe Ile Gly
    2270                2275                2280

Asp Asp Asn Ile Val His Gly Val Ile Ser Asp Lys Leu Met Ala
    2285                2290                2295

Glu Arg Cys Ala Ser Trp Val Asn Met Glu Val Lys Ile Ile Asp
    2300                2305                2310

Ala Val Met Gly Glu Lys Pro Pro Tyr Phe Cys Gly Gly Phe Ile
    2315                2320                2325

Val Phe Asp Ser Val Thr Gln Thr Ala Cys Arg Val Ser Asp Pro
    2330                2335                2340

Leu Lys Arg Leu Phe Lys Leu Gly Lys Pro Leu Thr Ala Glu Asp
    2345                2350                2355

Lys Gln Asp Glu Asp Arg Arg Arg Ala Leu Ser Asp Glu Val Ser
    2360                2365                2370

Lys Trp Phe Arg Thr Gly Leu Gly Ala Glu Leu Glu Val Ala Leu
    2375                2380                2385

Thr Ser Arg Tyr Glu Val Glu Gly Cys Lys Ser Ile Leu Ile Ala
    2390                2395                2400

Met Ala Thr Leu Ala Arg Asp Ile Lys Ala Phe Lys Lys Leu Arg
    2405                2410                2415

Gly Pro Val Ile His Leu Tyr Gly Gly Pro Arg Leu Val Arg
    2420                2425                2430

<210> SEQ ID NO 13
<211> LENGTH: 2435
<212> TYPE: PRT
<213> ORGANISM: Mayaro Virus
<220> FEATURE:
<221> NAME/KEY: misc_feature
<222> LOCATION: (1818)..(1818)
<223> OTHER INFORMATION: Xaa can be any naturally occurring amino acid

<400> SEQUENCE: 13

Met Ser Lys Val Phe Val Asp Ile Glu Ala Glu Ser Pro Phe Leu Lys
1               5                   10                  15

Ser Leu Gln Arg Ala Phe Pro Ala Phe Glu Val Glu Ala Gln Gln Val
            20                  25                  30

Thr Pro Asn Asp His Ala Asn Ala Arg Ala Phe Ser His Leu Ala Thr
        35                  40                  45

Lys Leu Ile Glu Gln Glu Thr Glu Lys Asp Thr Leu Ile Leu Asp Ile
    50                  55                  60

Gly Ser Ala Pro Ala Arg Arg Met Met Ser Glu His Thr Tyr His Cys
65                  70                  75                  80

Val Cys Pro Met Arg Ser Ala Glu Asp Pro Glu Arg Leu Leu Tyr Tyr
                85                  90                  95

Ala Arg Lys Leu Ala Lys Ala Ser Gly Glu Val Val Asp Arg Asn Ile
            100                 105                 110

Ala Ala Lys Ile Asp Asp Leu Gln Ser Val Met Ala Thr Pro Asp Asn
        115                 120                 125

Glu Ser Arg Thr Phe Cys Leu His Thr Asp Gln Thr Cys Arg Thr Pro
    130                 135                 140

Ala Glu Val Ala Val Tyr Gln Asp Val Tyr Ala Val His Ala Pro Thr
145                 150                 155                 160

Ser Leu Tyr Phe Gln Ala Met Lys Gly Val Arg Thr Ala Tyr Trp Ile
                165                 170                 175

Gly Phe Asp Thr Thr Pro Phe Met Phe Asp Thr Met Ala Gly Ala Tyr
            180                 185                 190

Pro Thr Tyr Ala Thr Asn Trp Ala Asp Glu Gln Val Leu Lys Ala Arg
        195                 200                 205

Asn Ile Gly Leu Cys Ser Ala Ala Leu Thr Glu Gly His Leu Gly Lys
    210                 215                 220

Leu Ser Ile Met Arg Lys Arg Met Glu Pro Ser Asp Gln Ile Met
225                 230                 235                 240

Phe Ser Val Gly Ser Thr Leu Tyr Thr Glu Ser Arg Arg Leu Leu Lys
                245                 250                 255

Ser Trp His Leu Pro Ser Val Phe His Leu Lys Gly Arg Gln Ser Tyr
            260                 265                 270

Thr Cys Arg Cys Asp Thr Ile Val Ser Cys Glu Gly Tyr Val Val Lys
        275                 280                 285

Lys Ile Thr Met Ser Pro Gly Val Phe Gly Lys Thr Ser Gly Tyr Ala
    290                 295                 300

Val Thr His His Ala Glu Gly Phe Leu Val Cys Lys Ile Thr Asp Thr
305                 310                 315                 320

Ile Ala Gly Glu Arg Val Ser Phe Pro Val Cys Thr Tyr Val Pro Ser
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ser Gln Ala Phe Ser Lys Trp Ala Lys Glu Tyr Arg Leu
385                 390                 395                 400

Asp Gln Glu Asp Glu Lys Asn Met Gly Met Arg Glu Arg Thr Leu Thr
                405                 410                 415

Cys Cys Cys Leu Trp Ala Phe Lys Ile His Lys Asn His Thr Met Tyr
            420                 425                 430

Lys Lys Pro Asp Thr Gln Thr Ile Val Arg Val Pro Ser Glu Phe Asn
        435                 440                 445

Ser Phe Val Ile Pro Asn Leu Trp Ser Ala Gly Leu Ser Ile Glu Ile
    450                 455                 460

Arg His Arg Ile Arg Leu Leu Gln Ser Arg Arg Ala Glu Pro Leu
465                 470                 475                 480

Val Pro Ser Met Asp Ala Ser Glu Ala Arg Ala Ala Glu Lys Glu Ala
                485                 490                 495

Ala Glu Ala Lys Glu Ala Glu Glu Thr Leu Ala Ala Leu Pro Pro Leu
            500                 505                 510

Ile Pro Thr Ala Pro Leu Leu Asp Asp Ile Pro Glu Val Asp Val Glu

-continued

```
            515                 520                 525
Glu Leu Glu Phe Arg Ala Gly Ala Gly Val Val Glu Thr Pro Arg Asn
        530                 535                 540

Ala Leu Lys Val Thr Pro Gln Asp Arg Asp Thr Met Val Gly Ser Tyr
545                 550                 555                 560

Leu Val Leu Ser Pro Gln Thr Val Leu Lys Ser Ala Lys Leu Gln Val
                565                 570                 575

Leu His Pro Leu Ala Glu Gln Val Lys Ile Ile Thr His Lys Gly Arg
                580                 585                 590

Ala Gly Arg Tyr Gln Val Asp Ala Tyr Asp Gly Arg Val Leu Ile Pro
            595                 600                 605

Thr Gly Ala Ala Ile Pro Val Pro Asp Phe Gln Ala Leu Ser Glu Ser
        610                 615                 620

Ala Thr Met Val Tyr Asn Glu Arg Glu Phe Ile Asn Arg Lys Leu Tyr
625                 630                 635                 640

His Ile Ala Val His Gly Ala Ala Leu Asn Thr Asp Glu Gly Tyr
                645                 650                 655

Glu Lys Val Arg Ala Glu Arg Thr Asp Ala Glu Tyr Val Phe Asp Val
            660                 665                 670

Asp Arg Lys Gln Cys Val Lys Arg Glu Asp Ala Glu Gly Leu Val Met
        675                 680                 685

Ile Gly Asp Leu Val Asn Pro Pro Phe His Glu Phe Ala Tyr Glu Gly
        690                 695                 700

Leu Lys Arg Arg Pro Ala Ala Pro Tyr Lys Thr Thr Val Val Gly Val
705                 710                 715                 720

Phe Gly Val Pro Gly Ser Gly Lys Ser Gly Ile Ile Lys Ser Leu Val
                725                 730                 735

Thr Arg Ala Asp Leu Val Thr Ser Gly Lys Arg Glu Asn Cys Gln Glu
            740                 745                 750

Ile Met Leu Asp Val Lys Arg Tyr Arg Asp Leu Asp Ile Thr Ala Lys
        755                 760                 765

Thr Val Asp Ser Val Leu Leu Asn Gly Val Lys Gln Thr Val Asp Val
        770                 775                 780

Leu Tyr Val Asp Glu Ala Phe Ala Cys His Ala Gly Thr Leu Leu Ala
785                 790                 795                 800

Leu Ile Ala Thr Val Arg Pro Arg Lys Lys Val Val Leu Cys Gly Asp
                805                 810                 815

Pro Lys Gln Cys Gly Phe Phe Asn Leu Met Gln Leu Gln Val Asn Phe
            820                 825                 830

Asn His Asn Ile Cys Thr Glu Val His His Lys Ser Ile Ser Arg Arg
        835                 840                 845

Cys Thr Leu Pro Ile Thr Ala Ile Val Ser Thr Leu His Tyr Glu Gly
        850                 855                 860

Lys Met Arg Thr Thr Asn Pro Tyr Asn Lys Pro Val Ile Ile Asp Thr
865                 870                 875                 880

Thr Gly Gln Thr Lys Pro Asn Arg Glu Asp Ile Val Leu Thr Cys Phe
                885                 890                 895

Arg Gly Trp Val Lys Gln Leu Gln Leu Asp Tyr Arg Gly His Glu Val
            900                 905                 910

Met Thr Ala Ala Ala Ser Gln Gly Leu Thr Arg Lys Gly Val Tyr Ala
        915                 920                 925

Val Arg Met Lys Val Asn Glu Asn Pro Leu Tyr Ala Gln Ser Ser Glu
        930                 935                 940
```

-continued

```
His Val Asn Val Leu Leu Thr Arg Thr Glu Gly Arg Leu Val Trp Lys
945                 950                 955                 960

Thr Leu Ser Gly Asp Pro Trp Ile Lys Thr Leu Ser Asn Ile Pro Lys
            965                 970                 975

Gly Asn Phe Thr Ala Thr Leu Glu Asp Trp Gln Gln Glu His Asp Ala
        980                 985                 990

Ile Met Arg Ala Ile Thr Gln Glu Ala Ala Pro Leu Asp Val Phe Gln
        995                 1000                1005

Asn Lys Ala Lys Val Cys Trp Ala Lys Cys Leu Val Pro Val Leu
    1010                1015                1020

Glu Thr Ala Gly Ile Arg Leu Ser Ala Ala Asp Trp Ser Ser Ile
    1025                1030                1035

Ile Leu Ala Phe Lys Glu Asp Arg Ala Tyr Ser Pro Glu Val Ala
    1040                1045                1050

Leu Asn Glu Ile Cys Thr Lys Val Tyr Gly Val Asp Leu Asp Ser
    1055                1060                1065

Gly Leu Phe Ser Ala Pro Arg Val Ser Leu His Tyr Thr Thr Asn
    1070                1075                1080

His Trp Asp Asn Ser Pro Gly Gly Arg Met Tyr Gly Phe Ser Val
    1085                1090                1095

Glu Ala Ala Asn Arg Leu Gln Arg His Pro Phe Tyr Arg Gly
    1100                1105                1110

Arg Trp Ala Ser Gly Gln Val Leu Val Ala Glu Arg Arg Thr Gln
    1115                1120                1125

Pro Ile Asp Ile Thr Cys Asn Leu Ile Pro Phe Asn Arg Arg Leu
    1130                1135                1140

Pro His Ala Leu Val Thr Glu Tyr His Pro Val Lys Gly Glu Arg
    1145                1150                1155

Val Glu Trp Leu Val Asn Lys Ile Pro Gly Tyr His Leu Leu Leu
    1160                1165                1170

Val Ser Glu Tyr Asn Leu Ile Leu Pro Arg Arg Lys Val Thr Trp
    1175                1180                1185

Ile Ala Pro Pro Thr Val Thr Gly Ala Asp Leu Thr His Asp Leu
    1190                1195                1200

Asp Leu Gly Leu Pro Pro Asn Ala Gly Arg Tyr Asp Leu Val Phe
    1205                1210                1215

Val Asn Met His Thr Pro Tyr Arg Leu His His Tyr Gln Gln Cys
    1220                1225                1230

Val Asp His Ala Met Lys Leu Gln Met Leu Gly Gly Asp Ala Leu
    1235                1240                1245

Tyr Leu Leu Lys Pro Gly Gly Ser Leu Leu Leu Arg Ala Tyr Gly
    1250                1255                1260

Tyr Ala Asp Arg Thr Ser Glu Ala Val Val Thr Ala Leu Ala Arg
    1265                1270                1275

Arg Phe Ser Ser Phe Arg Ala Val Arg Pro Pro Cys Val Thr Ser
    1280                1285                1290

Asn Thr Glu Val Phe Leu Leu Phe Ser Asn Phe Asp Asn Gly Arg
    1295                1300                1305

Arg Thr Val Thr Leu His Pro Thr Asn Gly Lys Leu Ser Ser Ile
    1310                1315                1320

Tyr Ala Gly Thr Val Leu Gln Ala Ala Gly Cys Ala Pro Ala Tyr
    1325                1330                1335
```

-continued

Thr Val Lys Arg Ala Asp Ile Ala Thr Ala Ile Glu Asp Ala Val
1340              1345              1350

Val Asn Ala Ala Asn His Arg Gly Gln Val Gly Asp Gly Val Cys
1355              1360              1365

Arg Ala Val Ala Arg Lys Trp Pro Gln Ala Phe Arg Asn Ala Ala
1370              1375              1380

Thr Pro Val Gly Thr Ala Lys Thr Val Lys Cys Asp Glu Thr Tyr
1385              1390              1395

Ile Ile His Ala Val Gly Pro Asn Phe Asn Asn Thr Ser Glu Ala
1400              1405              1410

Glu Gly Asp Arg Asp Leu Ala Ala Ala Tyr Arg Ala Val Ala Ala
1415              1420              1425

Glu Ile Asn Arg Leu Ser Ile Ser Ser Val Ala Ile Pro Leu Leu
1430              1435              1440

Ser Thr Gly Ile Phe Ser Ala Gly Lys Asp Arg Val His Gln Ser
1445              1450              1455

Leu Ser His Leu Leu Ala Ala Met Asp Thr Thr Glu Ala Arg Val
1460              1465              1470

Thr Ile Tyr Cys Arg Asp Lys Thr Trp Glu Gln Lys Ile Lys Thr
1475              1480              1485

Val Leu Gln Asn Arg Cys Ala Thr Glu Leu Val Ser Asp Glu Leu
1490              1495              1500

Gln Leu Glu Val Asn Leu Thr Arg Val His Pro Asp Ser Ser Leu
1505              1510              1515

Val Gly Arg Pro Gly Tyr Ser Thr Thr Asp Gly Thr Leu Tyr Ser
1520              1525              1530

Tyr Met Glu Gly Thr Lys Phe His Gln Ala Ala Leu Asp Met Ala
1535              1540              1545

Glu Ile Thr Thr Leu Trp Pro Arg Val Gln Asp Ala Asn Glu His
1550              1555              1560

Ile Cys Met Tyr Ala Leu Gly Glu Thr Met Asp Asn Ile Arg Ser
1565              1570              1575

Arg Cys Pro Val Glu Asp Ser Asp Ser Ser Thr Pro Pro Lys Thr
1580              1585              1590

Val Pro Cys Leu Cys Arg Tyr Ala Met Thr Pro Glu Arg Val Thr
1595              1600              1605

Arg Leu Arg Met His His Thr Lys Asp Leu Val Val Cys Ser Ser
1610              1615              1620

Phe Gln Leu Pro Lys Tyr Arg Ile Ala Gly Val Gln Arg Val Arg
1625              1630              1635

Cys Glu Lys Val Met Leu Phe Asp Ala Thr Pro Ala Ser Val
1640              1645              1650

Ser Pro Val Gln Tyr Leu Thr Ser His Ser Glu Thr Thr Val Ser
1655              1660              1665

Leu Ser Ser Phe Ser Ile Thr Ser Asp Ser Ser Leu Ser Thr
1670              1675              1680

Phe Pro Asp Leu Glu Ser Leu Glu Glu Leu Gly Asn Asp Pro Gln
1685              1690              1695

Ser Met Arg Met Asp Glu Ser Val Asn Gln Gln Pro Ile Pro Thr
1700              1705              1710

Ala Glu Pro Val Val Gln Pro Val Pro Pro Arg Pro Lys Arg
1715              1720              1725

Ala Arg Arg Leu Ala Ala Ala Arg Met Gln Val Gln Val Glu Val

```
            1730                1735                1740

His Arg Pro Pro Val Val Gln Arg Thr Lys Pro Val Pro Ala Pro
            1745                1750                1755

Arg Thr Ser Leu Arg Pro Val Pro Ala Pro Arg Ser Cys Met Pro
            1760                1765                1770

Arg Pro Ala Val Glu Leu Pro Trp Pro Gln Glu Thr Val Asp Val
            1775                1780                1785

Glu Phe Gly Ala Pro Thr Glu Glu Asp Ser Glu Ile Thr Phe Gly
            1790                1795                1800

Asp Phe Ser Ala Ser Glu Trp Glu Thr Ile Ser Asn Ser Ser Xaa
            1805                1810                1815

Leu Gly Arg Ala Gly Ala Tyr Ile Phe Ser Ser Asp Val Gly Pro
            1820                1825                1830

Gly His Leu Gln Gln Lys Ser Val Arg Gln His Asp Leu Glu Val
            1835                1840                1845

Pro Ile Met Asp Arg Val Val Glu Glu Lys Val Tyr Pro Pro Lys
            1850                1855                1860

Phe Asp Glu Ala Lys Glu Lys Gln Leu Leu Lys Leu Gln Met
            1865                1870                1875

His Ala Thr Asp Ala Asn Arg Ser Arg Tyr Gln Ser Arg Lys Val
            1880                1885                1890

Glu Asn Met Lys Ala Thr Ile Ile Asp Arg Leu Lys Gln Gly Ser
            1895                1900                1905

Ala Ser Tyr Ile Ser Ala Glu Ala Asp Lys Ala Val Thr Tyr His
            1910                1915                1920

Val Lys Tyr Ala Lys Pro Arg Tyr Ser Val Pro Val Met Gln Arg
            1925                1930                1935

Leu Ser Ser Ala Thr Thr Ala Val Ala Ala Cys Asn Glu Phe Leu
            1940                1945                1950

Ala Arg Asn Tyr Pro Thr Val Ala Ser Tyr Gln Ile Thr Asp Glu
            1955                1960                1965

Tyr Asp Ala Tyr Leu Asp Met Val Asp Gly Ser Glu Ser Cys Leu
            1970                1975                1980

Asp Arg Ala Asn Phe Cys Pro Ala Lys Leu Arg Cys Tyr Pro Lys
            1985                1990                1995

His His Ala Tyr His Val Pro Gln Ile Arg Ser Ala Val Pro Ser
            2000                2005                2010

Pro Phe Gln Asn Thr Leu Gln Asn Val Leu Ala Ala Thr Lys
            2015                2020                2025

Arg Asn Cys Asn Val Thr Gln Met Arg Glu Leu Pro Thr Leu Asp
            2030                2035                2040

Ser Ala Val Tyr Asn Val Glu Cys Phe Arg Lys Tyr Ala Cys Asn
            2045                2050                2055

Asn Glu Tyr Trp Glu Glu Phe Ala Ala Lys Pro Ile Arg Ile Thr
            2060                2065                2070

Thr Glu Asn Leu Thr Thr Tyr Val Thr Lys Leu Lys Gly Gly Lys
            2075                2080                2085

Ala Ala Ala Leu Phe Ala Lys Thr His Asn Leu Val Pro Leu Gln
            2090                2095                2100

Glu Val Pro Met Asp Arg Phe Val Met Asp Met Lys Arg Asp Val
            2105                2110                2115

Lys Val Thr Pro Gly Thr Lys His Thr Glu Glu Arg Pro Lys Val
            2120                2125                2130
```

```
Gln Val Ile Gln Ala Ala Glu Pro Leu Ala Thr Ala Tyr Leu Cys
    2135            2140            2145

Gly Ile His Arg Glu Leu Val Arg Arg Leu Asn Ala Val Leu Leu
    2150            2155            2160

Pro Asn Ile His Thr Leu Phe Asp Met Ser Ala Glu Asp Phe Asp
    2165            2170            2175

Ala Ile Ile Ser Glu His Phe Lys Pro Gly Asp His Val Leu Glu
    2180            2185            2190

Thr Asp Ile Ala Ser Phe Asp Lys Ser Gln Asp Asp Ser Leu Ala
    2195            2200            2205

Leu Thr Gly Leu Met Ile Leu Glu Asp Leu Gly Val Asp Asn Gln
    2210            2215            2220

Leu Leu Asp Leu Ile Glu Ala Ala Phe Gly Gln Ile Thr Ser Cys
    2225            2230            2235

His Leu Pro Thr Gly Thr Arg Phe Lys Phe Gly Ala Met Met Lys
    2240            2245            2250

Ser Gly Met Phe Leu Thr Leu Phe Ile Asn Thr Val Leu Asn Ile
    2255            2260            2265

Thr Ile Ala Ser Arg Val Leu Glu Ala Arg Leu Thr Asn Ser Ala
    2270            2275            2280

Cys Ala Ala Phe Ile Gly Asp Asp Asn Val Val His Gly Val Val
    2285            2290            2295

Ser Asp Lys Leu Met Ala Asp Arg Cys Ala Thr Trp Val Asn Met
    2300            2305            2310

Glu Val Lys Ile Ile Asp Ala Val Met Cys Ala Lys Pro Pro Tyr
    2315            2320            2325

Phe Cys Gly Gly Phe Leu Val Tyr Asp His Val Thr Arg Met Ser
    2330            2335            2340

Cys Arg Ile Ala Asp Pro Leu Lys Arg Leu Phe Lys Leu Gly Lys
    2345            2350            2355

Pro Leu Pro Ala Asp Asp Cys Gln Asp Glu Asp Arg Arg Arg Ala
    2360            2365            2370

Leu His Asp Glu Val Lys Lys Trp Phe Arg Ser Gly Leu Gly Ser
    2375            2380            2385

Glu Ile Glu Val Ala Leu Ala Thr Arg Tyr Glu Val Glu Gly Gly
    2390            2395            2400

Tyr Asn Leu Leu Leu Ala Met Ser Thr Phe Ala His Ser Met Lys
    2405            2410            2415

Asn Phe Ser Ala Leu Arg Gly Pro Val Ile His Leu Tyr Gly Gly
    2420            2425            2430

Pro Lys
    2435
```